(12) United States Patent
Riley et al.

(10) Patent No.: US 9,474,857 B2
(45) Date of Patent: Oct. 25, 2016

(54) MULTI-FLUID MEDICAL INJECTOR SYSTEM AND METHODS OF OPERATION

(71) Applicant: MEDRAD, Inc., Indianola, PA (US)

(72) Inventors: Michael A. Riley, Saxonburg, PA (US); Ralph H. Schriver, Tarentum, PA (US); William D. Barlow, Beaver Falls, PA (US); Thomas P. Joyce, Wilkins Township, PA (US); Andreas Maihoefer, Cheswick, PA (US)

(73) Assignee: Bayer HealthCare LLC, Whippany, NJ (US)

( * ) Notice: Subject to any disclaimer, the term of this patent is extended or adjusted under 35 U.S.C. 154(b) by 152 days.

(21) Appl. No.: 14/041,920

(22) Filed: Sep. 30, 2013

(65) Prior Publication Data

US 2014/0027009 A1 Jan. 30, 2014

Related U.S. Application Data

(62) Division of application No. 13/386,765, filed as application No. PCT/US2010/042501 on Jul. 20, 2010, now Pat. No. 8,945,051.

(60) Provisional application No. 61/228,294, filed on Jul. 24, 2009.

(51) Int. Cl.
*A61M 1/00* (2006.01)
*A61M 31/00* (2006.01)
(Continued)

(52) U.S. Cl.
CPC ............ *A61M 5/1782* (2013.01); *A61M 5/007* (2013.01); *A61M 5/1458* (2013.01);
(Continued)

(58) Field of Classification Search
CPC .. A61M 5/007; A61M 5/36; A61M 5/16831; A61M 5/1684; A61M 5/1782; A61M 5/14546; A61M 5/1458; A61M 5/16827; A61M 2005/1402; A61M 2005/1403; A61M 2005/14553; A61B 6/481; A61B 6/504; A61B 6/507
See application file for complete search history.

(56) References Cited

U.S. PATENT DOCUMENTS

| 2,112,160 A | 3/1938 | Johnson |
|---|---|---|
| 2,703,575 A | 3/1955 | Chibret et al. |

(Continued)

FOREIGN PATENT DOCUMENTS

| DE | 60113503 T2 | 6/2006 |
|---|---|---|
| DE | 69831596 T2 | 6/2006 |

(Continued)

OTHER PUBLICATIONS

The European Search Report dated Apr. 24, 2014 from corresponding EP Application No. 14155592.
(Continued)

*Primary Examiner* — Elmer Chao
(74) *Attorney, Agent, or Firm* — David Schramm; Joseph L. Kent; James R. Stevenson

(57) ABSTRACT

A multi-fluid injector system and methods of operation thereof are presented. One embodiment of such a fluid injector system includes an automatic refill procedure for a fluid injector system comprising a fluid injector and an operably engaged syringe. The procedure includes the step of determining, using an electronic control device operably controlling the fluid injector system, whether a fluid injection procedure involving the syringe is impending. If the electronic control device determines that the fluid injection procedure is not impending, such that the automatic refill will not interfere with the fluid injection procedure, an automatic refill of the syringe is initiated.

9 Claims, 91 Drawing Sheets

(51) Int. Cl.
 *A61M 37/00* (2006.01)
 *A61B 6/00* (2006.01)
 *A61M 5/178* (2006.01)
 *A61M 5/00* (2006.01)
 *A61M 5/145* (2006.01)
 *A61M 5/168* (2006.01)
 *A61M 5/14* (2006.01)

(52) U.S. Cl.
 CPC .... *A61M 5/14546* (2013.01); *A61M 5/16827* (2013.01); *A61B 6/507* (2013.01); *A61M 2005/1402* (2013.01); *A61M 2005/1403* (2013.01); *A61M 2005/14553* (2013.01)

(56) References Cited

U.S. PATENT DOCUMENTS

| | | |
|---|---|---|
| 3,754,644 A | 8/1973 | Hampel |
| 4,260,077 A | 4/1981 | Schroeder |
| 4,979,942 A | 12/1990 | Wolf et al. |
| 5,033,650 A | 7/1991 | Colin et al. |
| 5,116,315 A | 5/1992 | Capozzi et al. |
| 5,239,265 A | 8/1993 | Sugahara |
| 5,279,569 A | 1/1994 | Neer et al. |
| 5,300,031 A | 4/1994 | Neer et al. |
| 5,451,211 A | 9/1995 | Neer et al. |
| 5,456,669 A | 10/1995 | Neer et al. |
| 5,456,670 A | 10/1995 | Neer et al. |
| 5,464,014 A | 11/1995 | Sugahara |
| 5,505,707 A | 4/1996 | Manzie et al. |
| 5,569,181 A | 10/1996 | Heilman et al. |
| 5,573,515 A | 11/1996 | Wilson et al. |
| 5,658,261 A | 8/1997 | Neer et al. |
| 5,662,612 A | 9/1997 | Niehoff |
| 5,662,666 A | 9/1997 | Onuki et al. |
| 5,665,067 A | 9/1997 | Linder et al. |
| 5,665,074 A | 9/1997 | Kelly |
| 5,681,286 A | 10/1997 | Niehoff |
| 5,738,659 A | 4/1998 | Neer et al. |
| 5,739,508 A | 4/1998 | Uber, III |
| 5,743,872 A | 4/1998 | Kelly |
| 5,779,675 A | 7/1998 | Reilly et al. |
| 5,800,397 A | 9/1998 | Wilson et al. |
| 5,806,519 A | 9/1998 | Evans, III et al. |
| 5,840,026 A | 11/1998 | Uber, III et al. |
| 5,843,037 A | 12/1998 | Uber, III |
| 5,855,568 A | 1/1999 | Battiato et al. |
| 5,857,647 A | 1/1999 | Jakubowski, Jr. |
| 5,865,805 A | 2/1999 | Ziemba |
| 5,868,710 A | 2/1999 | Battiato et al. |
| 5,882,343 A | 3/1999 | Wilson et al. |
| 5,885,216 A | 3/1999 | Evans, III et al. |
| 5,902,276 A | 5/1999 | Namey, Jr. |
| 5,913,844 A | 6/1999 | Ziemba et al. |
| 5,916,165 A | 6/1999 | Duchon et al. |
| 5,920,054 A | 7/1999 | Uber, III |
| 5,925,022 A | 7/1999 | Battiato et al. |
| 5,928,197 A | 7/1999 | Niehoff |
| 5,938,638 A | 8/1999 | Passariello et al. |
| 5,968,015 A | 10/1999 | Yamamoto |
| 5,988,587 A | 11/1999 | Duchon et al. |
| 5,997,484 A | 12/1999 | Sugahara |
| 6,004,285 A | 12/1999 | Sugahara |
| 6,004,292 A | 12/1999 | Battiato et al. |
| 6,099,502 A | 8/2000 | Duchon et al. |
| 6,159,183 A | 12/2000 | Neer et al. |
| 6,196,999 B1 | 3/2001 | Goethel et al. |
| 6,221,045 B1 | 4/2001 | Duchon et al. |
| 6,254,572 B1 | 7/2001 | Knipfer et al. |
| 6,293,958 B1 | 9/2001 | Berry et al. |
| 6,312,410 B1 | 11/2001 | Yamamoto |
| 6,315,758 B1 | 11/2001 | Neer et al. |
| 6,344,030 B1 | 2/2002 | Duchon et al. |
| 6,355,024 B1 | 3/2002 | Small et al. |
| 6,361,528 B1 | 3/2002 | Wilson et al. |
| 6,368,307 B1 | 4/2002 | Ziemba et al. |
| 6,447,481 B1 | 9/2002 | Duchon et al. |
| 6,468,261 B1 | 10/2002 | Small et al. |
| 6,488,660 B1 | 12/2002 | Futterknecht |
| 6,511,459 B1 | 1/2003 | Fago |
| 6,530,907 B1 | 3/2003 | Sugahara et al. |
| 6,533,758 B1 | 3/2003 | Staats et al. |
| 6,558,125 B1 | 5/2003 | Futterknecht |
| 6,569,127 B1 | 5/2003 | Fago et al. |
| 6,623,445 B1 | 9/2003 | Nelson et al. |
| 6,626,862 B1 | 9/2003 | Duchon et al. |
| 6,635,030 B1 | 10/2003 | Bae et al. |
| 6,648,860 B2 | 11/2003 | Staats et al. |
| 6,650,929 B1 | 11/2003 | Nemoto et al. |
| 6,656,157 B1 | 12/2003 | Duchon et al. |
| 6,659,979 B2 | 12/2003 | Neer et al. |
| 6,669,679 B1 | 12/2003 | Savage et al. |
| 6,673,048 B1 | 1/2004 | Duchon et al. |
| 6,676,635 B2 | 1/2004 | Nemoto |
| 6,746,427 B2 | 6/2004 | Duchon et al. |
| 6,752,789 B2 | 6/2004 | Duchon et al. |
| 6,764,466 B1 | 7/2004 | Staats et al. |
| 6,780,170 B2 | 8/2004 | Fago et al. |
| 6,880,808 B2 | 4/2005 | McPeak et al. |
| 6,917,828 B2 | 7/2005 | Fukuda |
| 6,929,619 B2 | 8/2005 | Fago et al. |
| 6,945,959 B2 | 9/2005 | Duchon et al. |
| 6,969,865 B2 | 11/2005 | Duchon et al. |
| 7,001,354 B2 | 2/2006 | Suzuki et al. |
| 7,018,363 B2 | 3/2006 | Cowan et al. |
| 7,047,994 B2 | 5/2006 | McPeak et al. |
| 7,081,104 B2 | 7/2006 | Neer et al. |
| 7,101,352 B2 | 9/2006 | Duchon et al. |
| 7,128,729 B2 | 10/2006 | Duchon et al. |
| 7,137,967 B2 | 11/2006 | Nemoto |
| 7,153,288 B2 | 12/2006 | Duchon et al. |
| 7,169,135 B2 | 1/2007 | Duchon et al. |
| 7,686,800 B2 | 3/2010 | Savage et al. |
| 7,828,776 B2 | 11/2010 | Nemoto et al. |
| 7,887,513 B2 | 2/2011 | Nemoto et al. |
| 8,177,757 B2 | 5/2012 | Nemoto et al. |
| 8,211,067 B2 | 7/2012 | Nemoto |
| 8,361,040 B2 | 1/2013 | Spohn et al. |
| 2001/0011163 A1 | 8/2001 | Nolan et al. |
| 2002/0095117 A1 | 7/2002 | Wilson et al. |
| 2002/0115933 A1 | 8/2002 | Duchon et al. |
| 2002/0128601 A1 | 9/2002 | Reilly et al. |
| 2002/0143294 A1 | 10/2002 | Duchon et al. |
| 2002/0169415 A1 | 11/2002 | Staats et al. |
| 2002/0183616 A1 | 12/2002 | Toews et al. |
| 2002/0198496 A1 | 12/2002 | Duchon et al. |
| 2003/0007891 A1 | 1/2003 | Wilson |
| 2003/0028144 A1 | 2/2003 | Duchon et al. |
| 2003/0028145 A1 | 2/2003 | Duchon et al. |
| 2003/0028402 A1 | 2/2003 | Ulrich et al. |
| 2003/0122095 A1 | 7/2003 | Wilson et al. |
| 2004/0010229 A1 | 1/2004 | Houde et al. |
| 2004/0064040 A1 | 4/2004 | Masuda et al. |
| 2004/0064041 A1 | 4/2004 | Lazzaro et al. |
| 2004/0082919 A1 | 4/2004 | Nemoto |
| 2004/0087909 A1 | 5/2004 | Nemoto |
| 2004/0087910 A1 | 5/2004 | Nemoto |
| 2004/0092881 A1 | 5/2004 | Nemoto |
| 2004/0097905 A1 | 5/2004 | Savage et al. |
| 2004/0122369 A1 | 6/2004 | Schriver et al. |
| 2004/0133165 A1 | 7/2004 | Duchon et al. |
| 2004/0152979 A1 | 8/2004 | Sakakibara et al. |
| 2004/0162484 A1 | 8/2004 | Nemoto |
| 2004/0167469 A1 | 8/2004 | Nemoto |
| 2004/0199076 A1 | 10/2004 | Nemoto |
| 2004/0215490 A1 | 10/2004 | Duchon et al. |
| 2004/0225255 A1 | 11/2004 | Ono |
| 2004/0249276 A1 | 12/2004 | Nemoto et al. |
| 2004/0249344 A1 | 12/2004 | Nemoto et al. |
| 2004/0254533 A1 | 12/2004 | Schriver et al. |
| 2005/0000447 A1 | 1/2005 | Koninckx et al. |
| 2005/0015056 A1 | 1/2005 | Duchon et al. |
| 2005/0027238 A1 | 2/2005 | Fago et al. |
| 2005/0038386 A1 | 2/2005 | Fago et al. |

(56) References Cited

U.S. PATENT DOCUMENTS

| | | |
|---|---|---|
| 2005/0038389 A1 | 2/2005 | Fago et al. |
| 2005/0038390 A1 | 2/2005 | Fago et al. |
| 2005/0038468 A1 | 2/2005 | Panetta et al. |
| 2005/0049556 A1 | 3/2005 | Tanaka |
| 2005/0113754 A1 | 5/2005 | Cowan |
| 2005/0113766 A1 | 5/2005 | Mottola et al. |
| 2005/0143653 A1 | 6/2005 | Fukuda |
| 2005/0148867 A1 | 7/2005 | Neer |
| 2005/0148868 A1 | 7/2005 | Fago et al. |
| 2005/0148869 A1 | 7/2005 | Masuda |
| 2005/0182322 A1 | 8/2005 | Grispo |
| 2005/0182323 A1 | 8/2005 | Grispo et al. |
| 2005/0182371 A1 | 8/2005 | Wagner et al. |
| 2005/0194047 A1 | 9/2005 | Bausmith |
| 2005/0230575 A1 | 10/2005 | Zelenski et al. |
| 2005/0234407 A1 | 10/2005 | Spohn et al. |
| 2005/0234428 A1 | 10/2005 | Spohn et al. |
| 2005/0245873 A1 | 11/2005 | Nemoto |
| 2006/0079765 A1 | 4/2006 | Neer et al. |
| 2006/0079766 A1 | 4/2006 | Neer et al. |
| 2006/0079767 A1 | 4/2006 | Gibbs et al. |
| 2006/0079768 A1 | 4/2006 | Small et al. |
| 2006/0079842 A1 | 4/2006 | Small et al. |
| 2006/0106347 A1 | 5/2006 | Fago et al. |
| 2006/0138377 A1 | 6/2006 | McPeak et al. |
| 2006/0151049 A1 | 7/2006 | Nemoto |
| 2006/0167415 A1 | 7/2006 | Nemoto |
| 2006/0180202 A1 | 8/2006 | Wilson et al. |
| 2006/0184122 A1 | 8/2006 | Nemoto |
| 2006/0264744 A1 | 11/2006 | Neer et al. |
| 2006/0271014 A1 | 11/2006 | Hynes et al. |
| 2007/0100282 A1 | 5/2007 | Small et al. |
| 2007/0161970 A1 | 7/2007 | Spohn et al. |
| 2007/0197963 A1 | 8/2007 | Griffiths et al. |
| 2007/0203460 A1 | 8/2007 | Nemoto et al. |
| 2007/0276235 A1 | 11/2007 | Ono |
| 2008/0058720 A1 | 3/2008 | Spohn et al. |
| 2008/0086087 A1 | 4/2008 | Spohn et al. |
| 2008/0154202 A1 | 6/2008 | Nemoto et al. |
| 2008/0154214 A1 | 6/2008 | Spohn et al. |
| 2008/0161634 A1 | 7/2008 | Nemoto et al. |
| 2008/0225440 A1 | 9/2008 | Nemoto et al. |
| 2008/0287785 A1 | 11/2008 | Saitoh et al. |
| 2009/0014303 A1 | 1/2009 | Nemoto et al. |
| 2009/0022378 A1 | 1/2009 | Nemoto |
| 2009/0149744 A1 | 6/2009 | Nemoto et al. |

FOREIGN PATENT DOCUMENTS

| | | |
|---|---|---|
| DE | 69833269 T2 | 11/2006 |
| EP | 650738 A1 | 5/1995 |
| EP | 650739 A1 | 5/1995 |
| EP | 692766 A1 | 1/1996 |
| EP | 702966 A2 | 3/1996 |
| EP | 726789 A1 | 8/1996 |
| EP | 813429 A1 | 12/1997 |
| EP | 1145703 | 10/2001 |
| EP | 1380261 A2 | 1/2004 |
| EP | 1410815 A1 | 4/2004 |
| EP | 1475111 A2 | 11/2004 |
| EP | 1037682 B1 | 9/2005 |
| EP | 1570874 A2 | 9/2005 |
| EP | 1571519 A2 | 9/2005 |
| EP | 1602389 A2 | 12/2005 |
| EP | 1607112 A1 | 12/2005 |
| EP | 1021813 B1 | 1/2006 |
| EP | 1024847 B1 | 1/2006 |
| EP | 1611911 A1 | 1/2006 |
| EP | 1618907 A1 | 1/2006 |
| EP | 1688157 A1 | 8/2006 |
| EP | 1829576 A1 | 9/2007 |
| JP | S51 25894 | 2/1976 |
| JP | H05084296 A | 4/1993 |
| JP | H05329211 A | 12/1993 |
| JP | H06030905 A | 2/1994 |
| JP | H06038563 A | 2/1994 |
| JP | H06142199 A | 5/1994 |
| JP | H06142200 A | 5/1994 |
| JP | H06165776 A | 6/1994 |
| JP | H07100212 A | 4/1995 |
| JP | H07178169 A | 7/1995 |
| JP | H08164120 A | 6/1996 |
| JP | H08336592 A | 12/1996 |
| JP | H09131400 A | 5/1997 |
| JP | H09164203 A | 6/1997 |
| JP | H09285546 A | 11/1997 |
| JP | H11033113 A | 2/1999 |
| JP | H11076402 A | 3/1999 |
| JP | H11-511356 | 10/1999 |
| JP | 2001212241 A | 8/2001 |
| JP | 2001218842 A | 8/2001 |
| JP | 2002011096 A | 1/2002 |
| JP | 2002301063 A | 10/2002 |
| JP | 2002301065 A | 10/2002 |
| JP | 2003033437 A | 2/2003 |
| JP | 2003132766 A | 5/2003 |
| JP | 2003135452 A | 5/2003 |
| JP | 2003150138 A | 5/2003 |
| JP | 2003196390 A | 7/2003 |
| JP | 2003220136 A | 8/2003 |
| JP | 2003235970 A | 8/2003 |
| JP | 2003235974 A | 8/2003 |
| JP | 2003290343 A | 10/2003 |
| JP | 2003290347 A | 10/2003 |
| JP | 2003290348 A | 10/2003 |
| JP | 2003290349 A | 10/2003 |
| JP | 2003295961 A | 10/2003 |
| JP | 2003339695 A | 12/2003 |
| JP | 2004024476 A | 1/2004 |
| JP | 2004024482 A | 1/2004 |
| JP | 2004121467 A | 4/2004 |
| JP | 2004154235 A | 6/2004 |
| JP | 2004154238 A | 6/2004 |
| JP | 2004154239 A | 6/2004 |
| JP | 2004178065 A | 6/2004 |
| JP | 2004194802 A | 7/2004 |
| JP | 2004194877 A | 7/2004 |
| JP | 2004290455 A | 10/2004 |
| JP | 2004298550 A | 10/2004 |
| JP | 2004298610 A | 10/2004 |
| JP | 2004305361 A | 11/2004 |
| JP | 2004313243 A | 11/2004 |
| JP | 2004313579 A | 11/2004 |
| JP | 2004344472 A | 12/2004 |
| JP | 2004357748 A | 12/2004 |
| JP | 2005021431 A | 1/2005 |
| JP | 2005021495 A | 1/2005 |
| JP | 2005024423 A | 1/2005 |
| JP | 2005025556 A | 1/2005 |
| JP | 2005110906 A | 4/2005 |
| JP | 2005160857 A | 6/2005 |
| JP | 2005185311 A | 7/2005 |
| JP | 2005198808 A | 7/2005 |
| JP | 2005270579 A | 10/2005 |
| JP | 2005327539 A | 11/2005 |
| JP | 2006014804 A | 1/2006 |
| JP | 2006164772 A | 6/2006 |
| JP | 2006164865 A | 6/2006 |
| JP | 2008-521577 | 6/2008 |
| WO | 9511722 A1 | 5/1995 |
| WO | 9602739 A1 | 9/1996 |
| WO | 0060522 A2 | 10/2000 |
| WO | 0113785 A2 | 3/2001 |
| WO | 01/89634 | 11/2001 |
| WO | 02064194 A1 | 8/2002 |
| WO | 02064195 A2 | 8/2002 |
| WO | 02065114 A2 | 8/2002 |
| WO | 03050491 A2 | 6/2003 |
| WO | 2005051463 A1 | 6/2005 |
| WO | 2005086393 A1 | 9/2005 |
| WO | 2005088661 A1 | 9/2005 |
| WO | 2005097232 A1 | 10/2005 |
| WO | 2006051855 A1 | 5/2006 |
| WO | 2006051856 A1 | 5/2006 |

(56) References Cited

FOREIGN PATENT DOCUMENTS

| WO | 2006054650 | A1 | 5/2006 |
|---|---|---|---|
| WO | 2006054651 | A1 | 5/2006 |
| WO | 2006057089 | A1 | 6/2006 |
| WO | 2006059597 | A1 | 6/2006 |
| WO | 2006068171 | A1 | 6/2006 |
| WO | 2006109691 | A1 | 10/2006 |
| WO | 2006109692 | A1 | 10/2006 |
| WO | 2006109777 | A1 | 10/2006 |
| WO | 2006109778 | A1 | 10/2006 |
| WO | 2006109779 | A1 | 10/2006 |
| WO | 2007062315 | A2 | 5/2007 |
| WO | 2007076463 | A2 | 7/2007 |
| WO | 2009036413 | A1 | 3/2009 |
| WO | 2012124028 | | 9/2012 |

OTHER PUBLICATIONS

The Supplementary European Search Report from corresponding EP Application No. 10802740.0.
The Written Opinion, International Search Report, and International Preliminary Report on Patentability from corresponding PCT Application No. PCT/US10/42501.
The Extended European Search Report dated Nov. 11, 2015 from corresponding EP Application No. EP15180011.7.

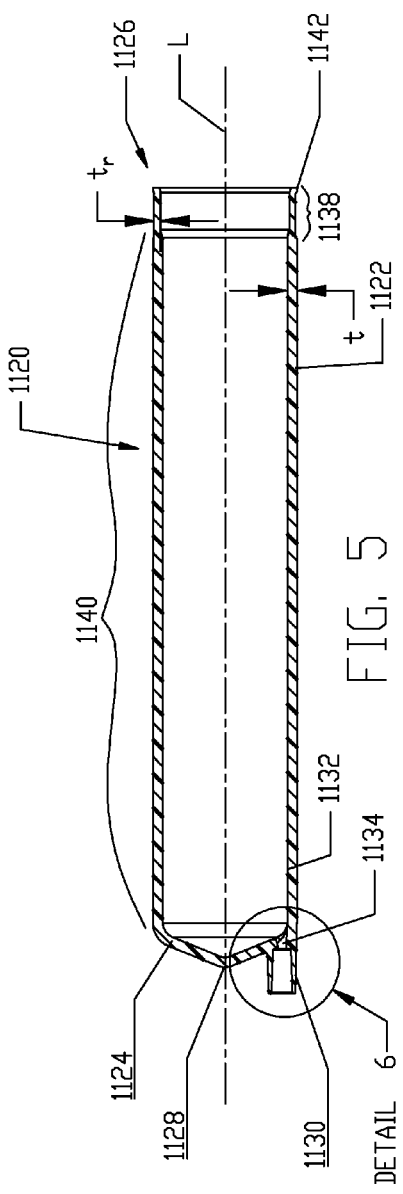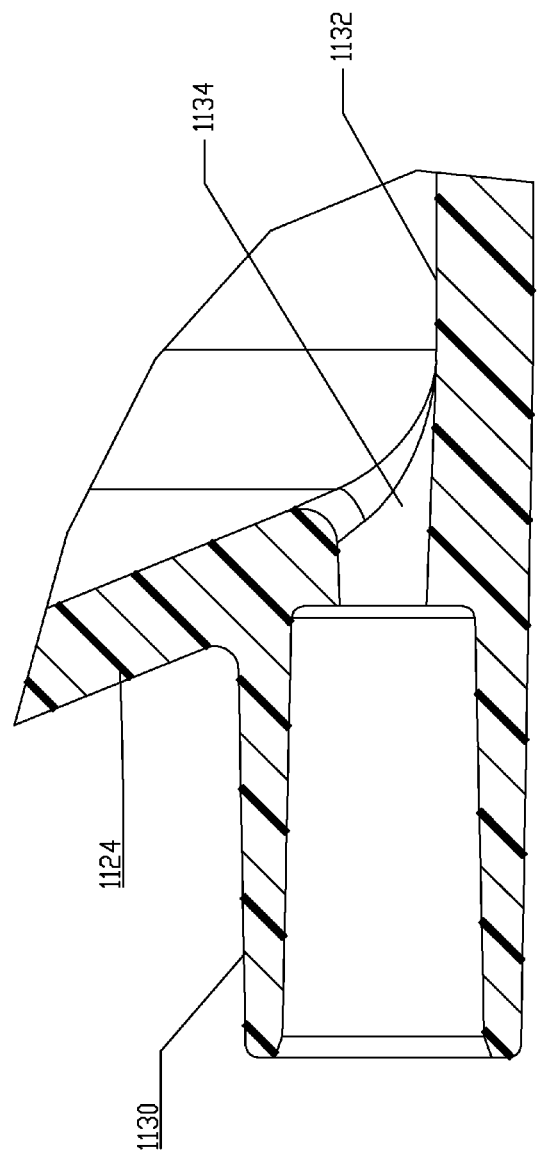

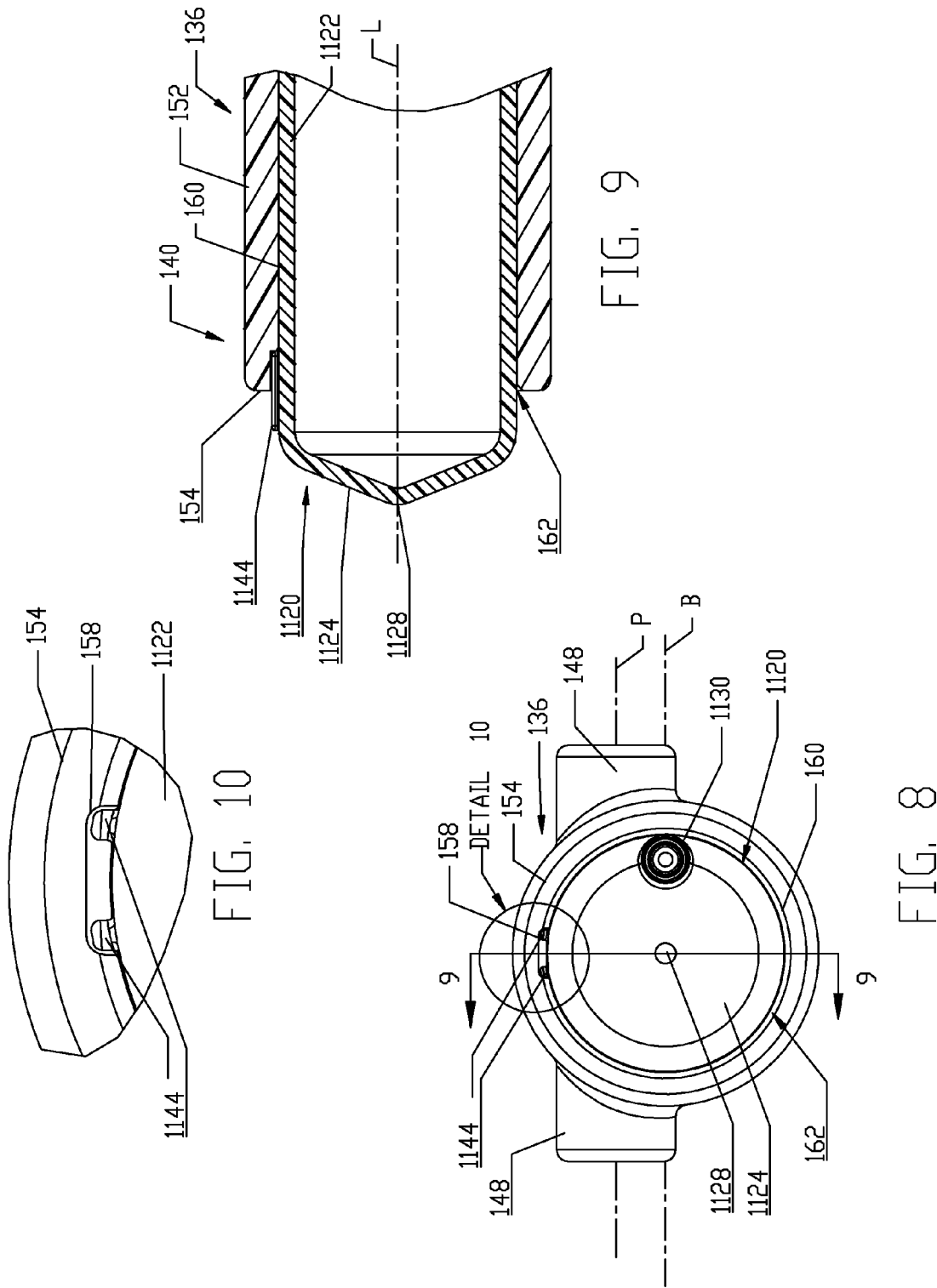

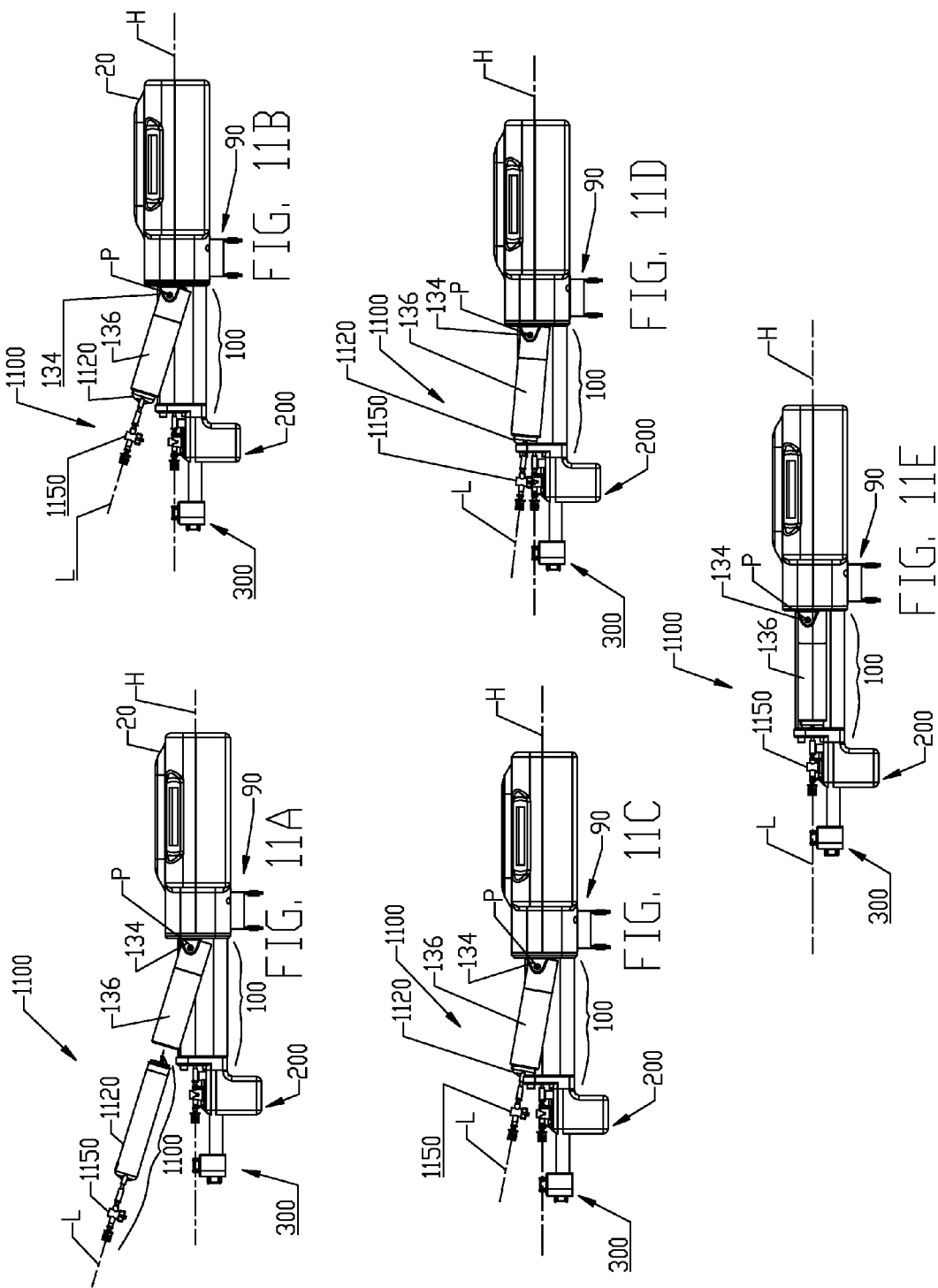

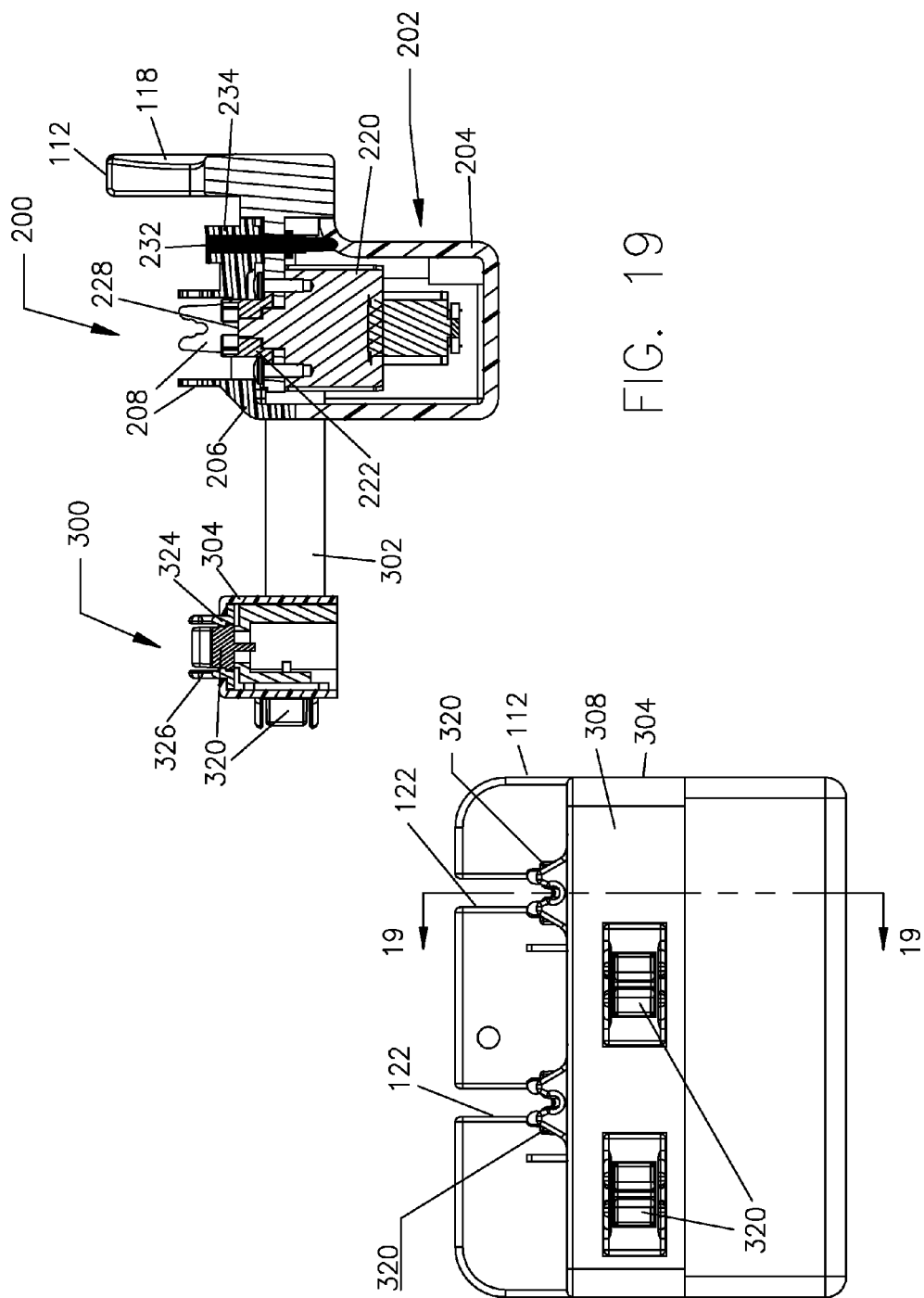

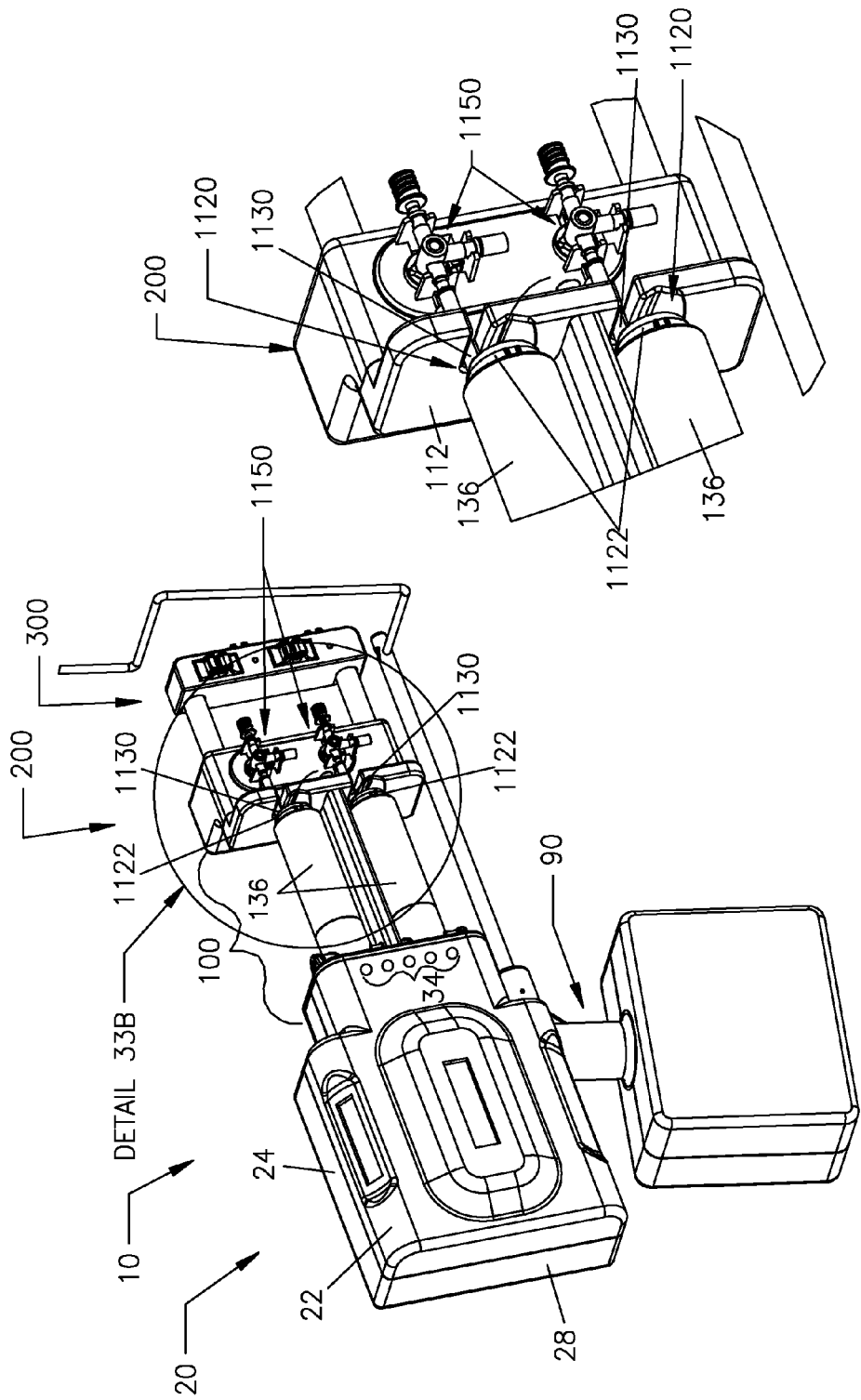

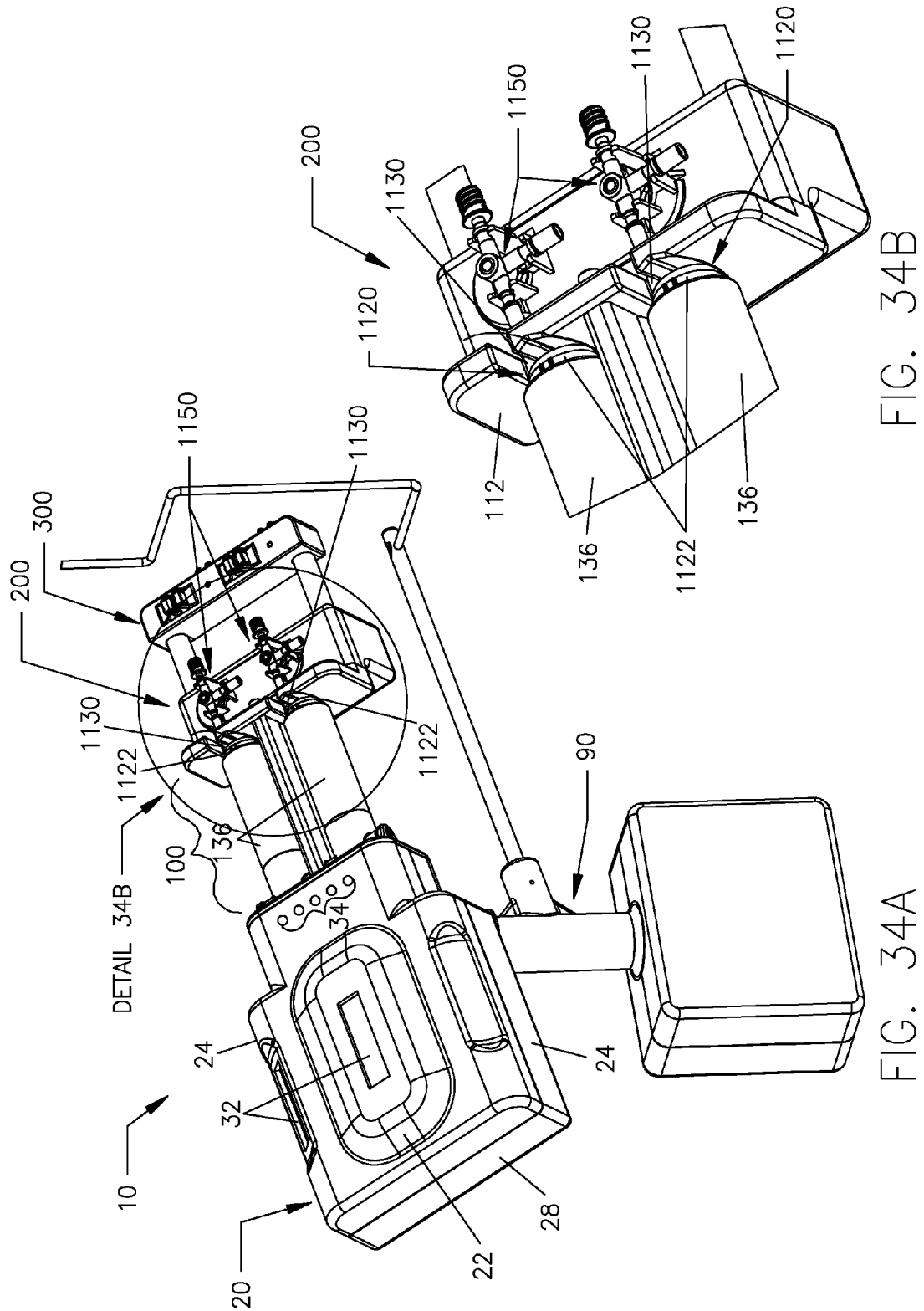

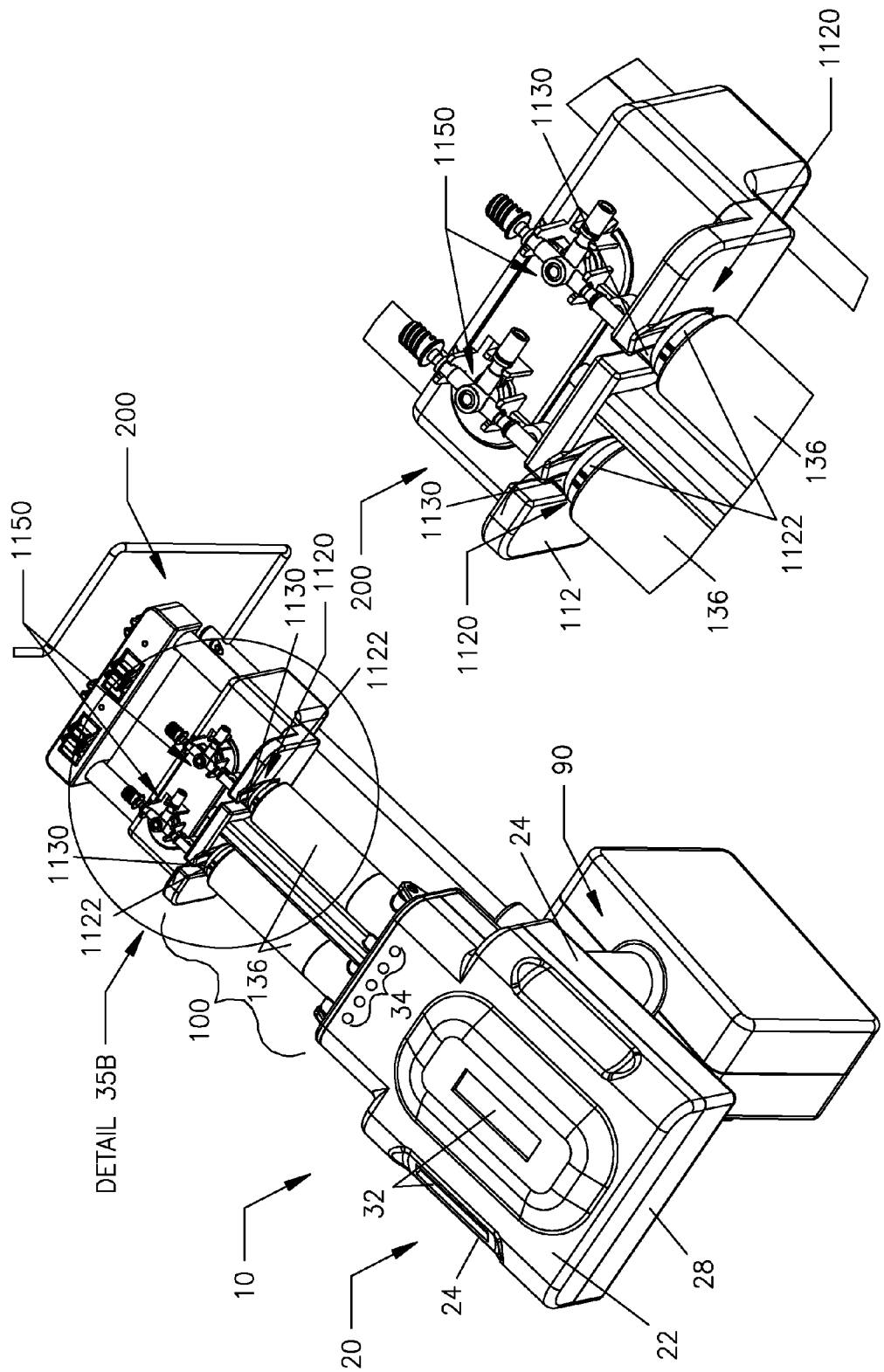

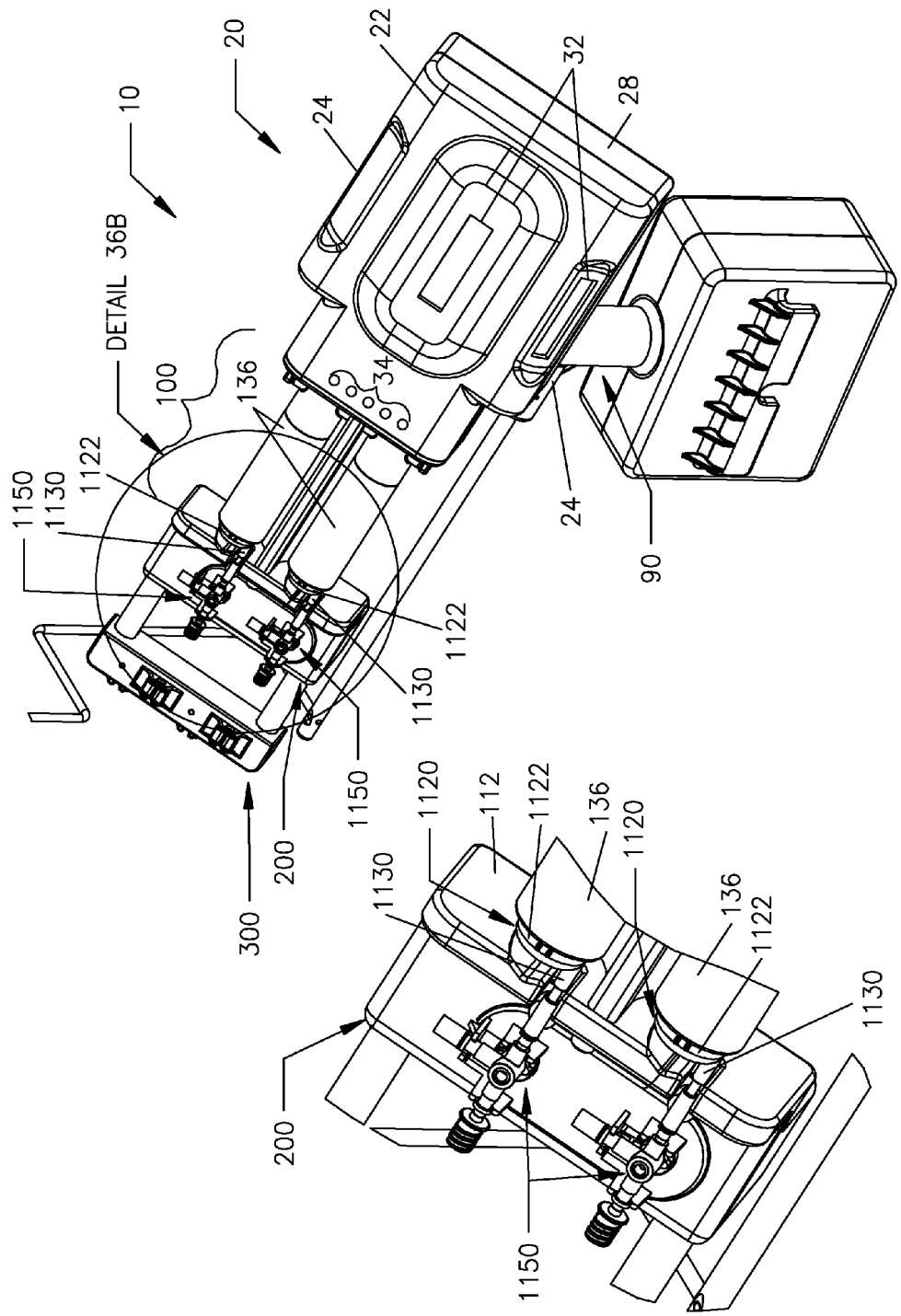

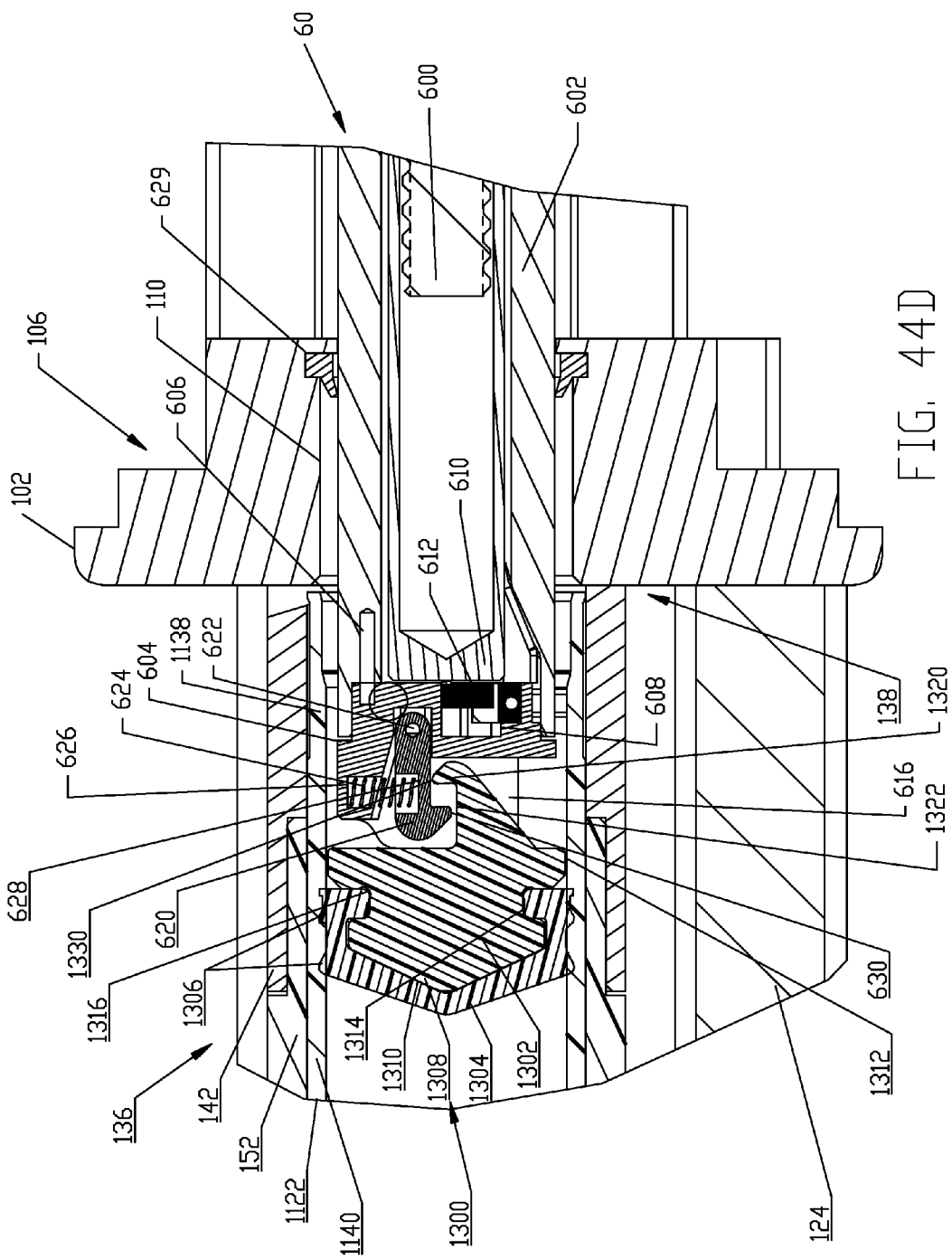

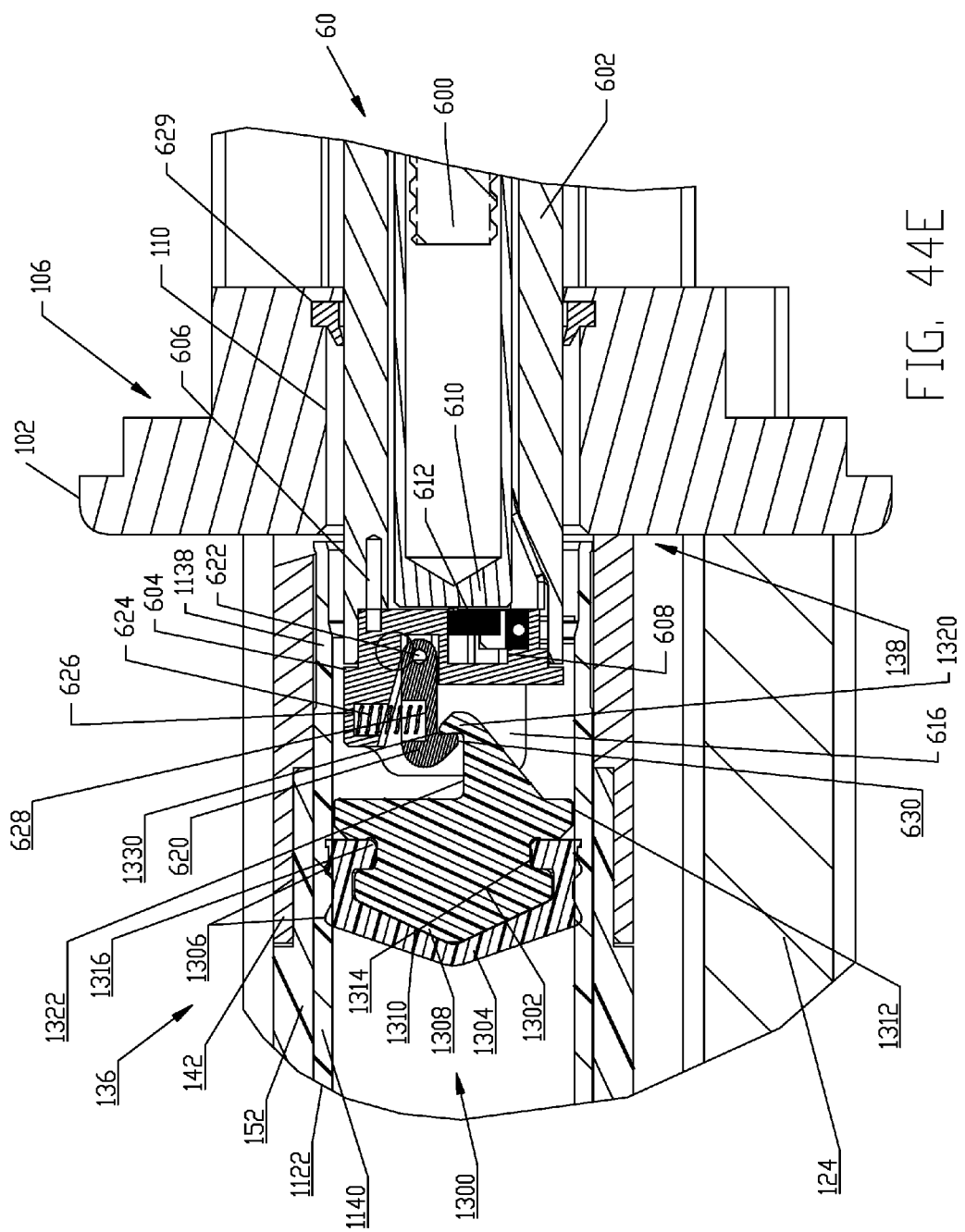

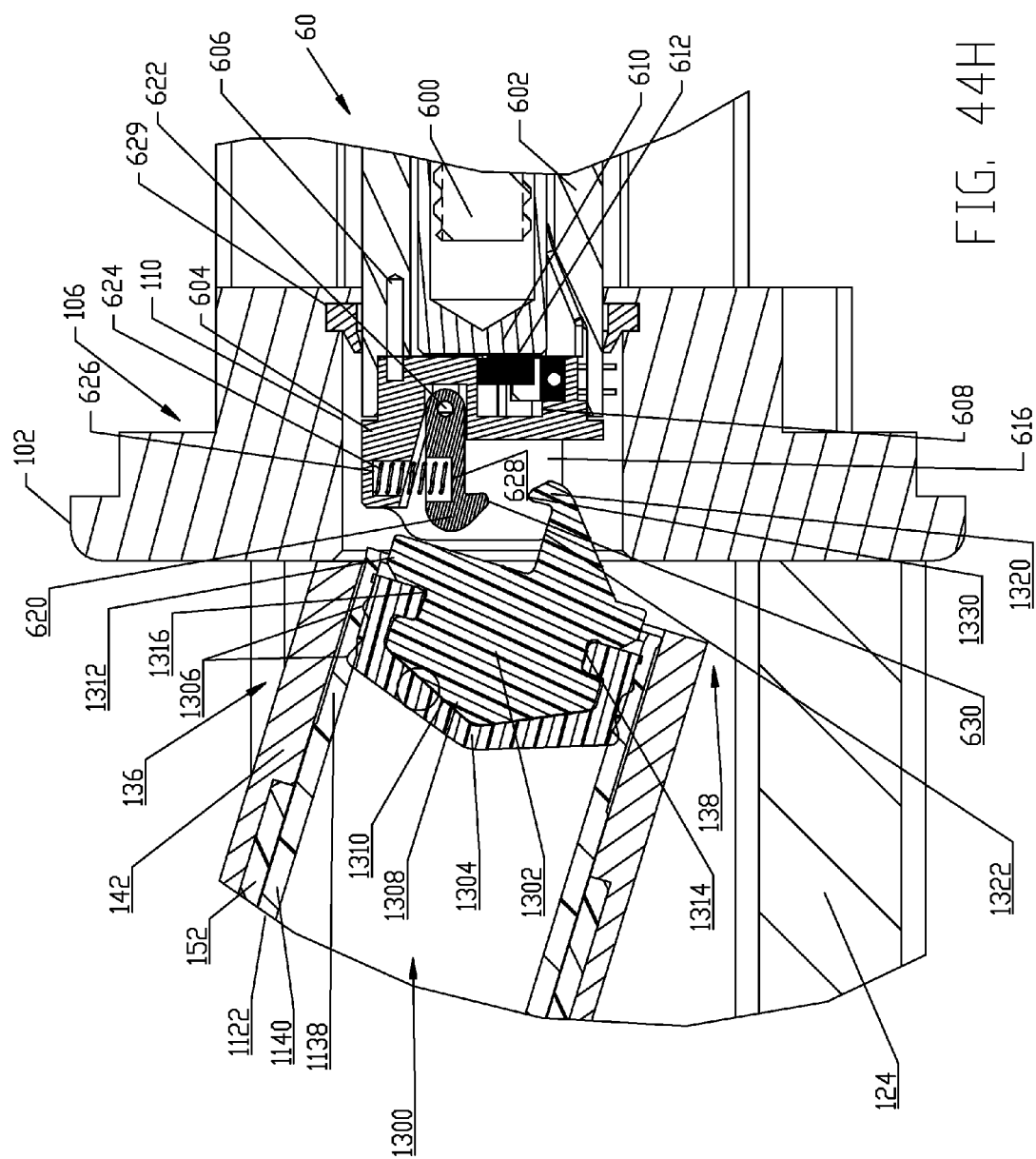

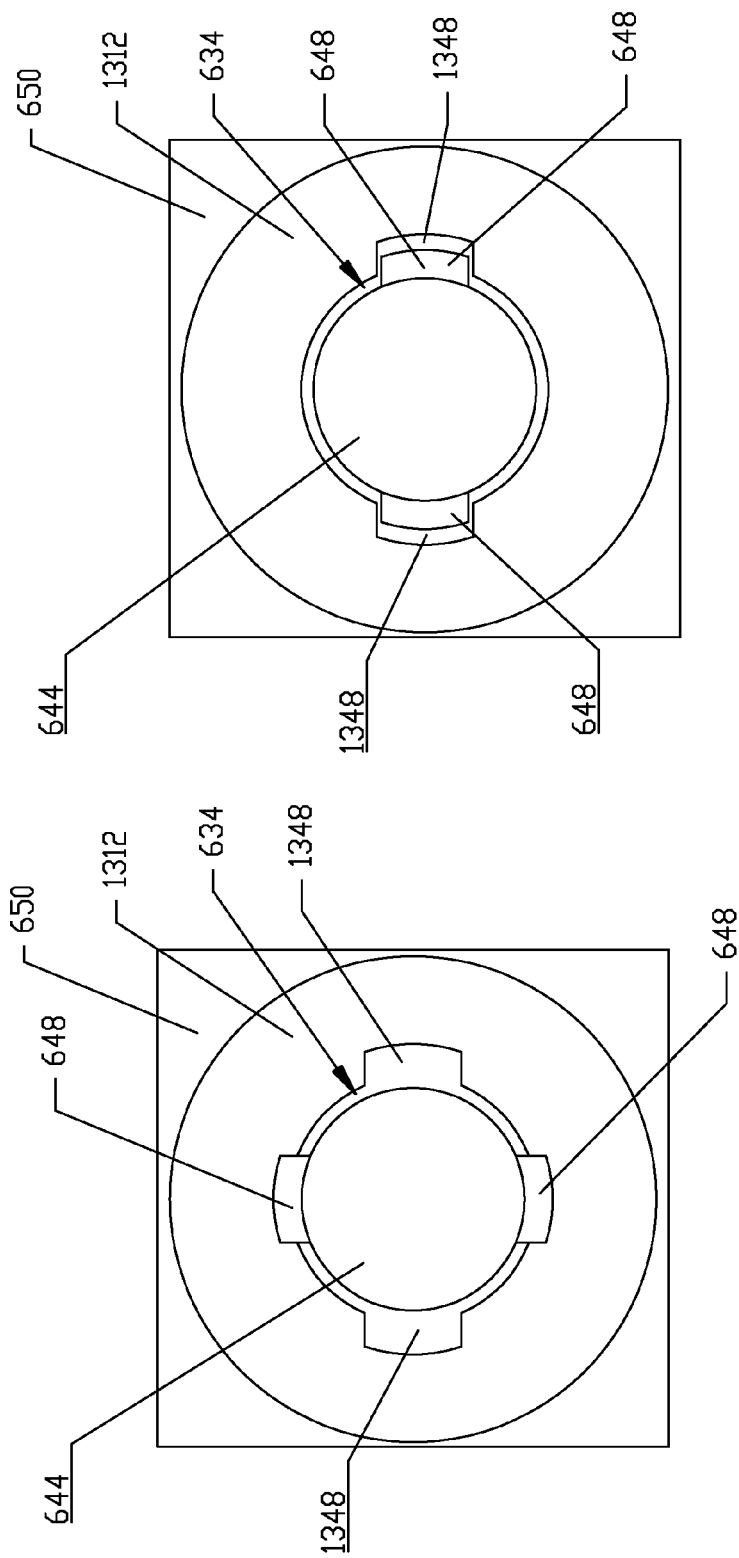

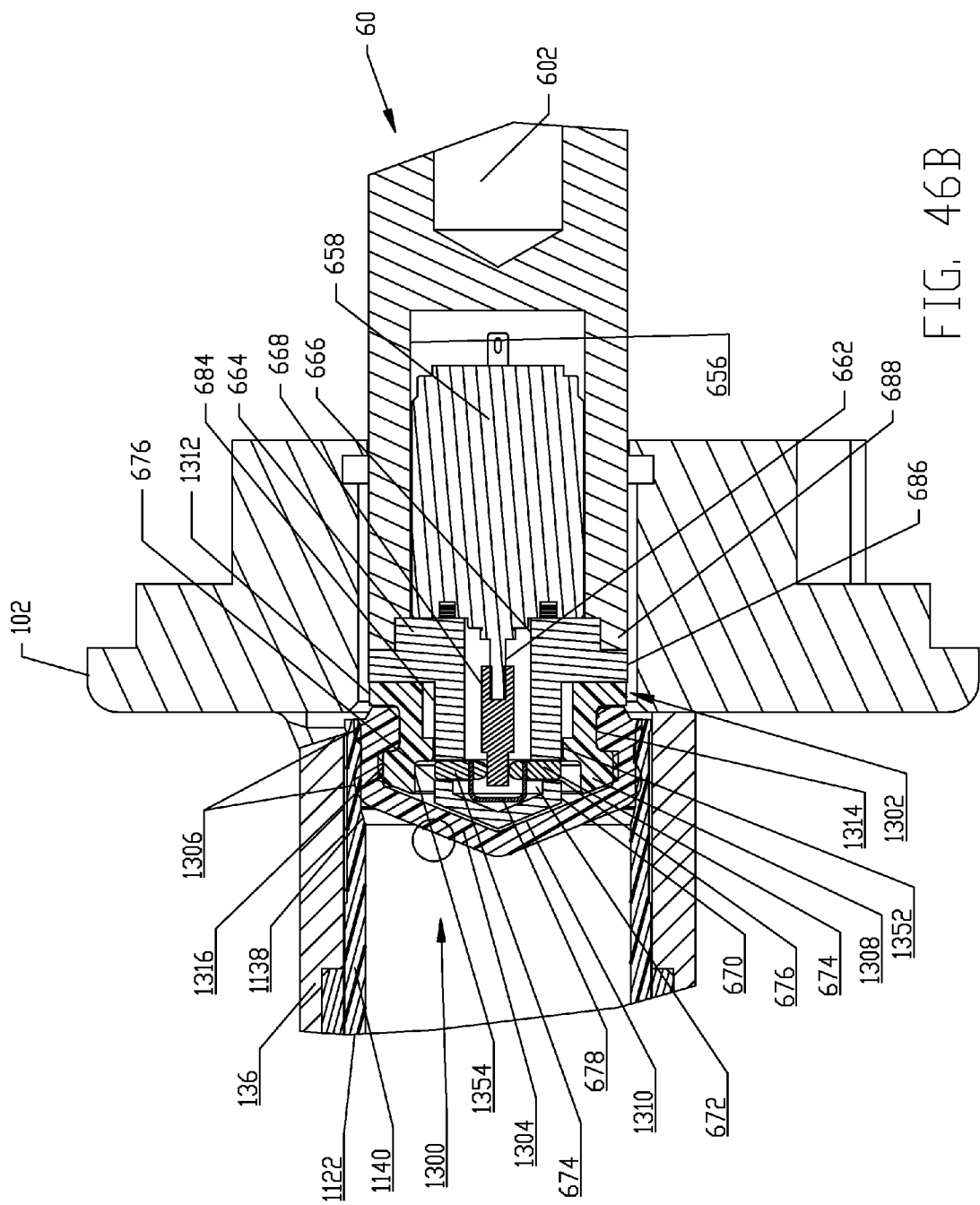

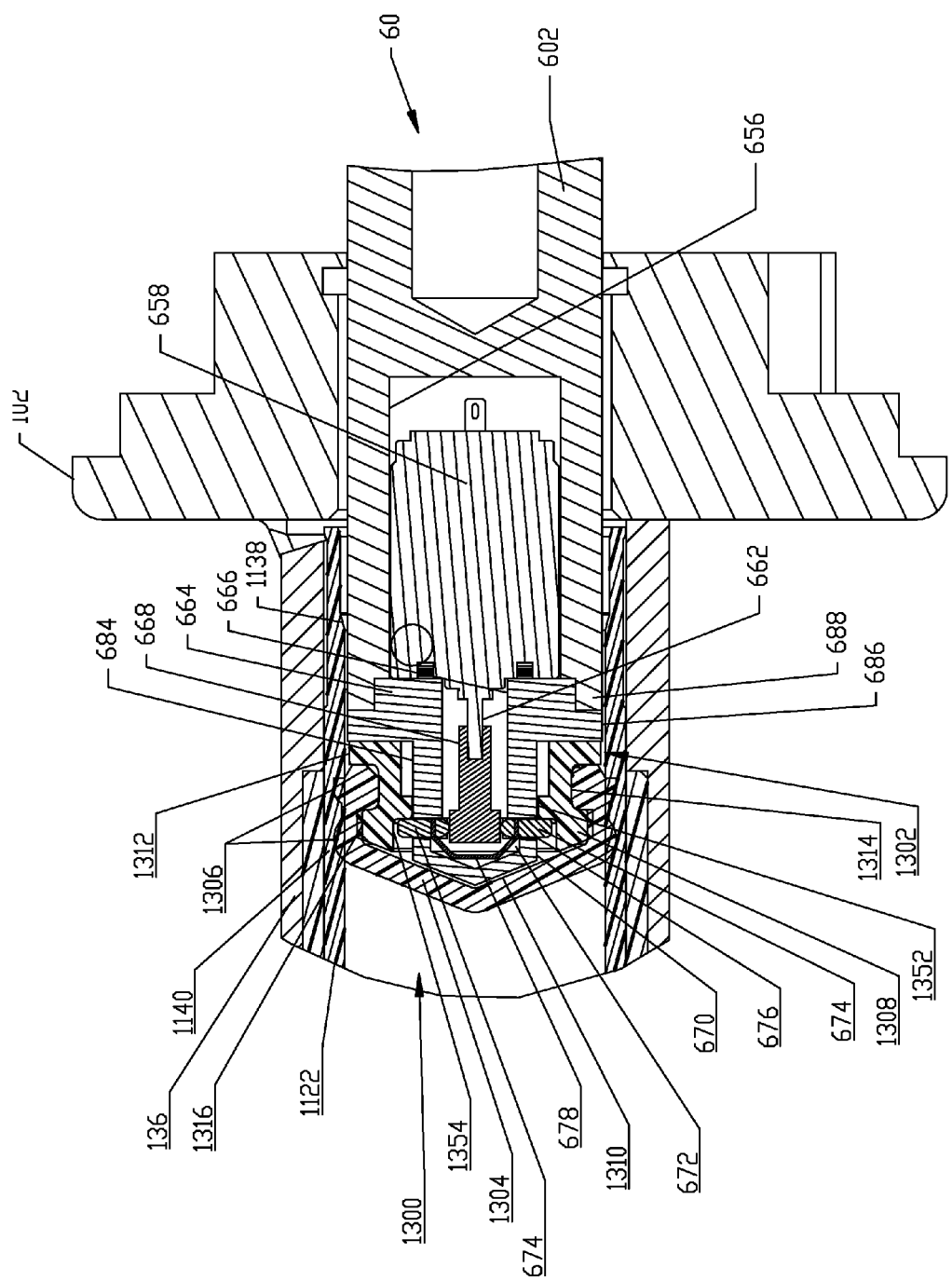

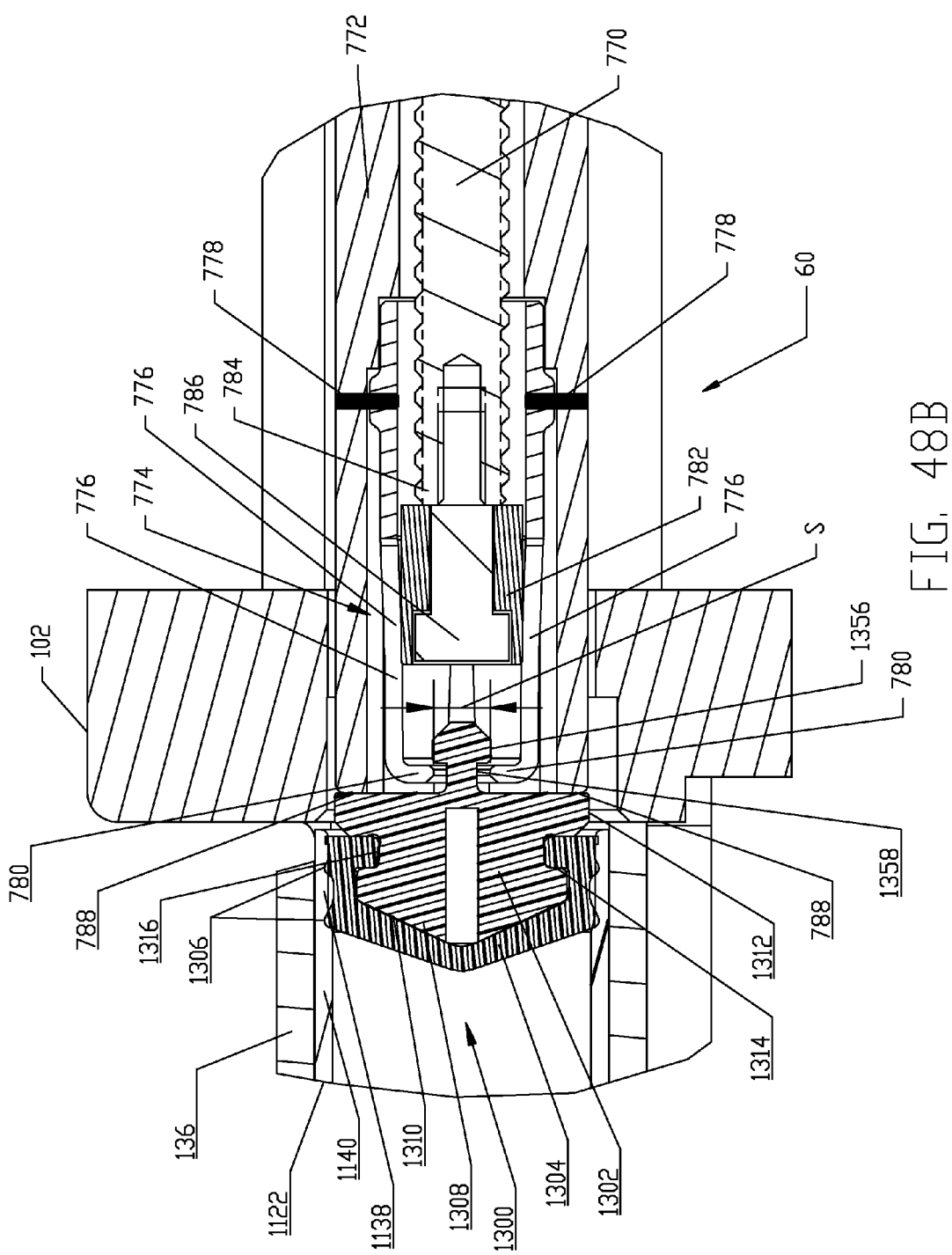

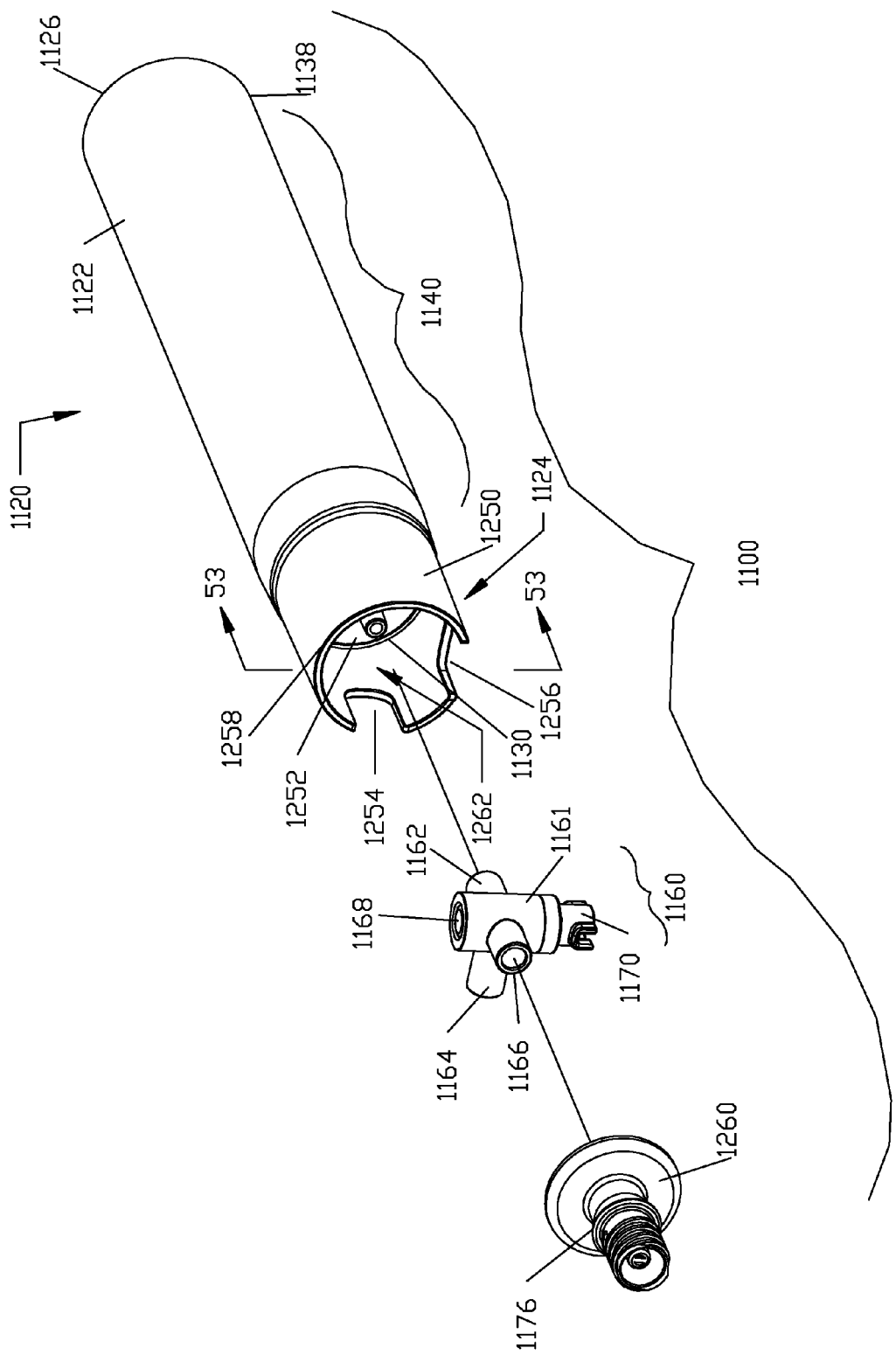

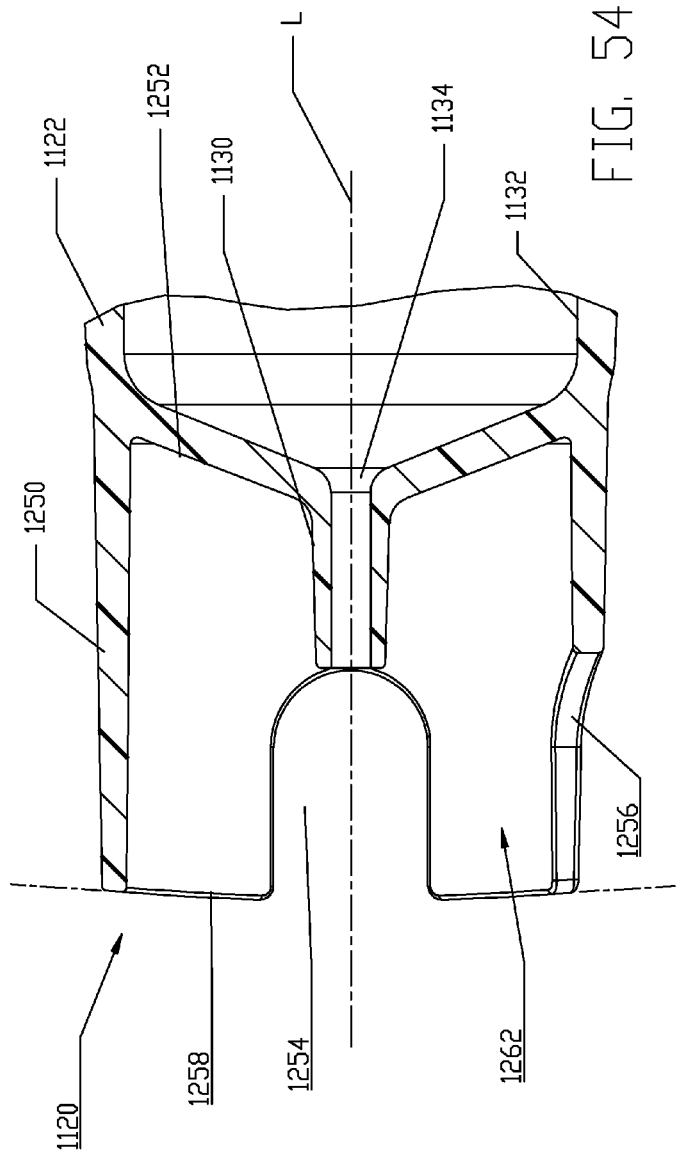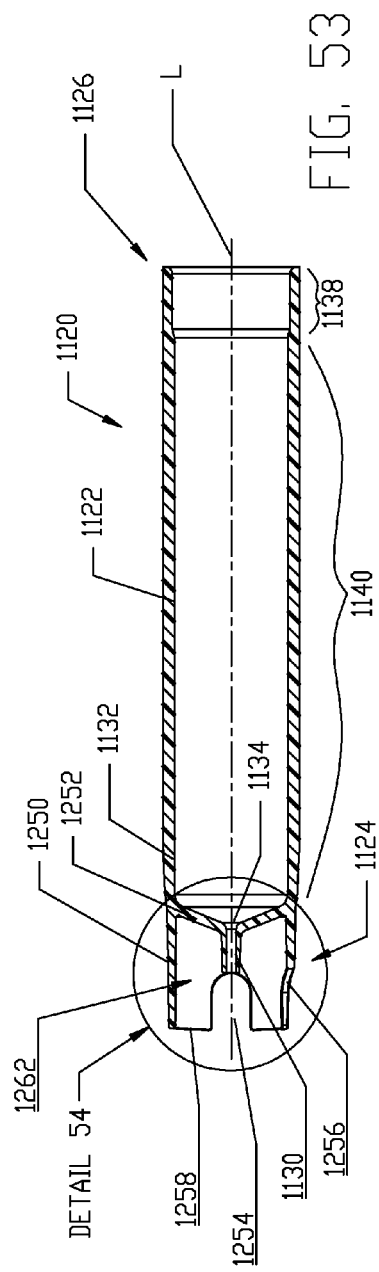

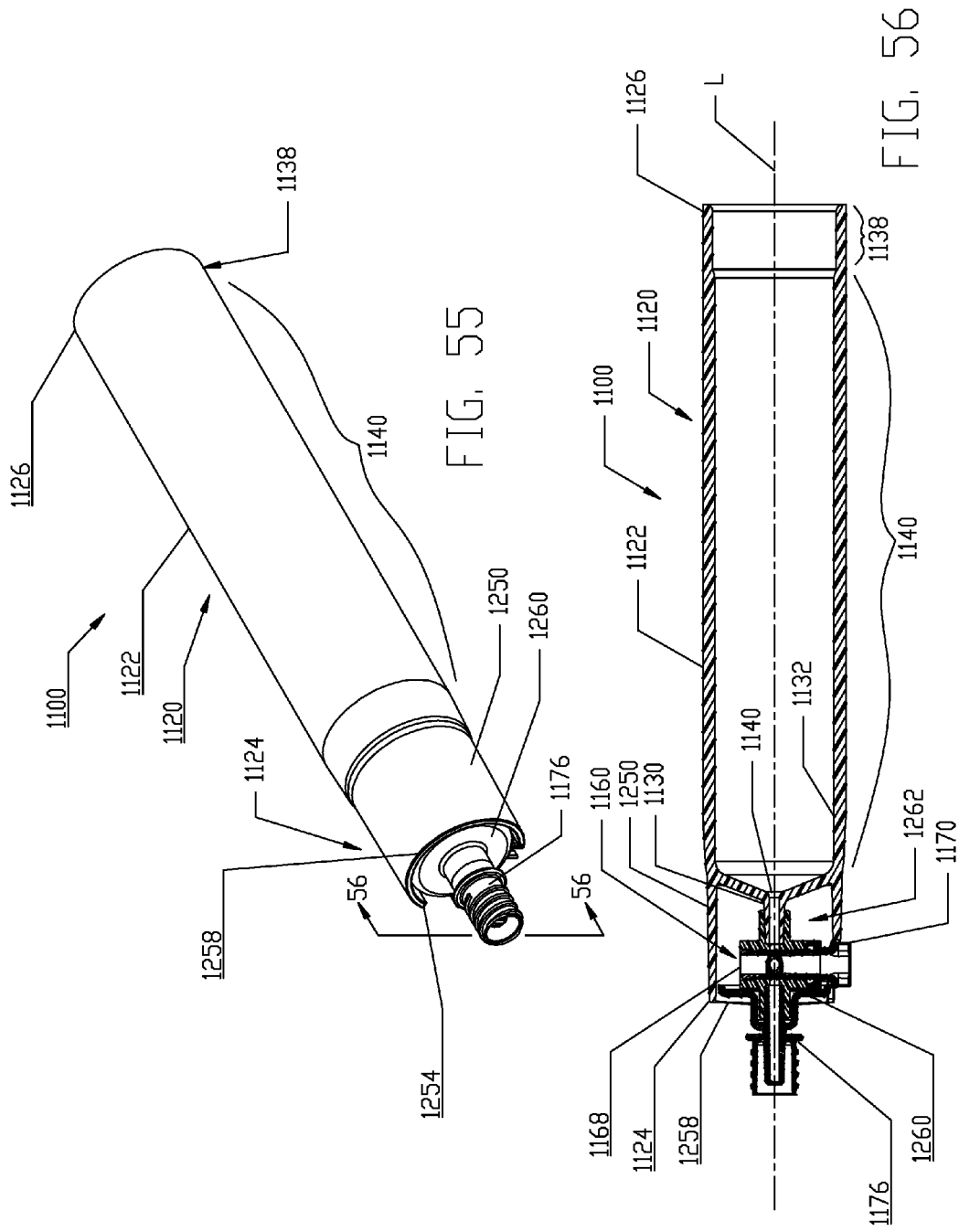

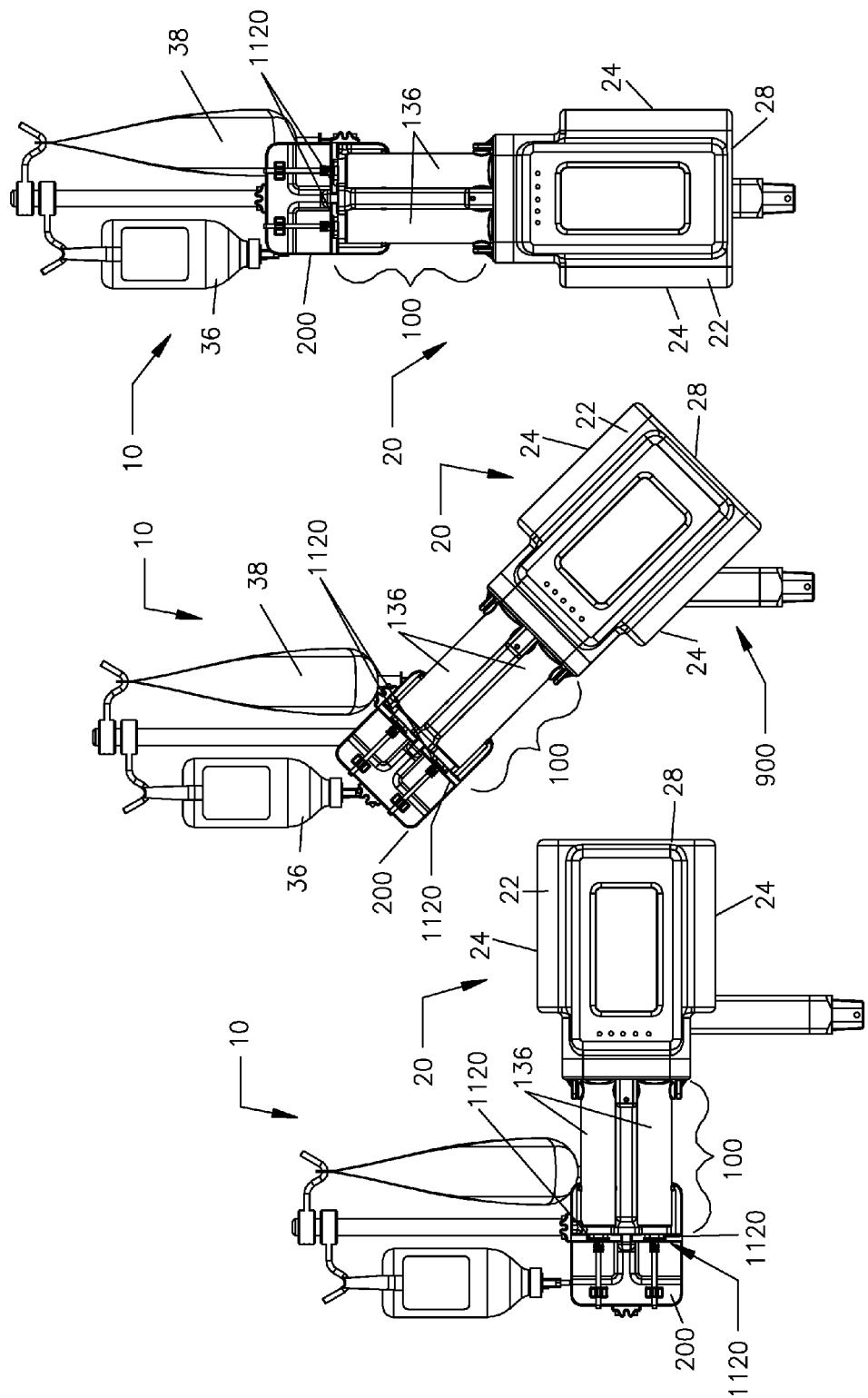

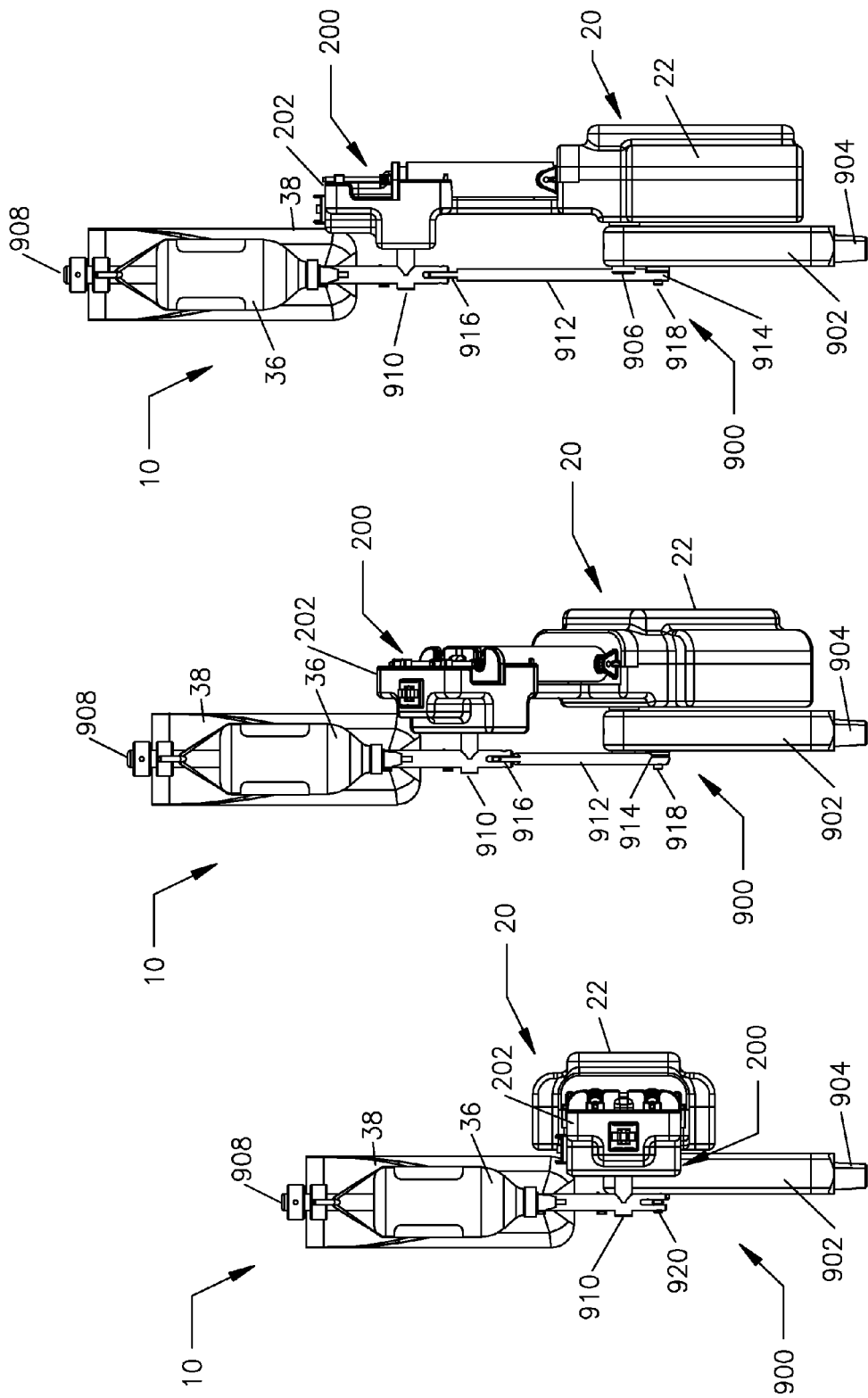

MULTI-FLUID MEDICAL INJECTOR SYSTEM AND METHODS OF OPERATION

CROSS REFERENCE TO RELATED APPLICATIONS

This patent application is a divisional of U.S. application Ser. No. 13/386,765, filed Jan. 24, 2012, "Multi-Fluid Medical Injector System and Methods of Operation", now U.S. Pat. No. 8,945,051, which is a national phase of International Patent Application No. PCT/US2010/042501, filed Jul. 20, 2010, entitled "Multi-Fluid Medical Injector System and Methods of Operation", which claims priority to U.S. Provisional Patent Application No. 61/228,294, filed Jul. 24, 2009, entitled "Multi-Fluid Medical Injector System and Methods of Operation," and all of which are hereby incorporated into this application by reference as if fully set forth herein.

BACKGROUND OF THE INVENTION

1. Field of the Invention

The invention described herein relates to medical fluid delivery applications and, particularly, the automated delivery of one or more medical fluids to a patient undergoing a medical diagnostic or therapeutic procedure.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media (often referred to simply as "contrast"), have been developed for use in procedures such as angiography, computed tomography (CT), ultrasound, and NMR/MRI. In general, these powered injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Nonetheless, automatic contrast injection mechanisms provide improved control over manual apparatus where successful use of such manual devices is dependent on the skill of the medical practitioner operating the device.

While manual and automated injectors are known in the medical field, improved fluid delivery systems adapted for use in medical diagnostic and therapeutic procedures where one or more fluids are supplied to a patient during the procedure continue to be in demand in the medical field. Additionally, improved fluid transfer sets and flow controlling and regulating devices associated therewith that may be used with fluid delivery systems for conducting and regulating fluids flows are also desired in the medical field. Moreover, the medical field continues to demand improved medical devices and systems used to supply fluids to patients during medical procedures such as angiography, computed tomography, ultrasound, and NMR/MRI.

SUMMARY OF THE INVENTION

While various embodiments of a fluid injector system, desirably a multi-fluid injector system and methods of operation thereof are described in detail herein, one embodiment of such a fluid injector system comprises a powered injector, a pressure jacket support, a syringe pressure jacket, and a syringe. The pressure jacket support comprises a front plate and a rear plate. The rear plate is connected to the injector and the front plate is spaced from the rear plate and defines a slot. The syringe pressure jacket has a proximal end pivotally connected to the rear plate so that a distal end of the pressure jacket pivots relative to the front plate. The syringe comprises a syringe body with a distally extending discharge conduit. With the syringe disposed in a barrel of the pressure jacket, pivotal movement of the pressure jacket distal end toward the front plate places the discharge conduit within the slot in the front plate.

In one variation, the discharge conduit may be offset from a central longitudinal axis of the syringe body. Additionally, the syringe body may comprise a conical distal end and the front plate may define a mating recess for the conical distal end such that the conical distal end engages the mating recess as the discharge conduit is received in the slot in the front plate. The mating recess may be offset from the slot. Alternatively, the slot in the front plate may generally bisect the mating recess. The front plate and the rear plate may be connected by a center beam. The syringe body may comprise a conical distal end and the front plate defines a mating recess for the conical distal end such that the conical distal end engages the mating recess and an apex of the conical distal end is received in an apex curve formed in the mating recess as the discharge conduit is received in the slot in the front plate.

The syringe body may comprise at least one key element and the pressure jacket may define at least one internal slot or keyway for receiving the at least one key element to orient the syringe body in the pressure jacket.

A fluid control valve may be connected to the discharge conduit extending from the syringe body, and the fluid control valve may comprise one of a stopcock, a piston valve, and a dual check valve.

In another embodiment, the fluid injector system comprises a powered injector, a pressure jacket support, a syringe pressure jacket, a syringe, and a fluid control module. The pressure jacket support comprises a front plate and a rear plate. The rear plate is connected to the injector and the front plate is spaced from the rear plate and defines a slot. The syringe pressure jacket has a proximal end pivotally connected to the rear plate so that a distal end of the pressure jacket pivots relative to the front plate. The syringe comprises a syringe body with a distally extending discharge conduit. The fluid control module is connected to the front plate. With the syringe disposed in a barrel of the pressure jacket, pivotal movement of the pressure jacket distal end toward the front plate places the discharge conduit within the slot in the front plate.

In one variation, the discharge conduit may be offset from a central longitudinal axis of the syringe body. Additionally, the syringe body may comprise a conical distal end and the front plate may define a mating recess for the conical distal end such that the conical distal end engages the mating recess as the discharge conduit is received in the slot in the front plate. The mating recess may be offset from the slot. Alternatively, the slot in the front plate may bisect the mating recess. The front plate and the rear plate may be connected by a center beam. The syringe body may comprise a conical distal end and the front plate defines a mating recess for the conical distal end such that the conical distal end engages the mating recess and an apex of the conical distal end is received in an apex curve formed in the mating recess as the discharge conduit is received in the slot in the front plate.

The syringe body may comprise at least one key element and the pressure jacket may define at least one internal slot or keyway for receiving the at least one key element to orient the syringe body in the pressure jacket.

A fluid control valve may be connected to the discharge conduit extending from the syringe body, and the fluid control valve may comprise one of a stopcock, a piston valve, and dual check valve. The pivotal movement of the pressure jacket distal end toward the front plate may operatively interface the fluid control valve with the fluid control module. The fluid control module may comprise a control valve actuator that operates the fluid control valve.

Various methods of operating the embodiments of the fluid injector system are described in detail in this disclosure. In one embodiment, the method comprises providing a powered injector. The powered injector comprises a pressure jacket support and a syringe pressure jacket. The pressure jacket support comprises a front plate and a rear plate, with the rear plate connected to the injector. The front plate is spaced from the rear plate and defines a slot. The syringe pressure jacket has a proximal end pivotally connected to the rear plate so that a distal end of the pressure jacket pivots relative to the front plate. In the method, the syringe is loaded into a barrel of the pressure jacket, and the syringe comprises a syringe body with a distally extending discharge conduit. The pressure jacket is then pivoted so that the pressure jacket distal end pivots toward the front plate to place the discharge conduit within the slot in the front plate.

In one variation, the discharge conduit may be offset from a central longitudinal axis of the syringe body. Additionally, the syringe body may comprise a conical distal end and the front plate may define a mating recess for the conical distal end such that the conical distal end engages the mating recess as the discharge conduit is received in the slot in the front plate. The mating recess may be offset from the slot. Alternatively, the slot in the front plate may bisect the mating recess.

When utilizing a syringe wherein the discharge conduit is offset from a central longitudinal axis of the syringe body, the method may further comprise pivoting the injector onto one lateral side to orient the discharge conduit to a top position on the syringe body and a fluid priming and an air purging procedure may be performed on the syringe. Additionally, the injector may be pivoted onto its opposing lateral side to orient the discharge conduit to a bottom position on the syringe body and a single-use fluid delivery set may be generally associated with the syringe. The method may further comprise performing a fluid priming and an air purging procedure on the single-use fluid delivery set.

A method of operating the fluid injector system is also detailed herein with a focus on fluid priming and air purging of components of the system. This method generally comprises providing a powered injector comprising a pressure jacket supporting a syringe. The syringe comprises a syringe body with a distally extending discharge conduit and the discharge conduit is offset from a central longitudinal axis of the syringe body. The injector is pivoted onto one lateral side to orient the discharge conduit to a top position on the syringe body and a fluid priming and an air purging procedure is performed on the syringe. Additionally, the injector may be pivoted onto its opposing lateral side to orient the discharge conduit to a bottom position on the syringe body for use in an injection procedure on a patient. Additionally, a single-use fluid delivery set may be placed in association with the syringe so as to be in fluid communication with the syringe body, a fluid priming and an air purging procedure may be performed on the single-use fluid delivery set.

Further details and advantages of the various embodiments detailed herein will become clear upon reviewing the following detailed description of the various embodiments in conjunction with the accompanying drawing figures.

BRIEF DESCRIPTION OF THE DRAWINGS

FIG. 5 is a longitudinal cross-sectional view of the syringe of FIG. 4 taken along Line 5-5 in FIG. 4.

FIG. 6 is a detail view of Detail 6 in FIG. 5.

FIG. 8 is a front view of the view shown in FIG. 7.

FIG. 9 is a cross-sectional view of a front portion of the pressure jacket and loaded syringe in the view of FIG. 7, as taken along Line 9-9 in FIG. 8.

FIG. 10 is a detail view of Detail 10 in FIG. 8.

FIGS. 11A-11E illustrate a loading sequence for loading the syringe into the pressure jacket.

FIG. 18 is a front view of the fluid control module shown in FIG. 17.

FIG. 19 is a cross-sectional view taken along Line 19-19 in FIG. 18.

FIG. 33A is a perspective view showing a fluid priming and air purging orientation of the fluid injector system of FIG. 1.

FIG. 33B is a detail view of Detail 33B in FIG. 33A.

FIG. 34A is a perspective view showing the fluid injector system of FIG. 1 in an intermediate position while transitioning to a generally horizontal orientation.

FIG. 34B is a detail view of Detail 34B in FIG. 34A.

FIG. 35A is a perspective view showing the fluid injector system of FIG. 1 in a generally horizontal orientation.

FIG. 35B is a detail view of Detail 35B in FIG. 35A.

FIG. 36A is a perspective view showing the fluid injector system of FIG. 1 in an intermediate position while transitioning to an injection orientation.

FIG. 36B is a detail view of Detail 36B in FIG. 36A.

FIGS. 44A-44I are respective cross-sectional views illustrating a sequence of interfacing a syringe plunger in the syringe of FIG. 4 with a piston element of a powered injector of the fluid injector system of FIG. 1 according to a first embodiment.

FIGS. 45A-45H are respective cross-sectional views illustrating a sequence of interfacing a syringe plunger in the syringe of FIG. 4 with a piston element of the powered injector of the fluid injector system of FIG. 1 according to a second embodiment.

FIGS. 46A-46I are respective cross-sectional views illustrating a sequence of interfacing a syringe plunger in the syringe of FIG. 4 with a piston element of the powered injector of the fluid injector system of FIG. 1 according to a third embodiment.

FIGS. 48A-48D are respective cross-sectional views illustrating a sequence of interfacing a syringe plunger in the syringe of FIG. 4 with a piston element of a powered injector of the fluid injector system of FIG. 1 according to a fifth embodiment.

FIG. 52 is an exploded perspective view of a syringe and fluid control valve adapted for use in the fluid injector system of FIG. 49.

FIG. 53 is a cross-sectional view of the syringe shown in FIG. 52 taken along Line 53-53 in FIG. 52.

FIG. 54 is a detail cross-sectional view of Detail 54 in FIG. 53.

FIG. 55 is an assembled perspective view of the syringe and fluid control valve shown in FIG. 52.

FIG. 56 is a cross-sectional view of the syringe and fluid control valve shown in FIG. 55 taken along Line 56-56 in FIG. 55.

FIGS. 57A-57C are front views of the fluid injector system of FIG. 49 illustrating movement of the fluid injector system from a generally horizontal orientation to a generally vertical orientation.

FIGS. 59A-59C are front side views of the fluid injector system of FIG. 49 illustrating the sequence of movement shown in FIGS. 57A-57C but from the front side of the fluid injector system.

DESCRIPTION OF THE INVENTION

Figure 1:
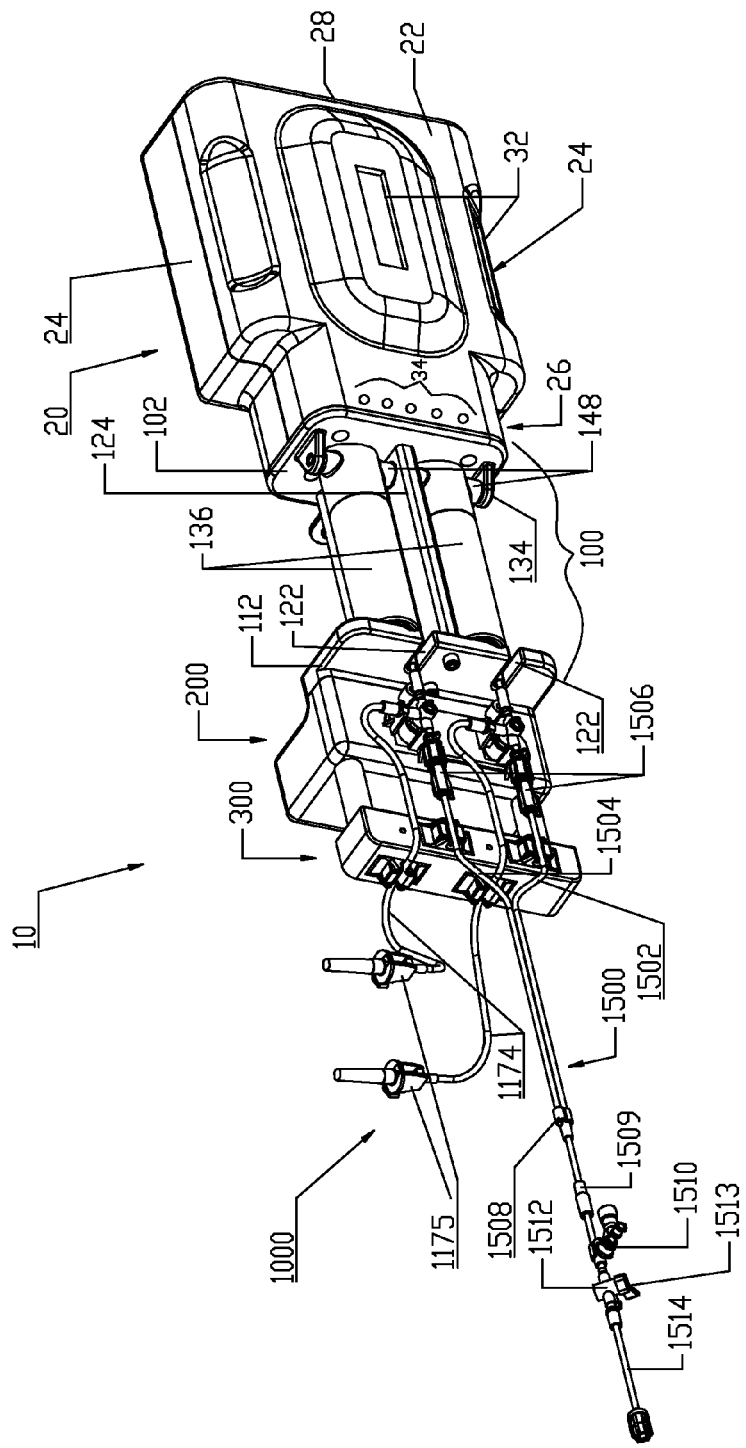
FIG. 1 is a perspective view of a fluid injector system according to one embodiment.

For purposes of the description hereinafter, spatial orientation terms, as used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific components, devices, and features illustrated in the accompanying drawing figures and described herein are simply exemplary and should not be considered as limiting.

Referring initially to FIGS. 1-14, an embodiment of a multi-fluid medical injection/injector system 10 is shown. Multi-fluid medical injection/injector system 10 (hereinafter "fluid injector system 10") comprises multiple components as individually described herein. Generally, fluid injector system 10 comprises a powered injector administrator or device 20 and a fluid delivery set 1000 intended to be associated with the injector 20 to conduct one or more fluids under pressure into a patient intravenously via a patient catheter. The various devices, components, and features of the injector 20 and the fluid delivery set 1000 are likewise described in detail herein. In fluid injector system 10, a pressure jacket support assembly or element 100 is supported to a distal end of the injector 20, a fluid control module 200 is supported from a distal end of the pressure jacket support assembly or element 100, and an air detector module 300 is disposed distally of the fluid control module 200 and supported thereto. The fluid delivery set 1000 is intended to be associated with the injector 20 so as to physically interface therewith and, further, physically interface with the pressure jacket support assembly or element 100, fluid control module 200, and air detector module 300.

While details of fluid delivery set 1000 are provided herein, the fluid delivery set 1000 generally comprises a multi-use fluid delivery set 1100 and a single-use fluid delivery set 1500.

Injector 20 is desirably at least a dual-syringe injector, wherein two fluid delivery syringes are oriented in a side-by-side relationship and which are separately actuated by respective piston elements associated with the injector 20. A suitable injector for this purpose is a Stellant™ injector manufactured by Medrad, Inc. of Pittsburgh, Pa. Details of the Stellant™ injector may be found in U.S. Pat. No. 7,018,363 (Cowan, et al.) and in United States Patent Application Publication Nos. 2004/0064041 (Lazzaro et al.) and 2005/0113754 (Cowan), each of which is incorporated herein by reference.

Generally, injector 20 comprises an injector housing 22 comprising opposed lateral sides 24, a distal end 26, and a proximal end 28. Injector housing 22 encloses the various mechanical drive components, electrical and power components necessary to drive the mechanical drive components, and control components such as electronic memory and electronic control devices (hereinafter "electronic control device(s)") used to discretely control operation of reciprocally movable piston elements 60 associated with injector 20 which are described later in this disclosure in connection with FIGS. 44-48. Such piston elements 60 may be reciprocally operable via electro-mechanical drive components such as a ball screw shaft driven by a motor, a voice coil actuator, a rack-and-pinion gear drive, a linear motor, and the like.

Injector 20 includes one or more display windows 32 desirably in the form of a graphical user interface (GUI) display window as is well-known in the powered medical injector field. Display window(s) 32, as is known in the powered medical injector field, may display information pertinent to a fluid injection procedure involving fluid injector system 10, such as current flow rate, fluid pressure, and volume remaining in fluid sources connected to fluid delivery set 1000, as non-limiting examples. Moreover, it will be appreciated that while the display windows 32 are shown on the injector housing 22, such display windows 32 may also be remote displays from the injector housing 22 that are wired or wirelessly linked to the injector 20. Additionally, injector 20 may comprise one or more (e.g., a plurality of) control buttons 34 for tactile operation by an attendant operator of injector 20. These control buttons may be hard-wired to the electronic control device(s) associated with injector 20 to provide direct input to the electronic control device(s). Such control buttons 34 may also be graphically part of the graphical user interface display window 32 as will be readily clear to one skilled in the powered medical injector field. In either arrangement, the control buttons 34 provide certain individual control features to the attendant operator of injector 20, such as but not limited to: (1) Acknowledge/Start; (2) Fill/Purge; (3) Forward; (4) Unload; and (5) Stop. Injector 20 also includes a pedestal support 90 comprising a support column 92 (see FIGS. 38-39 discussed herein) used to support the injector 20 and the fluid injector system 10 generally.

The distal end 26 of injector housing 22 defines an open distal end of the injector housing 22 for interfacing with pressure jacket support assembly/element 100, (hereinafter "pressure jacket support 100"). Pressure jacket support 100 may be a multi-component support structure for supporting a syringe pressure jacket 136 used to limit radial expansion of a syringe 1120 associated with multi-use fluid delivery set 1100 of fluid delivery set 1000 as described herein. As will be apparent from FIG. 1, pressure jacket support 100 is configured to support a pair of syringe pressure jackets 136 in side-by-side relationship which support respective syringes 1120 associated with multi-use fluid delivery set 1100. As is well-known in the powered medical injector field, the use of a syringe pressure jacket limits radial expansion of a syringe when under pressure which may lead to bursting or to leaks of the pressurized fluid around the seal(s) of the syringe plunger. Another function of pressure jacket support 100 is to limit and substantially prevent forward motion of syringes 1120 relative to injector 20 as the piston elements 60 associated with injector 20 move syringe plungers in the respective syringes 1120; the details of the syringes 1120 used with the injector 20 and the interfacing of piston elements 60 with the syringe plungers in the syringes 1120 is described in detail herein.

Pressure jacket support 100 generally comprises two opposed support plates 102, 112 joined by a center beam 124. The connection between support plates 102, 112 via center beam 124 provides an overall I-beam construction or shape for pressure jacket support 100 with the center beam 124 generally forming the web portion of the I-beam. With this construction, respective adjacent spaces 104 are defined on opposing sides of center beam 124 wherein the respective pressure jackets 136 are disposed and operable. Rear or proximal plate 102 may have a profiled shape 106 adapted to be inserted into the open distal end 26 of the injector housing 22. Such a profiled shape 106 may include terraced ledges 108 for interfacing with the open distal end 26 of injector 20. Additionally, respective front openings 110 are defined in rear plate 102 to allow passage of the piston elements 60 associated with the injector 20 so that the piston elements 60 may interface with syringe plungers in syringes 1120 that are loaded into the respective pressure jackets 136.

Front or distal plate 112 comprises a front or distal side 114 and a rear or proximal side 116. Respective recesses 118 are defined in rear side 116 to face pressure jackets 136 and the syringes 1120 are loaded therein as described herein. Recesses 118 comprise a central apex curve or area 120 to accommodate a distal tip of the respective syringes 1120 and lateral mating contact surfaces 121 are present on either side of central apex curve 120 to contact and interface with the distal end of each of the syringes 1120. Slots 122 are defined vertically in front plate 112 and are offset laterally from the respective recesses 118 to accommodate a discharge outlet extending from syringes 1120; specific features of the syringes 1120 adapted for use with pressure jackets 136 in pressure jacket support 100 are described herein. The front side 114 of front plate 112 provides a support/mounting location for the fluid control module 200 as described herein.

Center beam 124 generally defines an inverted T-shape in transverse cross-section which defines the respective pressure jacket operating spaces 104. While the rear plate 102, front plate 112, and center beam 124 are illustrated in the accompanying drawing figures and described in the foregoing as distinct elements, these individual components or elements may be formed as an integral, unitary component. However, the rear plate 102, front plate 112, and center beam 124 are typically mechanically connected together through use of conventional mechanical fasteners or joined via permanent joining methods such as by welding. It is desirable to form the rear plate 102, front plate 112, and center beam 124 from metal such as stainless steel of a grade suitable for use in medical environments but these components may alternatively be made of any material(s) that provides sufficient structural strength to withstand the operational pressures associated with operation of syringes 1120 in pressure jackets 136. As an example, a force of 2,400 pounds is typically required to restrain the forward motion of a 150 ml syringe with a cross-section of 2.0 in.sup.2 at 1,200 p.s.i. Mounting flanges 134 are provided on the front side of the rear plate 102 for mounting the respective pressure jackets 136 to the rear plate 102.

In the present embodiment, dual pressure jackets 136 are provided for the dual-syringe injector 20. Each pressure jacket 136 operates in a pressure jacket operating space 104 defined by the pressure jacket support 100. Each pressure jacket 136 generally has a proximal end 138 and a distal end 140. In the illustrated embodiment, each pressure jacket 136 is a composite two-piece structure comprised of a proximal cylindrical flange portion 142 and a distal cylindrical body portion 152. While the flange portion 142 and body portion 152 are illustrated as separate components, these components may alternatively be integrally formed as a unitary component. In the illustrated embodiment, flange portion 142 is desirably formed of metal such as aluminum or stainless steel selected from a grade suitable for medical environments and body portion 152 is desirably formed of a transparent plastic material such as polycarbonate and like relatively rigid plastic materials that are suited to restraining radial expansion of syringes 1120 loaded into pressure jackets 136. Flange portion 142 has a distal rim or end 144 and a proximal rim or end 146. Likewise, body portion 152 has a distal rim or end 154 and a proximal rim or end 156. An overlapping joint 170 is formed at the joining location of the flange portion 142 and the body portion 152 and the overlapped joint 170 may be secured by joining methods customary in the medical field such as by a suitable medical grade adhesive, solvent bonding, ultrasonic welding friction fit engagement, threaded engagement, etc. In particular, the overlapped joint 170 is formed between overlapping areas on the distal rim 144 of the flange portion 142 and the proximal rim 156 of the body portion 152. The flange portion 142 of each pressure jacket 136 further comprises two external and outward extending mounting hubs 148 for forming a pivotal connection with a corresponding mounting flange 134 on the front side of the rear plate 102 and with a pivot location on the center beam 124. As illustrated, each pressure jacket 136 is pivotally supported by mounting hubs 148 to one of the mounting flanges 134 on the rear plate 102 and a pivot location on the center beam 124 of pressure jacket support 100. Such pivotal connections may be made through the use of suitable mechanical fasteners. It is noted that the mounting hubs 148 on the flange portion 142 of each pressure jacket 136 are offset above a plane B which bisects the pressure jacket 136 longitudinally and, thus, a pivot axis P of each pressure jacket 136 is located above the bisecting plane B shown in FIG. 8. Mounting flanges 134 are similarly offset above such a bisecting horizontal plane B. As shown in the view of FIG. 11, when the respective pressure jackets 136 are disposed in a generally horizontal orientation within the respective pressure jacket operating spaces 104 and a horizontal plane H shown in these figures is coextensive with the longitudinal bisecting plane B passing through the pressure jacket 136. The purpose and function of the foregoing offset arrangements are described herein. Briefly, however, each pressure jacket 136 is adapted to pivot upward in its operating space 104 to allow loading of syringes 1120 therein. In order to permit this upward pivoting movement of the pressure jackets 136, the respective front openings 110 in rear plate 102 are positioned and sized to allow the proximal or rear rim 146 on the flange portion 142 of each pressure jacket 136 to pivot at least partially into the respective front openings 110. More particularly, front openings 110 are of sufficient size to allow clearance for the proximal or rear rim 146 on the flange portion 142 of each pressure jacket 136 as the pressure jackets 136 are pivoted upward to allow loading of syringes 1120 therein.

A further feature of each pressure jacket 136 comprises the provision of a keyway 158 defined in the distal rim 154 of the body portion 152 of each pressure jacket 136. The keyway 158 is defined in an interior surface 160 of the body portion 152 at the distal rim 154. Two slots or keyways 158 may be defined in the interior surface 160 of the body portion 152 of each pressure jacket 136 and extend substantially or generally parallel to one another. However, the accompanying figures illustrate only one keyway 158. As will be understood from the foregoing, the flange portion 142 and the body portion 152 of each pressure jacket 136 together generally define a receiving bore or barrel 162 of the pressure jacket 136 for receiving a syringe 1120 associated with multi-use fluid delivery set 1100 of fluid delivery set 1000.

As noted in the foregoing, fluid delivery set 1000 generally comprises a multi-use fluid delivery set 1100 and a single-use fluid delivery set 1500. While both the multi-use fluid delivery set 1100 and the single-use fluid delivery set 1500 are intended to be disposable items, it is envisioned that the multi-use fluid delivery set 1100 (hereinafter "multi-use set 1100") may be reused a set number of times and/or for a set number of patients whereas single-use fluid delivery set 1500 (hereinafter "single-use set 1500") is intended to be a single-use or per-patient use set pursuant to the concepts outlined in U.S. Pat. No. 5,840,026 (Uber, III); U.S. Pat. No. 5,843,037 (Uber, III); and U.S. Pat. No. 5,806,519 (Evans, III, et al.), all incorporated herein by reference in their entirety. As further noted in the foregoing, syringe 1120 is one component or part of multi-use set 1100, with additional components or parts thereof described herein. In the set-up or ready-for-use state of fluid injector system 10, two multi-use sets 1100 and one single-use set 1500 are typically installed, with each multi-use set 1100 comprising a syringe 1120 loaded into the receiving bore or barrel 162 of a corresponding pressure jacket 136. The following discussion describes one of the multi-use sets 1100 adapted for use with fluid injector system 10.

The syringe 1120 in each multi-use set 1100 comprises an elongated, cylindrical syringe body 1122 having a front or distal end 1124 and a rear or proximal end 1126. A syringe plunger 1300 is disposed within the syringe body 1122 and various embodiments of the syringe plunger 1300 are described herein in this disclosure for interfacing with the reciprocally operable piston elements 60 associated with injector 20. The distal end 1124 of the syringe body 1122 is generally conical-shaped and tapers to an apex or cone point 1128 which is adapted to interface with the central apex curve 120 formed in the recess(es) 118 defined in the rear or proximal side 116 of the front plate 112 as described further herein. Syringe apex or cone point 1128 is located along a central longitudinal axis L of the syringe body 1122. In one non-limiting embodiment, the tapered distal end 1124 of syringe body 1122 tapers at an angle of about 22.degree. In addition, the syringe body 1122 comprises a discharge outlet or conduit 1130 that is offset from the central longitudinal axis L of the syringe body. Discharge outlet or conduit 1130 is formed to extend distally from a sidewall 1132 of the syringe body 1122 so that a discharge port 1134 defined by the discharge outlet 1130 is situated immediately adjacent the sidewall 1132 of the syringe body 1122 and at the base of the cone defined by the conical-shaped distal end 1124 of the syringe body 1122. Discharge outlet 1130 may be formed with a conventional luer fitting-type connection to mate with additional downstream components of the multi-use set 1100 as described herein.

The proximal end 1126 of syringe body 1122 is desirably formed with an expansion section 1138. A generally cylindrical "working" section 1140 of syringe body 1122 connects the distal and proximal ends 1124, 1126 of the syringe body 1122 and is defined essentially forward or distal of the expansion or storage section 1138 of syringe body 1122. The cylindrical section 1140 of the syringe body 1122 has a relatively uniform outer diameter. The expansion section 1138 is provided generally as a storage section or area for the syringe plunger 1300. The expansion section 1138 is preferably formed at the proximal end 1126 of syringe body 1122 but may optionally be formed at a different location along the syringe body 1122. Generally, the expansion section 1138 is formed by the sidewall 1132 of syringe body 1122 narrowing to a reduced wall thickness $t_r$ from a thickness t of the sidewall 1132 in the main body cylindrical section 1140 of the syringe body 1122. Thus, an inner diameter of the expansion section 1138 is larger than an inner diameter of the main body cylindrical section 1140 of the syringe body 1122 and the resulting reduced wall thickness $t_r$ at the expansion section 1138 allows the expansion section 1138 to expand outward under radial force exerted by the syringe plunger 1300 during storage periods. The expansion section 1138 thereby accommodates plastic creep of the syringe body 1122 even after long periods of storage. Even after long storage periods, the syringe 1120 with a pre-positioned syringe plunger 1300 may be quickly and easily actuated to move from the storage/expansion section 1138 into the cylindrical section 1140 of the syringe body 1122. Typically, once the syringe 1120 is inserted into its receiving pressure jacket 136 in the manner to be described herein, the injector 20 is actuated to move the corresponding piston element 60 forward or distally to engage the syringe plunger 1300 stored within the storage/expansion section 1138 of the syringe body 1122 of the syringe 1120. Thereafter, the piston element 60 may move the engaged syringe plunger 1300 into the main body cylindrical section 1140 of the syringe body 1122 of the syringe 1120.

The proximal end 1126 of the syringe body 1122 is formed with an outward extending lip 1142 to provide strength and rigidity to the storage/expansion section 1138 of the syringe body 1122. The proximal or rear lip 1142 may perform other functions such as engaging contact sensor(s) and like components or devices associated with the injector 20 which may be used, for example, to determine if a syringe 1120 is present within the corresponding pressure jacket 136. However, it is preferred that the proximal or rear lip 1142 have an outer diameter approximately the same as the outer diameter of the main body cylindrical section 1140 of the syringe body 1122 so that the syringe 1120 may be smoothly accepted into the receiving barrel or bore 162 of the pressure jacket 136.

Additionally, the syringe body 1122 further comprises one or more key or tab elements 1144 formed on the main body or working section 1140 of the syringe body 1122 and immediately adjacent the conical distal end 1124 of the syringe body 1122. Key or tab elements 1144 are adapted to interface with the keyway 158 defined in the inner surface 160 of the body portion 152 of each pressure jacket 136 when the syringe 1120 is inserted into its receiving pressure jacket 136. Generally, as shown in several views of FIGS. 4-9, parallel key or tab elements 1144 are oriented approximately opposite (180.degree.) from the discharge outlet or conduit 1130. The syringe body 1122 may be formed of conventional materials used in the medical field to form syringe barrels such as polycarbonate, polypropylene, etc.

With the foregoing description of the pressure jacket support 100 and the syringe 1120 in mind, exemplary loading and unloading of a syringe 1120 into a receiving pressure jacket 136 will now be described, with specific reference to FIGS. 11-14. Initially, the receiving pressure jacket 136 is pivoted upward in its pressure jacket operating space 104 about the pivotal connection associated with the mounting hubs 148. Pivotal movement is continued until the distal rim or end 154 of the body portion 152 of the pressure jacket 136 is pivoted above the top of front plate 112 to provide clear access to the barrel or bore 162 of the pressure jacket 136. In this position, a central longitudinal axis of the pressure jacket 136 which is coaxial with the central longitudinal axis L of the syringe body 1122 defines an acute angle with the horizontal plane H which generally bisects the injector housing 22 as shown in FIGS. 11A-11E. With the barrel 162 of the receiving pressure jacket 136 now accessible, an attendant operator generally orients syringe body 1122 of syringe 1120 so that key or tab elements 1144 on the syringe body 1122 are aligned with the keyway 158 defined in the inner surface 160 of the body portion 152 of the receiving pressure jacket 136. Orienting the syringe body 1122 in this manner automatically orients discharge outlet 1130 extending distally from the syringe body 1122 vertically with the corresponding offset slot 122 defined in the front plate 112 of the pressure jacket support 100. The syringe 1120 may then be inserted into the barrel 162 of the pressure jacket 136 and engagement of the key elements 1144 in the keyway 158 defined in the inner surface 160 of the body portion 152 of the pressure jacket 136 limits insertion of the syringe body 1122 into the pressure jacket 136. The pressure jacket 136 is then pivoted downward in its pressure jacket operating space 104 about the pivotal connection associated with the mounting hubs 148, thereby decreasing the acute angle as shown in FIGS. 11A-11E. Pivotal movement is continued until the discharge outlet 1130 extending distally from the syringe body 1122 seats into the corresponding offset slot 122 defined in the front plate 112 of the pressure jacket support 100. In this position, the pressure jacket 136, now supporting the syringe 1120, is generally horizontal and places the syringe 1120 in a loaded position ready for use. The central longitudinal axis L of the pressure jacket 136 and syringe body 1122 now aligns with the horizontal plane H.

Figure 12:
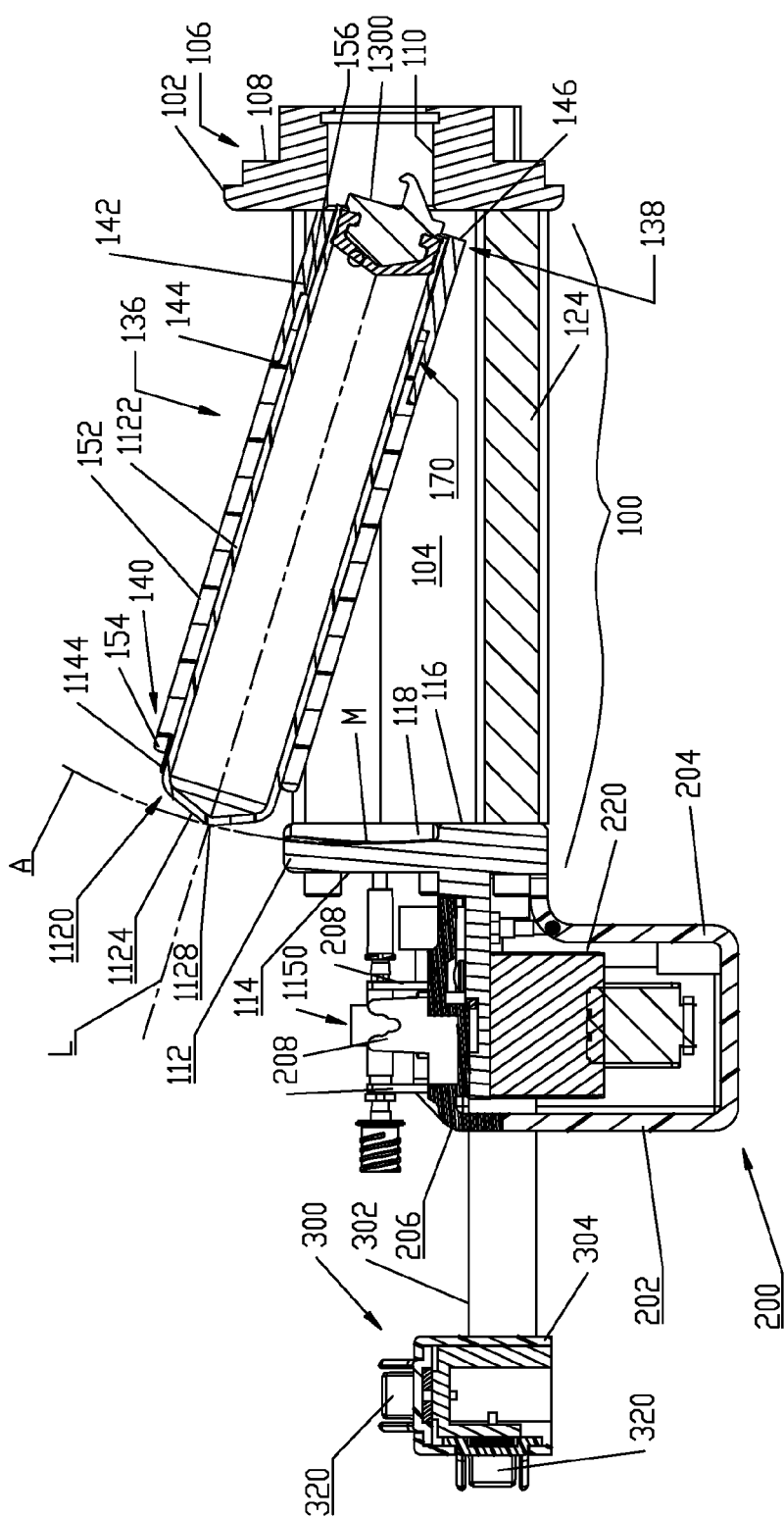
FIG. 12 is a cross-sectional view of the fluid injector system of FIG. 1 showing the syringe loaded into the pressure jacket.
Figure 13:
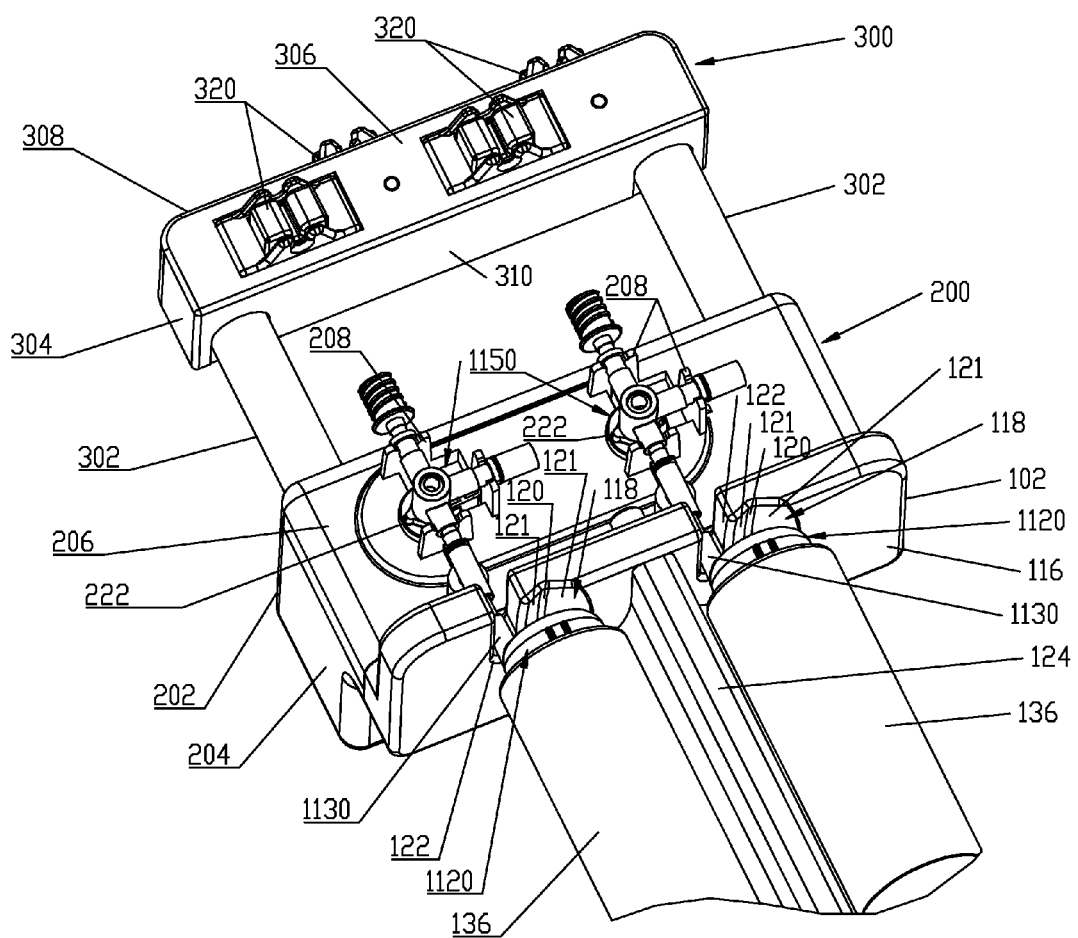
FIG. 13 is a top perspective view of the fluid injector system of FIG. 1 showing a pair of syringes interfaced with a front plate of a pressure jacket support in the fluid injector system of FIG. 1.
Figure 14:
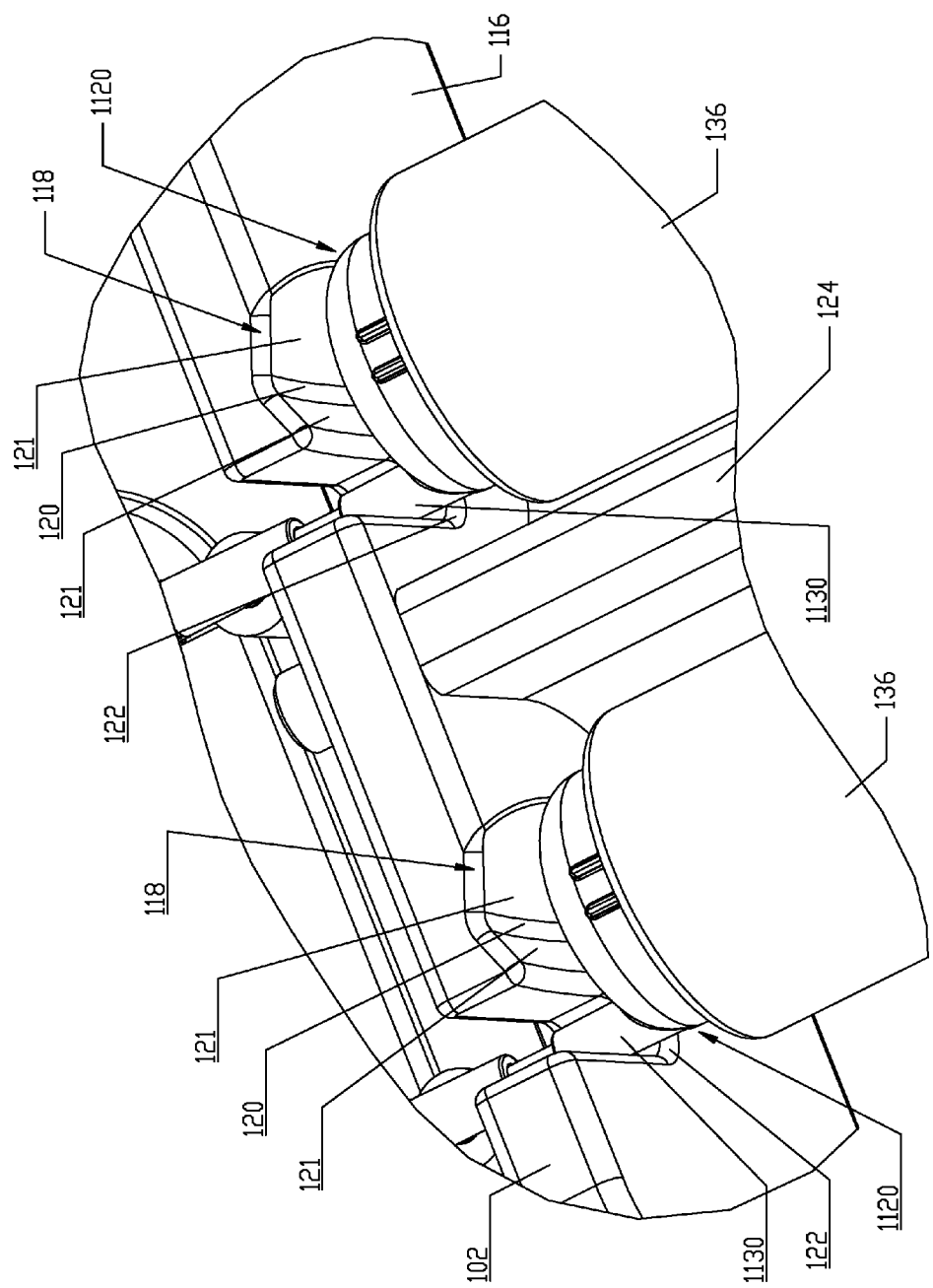
FIG. 14 is a close-up perspective of the view shown in FIG. 13.

As will be understood from FIG. 12 in particular, the apex or cone point 1128 at the distal end 1124 of syringe body 1122 defines an arcuate or arc-type movement as illustrated by arc path line A as the pressure jacket 136 is pivoted upward/downward from/into pressure jacket operating space 104 as described in the foregoing. As noted previously, the apex or cone point 1128 at the distal end 1124 of syringe body 1122 is adapted to interface with the central apex curve 120 formed in the corresponding receiving recess 118 defined in the rear or proximal side 116 of the front plate 112. This engagement and the mating engagement between the conical distal end 1124 of syringe body 1122 and the lateral mating surfaces 121 defined by the receiving recess 118 axially restrains the syringe body 1122 when under pressure. In particular, the central apex point 1128 at the distal end 1124 of the syringe body 1122 is seated within the central apex curve 120 approximately at a midpoint M of the curvature of this curve while the lateral mating surfaces 121 contact and support the conical distal end 1124 of the syringe body 1122. The foregoing mating features between the central apex point 1128 and the receiving central apex curve 120 and between the conical distal end 1124 and the lateral mating surfaces 121 ensures that when the syringe body 1122 is under pressure by action of the syringe plunger 1300, the syringe body 1122 remains centered against the front plate 112. The foregoing mating features provide a self-centering action for the syringe 1120 when loaded in the pressure jacket 136 in a ready-for-use state or condition. Without this self-centering action, if the syringe body 1122 were pressurized resulting in an upward directed force applied to the syringe body 1122, a potential exists for a corresponding torque force to be applied to the pressure jacket 136 which could cause the pressure jacket 136 to pivot upward about mounting hubs 148 and cause the potential dislodgment of the syringe 1120 from the pressure jacket 136.

Figure 15:
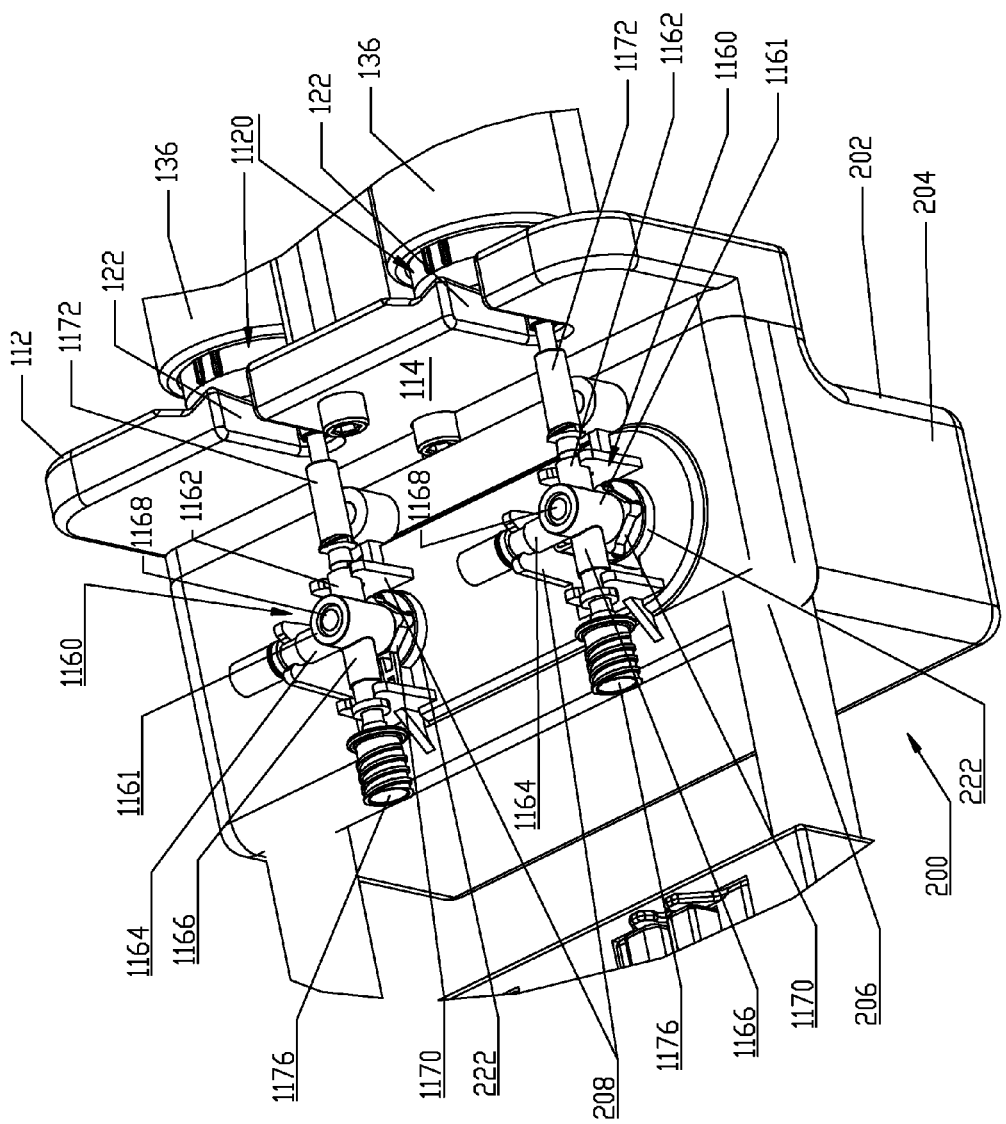
FIG. 15 is a top perspective view of the fluid injector system of FIG. 1 showing a fluid control module of the system and a first embodiment of a fluid control valve interfaced with the fluid control module.
Figure 16:
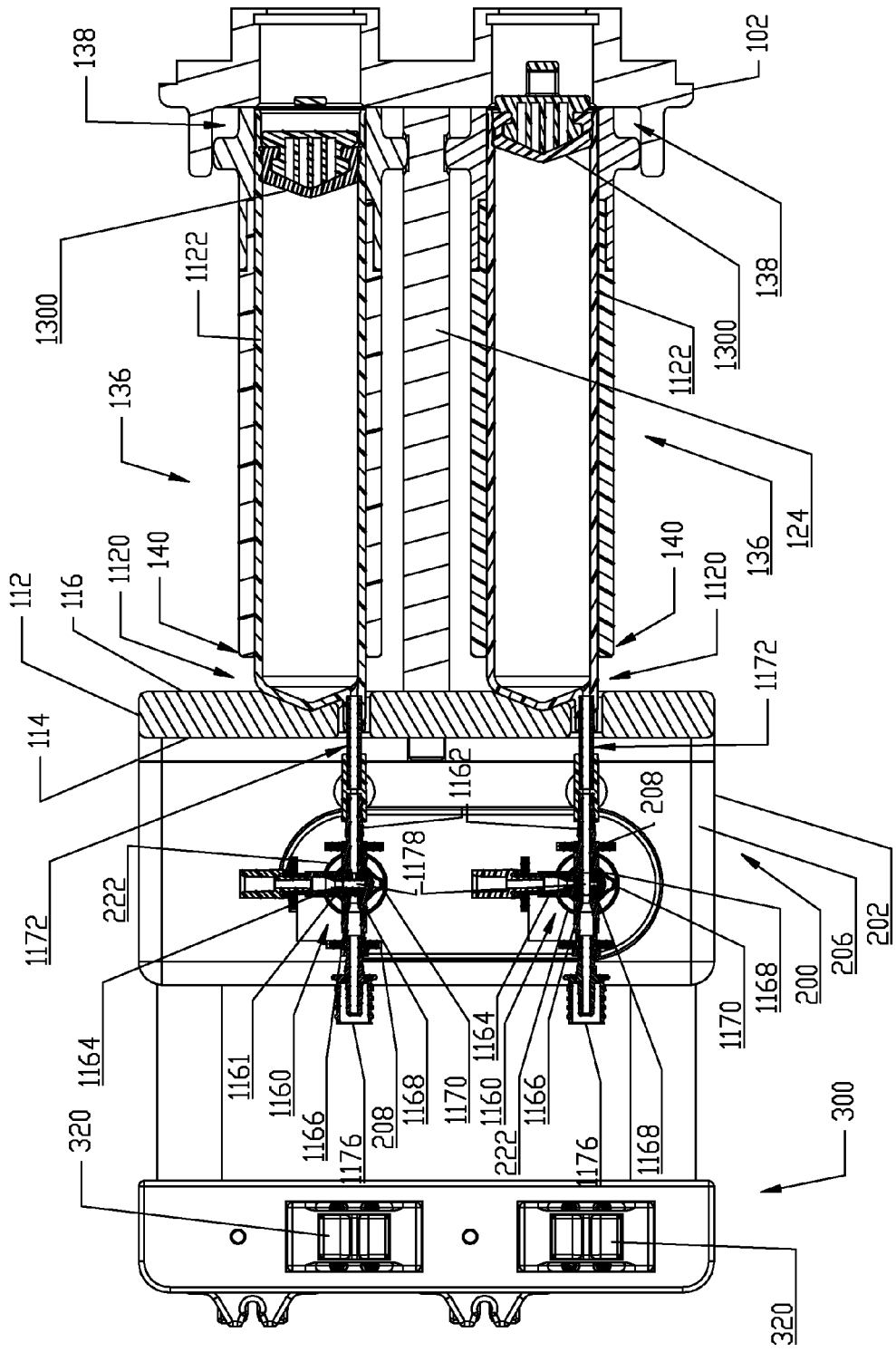
FIG. 16 is a longitudinal cross-sectional view of the fluid injector system shown in FIG. 1 and showing the fluid control module with the associated fluid control valve as shown in FIG. 15.
Figure 17:
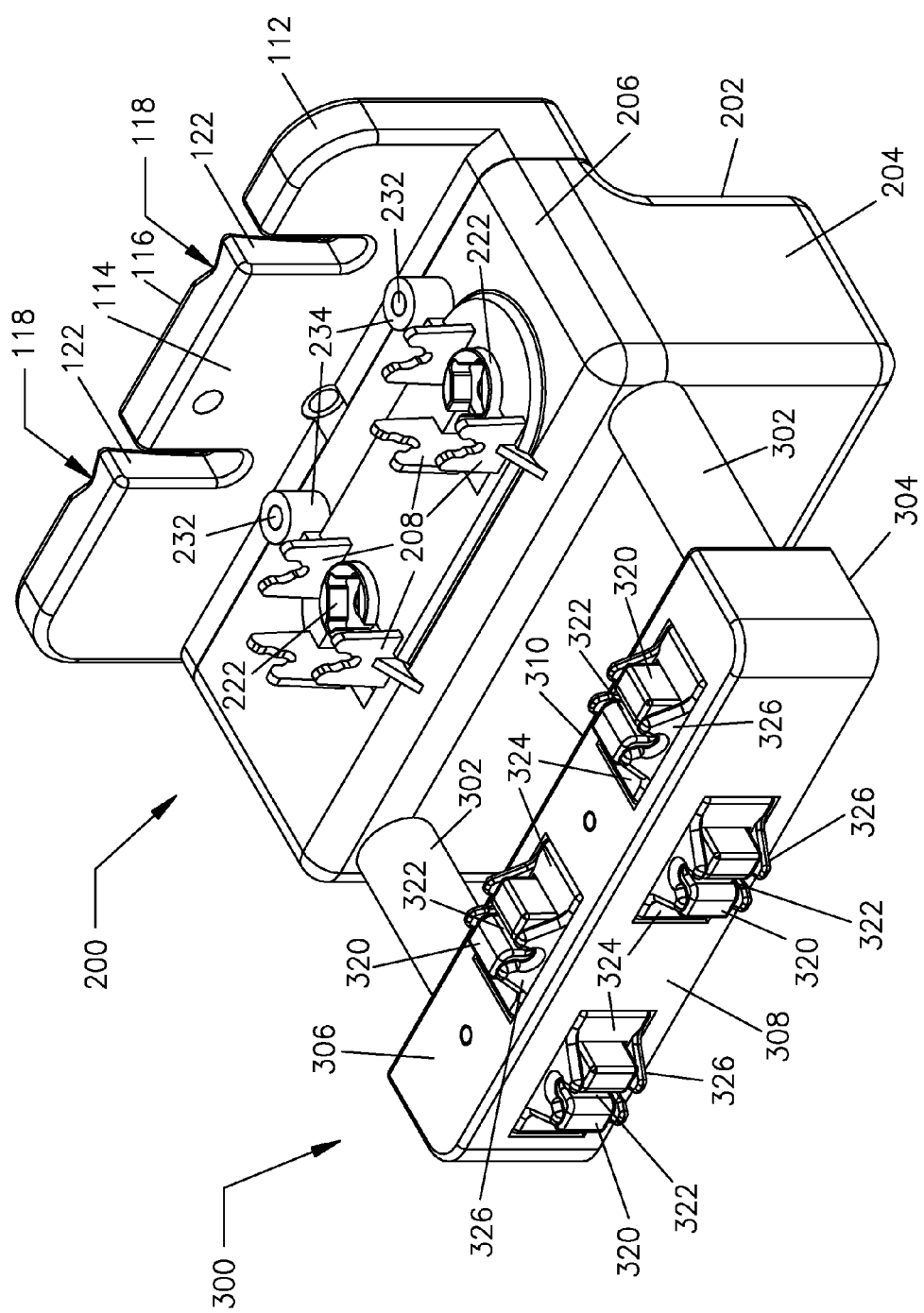
FIG. 17 is an isolation perspective view of the fluid control module of the fluid injector system of FIG. 1.

As noted in the foregoing, each multi-use set 1100 includes, as one component, the syringe 1120 as described previously. The multi-use set 1100 further comprises a fluid flow control device, namely, a fluid control valve 1150 which is adapted to interface with the fluid control module 200 as described further herein. Referring further to FIGS. 15-16, one embodiment of the fluid control valve 1150 is a three-way stopcock valve 1160. Stopcock valve 1160 comprises a valve body 1161 defining three ports, 1162, 1164, and 1166 and a plug 1168 actuated by an actuation handle 1170. First port 1162 is fluidly coupled to the discharge conduit 1130 on the syringe body 1122 of the syringe 1120 and this fluid coupling may be a permanent connection provided by an intermediate conduit element 1172 that is bonded to the first port 1162 and to the discharge conduit 1130 on the syringe body 1122, for example, by a medical grade adhesive, solvent bonding, ultrasonic welding, and like joining methods known in the medical field. Alternatively, a disconnecting connection may be provided between the first port 1162 and the discharge conduit 1130 on the syringe body 1122, for example, by a direct connection between the first port 1162 and the discharge conduit 1130 or via an intermediate conduit element similar to the illustrated intermediate conduit element 1172 but having suitable connector ports. Second port 1164 is fluidly coupled to a connecting tubing line 1174 having a conventional end connector spike 1175 via connecting tubing 1174 which is permanently joined to the second port 1164 via any of the joining methods set forth in the foregoing. Alternatively, a disconnecting arrangement may be made between the connecting tubing 1174 and the second port 1164 if desired. Third port 1166 is provided with a fluid connector 1176 which again is desirably permanently affixed to the third port 1166 via any of the conventional joining methods described in the foregoing or a disconnecting arrangement may be provided if desired. Due to the pressures generated during operation of the syringe 1120, a permanent and robust fluid connection between the third port 1166 and the fluid connector 1176 and between the first port 1162 and the discharge conduit 1130 on the syringe body 1122 of the syringe 1120 is generally preferred in accordance with this disclosure. Various suitable medical connectors for the fluid connector 1176 and details thereof may be found in United States Patent Application Publication No. 2008/0086087 (Spohn et al.) and/or in United States Patent Application Publication No. 2005/0234428 (Spohn et al.), both of which are incorporated herein by reference.

As described previously, two multi-use sets 1100 are provided to interface, respectively, with the two pressure jackets 136 supported to the injector 20 via the pressure jacket support 100. As further discussed in the foregoing, the fluid delivery set 1000 comprises a single-use set 1500 that interfaces and fluidly couples to the respective multi-use sets 1100 and provides a flow path from the multi-use sets 1100 to a patient. Single-use set 1500 comprises several components and, generally, a first input line 1502 and a second input line 1504 each terminating in a fluid connector 1506, a downstream Y-connector 1508, a gravity flow prevention diaphragm valve 1509, a pressure isolation valve 1510, a stopcock valve 1512 having an actuation handle 1513, and a catheter connector conduit 1514. Suitable medical connectors for fluid connectors 1506 that have mating features for interfacing with fluid connectors 1176 provided for the multi-use sets 1100 are also described in United States Patent Application Publication Nos. 2008/0086087 and 2005/0234428 (both to Spohn et al.). Details and operation of the pressure isolation valve 1510 may be found in United States Patent Application Publication Nos. 2008/0058720 and 2008/0154214 (both to Spohn et al.), each incorporated herein by reference. Additional desirable features for incorporation into single-use set 1500 for preventing gravity-flow situations may be found in International Application No. PCT/US2008/076378 (WO/2009/036413), incorporated herein by reference for this purpose. Moreover, additional aspects of single-use set 1500 may be found in United States Patent Application Publication Nos. 2007/0161970 and 2005/0234407 (both to Spohn et al.), each incorporated herein by reference. Downstream stopcock 1512 may have a number of functions including patient-isolation, waste-dumping, air aspiration, or, possibly, drug injection functions.

Referring further to FIGS. 17-20, fluid control module 200 generally comprises a housing 202 enclosing a pair of control valve actuators 220. A securing section or area is associated with the fluid control module 200 for interfacing with the fluid control valve 1150 provided with each multi-use set 1100. Generally, fluid control module housing 202 comprises a depending actuator enclosure 204, wherein the respective control valve actuators 220 are disposed, and a top cover or plate 206 for enclosing the actuator enclosure 204. Top cover or plate 206 defines two separate sets of attachment points or elements 208 arranged in a triad for interfacing with the fluid control valve 1150 provided with each multi-use set 1100. The attachment points or elements 208 are formed integrally with the cover plate 206 for securing the fluid control valve 1150 provided with each multi-use set 1100 to the fluid control module 200. In one embodiment, the attachment points or elements 208 are formed for a snap-fit/friction fit engagement with the respective stopcock valves 1160 and, in particular, via snap-fit engagement with ports 1162, 1164, 1166 on each stopcock valve 1160 as is well-known in the medical field.

Additionally, the front plate 112 of pressure jacket support 100 comprises a distal support flange 210 extending forward from the front or distal side 114 of the front plate 112 to provide an attachment or mounting location for the actuator enclosure 204 and top cover or plate 206. The respective control valve actuators 220 are also mounted to the distal support flange 210 beneath the distal support flange 210. As noted in the foregoing, fluid control module 200 is intended to enclose two control valve actuators 220 in actuator enclosure 204 for interfacing with the respective fluid control valves 1150 associated with the two multi-use sets 1100. The syringe 1120 for each such multi-use set 1100 interfaces with a pressure jacket 136 supported by pressure jacket support 100 as described in the foregoing. The cover plate 206 defines two top openings or apertures 212 to allow the respective control valve actuators 220 to interface with the respective fluid control valves 1150 in the multi-use sets 1100. The distal support flange 210 may be formed integrally with the front plate 112 of pressure jacket support 100 and, therefore, is desirably formed of aluminum or stainless steel of a grade suitable for medical applications as noted previously. Actuator enclosure 204 and cover plate 206 may be formed of a suitable medical grade plastic material and are mounted to the distal support flange 210 via mechanical fasteners 214. Each control valve actuator 220 comprises an actuator element 222 disposed in the respective openings 212 in the cover plate 206 enclosing actuator enclosure 204 for interfacing with the fluid control valve 1150.

As noted previously, orienting the syringe body 1122 in the proper configuration to align key or tab elements 1144 on the syringe body 1122 with the keyway 158 defined in the inner surface 160 of the body portion 152 of the pressure jacket 136 automatically orients the discharge outlet 1130 extending distally from the syringe body 1122 with the corresponding offset slot 122 defined in the front plate 112 of the pressure jacket support 100. Once the syringe 1120 is fully inserted into the barrel 162 of the receiving pressure jacket 136 and engagement of the key elements 1144 in the keyway 158 is complete, the pressure jacket 136 may then pivot downward. Pivotal movement is continued until the discharge outlet 1130 extending from the syringe body 1122 seats into the corresponding offset slot 122 defined in the front plate 112 of the pressure jacket support 100. This pivotal movement also automatically aligns the stopcock valve 1160, in the depicted embodiment, to interface with the corresponding attachment points or elements 208 on the cover plate 206 of the fluid control module housing 202. In particular, as the pressure jacket 136 containing a syringe 1120 is pivoted downward, ports 1162, 1164, and 1166 are aligned with the respective snap-fit/friction-fit attachment elements 208 on the cover plate 206 and, as the pressure jacket 136 is pivoted to a generally horizontal orientation, the respective ports 1162, 1164, and 1166 are in a position for connection to the attachment elements 208. Once the associated pressure jacket 136 reaches a generally horizontal orientation, the attendant operator may simply press on the valve body 1161 of the stopcock valve 1160 so that the respective ports 1162, 1164, and 1166 snap into engagement with the attachment elements 208. This snap-fit or frictional-fit connection also locates the actuation handle 1170 in a position to mechanically interface with the corresponding actuator element 222 of the control valve actuator 220 disposed within the actuator enclosure 204 of the fluid control module 200. As the actuation handle 1170 operates the stopcock plug 1168 of the stopcock valve 1160, operation of the actuation handle 1170 by the control valve actuator 220 places the stopcock plug 1168 in different operational states. As noted previously, the first port 1162 is fluidly coupled to the discharge conduit 1130 on the syringe body 1122 of the syringe 1120, the second port 1164 is fluidly coupled to a conventional connector spike 1175 via connecting tubing 1174, and the third port 1166 is provided with a fluid connector 1176 for interfacing with a mating fluid connector 1506 on a single-use set 1500. The foregoing loading sequence for interfacing stopcock valve 1160 with the fluid control module 200 is repeated for the second multi-use set 1100 to be associated with injector 20 via pressure jacket 136.

Stopcock valve 1160 is a conventional three-way stopcock wherein stopcock plug 1168 defines a T-shaped intersecting passageway 1178 so that any two ports 1162, 1164, and 1166 may be connected at any one time. In the view of FIG. 16, the stopcock valve 1160 associated with the "lower" or right side syringe 1120 is in a state to permit fluid flow from this syringe 1120 to the third or outlet port 1166, while the "upper" or left side syringe 1120 is in a state to permit fluid flow from a source of fluid connected to the connector spike 1175 to this syringe 1120. A shut-off condition for stopcock valve 1160 may also be provided by orienting the stopcock plug 1168 in a position where passageway 1178 blocks fluid communication between any of ports 1162, 1164, 1166. As the view in FIG. 16 further demonstrates, the connection between the respective multi-use sets 1100 and the single-use set 1500 is defined substantially at the fluid control module 200 and, more particularly, at the third or outlet port 1166 of the stopcock valve 1160 via a sterile mating fluid connector arrangement between mating fluid connectors 1176, 1506.

Figure 20:
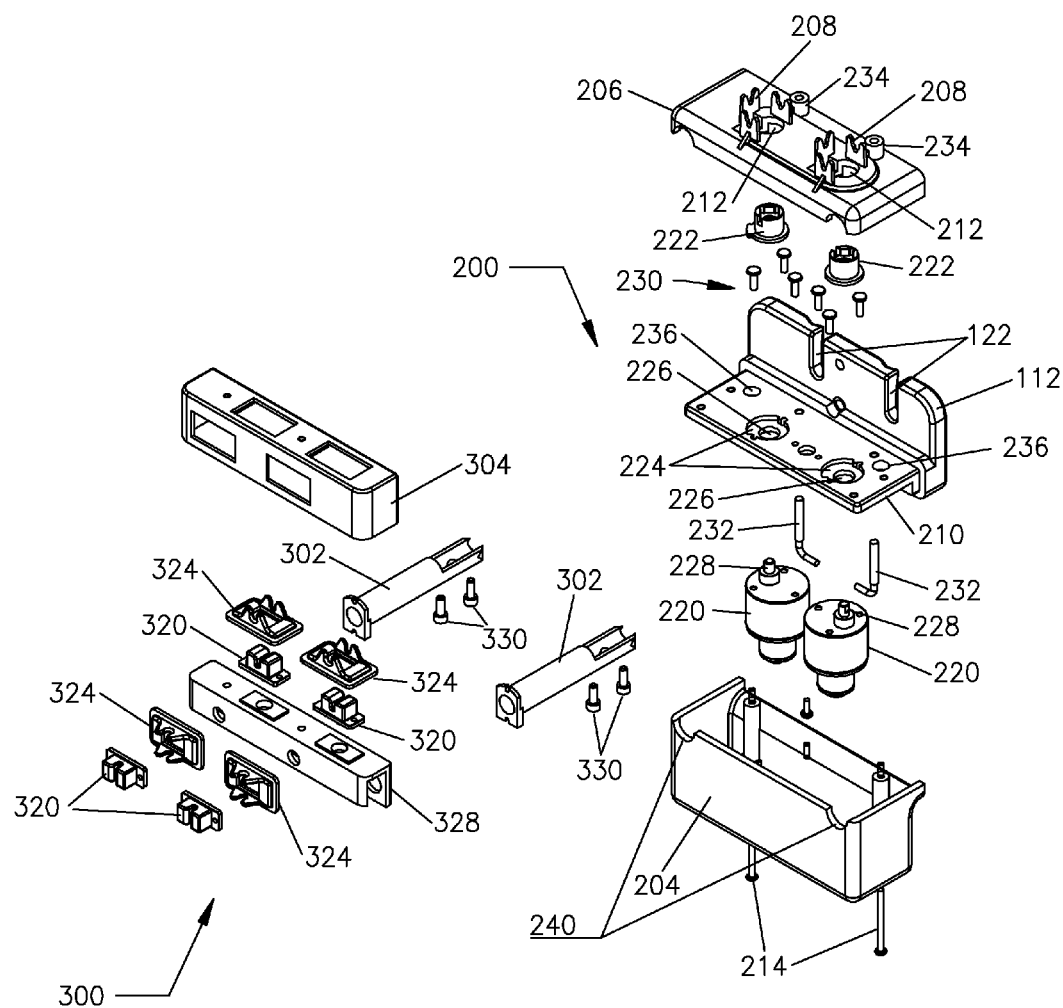
FIG. 20 is an exploded perspective view of the fluid control module shown in FIG. 17.

As shown in the exploded view in FIG. 20, the cover plate 206 is formed to seat onto distal support flange 210 extending from front plate 112 of pressure jacket support 100. The distal support flange 210 defines respective recesses 224 that correspond to the openings 212 in the cover plate 206 and which rotationally accept the respective actuator elements 222. In the illustrated embodiment, the actuator elements 222 comprise socket elements adapted to receive the stopcock actuation handle 1170 on the stopcock valves 1160. Additionally, openings 226 are defined in recesses 224 to allow the respective control valve actuators 220 to mechanically interface with the actuator elements 222. In particular, the control valve actuators 220 each comprise an output shaft 228 that mechanically interfaces with the respective actuator elements 222 to operationally control the position of the stopcock actuation handle 1170 and, thereby, the operational position of stopcock valve 1160.

Generally, each control valve actuator 220 is adapted to selectively position the stopcock actuation handle 1170 to achieve at least three set positions of the stopcock valve 1160, namely: (1) an inject or open position, wherein the first port 1162 is in fluid connection with the third or outlet port 1166; (2) a fill position, wherein the second port 1164 is in fluid connection with the first port 1162 to allow filling of syringe 1120 via the connector spike 1175 and connecting tubing 1174 associated with a fluid container; and (3) a closed or isolation position, wherein the first and second ports 1162 and 1164 are isolated from the third or outlet port 1166 and from one another. In an exemplary embodiment, the control valve actuators 220 may be a DC brush motor or a stepper motor secured by mechanical fasteners 230 to an underside of the distal support flange 210 extending from the front plate 112 of the pressure jacket support 100. In such an embodiment, the output shafts 228 from the motors comprising the control valve actuators 220 provide the motive forces for rotational movement of the socket actuating elements 222 and, thereby, cause operational movement of the stopcock actuation handle 1170.

A further feature of the fluid control module 200 comprises a pair of sensors 232 adapted to identify when the respective multi-use sets 1100 of the overall fluid delivery set 1000 are present in association with the fluid control module 200. The detector or proximity sensors 232 may be optical sensors that are seated and secured within a respective pair of annular mounts 234 formed as part of the cover plate 206 which encloses the actuator enclosure 204. The detector sensors 232 extend through a respective pair of receiving openings 236 in the distal support flange 210. As will be appreciated by those versed in the field of powered medical fluid injectors, detector sensors 232 are electronically coupled to electronic control device(s) used to discretely control operation of the reciprocally movable piston elements 60 associated with the injector 20 so that operation of the injector 20 may be based, at least in part, on inputs from the detector sensors 232. The detector sensor mounts 234 are positioned generally so as to allow the respective detector sensors 232 to identify when the first port 1162 of stopcock valve 1160 is positioned in its receiving attachment point or element 208 on the cover plate 206 or, desirably, when the connecting element 1172 between the first port 1162 and the discharge conduit 1130 extending from the syringe body 1122 is present near the detector sensor 232 which indicates that the discharge conduit 1130 is fully seated in the receiving slot 122 in the front plate 112 of the pressure jacket support 100. Mechanical fasteners 214 may be used to secure the cover plate 206 to the actuator enclosure 204 with the distal support flange 210 being sandwiched between these components and likewise held fixed by the mechanical fasteners. Furthermore, the actuator enclosure 204 may define two front recesses 240 to cooperate with support arms used to support the air detector module 300 distally outward from the fluid control module 200 as described herein.

The air detector module 300 is generally supported to the fluid control module housing 202 and, in particular, to the cover plate 206 via two distally extending support arms 302. The support arms 302 support a housing or body 304 that in turn supports a plurality of air column detectors 320, (hereinafter "air detectors 320"). In particular, the air detector module housing 304 is generally a rectangular, box-shaped housing structure that supports two air detectors 320 located on a top side of cover plate 306 and two air detectors 320 located on a front or distal side 308. The support arms 302 are joined to a rear or distal side 310 of the housing 304 to support the housing 304 to the fluid control module housing 202. The air detectors 320 may be conventional ultrasonic or optical air detector sensors and each define a detector recess 322 for receiving medical tubing associated with the multi-use set 1100 and the single-use set 1500. Each air detector 320 is provided with a mounting element 324 having a pair of attachment points 326 located on either side of the detector recess 322 for receiving and securing medical tubing associated with the multi-use set 1100 and the single-use set 1500. It is generally desirable for the top-mounted or top-located air detectors 320 on the air detector module housing 304 to interface with the input lines 1502, 1504 associated with the single-use set 1500 and for the front-mounted or front-located air detectors 320 on the air detector module housing 304 to interface with the respective connecting tubing lines 1174 associated with the second port 1164 of the respective stopcock valves 1160 in the multi-use sets 1100. In this manner, fluid drawn into and dispensed from the syringes 1120 during their operation is subject to air detection when in-coming to the syringes 1120 and outgoing from the syringes 1120. As will be appreciated by those skilled in the powered medical injector field, the respective air detectors 320 are linked to the electronic control device(s) associated with the injector 20 which is used to discretely control operation of the reciprocally movable piston elements 60 associated with injector 20 for safety and other purposes. A support bridge 328 may be disposed within the housing 304 to provide a supporting element or base within the housing 304 for attachment of the respective mounting elements 324 supporting the respective air detectors 320 as well as an anchoring location for the support arms 302 which, as illustrated, may pass through rear openings in the support bridge 328 to be affixed to the distal support flange 210 enclosed within the fluid control module housing 202 using conventional mechanical fasteners 330.

Figure 21:
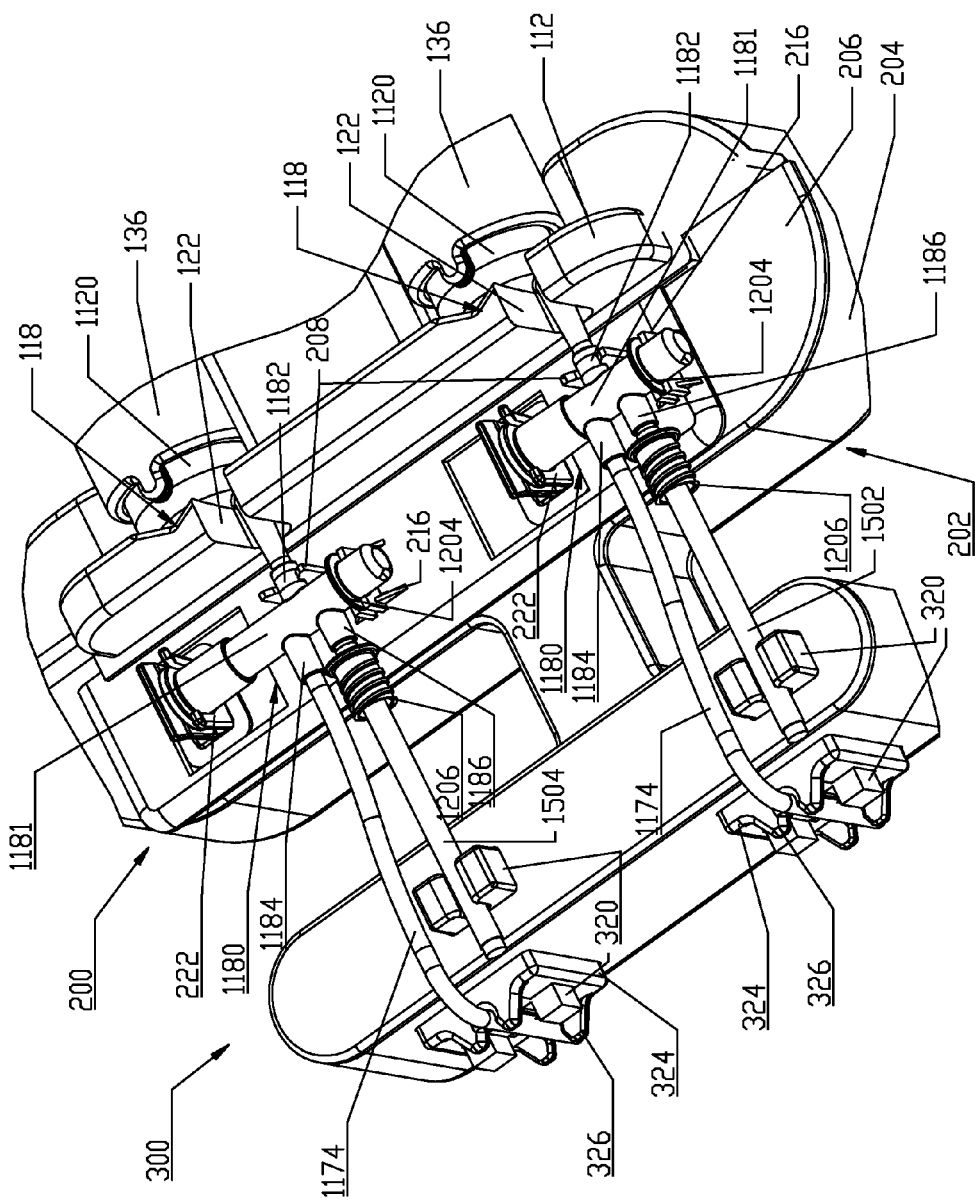
FIG. 21 is a top perspective view of a forward portion of the fluid injector system of FIG. 1 showing the fluid control module of the system and a second embodiment of a fluid control valve interfaced with the fluid control module.
Figure 22:
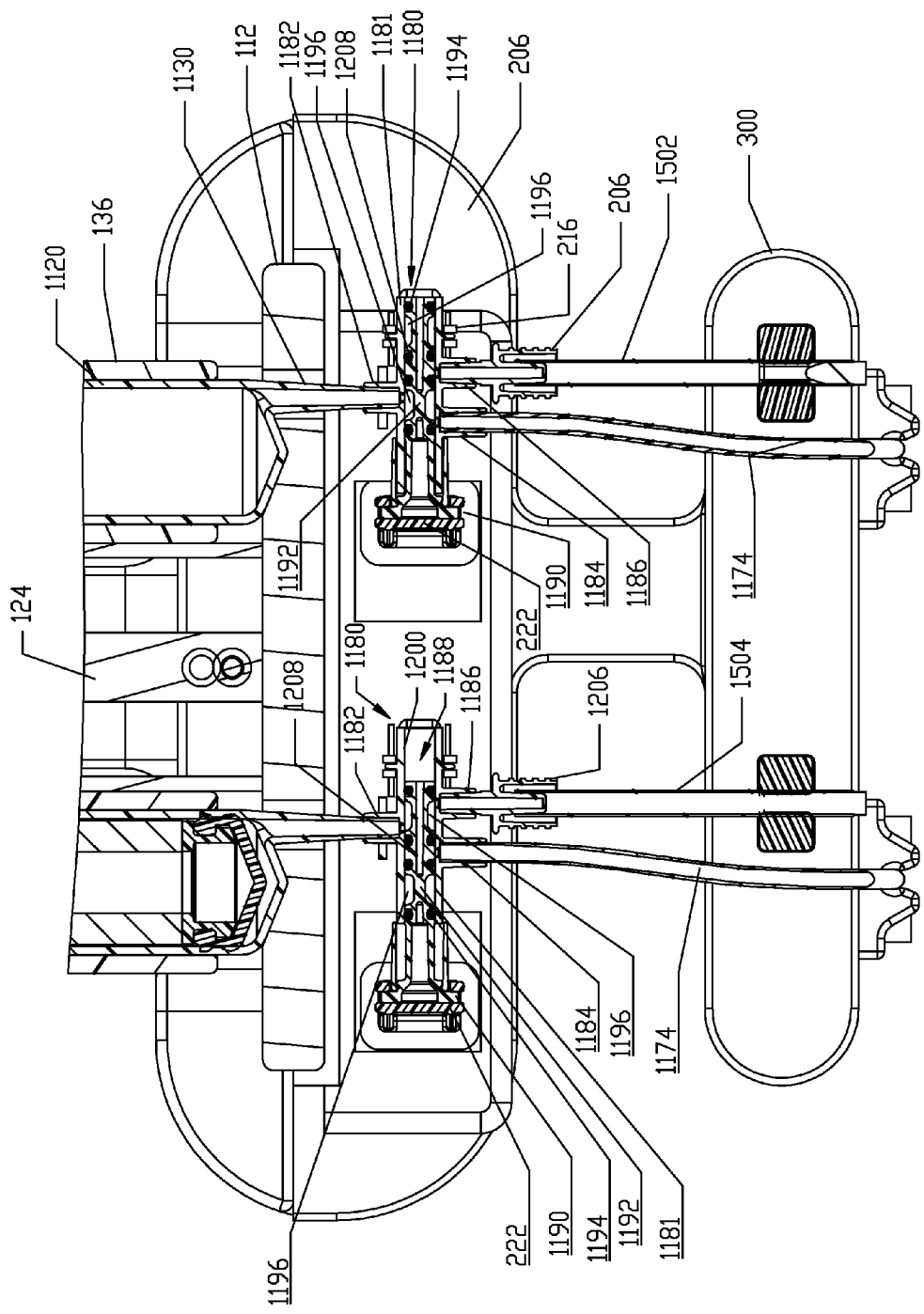
FIG. 22 is a longitudinal cross-sectional view of the fluid injector system shown in FIG. 1 and showing the fluid control module with the associated fluid control valve as shown in FIG. 21.

Referring next to FIGS. 21-22, another embodiment of the fluid control valve 1150 in the form of a piston valve 1180 is illustrated as forming part of the multi-use set 1100. The piston valve 1180 is another suitable embodiment of the fluid control valve 1150 for application in fluid injector system 10 with appropriate modifications to the fluid control module 200. The piston valve 1180 generally comprises a valve housing 1181 defining three ports 1182, 1184, and 1186 and a piston 1188. The piston 1188 comprises a piston head 1190 and a distally-extending piston stem 1192. The piston stem 1192 defines radial recesses at spaced apart locations along the piston stem 1192 where O-rings 1194 and like sealing elements may be seated for forming a fluid tight connection with an internal piston cavity or bore 1200 defined by the valve housing 1181. Two fluid connecting radial recesses 1196 are also defined in the piston stem 1192 at spaced apart axial locations to enable operation of the piston valve 1180. The piston head 1190 is formed to be engaged with a modified actuator element 222 of the control valve actuator 220 according to a modified embodiment of the control valve actuator 220 adapted for interfacing with piston valve 1180, as described herein.

The piston valve 1180 is secured to the cover plate 206 of the fluid control module housing 202 in an analogous manner to the manner in which the stopcock valve 1160 is secured to the cover plate 206 but with certain modifications as now described. In particular, one of the attachment elements 208 on the cover plate 206, in the present embodiment, is adapted for a snap-fit or friction-fit engagement with the first port 1182 in an analogous arrangement to the snap-fit/friction-fit engagement used to secure the first port 1162 of the stopcock valve 1160. However, the piston valve housing 1181 comprises a radial securing flange 1204 for further securing the piston valve housing 1181 to a second, modified attachment element 216 on the cover plate 206 which comprises two opposing walls adapted to receive the radial securing flange 1204 therebetween. Further, the modified actuator element 222 of the control valve actuator 220 may be formed for a snap-fit/friction-fit engagement with the piston head 1190 in a similar manner to the conventional attachment element 208 or, desirably, the second, modified attachment element 216 on the cover plate 206.

The first port 1182 of the piston valve 1180 is fluidly coupled to the discharge conduit 1130 on syringe body 1122 of syringe 1120 and this fluid coupling may be a permanent connection, for example, by a medical grade adhesive, solvent bonding, ultrasonic welding, and like joining methods known in the medical field. Alternatively, a disconnecting connection may be provided between the first port 1182 and the discharge conduit 1130 on the syringe body 1122, for example, by a direct connection between the first port 1182 and the discharge conduit 1130 or via an intermediate conduit element similar to the intermediate conduit element 1172 discussed previously in connection with stopcock valve 1160. The second port 1184 is fluidly coupled to the conventional connector spike 1175 via connecting tubing 1174 in the same manner described previously in connection with stopcock valve 1160. This fluid connection may be a permanent connection via any of the methods discussed previously but, alternatively, a disconnecting arrangement may be made between the connecting tubing 1174 and the second port 1184 if desired. The third port 1186 is provided with a fluid connector 1206 which again may be permanently affixed to the third port 1186 via any of the conventional joining methods described in the foregoing. Nonetheless, a disconnecting arrangement may be employed if desired. Due to the pressures generated during actuation of the syringe 1120, a permanent and robust fluid connection between the third port 1186 and the fluid connector 1206 between the first port 1182 and the discharge conduit 1130 on the syringe body 1122 of the syringe 1120 is generally preferred in accordance with this disclosure. Fluid connector 1206 is similar to fluid connector 1176 described previously and is adapted in like manner to fluid connector 1176 to interface with mating fluid connector(s) 1506 associated with single-use set 1500; the details for fluid connectors 1176, 1206 and mating fluid connector 1506 may be found in United States Patent Application Publication No. 2008/0086087 and/or in United States Patent Application Publication No. 2005/0234428, both of which were incorporated herein previously by reference.

The fluid connecting radial recesses 1196 in piston valve 1180 permit the first port 1182 to alternately be placed in fluid connection with ports 1184, 1186. In the view of FIG. 22, the piston valve 1180 associated with the "left" side syringe 1120 is in a state to permit fluid flow from this syringe 1120 to the third or outlet port 1186, while the "right" side syringe 1120 is in a state to permit fluid flow from a source of fluid connected to the connector spike 1175 to this syringe 1120. An intermediate portion 1208 of the piston stem 1192 defined between the radial recesses 1196 may be used to block or isolate the first port 1182 when this intermediate portion 1208 is generally centered over the first port 1182. In this location, the second and third ports 1184, 1186 are also isolated from one another. Operation of the piston 1188 to move the piston stem 1192 to achieve the various foregoing fluid connections is effected by engagement of the modified actuator element 222 of the control valve actuator 220 with the piston head 1190. In the present embodiment, it will be apparent that the associated control valve actuator 220 useful for operation of the piston valve 1180 is desirably a linear actuator capable of imparting linear reciprocal movement to the piston stem 1192 via the piston head 1190.

Figure 23:
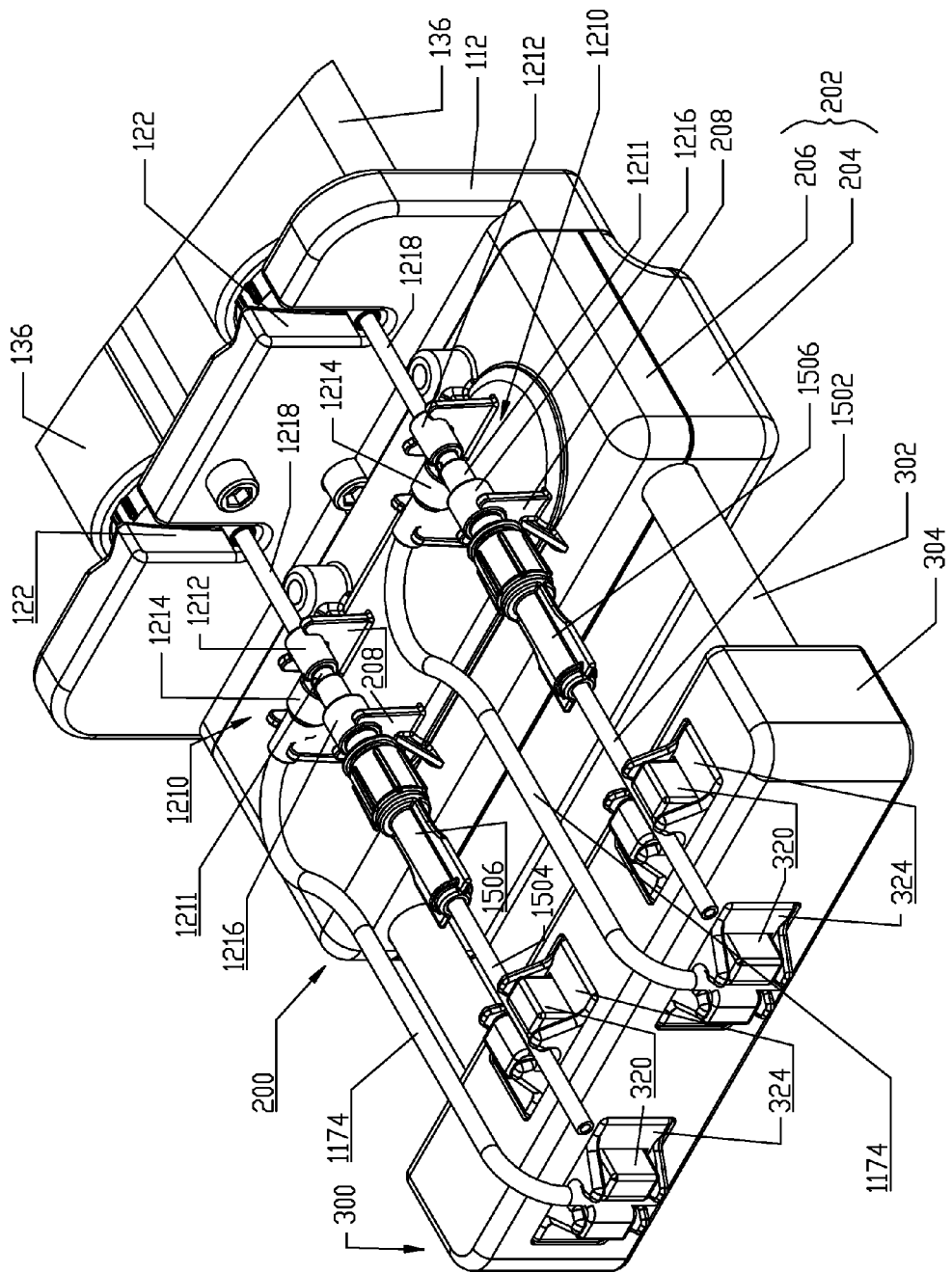
FIG. 23 is a top perspective view of a forward portion of the fluid injector system of FIG. 1 showing the fluid control module of the system and a third embodiment of a fluid control valve interfaced with the fluid control module.
Figure 24A:
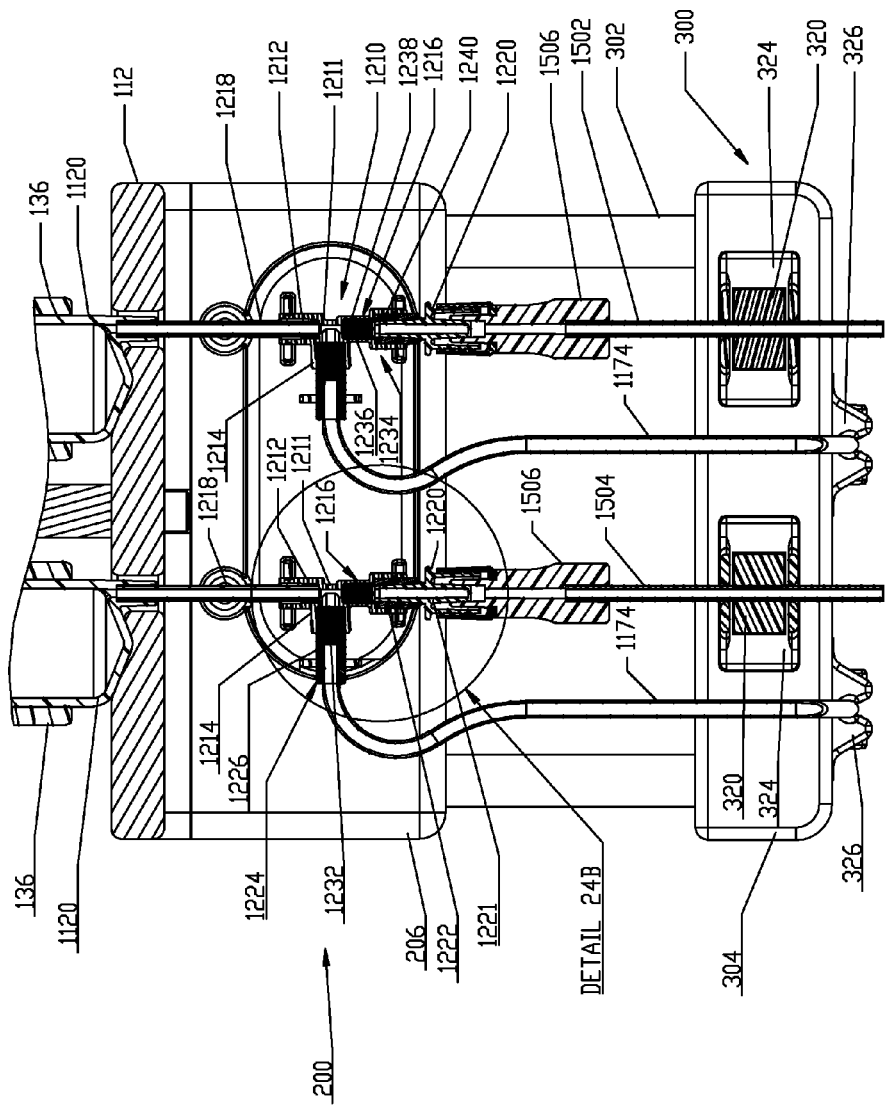
FIG. 24A is a longitudinal cross-sectional view of the fluid injector system shown in FIG. 1 and showing the fluid control module with the associated fluid control valve as shown in FIG. 23.
Figure 24B:
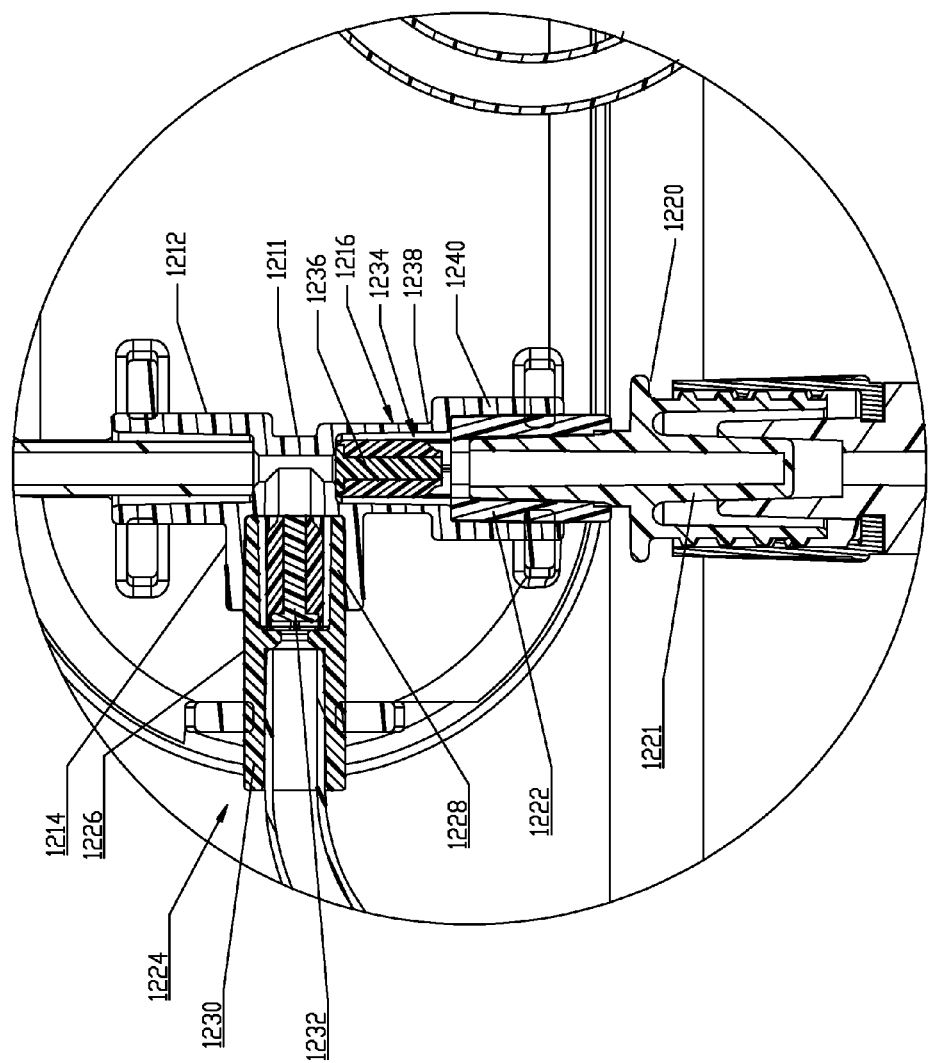
FIG. 24B is a detail view of Detail 24B in FIG. 24A.

Referring next to FIGS. 23-24, another embodiment of the fluid control valve 1150 is a dual or double check valve 1210. Dual check valve 1210 comprises a valve body 1211 defining three ports, 1212, 1214, and 1216, in like manner to stopcock valve 1160 discussed previously. The first port 1212 is fluidly coupled to the discharge conduit 1130 on the syringe body 1122 of the syringe 1120 and this fluid coupling may be a permanent connection provided by an intermediate conduit element 1218 that is bonded to the first port 1212 and to the discharge conduit 1130, for example, by a medical grade adhesive, solvent bonding, ultrasonic welding, and like joining methods known in the medical field. Alternatively, a disconnecting connection or like connection may be provided between the first port 1212 and the discharge conduit 1130, for example, by a direct but disconnecting connection between the first port 1212 and the discharge conduit 1130 or via a disconnecting intermediate conduit element similar to the illustrated intermediate conduit element 1218 but having suitable connector ports. The second port 1214 is fluidly coupled to a conventional connector spike 1175 via connecting tubing 1174 in a similar manner to the previously discussed embodiments of the fluid control valve 1150. The third port 1216 is provided with a connector element 1220 similar to connector element 1206 described previously in connection with the piston valve 1180 and the fluid connector 1176 described previously in connection with the stopcock valve 1160, and is adapted in like manner to connector elements 1206, 1176 to interface with mating fluid connector(s) 1506 associated with the single-use set 1500; the details for fluid connectors 1176, 1206, 1220 and mating fluid connector 1506 may be found in United States Patent Application Publication No. 2008/0086087 and/or in United States Patent Application Publication No. 2005/0234428, both of which were incorporated herein previously by reference. In view of the foregoing, it will be appreciated that fluid connectors 1176, 1206, 1220 are identical fluid connectors but are given different reference numerals for identity with the respective embodiments of fluid control valve 1150. In the illustrated embodiment, the connector element 1220 comprises a connector conduit 1221 extending proximally from connector element 1220 to interface with the third or outlet port 1216 via an interfacing bushing 1222. Ports 1212, 1214, and 1216 each interface via snap-fit/friction-fit engagement with the respective attachment elements 208 on the cover plate 206 of the fluid control module housing 202 in generally the same manner as described previously in connection with the stopcock valve 1160.

A first check valve 1224 is disposed in the second port 1214 of the dual check valve 1210. The first check valve 1224 comprises a unitary connector body 1226 having a first annular portion 1228 secured within the second port 1214, and a second annular portion 1230 wherein the connecting tubing 1174 connected to connector spike 1175 is disposed and secured. Securing of the first annular portion 1228 of the connector body 1226 within the second port 1214 and securing of the connecting tubing 1174 within the second annular portion 1230 of the connector body 1226 may be by any of the conventional joining methods described previously in this disclosure. A first check valve member 1232 is disposed within the first annular portion 1228 of the connector body 1226. Correspondingly, a second check valve 1234 is associated with the third or outlet port 1216 of the dual check valve 1210. In particular, the second check valve 1234 comprises a second check valve member 1236 seated within a first annular portion 1238 of the third port 1216. The third port 1216 further defines a second, larger annular portion 1240 for interfacing with the connector conduit 1221 extending proximally from the connector element 1220 via intermediate or intervening bushing 1222. The bushing 1222 may further be used to maintain the positioning of the second check valve member 1236 within the first annular portion 1238 of the third or outlet port 1216. The check valve members 1232, 1236 are oppositely operable from one another so that the first check valve member 1232 permits fluid flow from a fluid source connected to the connecting tubing 1174 via connector spike 1175 to enter the valve body 1211 of the dual check valve 1210 but reverse flow into the connecting tubing 1174 is prevented by the first check valve member 1232, for example, when the syringe 1120 is operating to dispense or inject fluid via discharge conduit 1130. Similarly, the second check valve member 1236 is operable to permit fluid flow to enter the third port 1216 and the connector element 1220 and to pass to the single-use set 1500, but prevents reverse flow into the connector element 1220 from the single-use set 1500 and, particularly, any reverse flow from the respective input lines 1502, 1504 of the single-use set 1500 toward syringe 1120.

A modified version multi-fluid medical injection/injector system 10 is shown in FIGS. 25-29, which will now be described. The modified version of fluid injector system 10 comprises the same powered injector device 20 and pressure jacket support 100 discussed previously but has certain modifications to the fluid control module 200 and air detector module 300 which results in certain modifications to the fluid delivery set 1000. The present embodiment of the fluid injector system 10 comprises a combined fluid control module 200 and air detector module 300, wherein the components of the previously discussed air detector module 300 are incorporated into the housing structure of the fluid control module 200.

With respect to the combined fluid control module 200 and air detector module 300 in the modified embodiment of the fluid injector system 10, the fluid control module 200 now generally comprises a pair of top and bottom cover plates 242, 244 between which the distal support flange 210 extending from the front plate 112 of the pressure jacket support 100 is sandwiched and secured in a similar manner to that described previously in this disclosure. Additionally, the depicted fluid control module 200 comprises the same basic components as described previously, with the top cover plate 242 comprising attachment points or elements 208 for the respective ports 1162, 1164, 1166 on stopcock valves 1160, similar detector sensors 232 as described previously and, moreover, similar control valve actuators 220 as described previously. However, each control valve actuator 220 comprises its own actuator enclosure 246 which is formed integrally with the bottom cover plate 244.

In the combined fluid control module 200 and air detector module 300, the top cover plate 242, the bottom cover plate 244, and the distal support flange 210 are elongated over the previously described embodiment of the fluid control module 200 and, further, define front slots or recesses 248 for receiving and supporting two pivotal air detector assemblies 336 adapted for use with input lines 1502, 1504 of single-use set 1500. As in the previously discussed embodiment of the air detector module 300, two front-located air detectors 320 are provided in substantially the same location as described previously, for association with the respective connecting tubing lines 1174 used to conduct fluid from the fluid sources to the respective syringes 1120 loaded in pressure jackets 136. These front-mounted air detectors 320 may be supported between the top and bottom cover plates 242, 244 in like manner to that described previously. The respective air detector assemblies 336 are each comprised of an air detector 340 defining a detector recess 342 for receiving medical tubing associated with the single-use set 1500. Each air detector 340 is identical to air detectors 320 described previously and is supported by a mounting element 344 having a pair of tubing attachment elements 346 located on either side of the detector recess 342 for receiving and securing medical tubing. Each mounting element 344 is connected to a pivotal support arm 348, pivotally secured within the respective front-located receiving slots/recesses 248.

The respective air detector assemblies 336 are pivotal in front slots or recesses 248 from a position wherein the respective air detectors 340 are generally horizontally aligned between the top cover plate 242 and bottom cover plate 244 to a pivoted position engaging one of the input lines 1502, 1504 of single-use set 1500. The air detector assemblies 336 are in a non-use position when the respective air detectors 340 are generally horizontally aligned or positioned in the respective front end slots or recesses 248. The use position of the air detector assemblies 336 is defined when the respective air detector assemblies 336 are pivoted upward to define an upstanding, generally vertical orientation of the support arms 348 whereby the air detectors 340 may interface with the input lines 1502, 1504 of the single-use set 1500.

The vertically-pivoted, use position of the air detector assemblies 336 desirably provides an additional function in the present embodiment of the fluid injector system 10. In particular, in the vertically-pivoted, use position of the air detector assemblies 336, the attachment elements 346 of mounting elements 344, which act as tubing securing elements or flanges, also secure the fluid connection between the single-use set 1500 and the respective multi-use sets 1100 provided by an alternative fluid connector 1516 shown in detail in FIGS. 27-29. These fluid connectors 1516 may be provided as an alternative to fluid connectors 1506 described previously and are mounted to input lines 1502, 1504 and, further, are provided in place of the fluid connectors 1176 described previously provided as part of the third or outlet port 1166 of the respective stopcock valves 1160 in the multi-use sets 1100.

Each fluid connector 1516 comprises a cylindrical body portion 1518 having a closed bottom end 1520, an open top end 1522, and a side wall 1524 defining a receiving bore or barrel 1526. A side port 1528 extends from the side wall 1524 and is generally adapted to interface with the third port 1166 of the stopcock valve 1160 in each of the multi-use sets 1100. The side port 1528 may be configured, for example, for a mating connection with the third or outlet port 1166 of a stopcock valve 1160. Alternatively, the side port 1528 may have a permanent connection to the third port 1166 and, hence, be part of the stopcock valve 1160 in the multi-use sets 1100. A cap portion 1530 is adapted to cooperate with the cylindrical body portion 1518. The cap portion 1530 has a T-shaped conduit 1532 for fluid communication with the side port 1528. A top port 1534 of the cap portion 1530 forms a connection port for connection to the fluid lines 1502, 1504 of the single-use set 1500. The cap portion 1530 may be provided as part of the single-use set 1500, with each fluid line 1502, 1504 carrying a cap portion 1530 in place of the fluid connectors 1506 described previously. The cap portion 1530 comprises an elongated stem 1536 adapted for insertion into the barrel 1526 of the cylindrical body portion 1518. The stem 1536 defines a pair of annular receiving recesses 1538 for accepting sealing O-rings 1540 so that a generally fluid-tight seal may be established between the cap portion 1530 and the cylindrical body portion 1518 when these components are joined together. The cap portion 1530 is adapted for removable insertion into the barrel 1526 of the cylindrical body portion 1518 and this engagement is secured as described herein. A shoulder 1542 on the stem 1536 has an outer diameter to fit snugly within the diameter of the barrel or bore 1526 in the cylindrical body portion 1518. Further, the cap portion 1530 comprises an outward-extending radial flange 1544 which is provided as a contact surface for interfacing with one of the attachment elements 346 on the mounting element 344 associated with the air detector 340 in each of the air detector assemblies 336 which secures the engagement between the cylindrical body portion 1518 and the cap portion 1530, as described herein.

Figure 25:
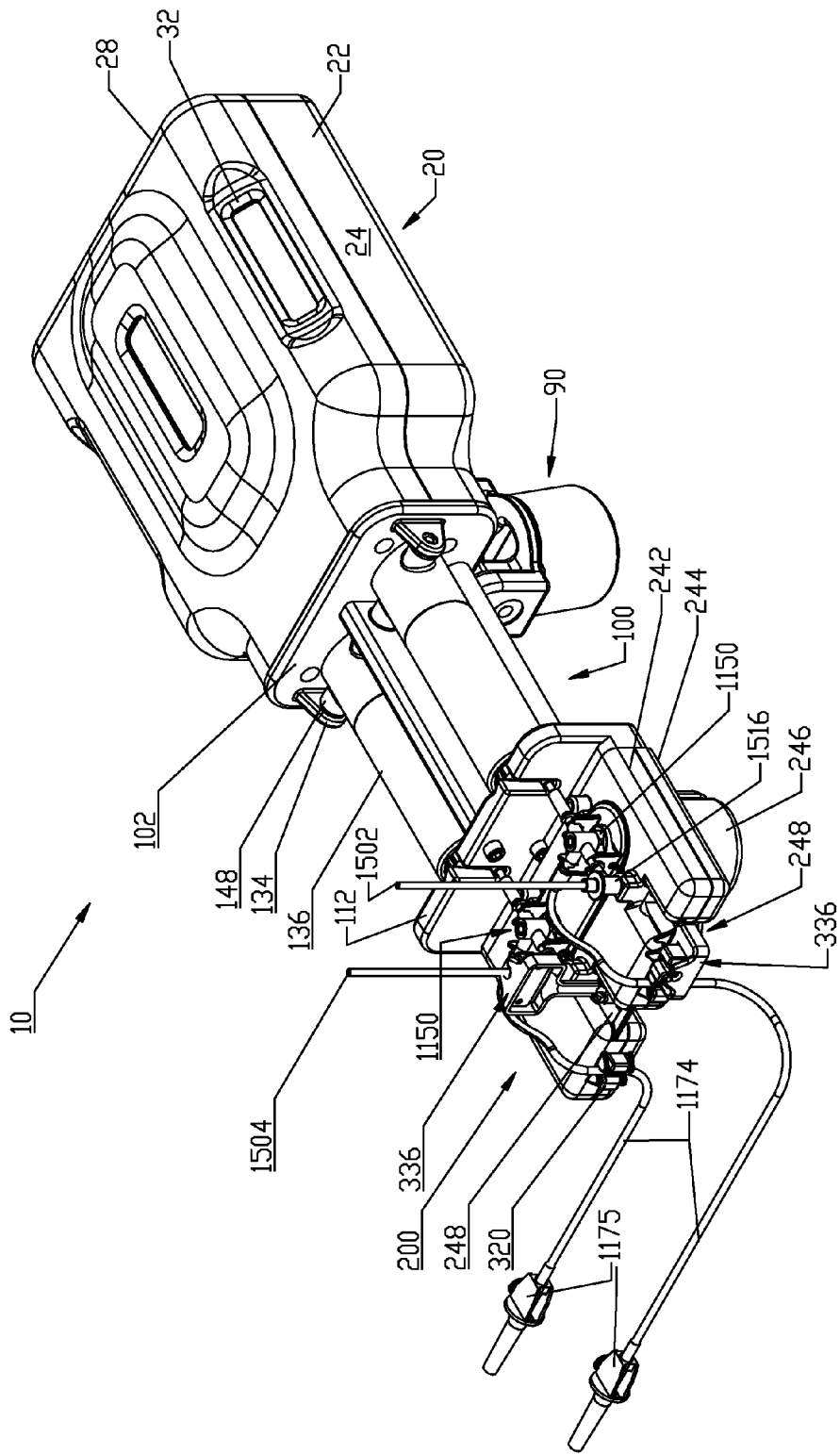
FIG. 25 is a perspective view of another embodiment of the fluid injector system of FIG. 1.
Figure 26:
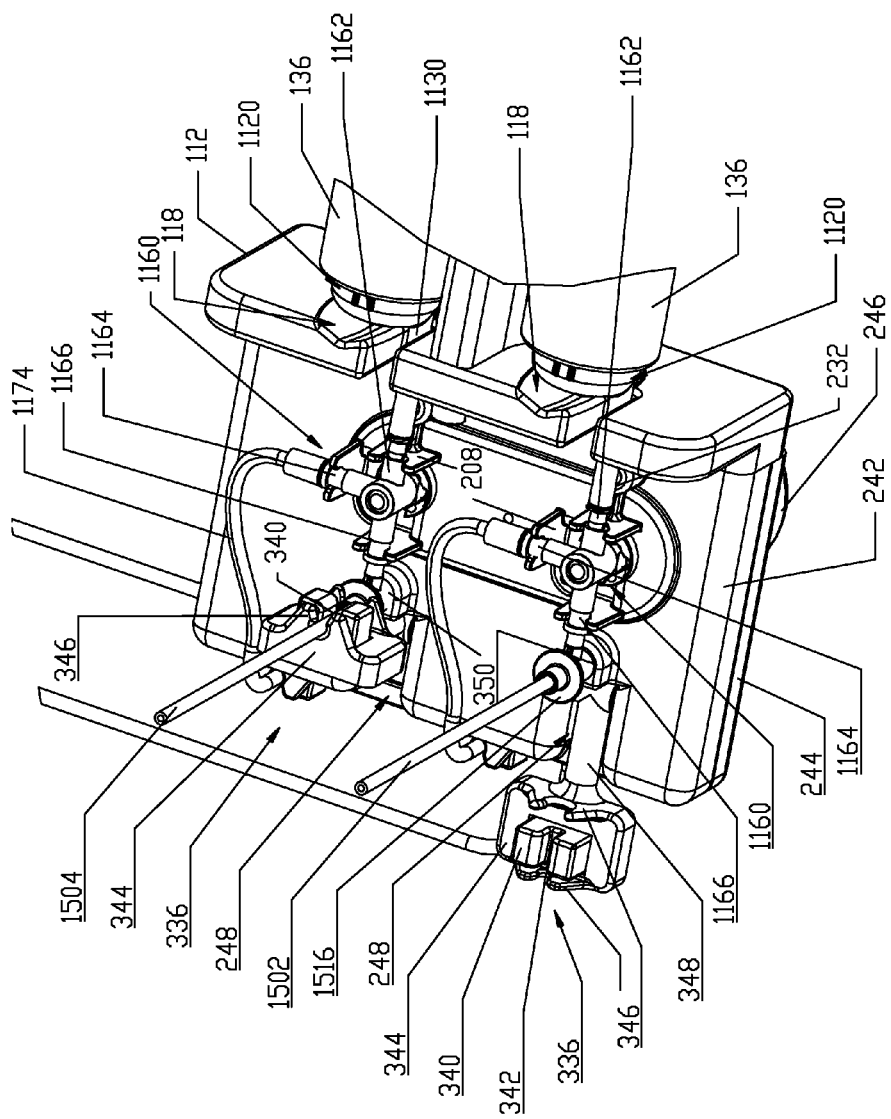
FIG. 26 is a perspective view of a forward portion of the fluid injector system of FIG. 25.
Figure 27:
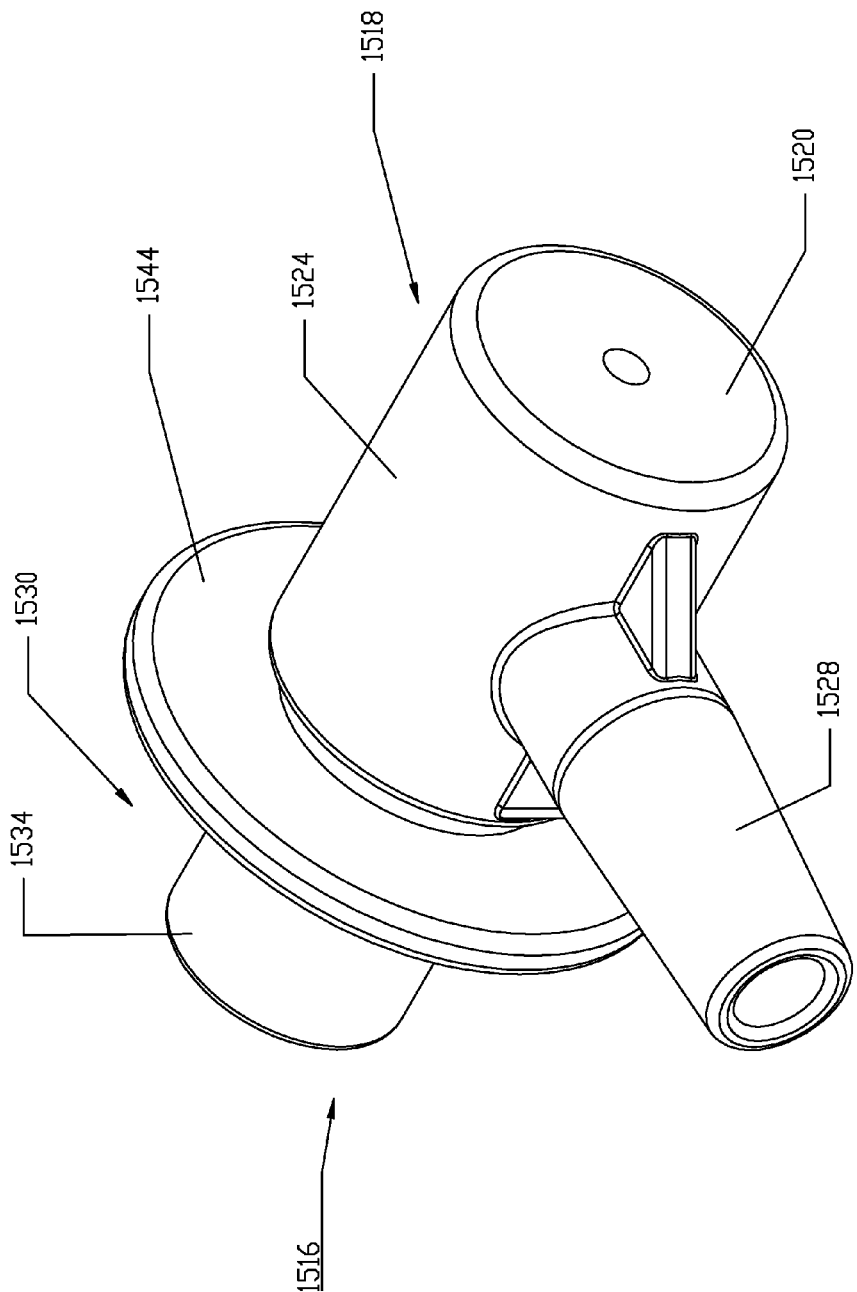
FIG. 27 is a perspective view of a fluid connector used to make fluid connections in the fluid injector system of FIG. 25.
Figure 28:
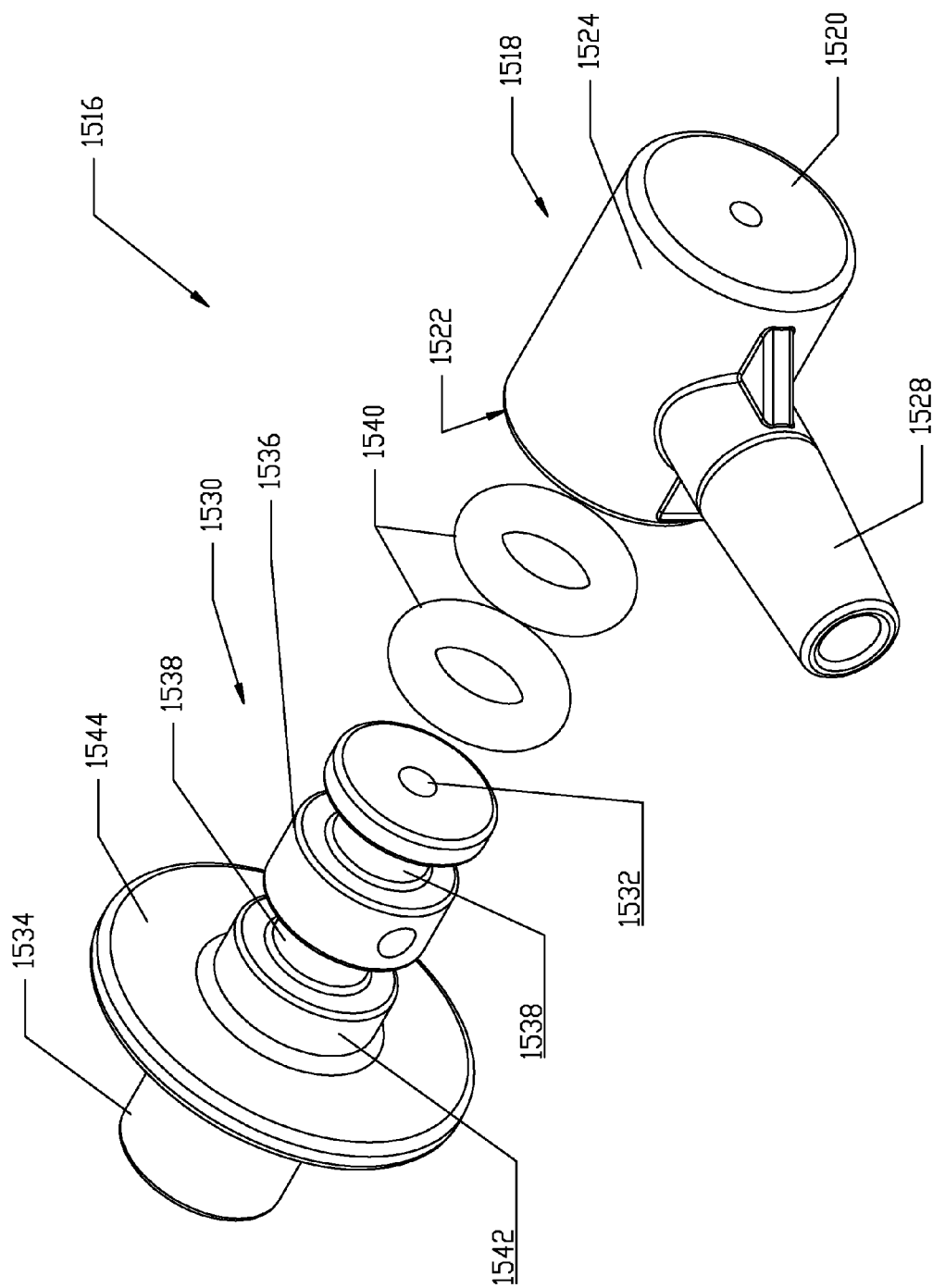
FIG. 28 is an exploded perspective view of the fluid connector shown in FIG. 27.
Figure 29:
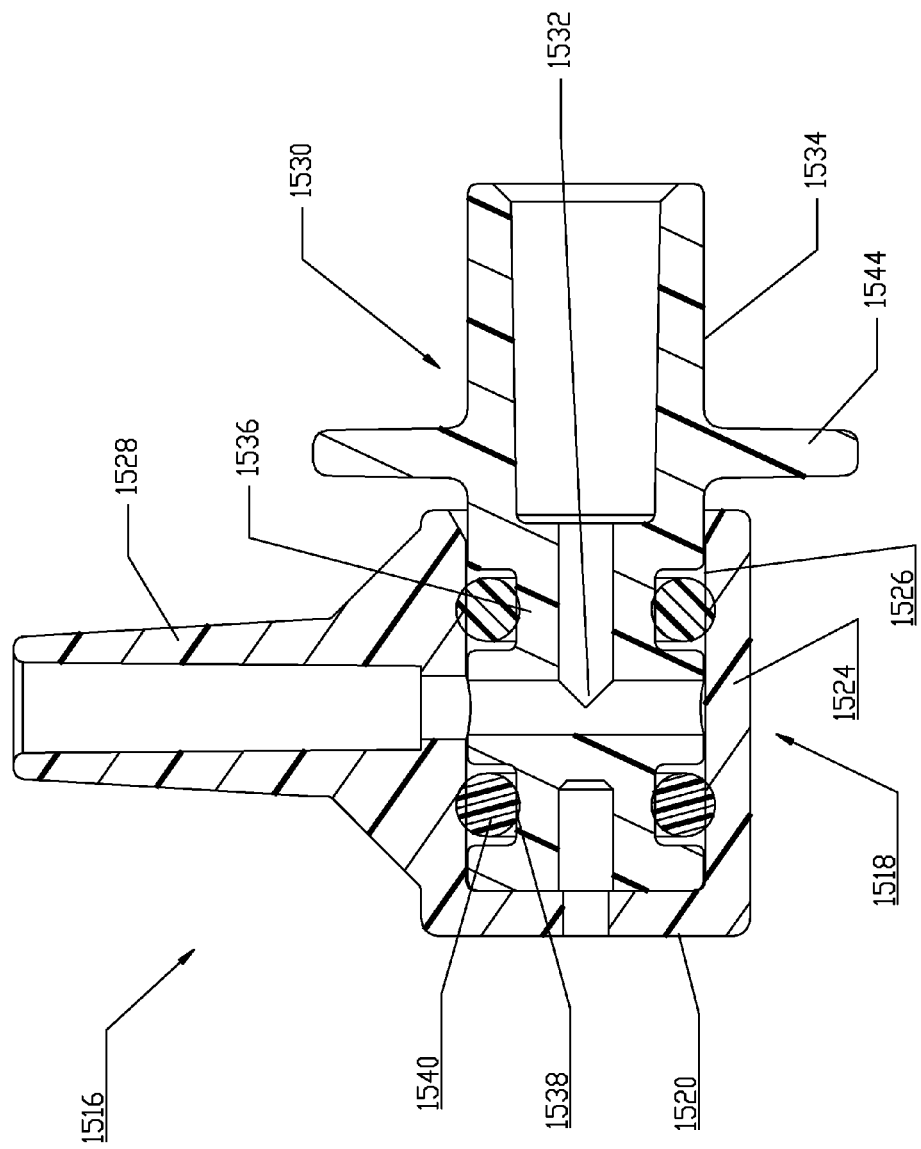
FIG. 29 is a cross-sectional view of the fluid connector shown in FIG. 27.

Based on the foregoing, it will be appreciated that each input line 1502, 1504 in single-use set 1500 is provided with a cap portion 1530 adapted for fluid connection with a corresponding cylindrical body portion 1518 which is interfaced (either in a removable fashion or in permanent connection) with the third port 1166 on a stopcock valve 1160 in one of the multi-use sets 1100. Accordingly, to make the desired fluid connections using the fluid connectors 1516 as shown in FIG. 25, the side port 1528 on the cylindrical body portion 1518 for each fluid connector 1516 is placed in fluid connection or engagement with the corresponding third port 1166 on one of the respective stopcock valves 1160 of the multi-use sets 1100 and the cylindrical body portion 1518 is situated on the top cover plate 242. The top cover plate 242 is formed with a pair of mounts 350 to provide a seating location for the cylindrical body portion 1518. The mounts 350 receive the cylindrical body portion 1518 for each fluid connector 1516 once the side port 1528 is inserted or otherwise associated with the corresponding third port 1166 on the respective stopcock valves 1160. Alternatively, as described in the foregoing, if the cylindrical body portion 1518 is connected to the stopcock valve 1160 via permanent connection between the side port 1528 and the third or outlet port 1166 on the stopcock valve 1160, the association of the stopcock valve 1160 with the attachment points or elements 208 on the cover plate 206 places the cylindrical body portion 1518 in the corresponding receiving mount 350 on the cover plate 206.

Next, the cap portions 1530, which are connected to the respective input lines 1502, 1504 of the single-use set 1500 via their respective top ports 1534, are inserted into the barrel 1526 in the receiving cylindrical body portions 1518. Once these fluid connections are made, the corresponding pivotal support arm 348 may be pivoted upward to the use position of the support arm 348, wherein the corresponding input lines 1502, 1504 of the single-use set 1500 are received in operative engagement with the air detector 340 supported by the respective mounting elements 344 carried by the respective support arms 348 and the attachment elements 346 engage the tubing forming the corresponding input lines 1502, 1504 to secure the tubing within the detector recess 342 of the air detector 340. At the same time, the "lower" attachment element 346 on each mounting element 344 engages the top port 1534 on the cap portion 1530 and, further, abuts against the contact surface defined by the radial flange 1544 extending about the cap portion 1530. With this contact engagement, the "lower" engaging attachment element 346 secures the fluid connection between the cap portion 1530 and the cylindrical body portion 1518 in the respective fluid connectors 1516.

Figure 30:
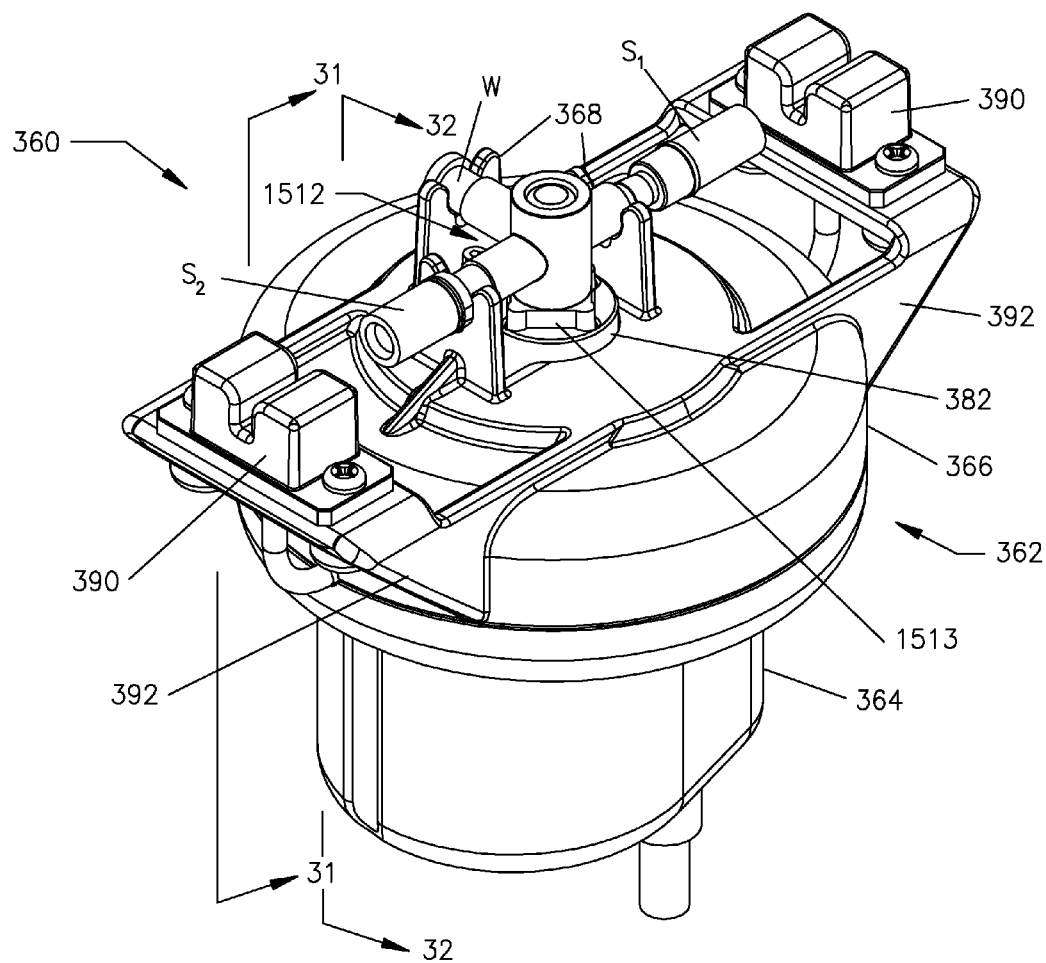
FIG. 30 is a perspective view of a secondary air detector module adapted for use with the various embodiments of the fluid injector system.
Figure 31:
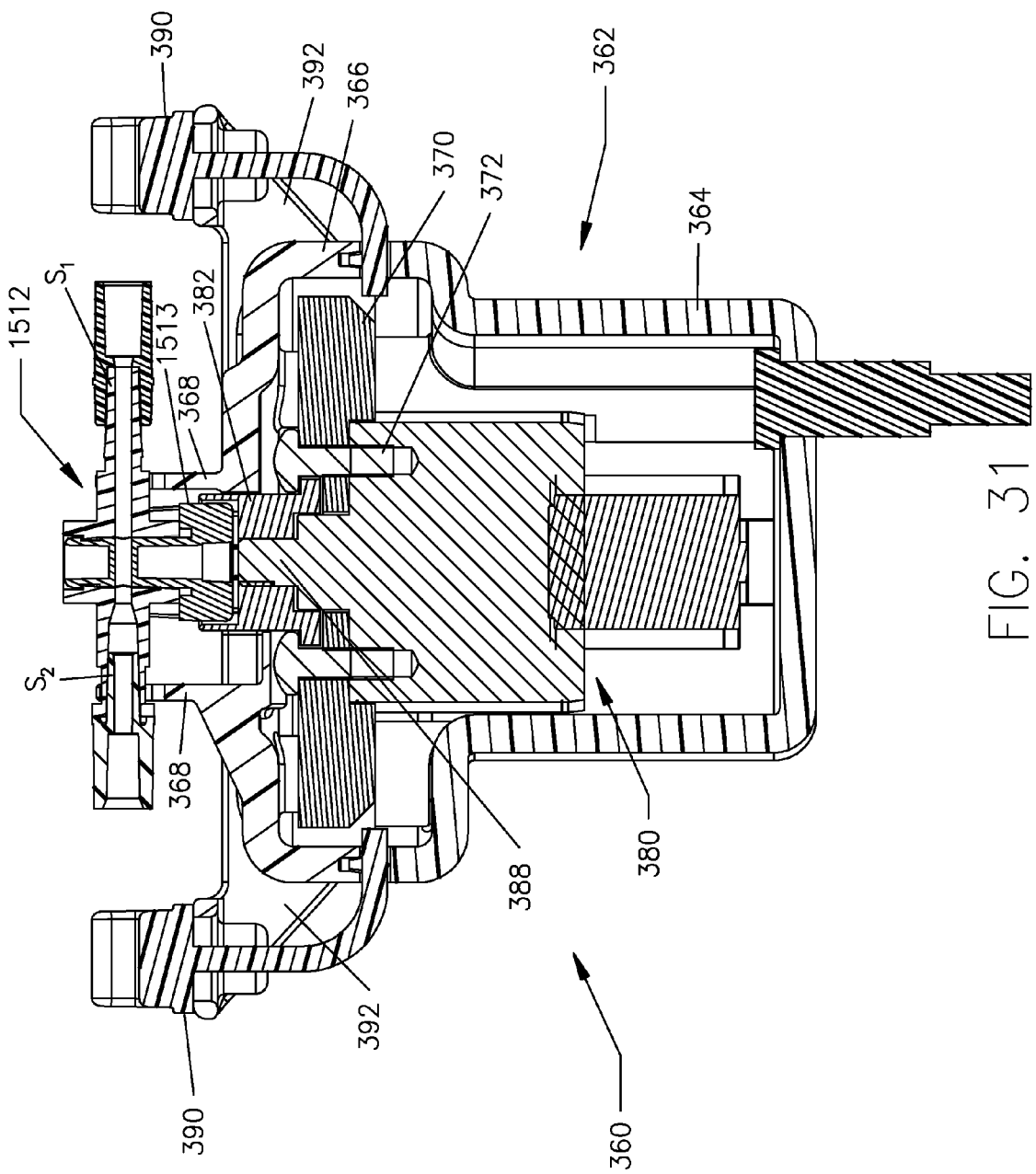
FIG. 31 is a cross-sectional view taken along Line 31-31 in FIG. 30.
Figure 32:
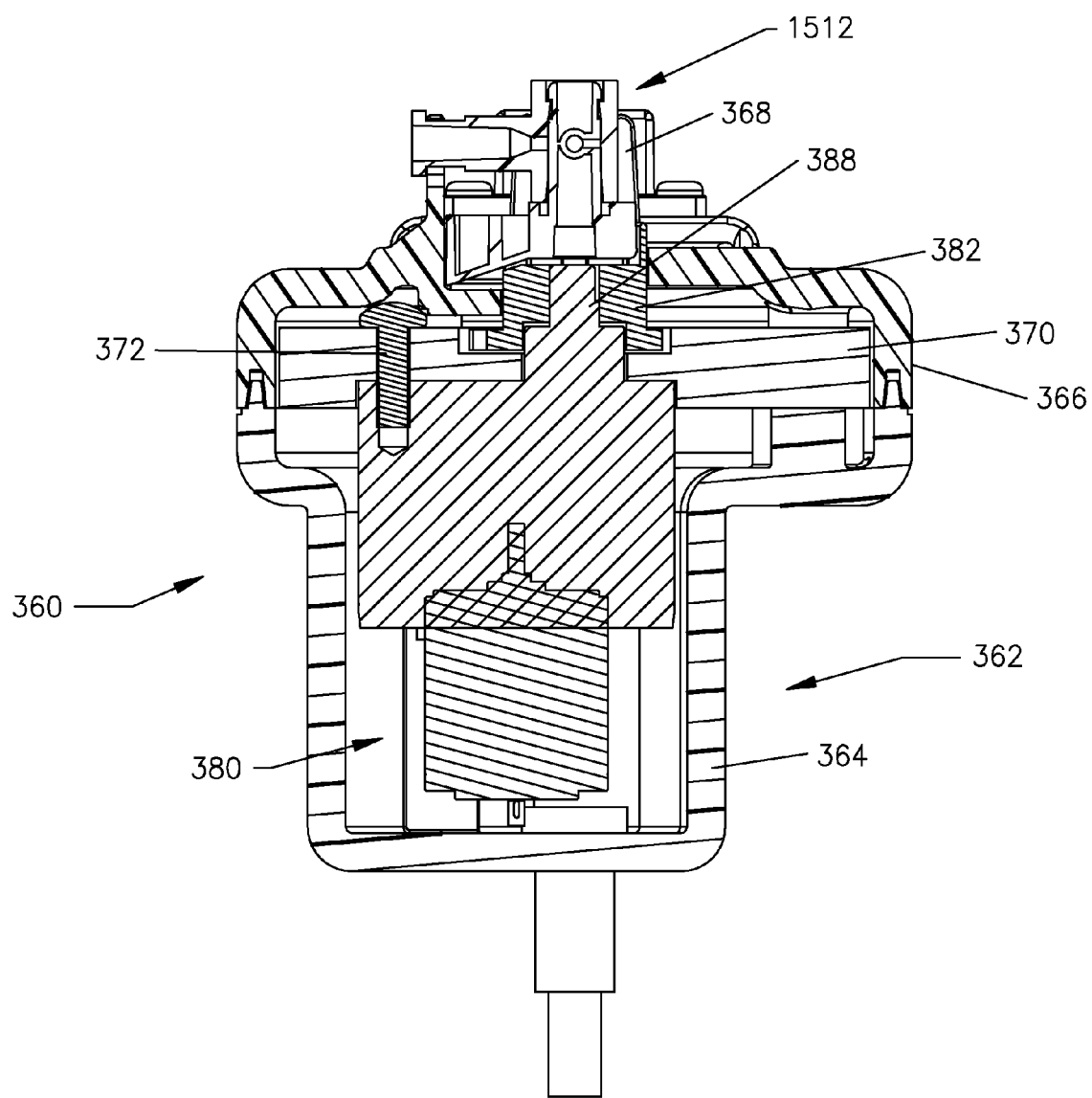
FIG. 32 is a cross-sectional view taken along Line 32-32 in FIG. 30.

Referring further to FIGS. 30-32, it may be desirable to provide additional or enhanced air injection protection in accordance with this disclosure by utilizing a downstream or secondary air detector module 360 which is dedicated to the single-use set 1500. Secondary air detector module 360 desirably includes a shut-off feature whereby, should air be detected in the tubing leading to the downstream shut-off or isolation stopcock 1512, this stopcock 1512 may be quickly and automatically turned to a closed position to isolate the catheter connector conduit 1514 and, thereby, shield a patient from a possible air injection situation. Accordingly, air detector module 360 may be considered to be an air detector and protection module 360, (hereinafter "secondary air detector module 360"). Secondary air detector module 360 comprises a module housing 362 comprising a depending actuator enclosure 364 wherein a valve actuator 380 is disposed for controlled operation of isolation stopcock 1512. A top cover or plate 366 encloses actuator enclosure 364 and comprises a series of attachment points or elements 368 for interfacing with the ports of the isolation stopcock 1512 to mechanically secure the isolation stopcock 1512 to the module housing 304. This mechanical arrangement is similar to the way stopcock valve 1160 interfaces with the cover plate 206 of fluid control module 200 described previously.

Cover plate 306 and actuator enclosure 364 are connected in a removable fashion and, further, together enclose a supporting mounting plate 370 to which valve actuator 380 is secured using conventional mechanical fasteners 372. Valve actuator 380 is mechanically interfaced with a socket actuator element 382 via an output shaft 388 extending from the valve actuator 380 to impart rotational motion to the socket actuator element 382. Socket actuator element 382 is configured to engage the actuation handle 1513 used to control operation of stopcock 1512 in a similar manner to the way socket actuator element 222 associated with the respective control valve actuators 220 interfaces with the actuation handle 1170 of the stopcock valve 1160 described previously. Mounting plate 370 defines an aperture to allow passage of output shaft 388 for engaging socket actuator element 382 to operationally control the position of the stopcock actuating handle 1513 and, thereby, the operational position of isolation stopcock 1512. Generally, valve actuator 380 is adapted to selectively position the stopcock actuating handle 1513 in at least one of three positions, namely: (1) open position, wherein fluid flow is permitted to catheter connector conduit 1514 from port $S_1$ of isolation stopcock 1512 to port $S_2$ of isolation stopcock 1512; (2) a closed or isolation position, wherein the catheter connector conduit 1514 is isolated from upstream components (e.g., port $S_2$ is blocked); and (3) a waste position, wherein a waste port W of isolation stopcock 1512 is open to allow draining of fluid from single-use set 1500, if desired. In an exemplary embodiment, valve actuator 380 may be a DC brush motor or a stepper motor or like device to provide the motive forces for rotational movement of socket actuating element 382 and, thereby, cause operational movement of the stopcock actuation handle 1513.

Additionally, the secondary air detector module 360 comprises a pair of air detectors 390 mounted to flanges 392 connected to the cover plate 306. Air detectors 390 are similar to air detectors 320, 340 described previously and are adapted to sense the presence of air in the tubing connected to port $S_1$ of isolation stopcock 1512 and in the tubing of catheter connector conduit 1514. Such an air detector arrangement on both sides of isolation stopcock 1512 provides dual redundancy to the air protection function. Further, air detectors 390 are linked to the electronic control device(s) associated with the injector 20 to provide inputs to the electronic control device(s) regarding the presence or air in proximity to isolation stopcock 1512 Likewise, valve actuator 380 is electronically coupled to the electronic control device(s) so that, should the electronic control device(s) receive input(s) that air is present in proximity to the isolation stopcock 1512, the valve actuator 380 may be controlled to place the isolation stopcock 1512 in the closed or isolation position discussed previously.

As described previously, loading of the respective multi-use sets 1100 used with the injector 20 comprises inserting the respective syringes 1120 into the corresponding pressure jackets 136 according to the loading steps described previously. The loading steps result in the discharge outlet 1130 extending distally from the syringe body 1122 of each syringe 1120 being seated into the corresponding offset slot 122 defined in the front plate 112 of the pressure jacket support 100. Likewise, the stopcock valve 1160 for each multi-use set 1100 is associated with the fluid control module 200 in the manner described previously, wherein the actuation handle 1170 of the respective stopcock valves 1160 is mechanically interfaced with the socket actuator element 222 of the corresponding or actuating control valve actuator 220 and so that the respective ports 1162, 1164, and 1166 on the stopcock valves 1160 are in engagement with the securing attachment elements 208 provided on the cover plate 206 of the fluid control module housing 202. Each of the two multi-use sets 1100 used with the powered injector 20 are loaded in a similar manner as described previously in this disclosure, which results in the syringes 1120 being loaded into the corresponding pressure jackets 136 and the stopcock valves 1160 being interfaced and secured in an operable state with the fluid control module 200.

Referring further to FIGS. 33-39, a generally horizontal orientation of injector 20, as shown in FIGS. 35A-35B, is believed to be the most convenient orientation to load the multi-use sets 1100 as described in the foregoing. A generally horizontal orientation is a desirable position for ergonomic reasons. A proximity sensor, such as a contact sensor or an optical sensor and the like, is used to determine whether the syringe plunger 1300 in the syringe body 1122 of each syringe 1120 is in the correct position for engagement by the piston elements 60, desirably, in the storage/expansion section 1138 at the proximal end 1126 of the syringe body 1122. If the syringe plungers 1300 are not so located in the storage/expansion section 1138, this could indicate that the syringes 1120 are not new syringes 1120 but may have been used previously, or that one or both of the syringes 1120 have been removed and brought back later for use as described pursuant to a possible "reuse-case" as set forth later in this disclosure. As a result, a visual or audible prompt may be provided by the electronic control device(s) in injector 20 to the attendant operator via the display windows 32 on the injector housing 22, and/or on a remote display window, indicating that the syringes 1120 may have been used previously and are possibly unsterile. Such electronic control device(s) may disable operation of the injector 20 until an override prompt or button is actuated by the attendant operator authorizing further use of the syringes 1120. The electronic control device(s) may then cause the piston elements 60 to extend forward or distally to fully capture the syringe plungers 1300 in the syringe body 1122 of the respective syringes 1120 loaded into the receiving pressure jackets 136. Additionally, the detector sensors 232 described previously also identify to the electronic control device(s) associated with injector 20 that two multi-use sets 1100 are correctly interfaced with the fluid control module 200 and pressure jackets 136. Further, the connecting tubing 1174 connected with the second port 1164 of each stopcock valve 1160 is placed in operative association with the front-mounted air detectors 320 of the air detector module 300. If desired, other fluid delivery set 1000 installation steps may occur while the injector 20 remains in a generally horizontal configuration such as interfacing the single-use set 1500 to the multi-use sets 1100, but this interfacing step may more desirably be carried out during a later step as described herein. The horizontal orientation of injector 20 is also believed to be the best orientation to unload the multi-use sets 1100 when their useful life is exhausted.

Figure 2:
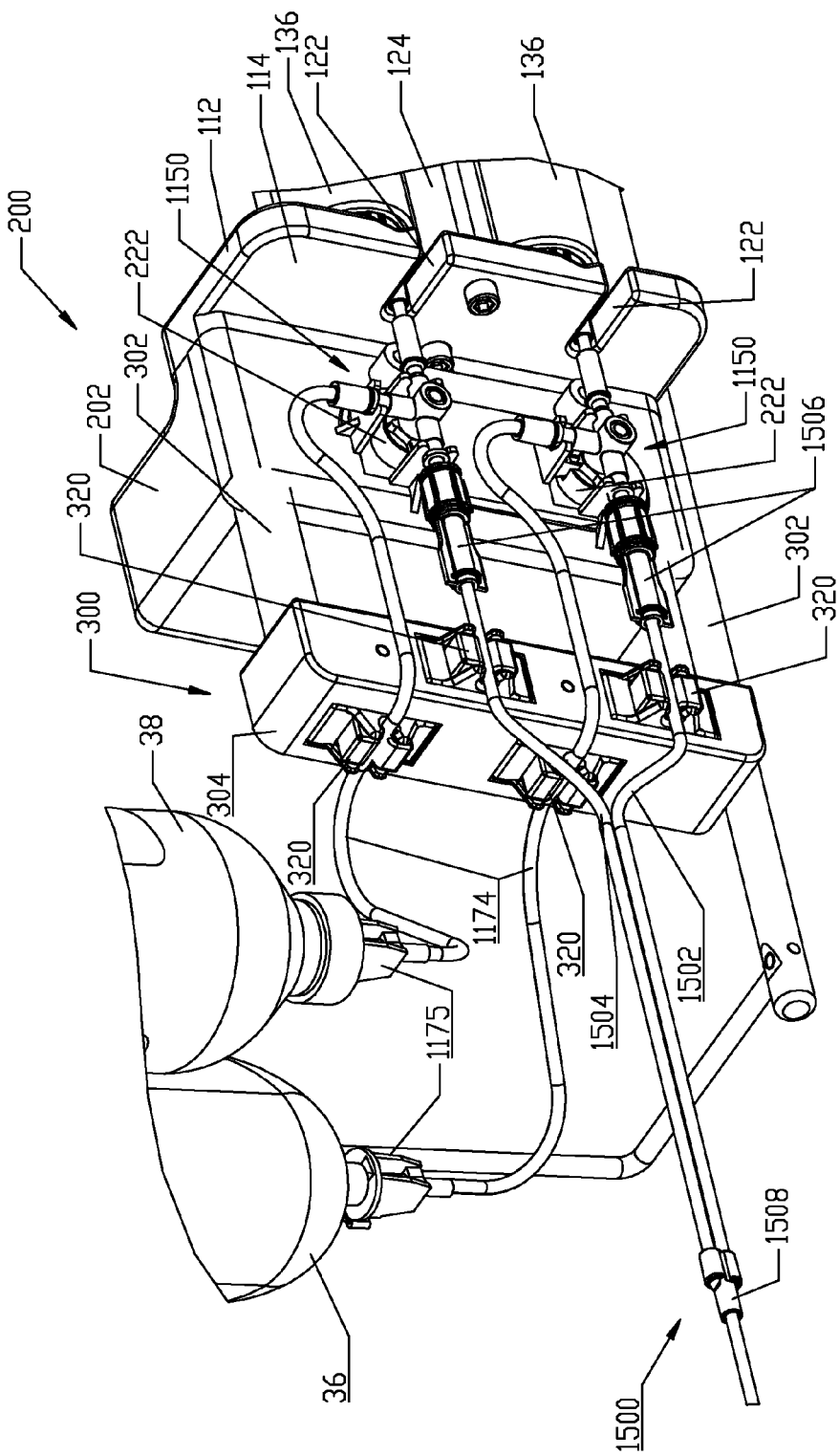
FIG. 2 is a front perspective view of a forward portion of the fluid injector system of FIG. 1.
Figure 3:
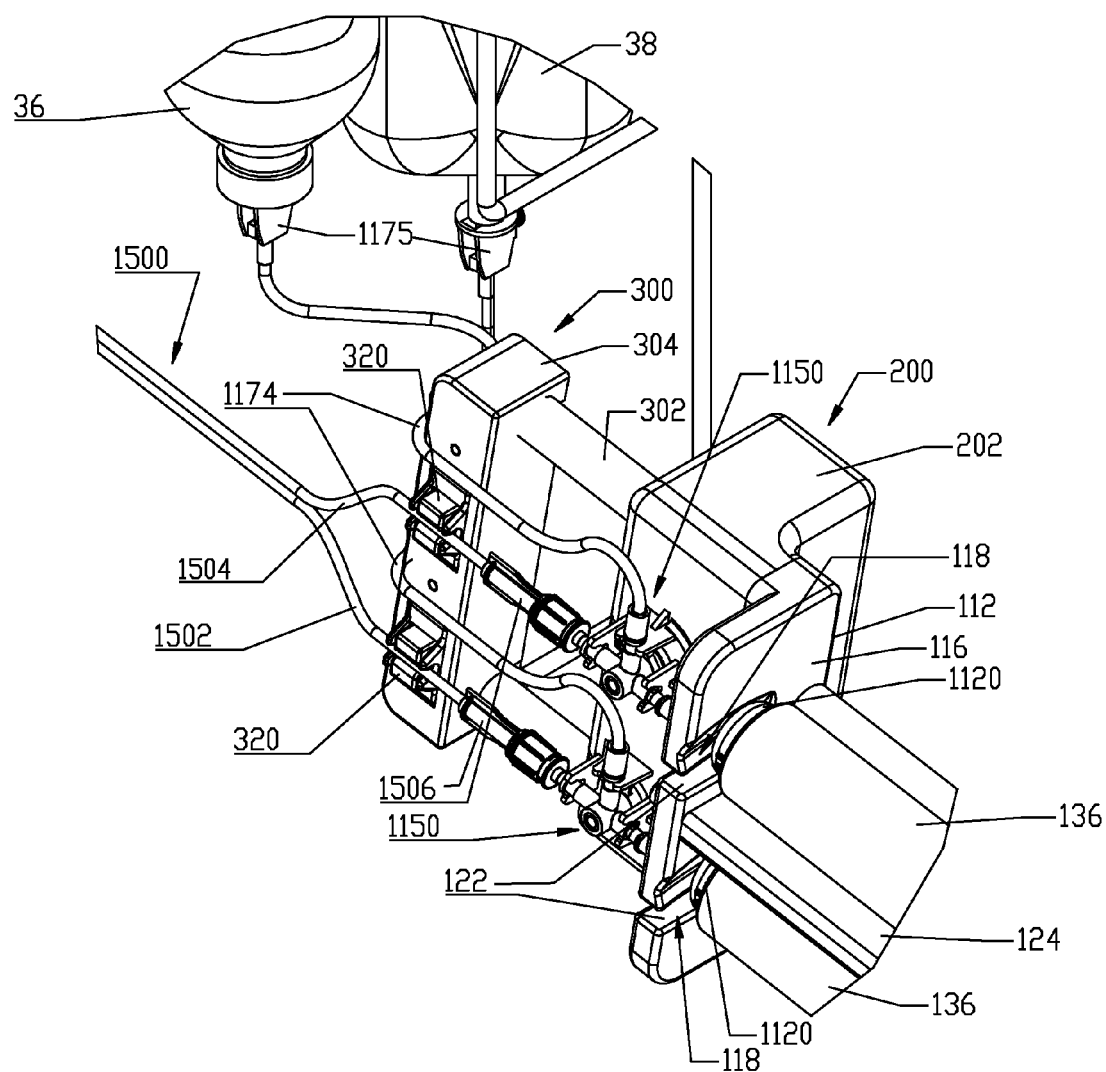
FIG. 3 is a top perspective view of the forward portion of the fluid injector system of FIG. 1.
Figure 4:
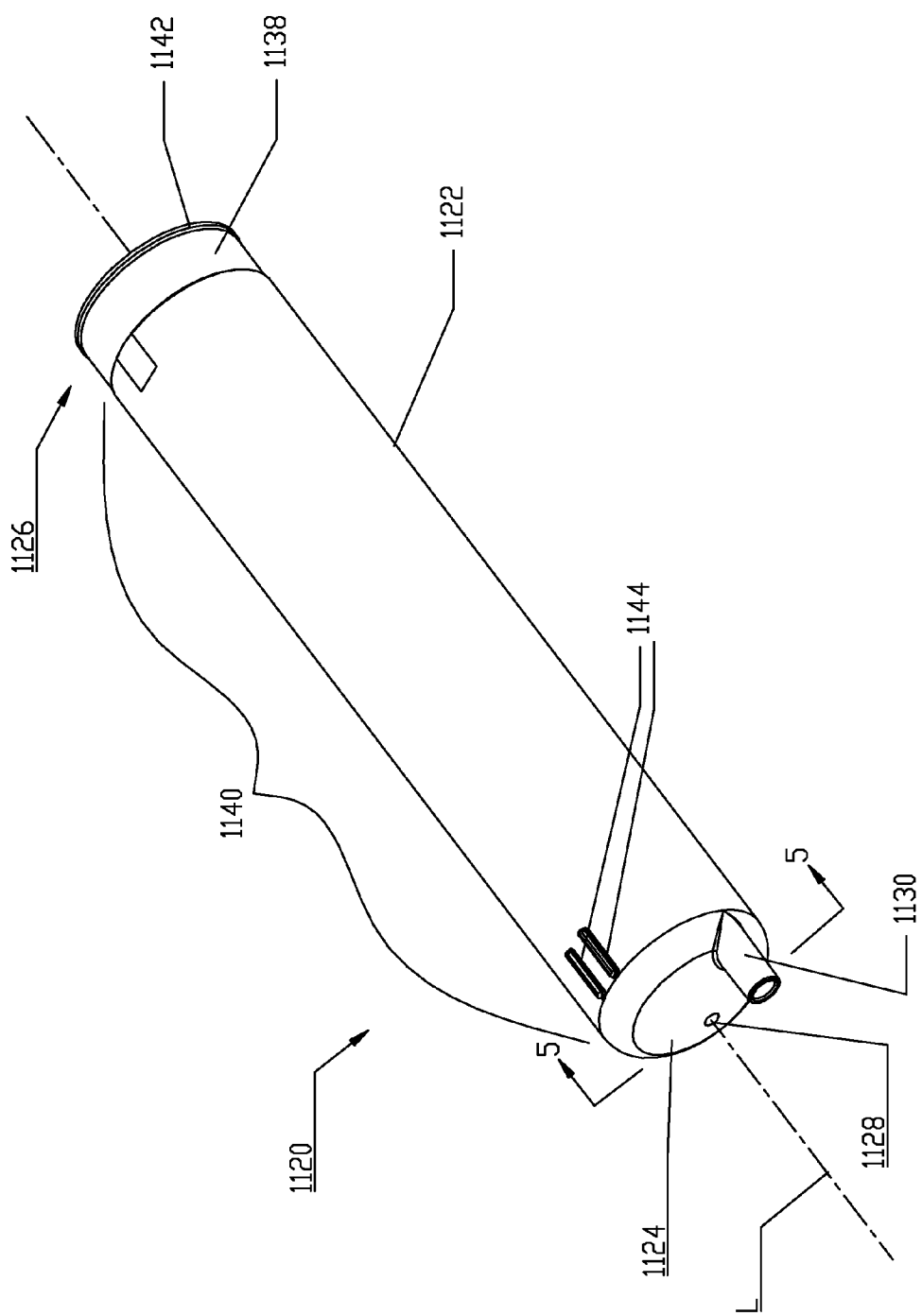
FIG. 4 is a perspective view of a syringe adapted for use in the fluid injector system of FIG. 1.
Figure 7:
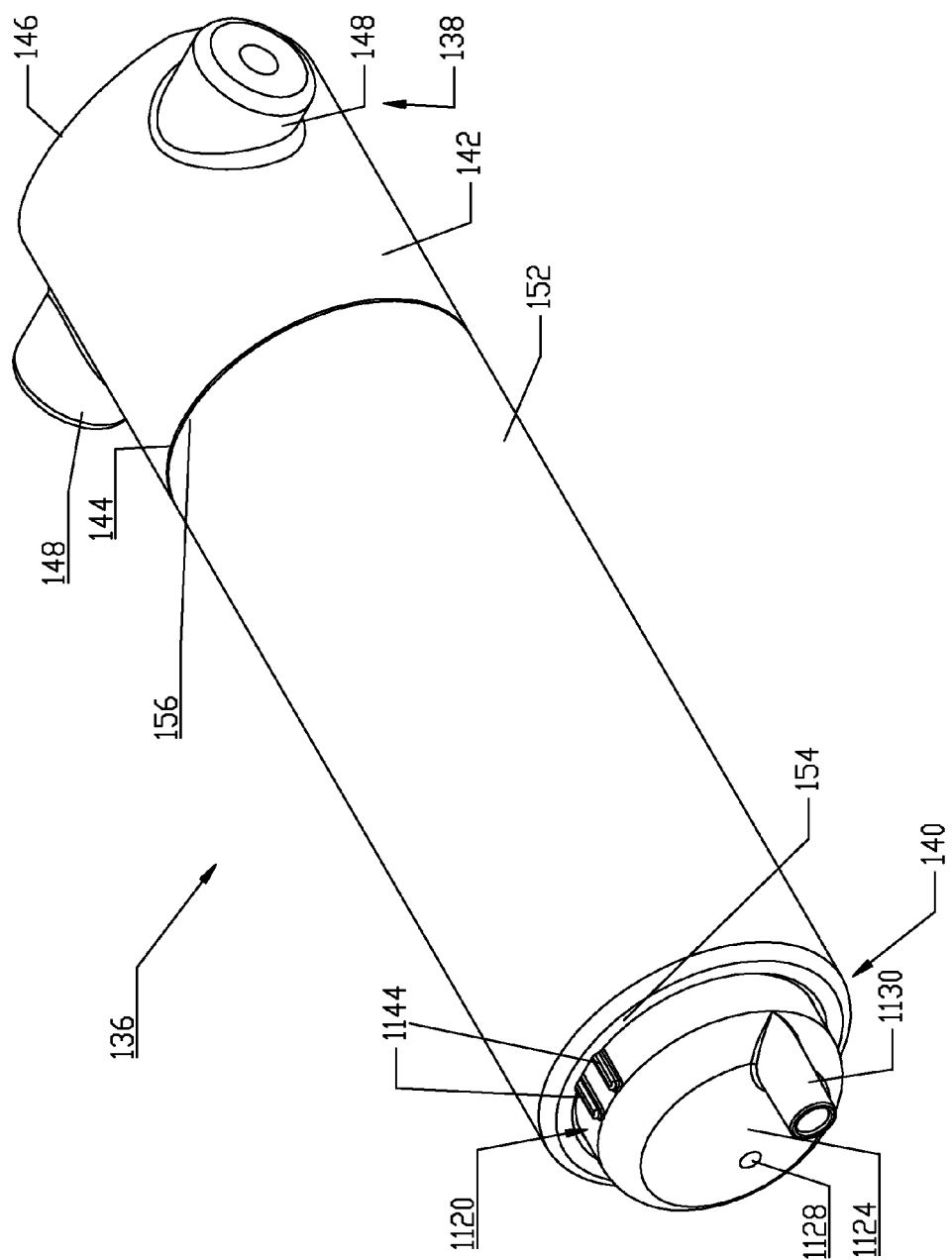
FIG. 7 is a perspective view showing the syringe of FIG. 4 loaded into a pressure jacket of the fluid injector system of FIG. 1.

Once the multi-use sets 1100 have been installed, the electronic control device(s) associated with the injector 20 cause the piston elements 60 to drive the captured syringe plungers 1300 distally forward to contact and seat against the conical distal end 1124 of the syringe body 1122. The connector spikes 1175 provided at the distal end of the connecting tubing 1174 and connected with the second port 1164 on each stopcock valve 1160 of the two respective multi-use sets 1100 may then be placed in fluid connection with two fluid supply containers 36, 38, as shown in FIGS. 2-3, which may be like fluids or different fluids and, typically, comprise saline and radiographic contrast media. Once the foregoing initial set-up sequence is completed, the injector 20 may be rotated to a fluid priming and air purge position to conduct a fluid priming and air purge procedure as discussed next in this disclosure.

Figure 38:
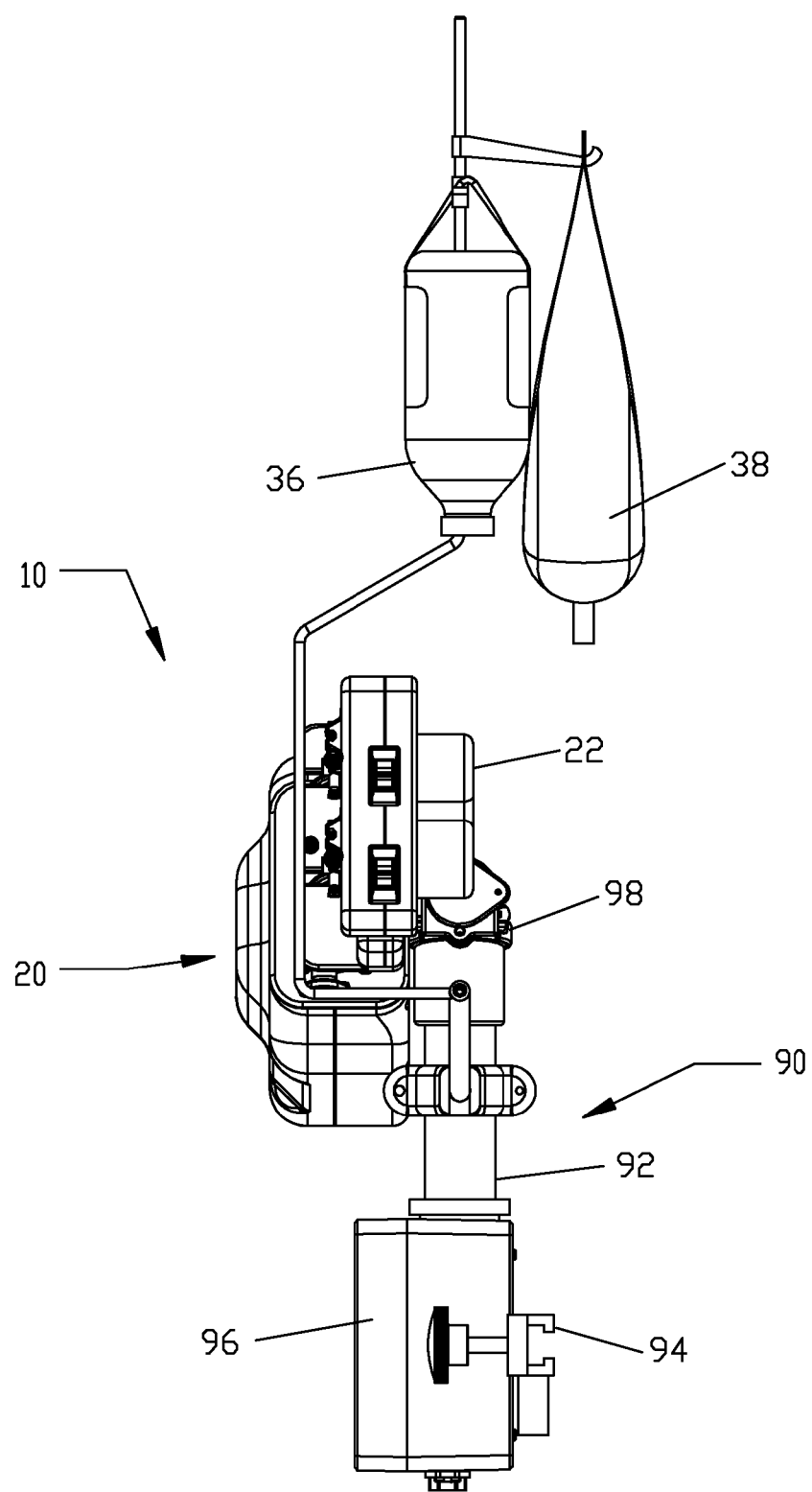
FIG. 38 is a front view of the fluid injector system of FIG. 1 showing a pedestal support for supporting the fluid injector system.
Figure 39:
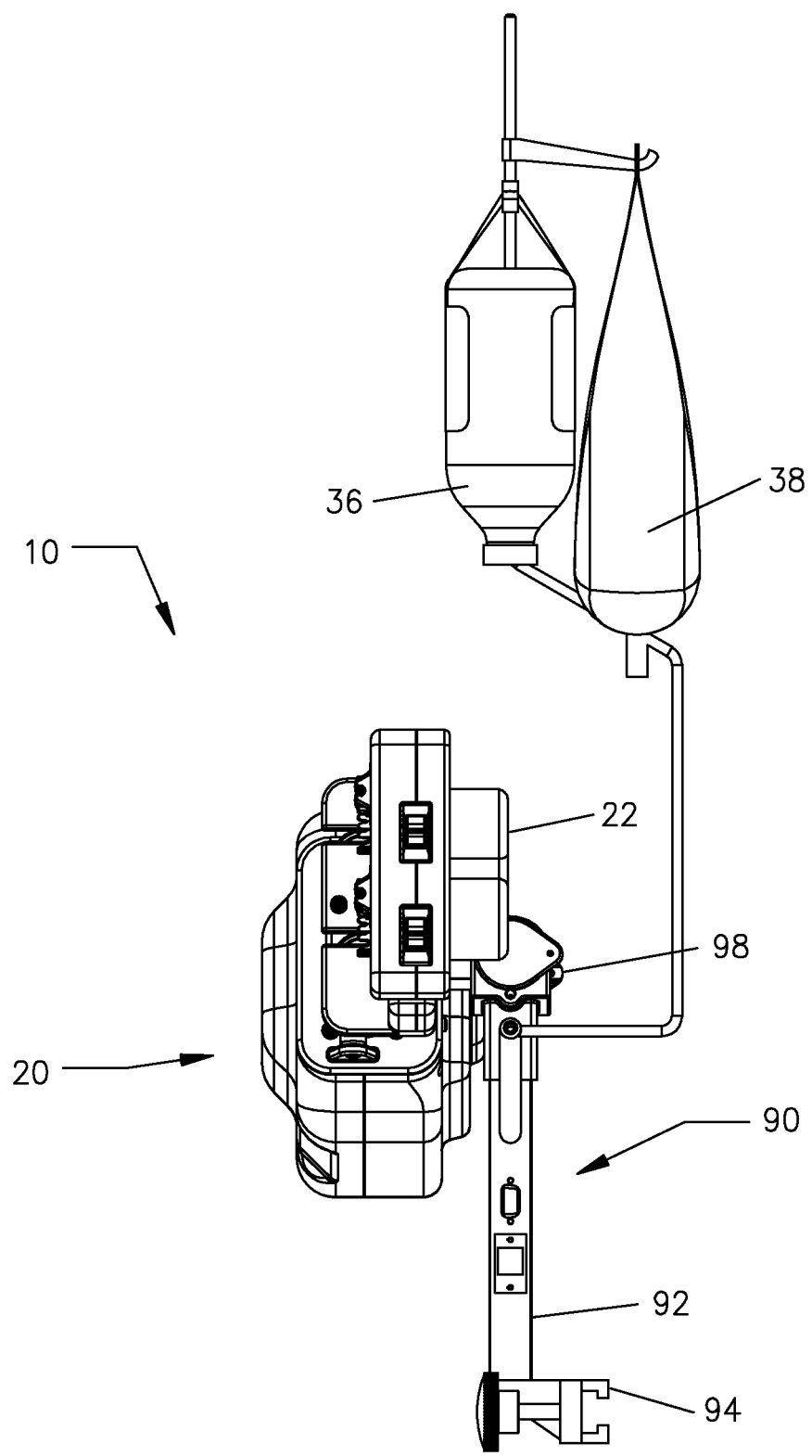
FIG. 39 is a front view of the fluid injector system of FIG. 1 showing a variation of the pedestal support shown in FIG. 38.
Figure 40:
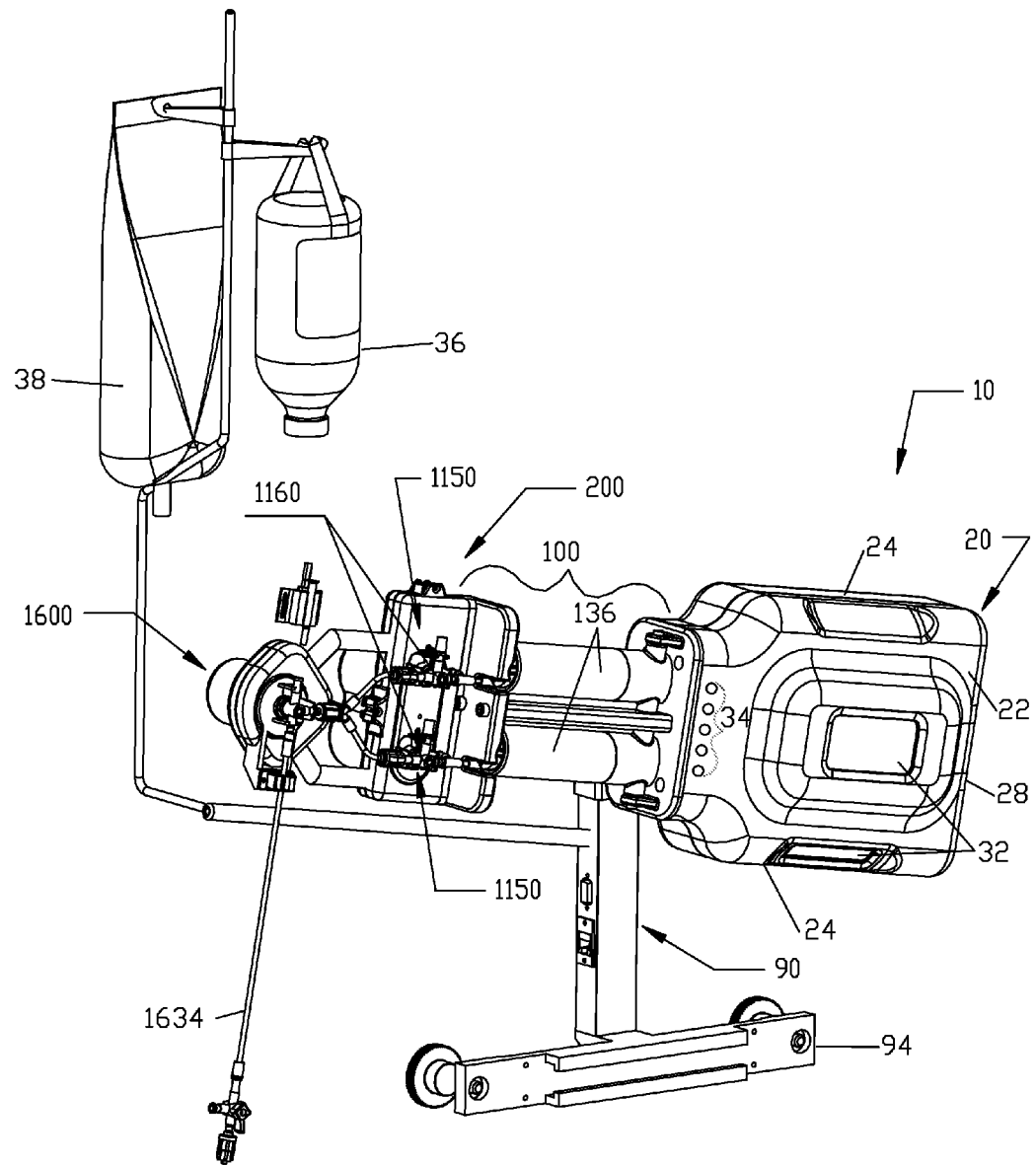
FIG. 40 is a perspective view of another embodiment of the fluid injector system of FIG. 1.
Figure 41:
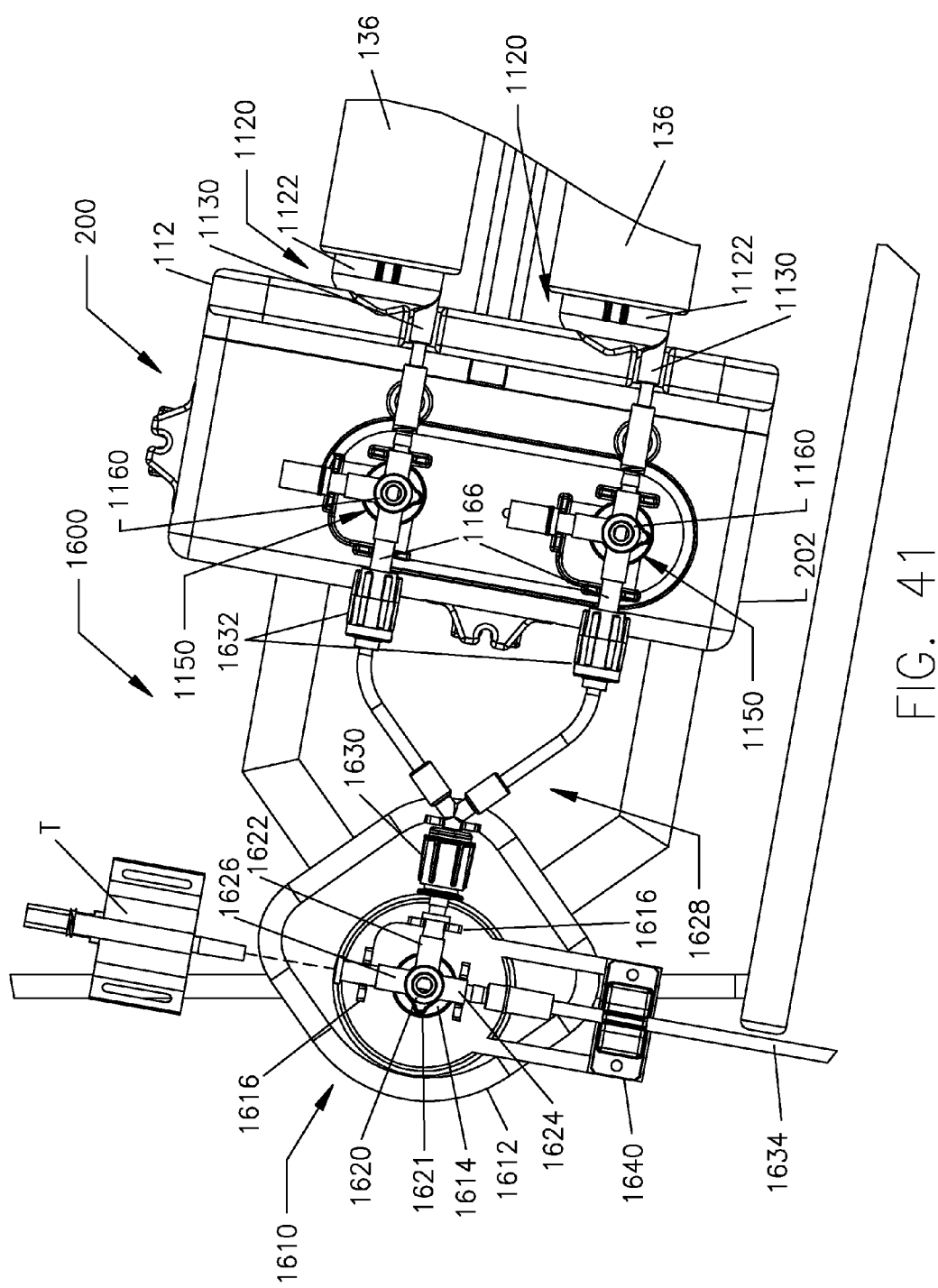
FIG. 41 is a top view of a forward portion of the fluid injector system shown in FIG. 40 and illustrating a fluid delivery set used in the system.
Figure 42:
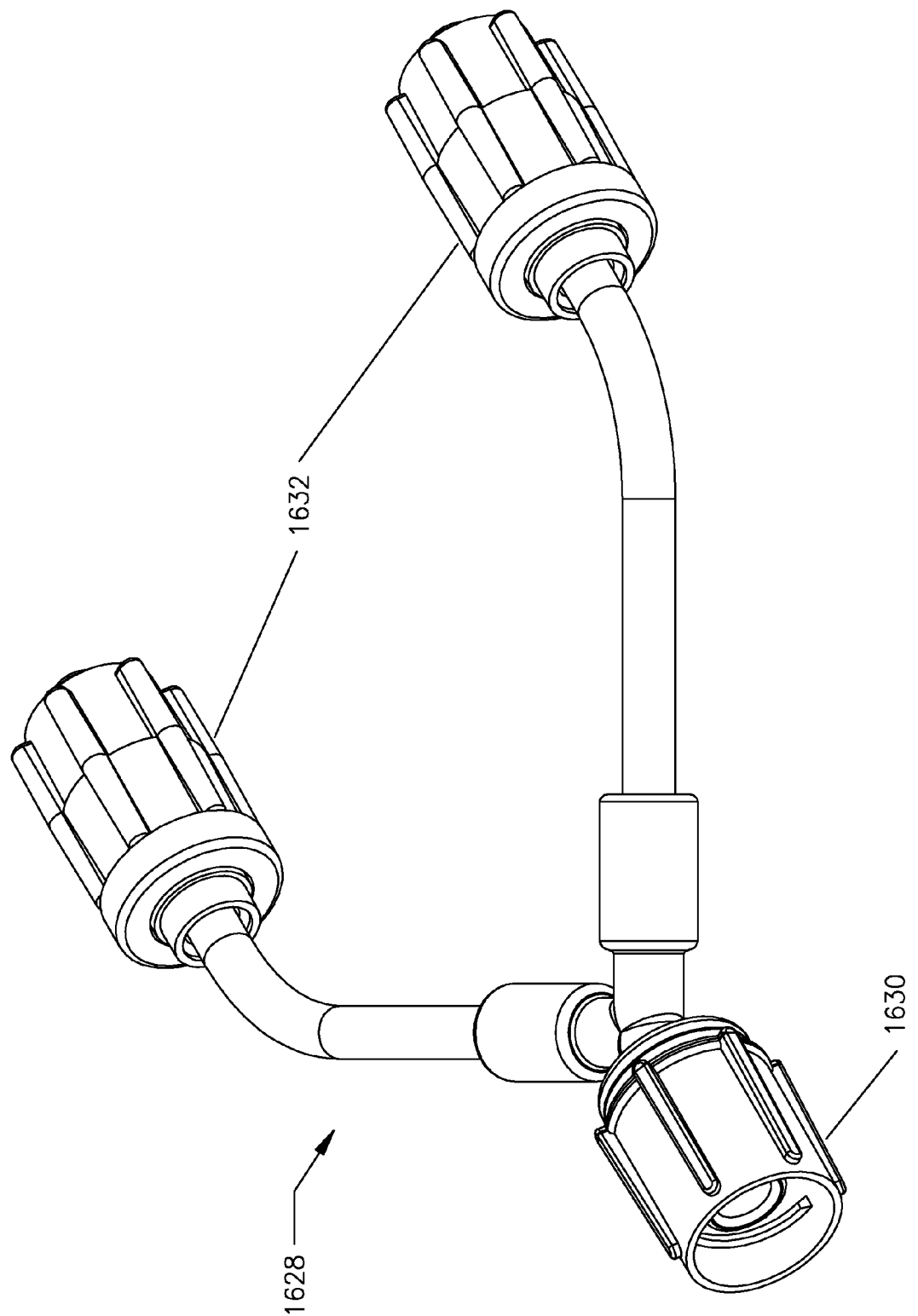
FIG. 42 is a perspective view of a Y-connector conduit used in the fluid delivery set shown in FIG. 40.
Figure 43:
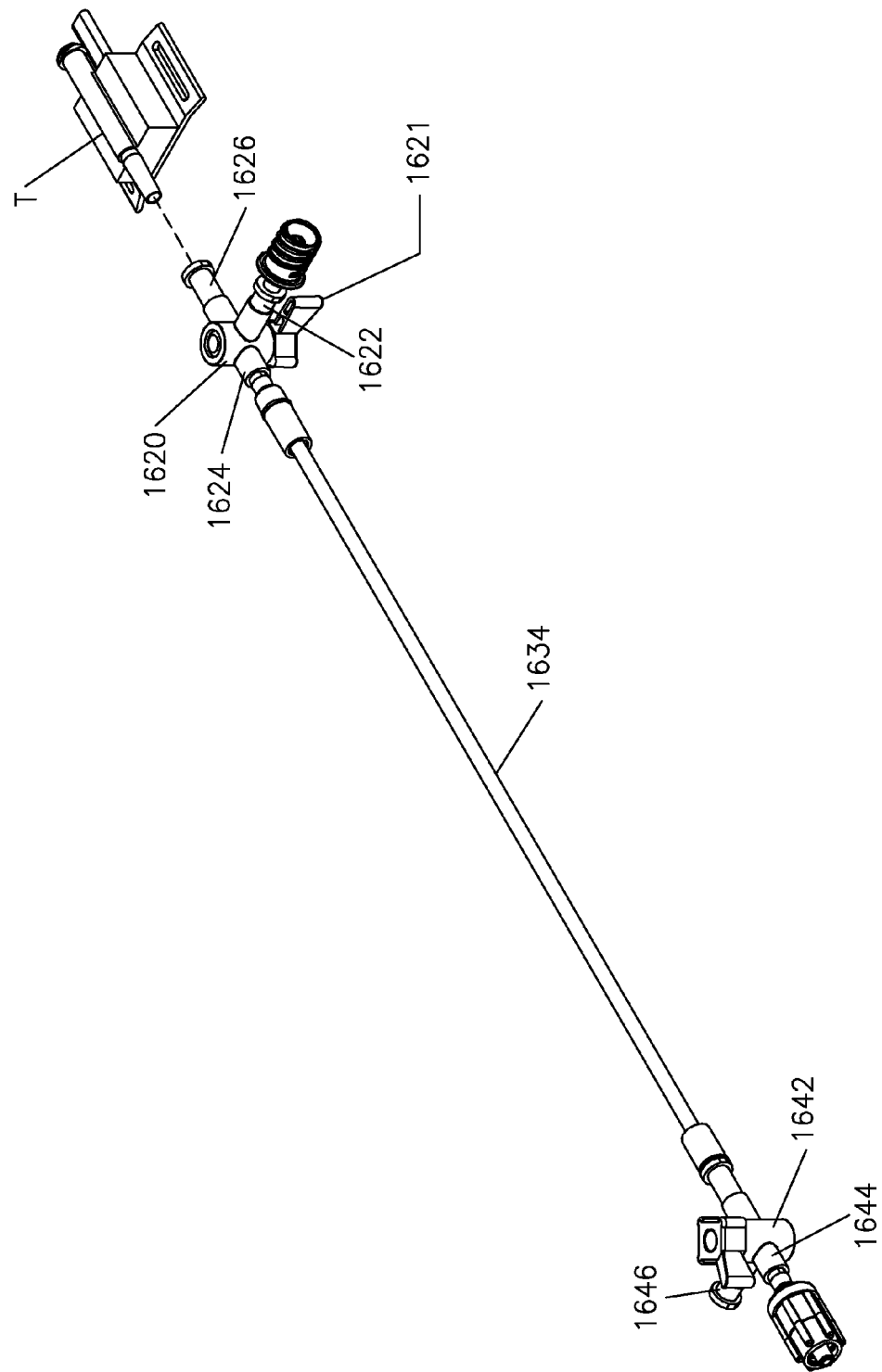
FIG. 43 is a perspective view of additional components of the fluid delivery set of FIG. 40.

In the fluid priming and air purge sequence, the injector 20 is pivoted about pedestal support 90 to a purge position or orientation. As discussed previously, pedestal support 90 comprises a support column 92 for supporting the injector 20 adjacent a patient supporting surface such as an examination table. As shown in FIGS. 38-39, the support column 92 may comprise a clamp 94 for attaching the support column 92 to a patient examination table or like surface having a rail for attaching equipment to the examination table. FIG. 38 shows that a storage compartment 96 may be integrated with the support column 92 for storing ancillary equipment associated with fluid injector system 10. A pivot joint 98 is secured to the underside of the injector housing 22 and connects the injector 20 to the support column 92. Electro-mechanical components reside in the injector housing 22 to effect operation of the pivot joint 98 to allow the injector 20 to exhibit pivoting movement on the pedestal support 90. Alternatively, the injector 20 may be pivoted manually if desired.

To reach the fill and purge position, the injector 20 pivots about pedestal support 90, typically in a direction away from the patient support surface (not shown), so that the discharge conduit 1130 extending from the syringe body 1122 of each syringe 1120 loaded into the respective pressure jackets 136 is positioned at the top of the syringe body 1122 or at a high point for each loaded syringe 1120. The pivoting movement of the injector 20 results in the injector 20 "rolling" away from the patient support surface in the present scenario. With the syringes 1120 positioned with the discharge conduit 1130 on each syringe body 1122 in a top position, any air bubbles remaining from the priming of the respective syringes 1120, as described herein, will be present at the top of the syringe body 1122 of each syringe 1120 and in a position for easy viewing and purging from the syringe body 1122. Once the injector 20 is placed in the fluid priming and air purge position or orientation, the attendant operator may press the "Fill/Purge" hard-wired control button 34 on the injector 20 to automatically fill the respective syringes 1120 with fluid and purge out air remaining in the syringe body 1122 of each syringe 1120. In an exemplary automated sequence for this cycle, once the attendant operator depresses the "Fill/Purge" control button 34, the respective stopcock valves 1160 in the multi-use sets 1100 open to a fill position wherein the second port 1164 is in fluid connection with first port 1162 to allow filling of syringe 1120 via connector spike 1175 and connecting tubing 1174 associated with a fluid container, typically fluid supply containers 36, 38 as shown in FIGS. 2-3. In various embodiments shown in the accompanying figures, the respective fluid supply containers desirably contain contrast and saline so that different fluids are loaded into the respective syringes 1120. Such different fluids may be contrast and saline or, possibly, different concentrations of contrast, or possibly other types of fluid entirely, such as a radiopharmaceutical drug and saline.

Next, the electronic control device(s) associated with the injector 20 actuates the piston elements 60 to retract the syringe plungers 1300 seated within the syringe body 1122 of each syringe 1120 so that the syringe plungers 1300 move proximally or rearward in the syringe body 1122 of each syringe 1120. This proximal movement may continue until a desired amount of filling fluid is drawn into the syringe body 1122 of each syringe 1120 from the external fluid sources. In one non-limiting example, the respective piston elements 60 move at 1 ml/s to introduce approximately 15 ml of fluid and accompanying air into the respective syringes 1120. The piston elements 60 are then actuated by the electronic control device(s) associated with injector 20 to move distally or forward so that the syringe plunger 1300 in each syringe body 1122 moves distally or forward in the syringe body 1122 thereby purging air present in the syringe body 1122 back into the respective fluid supply containers via the fluid path defined by stopcock valve 1160, connecting tubing 1174, and connector spike 1175. Such air-purging or forward movement may occur by the respective piston elements 60 moving distally or forward at 5 ml/s until fluid is detected with air sensor 320, and then piston element 60 moves further forward the volume of the disposable elements from the air sensor 320 to the tip of the spike 1175. The piston elements 60 are then actuated to reverse direction and move proximally or rearward, which causes the captured syringe plunger 1300 associated with each piston element 60 to move proximally or rearward in the syringe body 1122 of each syringe 1120 to begin filling the syringe body 1122 with fluid from the connected fluid supply container 36, 38. This movement desirably continues until the syringe body 1122 of each syringe 1120 is substantially filled with fluid to a desired level. Thereafter, the piston elements 60 are actuated to move forward a small amount, for example, to eject approximately 1.5 ml of fluid from the syringe body 1122 of each syringe 1120 for slack correction purposes. The respective stopcock valves 1160 in the multi-use sets 1100 are then operated by the electronic control device(s) associated with the injector 20 to the closed or isolation position, wherein both the first and second ports 1162 and 1164 are isolated from the third or outlet port 1166.

To reach an injection position or orientation, the injector 20 is pivoted about pedestal support 90, but now in a direction toward the patient support surface in the present scenario, so that the discharge conduit 1130 extending from the syringe body 1122 of each syringe 1120 loaded into the respective pressure jackets 136 is positioned on the bottom of the asymmetrical syringe body 1122. FIGS. 33-37 show the sequential movement of the injector 20 as it pivots from the fluid priming and air purge orientation shown in FIG. 33 to the inject orientation shown in FIG. 37. To reach the injection position, the pivoting movement of injector 20 results in the injector 20 "rolling" toward the patient support surface in the present scenario and traverses approximately 180.degree. of rotation. In the inject position, the discharge conduit 1130 extending from the syringe body 1122 of each syringe 1120 is at the lowest point, making injection of air difficult. It is when the injector 20 is rotated to the inject position that it is desirable to connect the single-use set 1500 to the respective multi-use sets 1100, which are operatively associated with the injector 20, fluid control module 200, and air detector module 300. This connection step generally includes connecting the respective input lines 1502, 1504 of the single-use set 1500 to the third or outlet ports 1166 of the respective stopcock valves 1160 in the multi-use sets 1100. In particular, the fluid connectors 1506 provided at the proximal end of each input line 1502, 1504 are joined to the mating fluid connector 1176 on the outlet port 1166 of each stopcock valve 1160 in the respective multi-use sets 1100. Additionally, the input lines 1502, 1504 are placed in operative association with the top-located air detectors 320 on the air detector module 300 in the manner described previously. While the single-use set 1500 could potentially be connected to the multi-use sets 1100 in the fluid priming and air purge position of the injector 20 described previously, there is a possibility that the single-use set 1500 may fall outside the sterile area surrounding the fluid injector system 10 during the pivoting movement of the injector 20. It is noted that the foregoing rolling motion of the injector 20 has distinct advantages in that the fluid supply containers 36, 38 may be kept close to the syringes 1120 thereby decreasing the tubing lengths between the fluid supply container 36, 38 and syringes 1120 and, as a result, decreasing the fill or refill time for the syringes 1120.

Once the single-use set 1500 is joined to the respective multi-use sets 1100 and, further, associated with the appropriate air detectors 320 in the air detector module 300, the single-use set 1500 is ready to be primed with fluid and purged of air. The fluid priming and air purging of the single-use set 1500 may include certain preliminary steps such as connecting a pressure transducer (not shown) to the pressure isolation valve 1510 and removing air from the pressure transducer and the pressure isolation valve 1510 via manual flush. To commence the fluid priming and air purging of the single-use set 1500, the attendant operator again presses the "Fill/Purge" control button 34. In an exemplary automated sequence for the fluid priming and air purging of the single-use set 1500, once the attendant operator depresses the "Fill/Purge" control button 34, the respective stopcock valves 1160 in the multi-use sets 1100 move to an inject position, wherein the first port 1162 of each stopcock valve 1160 is placed in fluid connection with the third or outlet port 1166. The respective stopcock valves 1160 are each placed in the foregoing inject position by the respective control valve actuators 220 which rotate the actuation handle 1170 of each stopcock valve 1160 via the socket actuator element 222 so that the T-shaped passageway in the stopcock valves 1160 is in an orientation where the first and third ports 1162, 1166 are in fluid communication. The control valve actuators 220 are controlled by the electronic control device(s) associated with the injector 20 as described previously. The electronic control device(s) associated with the injector 20 further causes the piston elements 60 to move distally or forward whereby fluid from the respective syringes 1120 enters the single-use set 1500 and, in particular, the respective input lines 1502, 1504. Movement of fluid in the input lines 1502, 1504 continues until fluid in each line reaches a point just distal or forward of Y-connector 1508. Typically, contrast and saline are respectively present in input lines 1502, 1504 (e.g., each input line 1502, 1504 carries a different fluid therein). Once the respective fluids reach the point just distal or forward of the Y-connector 1508, the stopcock valve 1160 fluidly coupled to the fluid supply container 36, 38 containing contrast is operated to the closed or isolation position, wherein the first port 1162 is isolated from the third or outlet port 1166. The stopcock valve 1160 that is fluidly coupled to the saline fluid supply container 36, 38 desirably remains in an open or inject position and the associated syringe 1120 continues to supply saline to the single-use set 1500 thereby priming the remainder of the downstream components of the single-use set 1500, namely, the pressure isolation valve 1510, isolation stopcock 1512, and catheter connector conduit 1514 where the patient catheter is to be connected. Thereafter, the second "saline" stopcock valve 1160 is operated to a closed position.

While the foregoing discussion identifies the steps used to initially prime the respective multi-use sets 1100 and single-use set 1500 with fluid and, further, purge air from the multi-use sets 1100, including syringes 1120, and from the single-use set 1500, it is desirable to permit refilling of the syringes 1120 during operation of fluid injector system 10 so that the respective multi-use sets 1100 may be reused typically for a set number of uses and/or a set number of patients. Refilling of the syringes 1120 is often needed in practice because some interventional procedures involving fluid injector system 10 can use more contrast than is present in a single "charge" of contrast in one filled syringe 1120 according to the foregoing discussion. In a refill situation, it is desirable that refilling of one or both syringes 1120 be done during a time that is convenient for the attendant operator of the fluid injector system 10. With the arrangement of the twin multi-use sets 1100 and single-use set 1500 and pivoting motion of the injector 20 as described in the foregoing, the respective fluid supply containers 36, 38 are always in close proximity to the discharge conduit 1130 extending from the syringe body 1122 of each syringe 1120 and the lengths of medical tubing needed to conduct fluids to the syringes 1120 may be made shorter. Thus, refill rates are faster. In particular, it is known that for a given inner diameter (ID) tube, the shorter the length of tubing the faster the refill rate may be before vaporizing the fill liquid with a vacuum.

A standard refill method for syringes 1120 according to the present disclosure may include a hard-wired "Refill" control button 34 on the injector 20 which the attendant operator depresses to cause refilling of one or both of the syringes 1120. This functionality may also be incorporated into the graphical user interface (GUI) display windows 32 on the injector 20, for example, as a user option on the graphical user interface (GUI) display windows 32. Refill rate and volume to refill the syringes 1120 may be preprogrammed by the attendant operator of the fluid injector system 10 as part of an initial data entry set-up for the electronic control device(s) associated with injector 20, or be preprogrammed into the electronic control device(s). The manual refill procedure may be stopped either automatically by the electronic control device(s) according to a preprogrammed parameter or, alternatively, may be interrupted by pressing the "Stop" control button 34 on the injector 20 or by actuation of another device associated with the injector 20 such as a hand controller (not shown) operatively connected to the injector 20 and electronically coupled to the electronic control device(s).

The electronic control device(s) associated with injector 20 may also be preprogrammed so that automatic refill occurs based upon a preprogrammed trigger minimum volume in the respective syringes 1120. For example, when the volume of fluid remaining in (one or both of) the respective syringes 1120 is less than a programmed volume, a syringe refill procedure is automatically initiated by the electronic control device(s). The electronic control device(s) associated with injector 20 may determine that the preprogrammed trigger minimum volume has been reached by tracking the fluid volume dispensed from the respective syringes 1120 during operation of the fluid injector system 10. Alternatively, optical fluid level sensors may be incorporated into the pressure jackets 136 supporting the respective syringes 1120 and inputs from these fluid level sensors may be provided to the electronic control device(s) so that the electronic control device(s) may determine when the preprogrammed trigger minimum volume has been reached in one or both of the syringes 1120. The fill volume and rate of refill can be preprogrammed in the electronic control device(s). The automatic refill procedure can be stopped either automatically by the electronic control device(s) as described in the foregoing or may be manually interrupted by pressing the "Stop" control button 34 on the injector 20 or by actuation of another device associated with the injector 20 such as a hand controller (not shown) operatively connected to the injector 20. In addition, an automatic refill procedure may be initiated when, at the completion of a fluid injection procedure, there is not enough fluid in one or both syringes 1120 to perform the next programmed fluid injection procedure, for example, that the next preprogrammed injection volume exceeds the actual volume in the syringe(s) 1120.

In a variation of the foregoing automatic refill procedure, the electronic control device(s) associated with the injector 20 may include a timer and associated programming to initiate a refill procedure when the electronic control device(s) determines that a fluid injection procedure involving syringes 1120 is not likely to occur in the near future. In other words, the programming of the electronic control device(s) desirably anticipates that inactivity of certain components of the fluid injector system 10 or certain states or conditions of the fluid injector system 10 indicate that a fluid injection procedure is not likely to occur and automatic or "invisible" refilling of one or both of the syringes 1120 may commence without interfering with an impending fluid injection procedure. For example, one triggering event could be the inactivity of a hand controller for a certain period of time. Based on this inactivity, the electronic control device(s) may trigger the automatic or "invisible" refill. In another example, a position or orientation sensor, such as an accelerometer, in a hand controller could identify to the electronic control device(s) that the hand controller has been set down; other possible sensor embodiments include a capacitance touch sensor or thermal sensor. As with previous refill procedures, once the foregoing refill procedure is commenced, the fill volume and refill rate can be based on preprogrammed parameters and interruption of the refill procedure. The foregoing automatic or "invisible" refill procedure may also be interrupted by any of the interrupt events discussed previously in this disclosure. Moreover, control of the foregoing automatic or "invisible" refill procedure may be conducted by the electronic control device(s) associated with the injector 20 such that when a fluid injection procedure is requested, the injector 20 can transition so quickly from the refill procedure to the fluid injection procedure that the attendant operator would not perceive a time lag. This result may be accomplished by conducting the refill procedure very slowly so as not to have to dissipate a vacuum when transitioning to an inject state.

During a refill procedure, it is possible that one or both of the fluid supply containers 36, 38 associated with the respective syringes 1120 may become empty (e.g., initially lack sufficient fluid to complete a full refill of the syringes 1120). A replacement fluid supply container 36, 38 is, therefore, necessary and replacement of such a fluid supply container 36, 38 is desirably made quickly and without introducing air into any components of fluid delivery set 1000. An exemplary procedure for carrying out a fluid supply container change is as follows. Initially, a refill procedure has been triggered in some fashion, for example, a manual, an automatic, or an automatic-invisible refill procedure. Additionally, the stopcock valve 1160 associated with the syringe 1120 requiring refilling is actuated to the fill position wherein the second port 1164 is in fluid communication with the first port 1162 to allow filling of the syringe 1120 via the connector spike 1175 and connecting tubing 1174 associated with the present partially used fluid supply container 36, 38. The associated piston element 60 interfaced with the syringe plunger 1300 in the syringe body 1122 of the refilling syringe 1120 moves proximally or rearward to begin refilling the syringe 1120. As the fluid supply container 36, 38 empties of fluid, air is drawn into connecting tubing 1174 and, as this air column reaches the in-line air detector 320 on the air detector module 300, the air detector 320 alerts the electronic control device(s) associated with the injector 20 which stops and reverses movement of the associated piston element 60 to push fluid back through the connecting tubing 1174 to the connector spike 1175. The electronic control device(s) then actuates the stopcock valve 1160 to the closed or off position isolating the outlet port 1166 from the first and second ports 1162, 1164. A prompt is given to the attendant operator via the graphical user interface (GUI) display windows 32 on the injector 20 to remove the fluid supply container 36, 38 and spike a new fluid supply container 36, 38 with the connector spike 1175. The electronic control device(s) then actuates the stopcock valve 1160 to the fill position described previously and actuates the associated piston element 60 engaged with the syringe plunger 1300 in the syringe body 1122 of the refilling syringe 1120 to move forward a small amount to purge any air remaining in the connector spike 1175 or connecting tubing 1174. Refilling of the syringe 1120 then continues according to the methodology described hereinabove.

An advantage of the multi-use sets 1100 described in this disclosure is that each such set 1100 is easily removed from association with the injector 20, fluid control module 200, and air detector module 300 so that, for example, contrast media changes may be made for a single patient (intra-patient) or contrast media changes may easily be made between patients. Moreover, the multi-use sets 1100 described in this disclosure allow for removal of a used multi-use set 1100 and its temporary storage for re-use, typically the same day, without compromising sterility. In particular, a contrast-containing multi-use set 1100 and its associated fluid supply container 36, 38 containing contrast media form a closed system which may be removed for temporary storage with the only additional sterility protection required being a sterile cap or cover used to enclose the fluid connector 1176 on the third or outlet port 1166 of the stopcock valve 1160.

An exemplary procedure for removing, storing, and reusing a used multi-use set 1100 as described in the preceding paragraph will now be described. In the following discussion, it is assumed that the current patient is finished with the current interventional study and, as a result, the single-use set 1500 may be removed from connection with the dual multi-use sets 1100 and discarded as medical waste. Sterile caps, as noted in the foregoing, are added to the fluid connector 1176 on the third or outlet port 1166 of the stopcock valve 1160 in each multi-use set 1100. The attendant operator then actuates the "Unload" control button 34 on the injector 20. The "Unload" control button 34 then causes a sequence of actions to occur, as described herein, which permits both multi-use sets 1100 to be removed if desired. However, it may also be desirable to provide two "Unload" control buttons 34, one for each multi-use set 1100, to allow removal of one or the other of the multi-use sets 1100 from the injector 20, for example, if it is desired to remove the multi-use set 1100 containing contrast media while the multi-use set 1100 containing saline remains engaged with the injector 20, fluid control module 200, and air detector module 300. The following discussion describes the removal sequence for one multi-use set 1100 for exemplary purposes.

Once the "Unload" control button 34 is actuated, the control valve actuator 220 is controlled by the electronic control device(s) associated with the injector 20 to move the stopcock valve 1160 to the fill position described previously and then actuates the piston element 60 engaged with the syringe plunger 1300 in the syringe body 1122 of the syringe 1120 to move proximally or rearward to a storage position. The storage position of the piston element 60 corresponds to placement of the syringe plunger 1300 to a set position in the storage/expansion section 1138 of the syringe body 1122 of the syringe 1120, and this position is typically a different axial position from a "new" syringe 1120 with a factory-set axial position. The electronic control device(s) then causes the control valve actuator 220 to place the stopcock valve 1160 in the closed or off position where the third or outlet port 1166 is isolated from the first and second ports 1162, 1164. At this point, the stopcock valve 1160 may be disengaged from the attachment elements 208 on the cover plate 206 of the fluid control module 200 and the corresponding pressure jacket 136 may be pivoted upward in the manner described previously to permit removal of the syringe 1120 from the barrel 162 of the pressure jacket 136. The syringe 1120, stopcock valve 1160, and connector spike 1175 with attached connecting tubing 1174 are then stored as one unit along with the fluid supply container 36, 38 connected to the connector spike 1175.

As will be appreciated from the foregoing, each time a syringe 1120 is loaded into a pressure jacket 136 in the fluid injector system 10 and the corresponding piston element 60 is extended to engage the syringe plunger 1300 in the syringe 1120, a determination may be made as to whether the syringe 1120 is an entirely new syringe 1120, meaning that the syringe 1120 has not been previously used, or is a previously used syringe 1120 and has been previously unloaded. The electronic control device(s) associated with the injector 20 can make this determination via a position or proximity sensor, for example, a contact or optical sensor, integrated into piston elements 60 of the injector 20, which can provide information to the electronic control device(s) as to the position of the syringe plunger 1300 in the syringe body 1122 of the syringe 1120. If the position of the syringe plunger 1300 corresponds to an initial position as set during manufacturing of the syringe 1120, the electronic control device(s) determines the syringe 1120 is an unused syringe 1120. If the syringe plunger 1300 is located at the storage position described previously arrived at as a result of a syringe unloading procedure, the electronic control device(s) determines that the syringe 1120 is a previously used syringe 1120 and fluid is most likely contained therein. It will be appreciated that the initial or factory set position of the syringe plunger 1300 in the syringe body 1122 of the syringe 1120 is also located within the storage/expansion section 1138 of the syringe body 1122 but at a different axial location from the storage position resulting from a syringe unloading procedure.

Initially, the injector 20 is pivoted on the pedestal support 90 to a generally horizontal orientation as described previously and this step is the same whether the syringe 1120 to be associated with the injector 20 is a new syringe 1120 or a previously-used syringe 1120. The syringe 1120 is then loaded into the receiving pressure jacket 136 and the stopcock valve 1160 of the multi-use set 1100 is physically interfaced with the fluid control module 200 according to the methodology described previously in this disclosure. The electronic control device(s) associated with the injector 20 then actuates the corresponding piston element 60 to move distally or forward until the syringe plunger 1300 in the syringe body 1122 of the syringe 1120 is encountered via the proximity sensor on the piston element 60. A suitable proximity sensor for this purpose is described in U.S. Pat. No. 7,018,363 (Cowan, et al.) and in United States Patent Application Publication Nos. 2004/0064041 (Lazzaro et al.) and 2005/0113754 (Cowan), each of which was previously incorporated herein by reference. If it is determined that the syringe 1120 has been previously used, the following exemplary procedure may be used to reload the syringe 1120 to the injector 20 and associate the other components of the multi-use set 1100 with the fluid control module 200 and air detector module 300.

Once it is determined that the encountered syringe 1120 is a previously-used syringe, the piston element 60 does not proceed to drive the syringe plunger 1300 forward to a distal-most position in the syringe body 1122 as described previously in connection with an entirely new syringe 1120. In contrast, movement of the piston element 60 stops upon interfacing engagement with the syringe plunger 1300. The electronic control device(s) associated with the injector 20 then causes the injector 20 to pivot or roll to the fill and purge position (or an attendant operator does this step manually), as shown in FIGS. 33A-33B, which orients the offset discharge conduit 1130 on the syringe body 1122 to a top or purge position. The attendant operator then actuates the "Purge" control button 34 and a prompt or other display is presented to the attendant operator to manually control the piston element 60 to move the piston element 60 forward. The stopcock valve 1160 is substantially simultaneously actuated by the electronic control device(s) to move to the inject position so that an air purging step may occur. Visual detection by the attendant operator helps ensure that no air is trapped in the syringe 1120. The stopcock valve 1160 is then actuated by the electronic control device(s) to the fill position and the syringe 1120 is then refilled according to the procedures outlined previously in this disclosure. If the syringe 1120 is entirely empty of fluid, which is one possible state of the syringe 1120 in the unloading procedure discussed previously, the initial fill sequence described previously in connection with a new syringe 1120 may alternatively be followed to completely fill the syringe 1120 with fluid, typically contrast media.

In the foregoing, single-use set 1500 was described generally and reference is made to certain United States and international publications for details of the single-use set 1500. An improvement to the single-use set 1500 is shown in FIGS. 40-43 and is generally designated with reference numeral 1600. When comparing single-use set 1500 to single-use set 1600, generally the flow-based pressure isolation valve 1510 is replaced with a pressure isolating stopcock assembly or device 1610, as described herein, which enhances air-purging operations, as air-purging of the associated pressure transducer (not shown) may be done automatically. Additionally, air sensor(s) may be provided on a downstream side of the stopcock pressure isolation valve, and possibly on the pressure isolation port itself on the stopcock for enhanced safety purposes. Furthermore, the stopcock pressure isolation valve is desirably made of hard plastic so that hemodynamic pressure signals are not as attenuated as much as in a more compliant pressure isolation valve. Moreover, positive closure features provided by the stopcock pressure isolation valve prevent cross contamination and density exchange of fluids (e.g., contrast media and saline or blood in most applications). The foregoing advantages provided by single-use set 1600 are exemplary and non-exhaustive.

Generally, multi-use sets 1100 remain unchanged from that described previously in this disclosure with the addition of a Y-connector as described herein. FIGS. 40-43 illustrate the respective stopcock valves 1160 associated with the multi-use sets 1100 operationally interfaced with fluid control module 200. However, connecting tubing 1174 associated with the second port 1164 of each stopcock valve 1160 is omitted for clarity purposes in these figures. The pressure isolating stopcock assembly or device 1610 comprises a control valve actuator device 1612 that is supported from the distal or front end of the fluid control module housing 202 via a pair of support arms in a manner similar to the way air detector module 300 is supported to the fluid control module housing 202. The control valve actuator device 1612 (hereinafter "actuator device 1612") is generally similar to the control valve actuators 220 described previously. The actuator device 1612 comprises an interfacing actuator element 1614 and attachment points or elements 1616. A pressure isolating stopcock 1620 mechanically interfaces with the actuator element 1614 via an actuation handle 1621 and is secured to the actuator device 1612 via the attachment elements 1616 in a similar manner to the mechanical interfacing of stopcock valves 1160 with the actuator elements 222 and attachment elements 208 of fluid control module 200 described previously. Accordingly, the pressure isolating stopcock 1620 is an automated stopcock valve operable between several positions or states in a similar manner to the operation of the stopcock valves 1160 described previously. Operation of the actuator device 1612 is desirably effected by the electronic control device(s) associated with injector 20. The operational states of the pressure isolating stopcock 1620 are described herein.

The pressure isolating stopcock 1620 is generally a three-position automated stopcock valve comprising a first or inlet port 1622, a second or outlet port 1624, and a third or pressure isolating port 1626 to which a pressure transducer T to be fluidly isolated from high pressure flows is connected. The pressure transducer T may be mounted to a height adjusting pole to align with a patient's chest cavity. The first or inlet port 1622 is connected via Y-connector conduit 1628 to the respective third outlet ports 1166 of stopcock valves 1160. Y-connector conduit comprises a Y-connector with a distal fluid connector 1630 adapted to interface with the first or inlet port 1622. The first or inlet port 1622 and distal fluid connector 1630 may have a similar mating configuration to mating fluid connectors 1176, 1516 described previously, or may be standard luer connections as is well-known in the medical field. Y-connector conduit 1628 also comprises proximal fluid connectors 1632 adapted to fluidly couple to fluid connectors 1176 provided on the third or outlet ports 1166 of the stopcock valves 1160 of the multi-use sets 1100 and, therefore, may have specific mating connections for interfacing with the fluid connectors 1176 or, alternatively, may be standard luer connections as is well-known in the medical field. With the Y-connector conduit 1628 in place, mixing of fluids in the single-use set 1600 is accomplished just prior to the pressure isolating stopcock 1620. While Y-connector conduit 1628 may be provided as part of the single-use set 1600, it may also be provided as part of the multi-use set 1100 described previously as desired. If the Y-connector conduit 1628 is provided as part of the multi-use sets 1100, the sterility break or connection point resides at the distal fluid connector 1630. If the Y-connector conduit 1628 is provided as part of the single-use set 1600, the sterility break or connection point resides at the proximal fluid connectors 1632. An outlet catheter connector 1634 is fluidly coupled to the second or outlet port 1624 of the pressure isolating stopcock 1620.

In the foregoing fluid connections, it may be desirable to form the connections between the third or pressure isolating port 1626 and the pressure transducer T and between the second or outlet port 1624 and the catheter connector conduit 1634 as integral or permanent connections via any of the suitable joining techniques described previously. Typically, the connection between the first or inlet port 1622 and the Y-connector conduit 1628 is detachable in accordance with this disclosure for the reasons detailed previously. Accordingly, the single-use set 1600 generally comprises the pressure isolating stopcock 1620, the catheter connector conduit 1634, optionally the pressure transducer T, and, optionally, includes Y-connector conduit 1628. If desired, the connections between the third or pressure isolating port 1626 and the pressure transducer T and between the second or outlet port 1624 and catheter connector conduit 1634 may also be detachable connections as provided, for example, via interfacing luer connections as is well-known in the medical field.

An air detector 1640 is mounted to the actuator device 1612 to interface with the catheter connector conduit 1634 connected to the second or outlet port 1624 of the pressure isolating stopcock 1620. Air detector 1640 is interfaced with the electronic control device(s) associated with injector 20 to identify the presence of air in the catheter connector conduit 1634. The actuator device 1612 or, optionally, the air detector 1640 comprises a detector sensor to identify the presence of the pressure isolating stopcock 1620 and such a detector sensor may be incorporated into actuator device 1612 in a similar manner to detector sensors 232 associated with the fluid control module 200 described previously. Alternatively, such a detector sensor may simply determine whether the catheter connector conduit 1634 is associated with the air detector 1640. A downstream isolation stopcock valve 1642 may be provided as part of catheter connector conduit 1634 and provide similar patient-isolating, waste-dumping, air aspiration, or, possibly, drug injection functions to stopcock valve 1512 described previously. It will be appreciated that any of the various features and attributes described previously in connection with the stopcock valve 1512 may be applied to stopcock valve 1642, such as interfacing with the second or downstream air detector module 360 with the stopcock 1642.

With the various features of single-use set 1600 now described, exemplary operational use of single-use set 1600 will now be set forth. In use during a fluid delivery or injection procedure, pressure isolating stopcock 1620 is engaged with the actuator device 1612 with the actuation handle 1621 in operative engagement with the actuator element 1614 whereby operation of the actuation handle 1621 may place the first or inlet port 1622 in fluid communication with the second or outlet port 1624. Fluid flow entering the pressure isolating stopcock 1620 may pass to the catheter connector conduit 1634 and, ultimately, a patient catheter connected to the catheter connector conduit 1634, while the pressure isolating port 1626 and the pressure transducer T connected thereto are isolated from any pressurized fluid flow in the stopcock 1620. If an arterial or venous blood pressure reading is desired, pressure isolating stopcock 1620 may be operated via the electronic control device(s) associated with injector 20 to place the pressure isolation port 1626 in fluid communication with the second or outlet port 1624 and, thereby, allow blood vessel pressure measurements to be taken. Moreover, the pressure isolating stopcock 1620 may be operated so as to place the third or pressure isolation port 1626 in fluid communication with the first or inlet port 1622 so that air residing in the tubing connected to the pressure transducer T may be purged. The downstream stopcock 1642 comprises a rotating catheter connection port 1644 for connecting to a patient catheter (not shown) and a side port 1646 that can perform several functions including as a waste port (e.g., aspiration port), drug injection port, etc.

An exemplary air-purging procedure for the single-use set 1600 now follows. The following discussion generally assumes that the single-use set 1600 is interfaced with the multi-use sets 1100 according to the foregoing discussion, and that the respective multi-use sets 1100 have been purged of air according to the techniques described previously. With the injector 20 in an "inject" position, the distal end of the pressure transducer T is placed or maintained in an open state, open to atmospheric pressure and the pressure isolating stopcock 1620 is in a state or position where fluid communication is present between the first or inlet port 1622 and the third or isolation port 1626. The injector 20 is activated to "push" a desired fluid, typically saline, from one of the corresponding multi-use sets 1100 into the single-use set 1600, whereby the flushing fluid passes through the pressure isolating stopcock 1620 and into the tubing connected to the pressure transducer T and out through the pressure transducer T. The attendant operator, once confirming that fluid has passed out from the pressure transducer T, then stops further injection of flushing fluid from injector 20. The electronic control device(s) associated with the injector 20 then operates the pressure isolating stopcock 1620 into the inject position, wherein the first or inlet port 1622 and second or outlet port 1624 are in fluid communication and the injector 20 is again actuated to inject the second fluid, typically contrast media, associated with the second multi-use set 1100 so that a volume of fluid equivalent to the volumetric capacity of the second multi-use set 1100 passes through the first or inlet port 1622 of the pressure isolating stopcock 1620 (e.g., past the first port 1622). This second injection procedure is ceased and the injector 20 recommences pushing of flushing fluid via the first multi-use set 1100 and pushes a volume of fluid equivalent to the volumetric capacity of the single-use set 1600. The air detector 1640 provides confirmation when the last air bubble or volume from the contrast-filling procedure passes into the single-use set 1600 and, therefore, "pushing" a volume of flushing fluid equivalent to the volumetric capacity of the single-use set 1600 is sufficient to purge air entirely from the single-use set 1600.

Referring next to FIGS. 44-48, this disclosure now sets forth several implementations for detachably joining or interfacing a syringe plunger 1300 disposed within the syringe body 1122 of a syringe 1120 to one of the piston elements 60 associated with injector 20. These several implementations are set forth hereinafter and any one of the following implementations may be utilized in accordance with this disclosure in fluid injector system 10. FIGS. 44A-44I show a first implementation wherein a hook-type interface is generally provided between the syringe plunger 1300 and piston element 60. Initially, it is noted that syringe plunger 1300 generally comprises a plunger element 1302 surrounded by an elastomeric cover 1304 defining a plurality of circumferential sealing ribs 1306. In the hook-interface embodiment, plunger element 1302 is desirably solid and comprises a tapered distal portion or end 1308 which is seated within a tapered cavity 1310 in cover 1304 and an external or rear flange portion 1312 which seats against a proximal end of the cover 1304. A circumferential recess 1314 is defined between and separates the tapered distal portion or end 1308 and the external or flange portion 1312 wherein an inward extending radial rib 1316 of the cover 1304 is seated and secured to secure the engagement between the plunger element 1302 and cover 1304. A proximal or rear hook element 1320 extends proximally or rearward from the flange portion 1312 of the plunger element 1302, with hook element 1320 defining a hook interface recess 1322 inward from a hook tip 1330.

The opposing piston element 60 is adapted for engagement with the hook element 1320 on the plunger element 1302 as now described. Piston element 60 generally comprises a ball screw shaft 600 surrounded by an outer sleeve 602 as is conventional in the powered medical injector field. A plunger interface element 604 is secured via a mechanical fastener 606 to the outer sleeve 602. The plunger interface element 604 defines an internal cavity 608 facing a distal end 610 of ball screw shaft 600 and, wherein, a proximity sensor 612 is disposed. Proximity sensor 612 is provided to identify the axial location of the syringe plunger 1300 within the syringe body 1122 of the syringe 1120 and, as discussed previously, may be a physical contact sensor, optical sensor, and like proximity sensors. As described previously, the proximity sensor 612 can provide information to the electronic control device(s) as to the position of the syringe plunger 1300 in the syringe body 1122 of the syringe 1120. If the position of the syringe plunger 1300 corresponds to an initial position as set during manufacturing of the syringe 1120, the electronic control device(s) determines the syringe 1120 is an unused syringe 1120. If the syringe plunger 1300 is located at the storage position described previously arrived at as a result of a syringe unloading procedure, the electronic control device(s) determines that the syringe 1120 is a previously used syringe 1120.

The plunger interface element 604 comprises a side plate 616 which may be integrally formed therewith. A pivotal hook element 620 is pivotally connected to the side plate 616 at a pivot point 622 and a compression spring 624 acts on the pivotal hook element 620. Compression or backing spring 624 is secured in opposing recesses 626, 628 defined, respectively, in the plunger interface element 604 and the hook element 620; the opposing ends of backing spring 624 may be secured in the opposing recesses 626, 628 by conventional methods. A sealing skirt 629 may be provided around the outer sleeve 602 of the piston element 60 and secured in a recess or cavity in the rear plate 102 of the pressure jacket support 100 for sterility purposes. The hook element 620 has a hook tip 630.

Figure 44A:
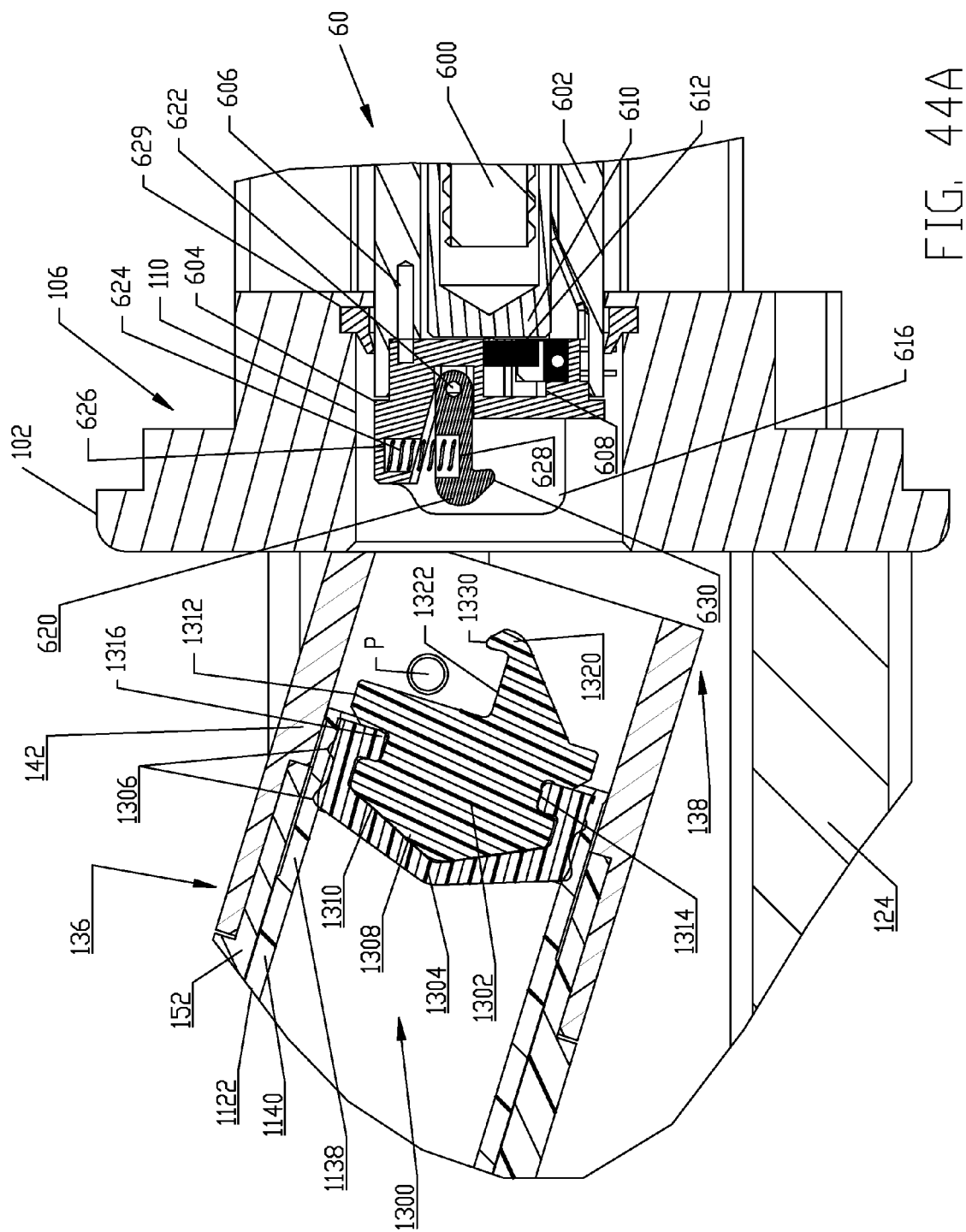
Figure 44B:
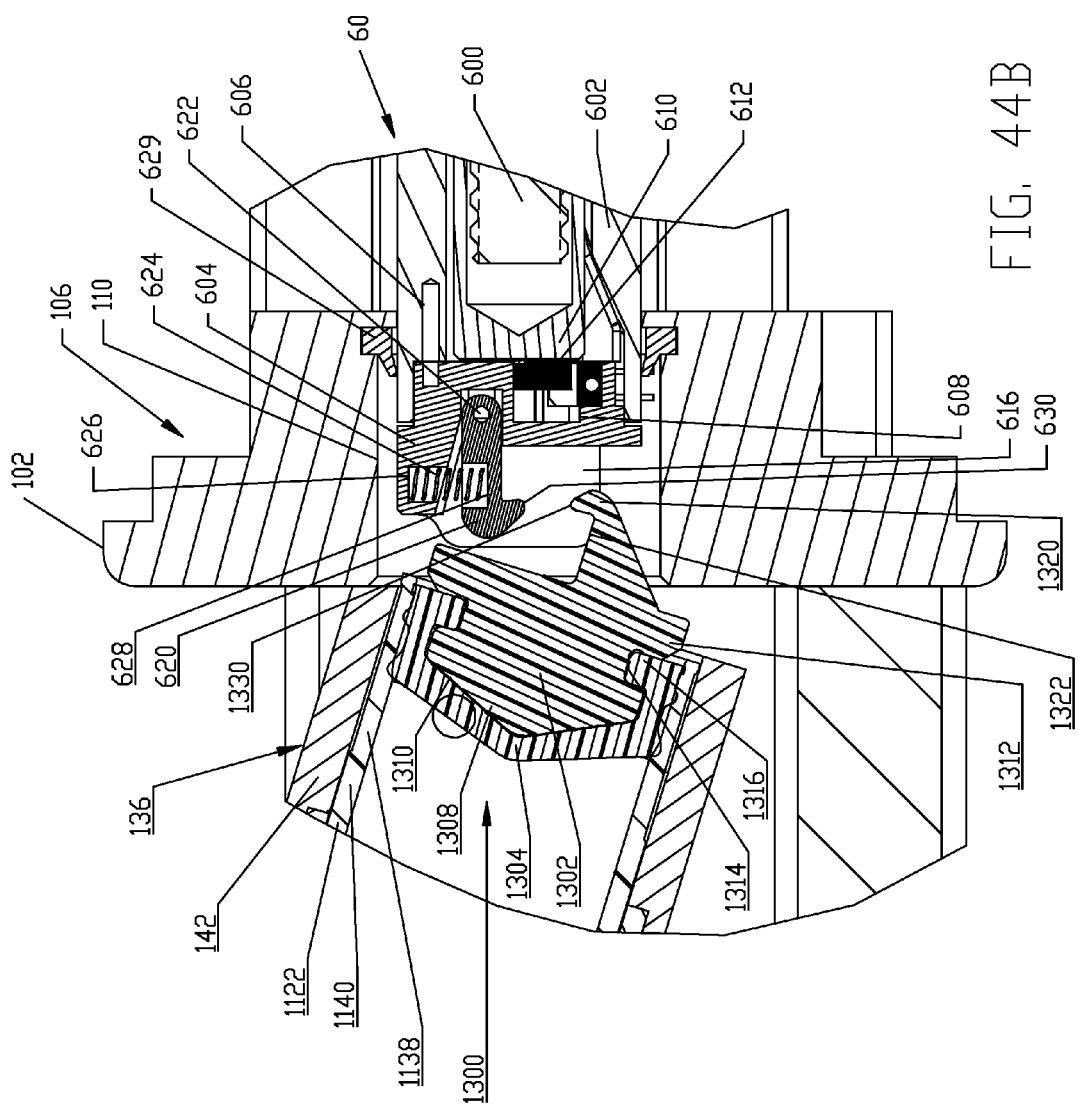
Figure 44C:
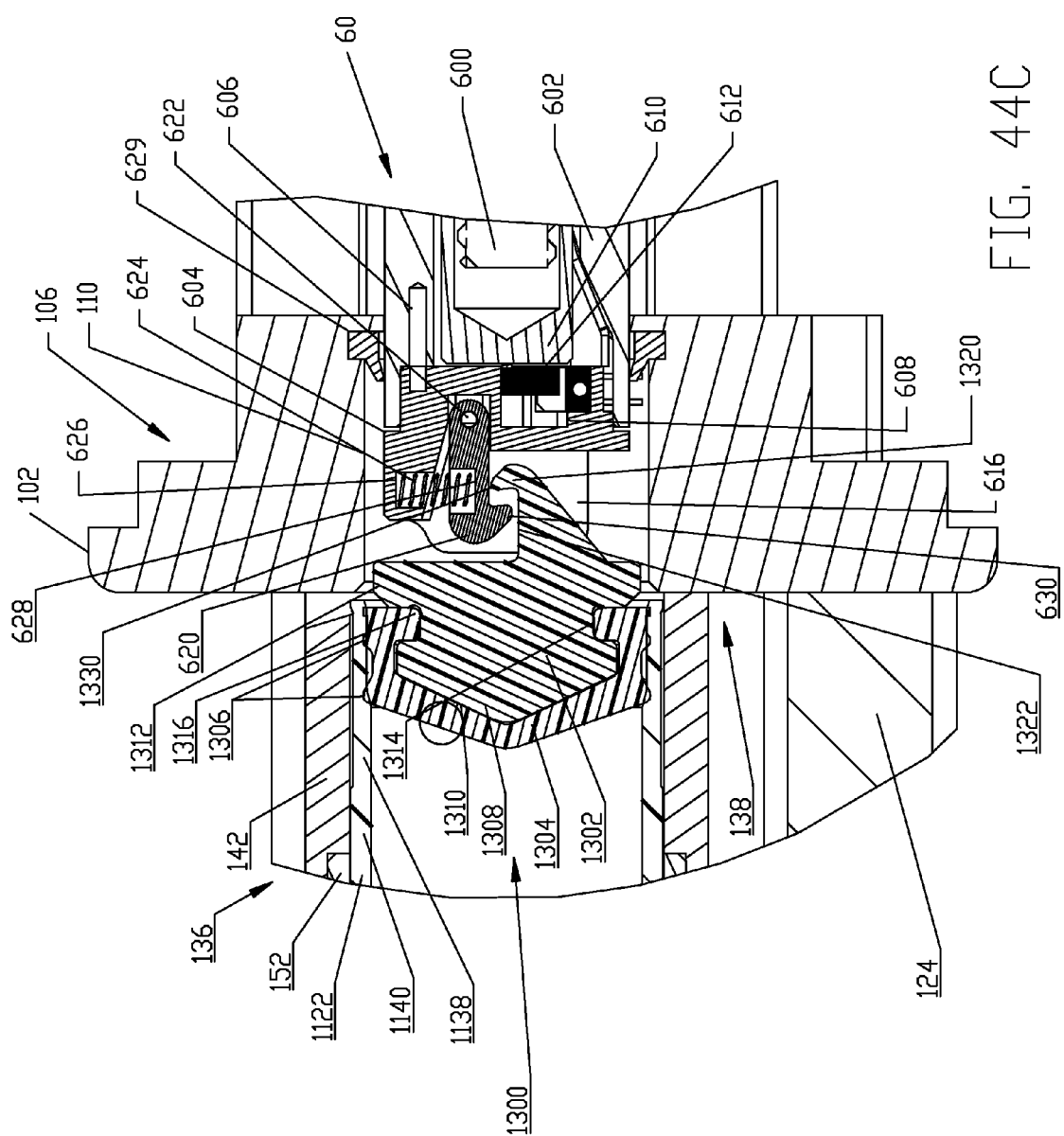
Figure 44F:
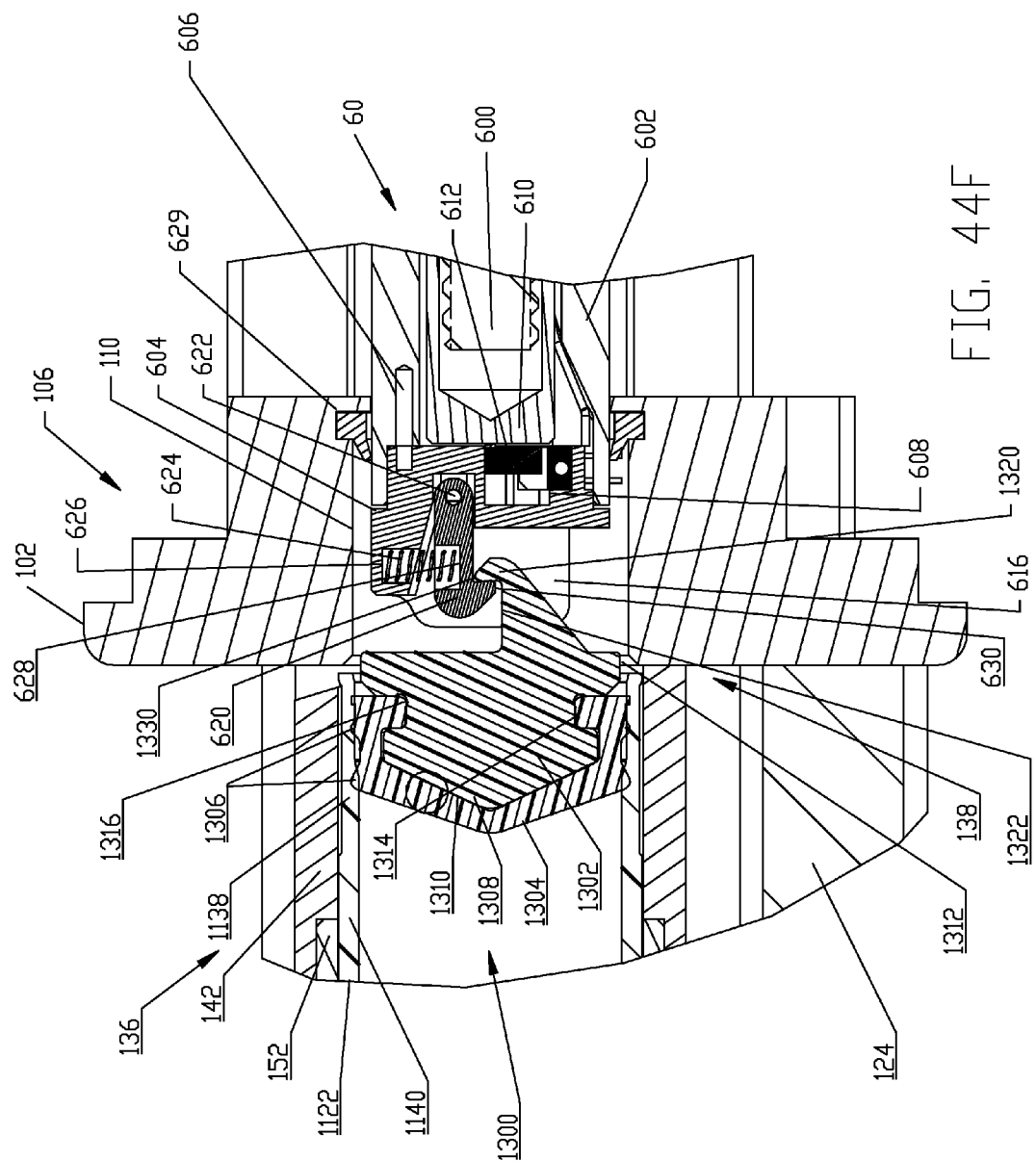

With the respective interfacing components of the syringe plunger 1300 and piston element 60 now set forth for the depicted hook interface implementation used to interface the syringe plunger 1300 and piston element 60, the operational sequence for the hook interface implementation will now be described. FIG. 44A illustrates the initial loading of the syringe 1120 into pressure jacket 136 wherein the syringe 1120 is received into the barrel 162 of the pressure jacket 136. Insertion of the syringe 1120 is generally complete with the engagement of the key elements 1144 in the keyway 158 defined in the inner surface 160 of the body portion 152 of the pressure jacket 136 as this limits insertion of syringe body 1122 into the pressure jacket 136, as described previously. As the pressure jacket 136 is pivoted downward in the manner described previously, the hook tip 630 on the hook element 620 is disposed in the hook recess 1322 defined by the hook element 1320 extending proximally from the plunger element 1302 of the syringe plunger 1300, as shown in FIG. 44C. Backing spring 624 maintains this arrangement by providing a backing force against the hook element 1320. A small space or clearance is defined between the hook tip 1330 of the hook element 1320 and the hook tip 630 of the hook element 620 to permit inter-engagement between hook elements 1320, 620. With the hook interface between the syringe plunger 1300 and piston element 60 now formed, movement of the piston element 60 in a distal or forward direction imparts linear movement to the syringe plunger 1300. In particular, as the piston element 60 moves in a distal or forward direction, as shown between FIG. 44C and FIG. 44D, the side plate 616 contacts the rear flange portion 1312 of the plunger element 1302 and this contact engagement imparts distal or forward movement to the syringe plunger 1300. If the piston element 60 moves in a proximal or rearward direction, as shown in FIG. 44E and FIG. 44F, hook element 620 contacts and engages the opposing hook element 1320 extending from the rear flange portion 1312 of the plunger element 1302 and this inter-engagement imparts proximal or rearward movement to the syringe plunger 1300, with the inter-engagement of the respective hooks 620, 1320 being maintained by backing spring 624.

Figure 44G:
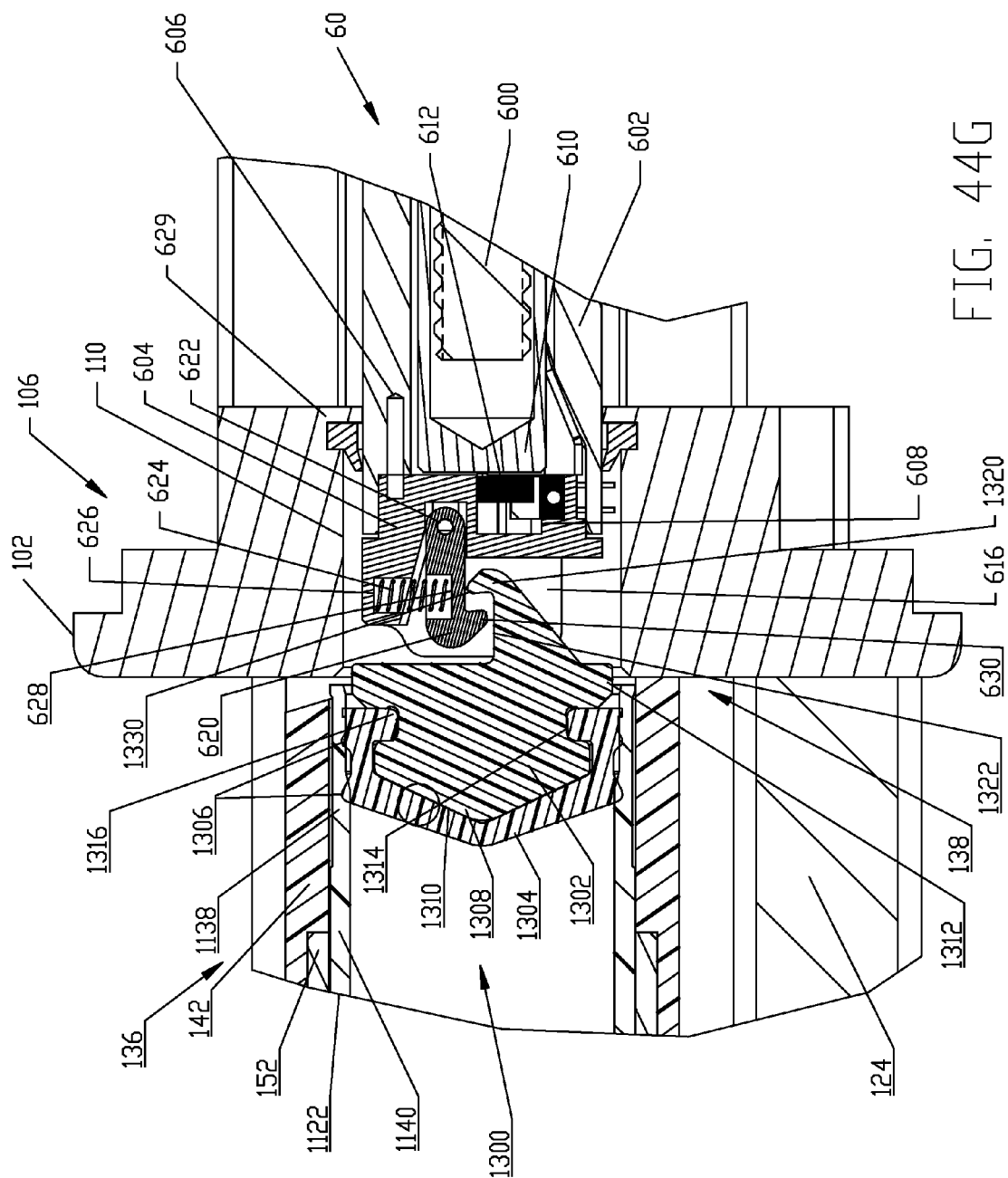
Figure 44I:
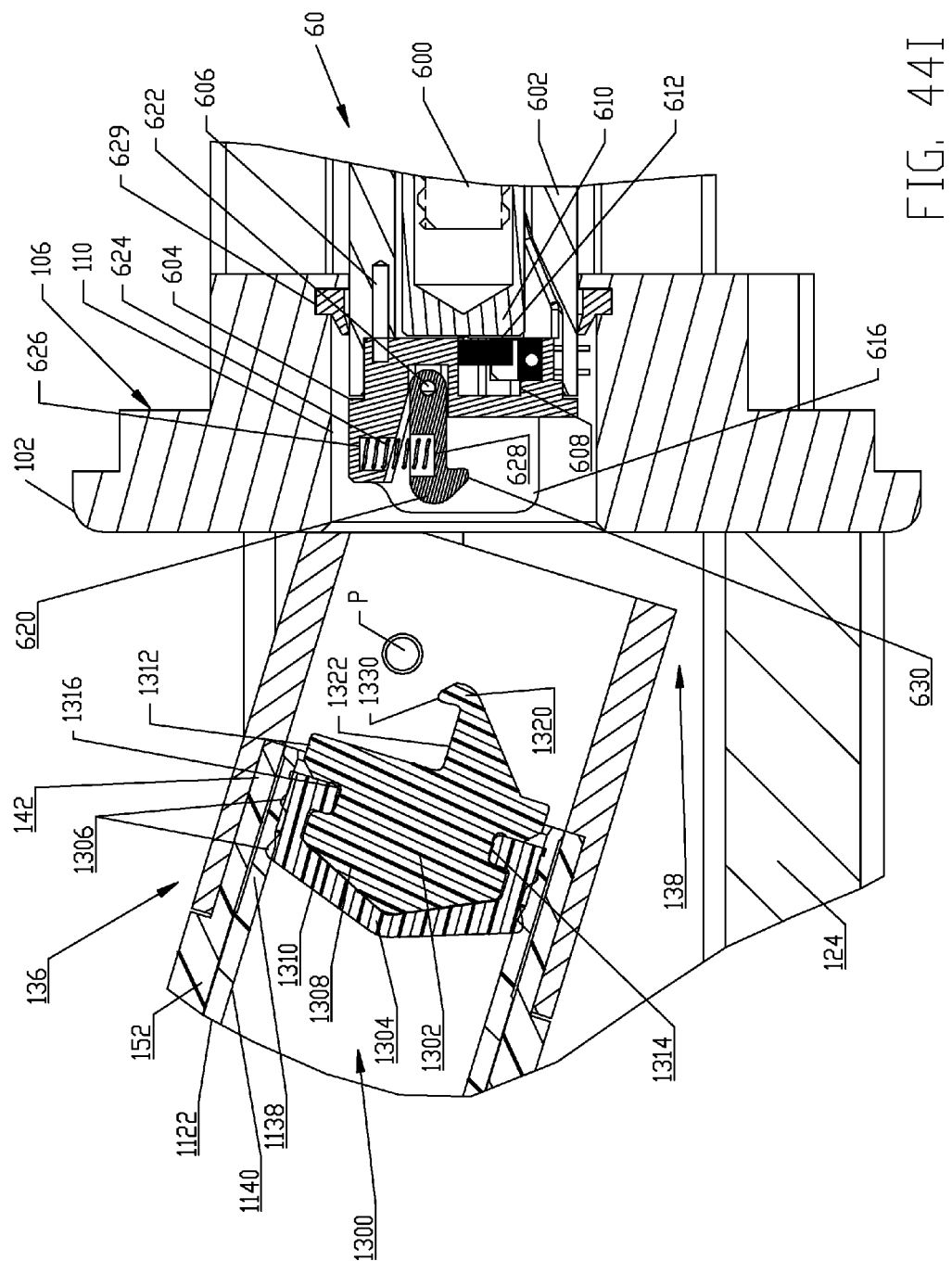

FIGS. 44G-44I, illustrate the unloading sequence for the syringe 1120 when removing the syringe 1120 from the receiving pressure jacket 136, and this sequence just reverses the sequence described in the foregoing for loading the syringe 1120 into the pressure jacket 136. In the removal sequence, a small space or clearance is again defined between the hook tip 1330 of the hook element 1320 and the hook tip 630 of the hook element 620 to permit pivotal disengagement between hook elements 1320, 620. In particular, if it is desired to release the interference engagement between the syringe plunger 1300 and piston element 60, the syringe plunger 1300 is first retracted to the storage position by the piston element 60 which corresponds to placement of the syringe plunger 1300 in the storage/expansion section 1138 of the syringe body 1122 of the syringe 1120 as described previously. In this position, the piston element 60 is withdrawn so that the plunger interface element 604 is positioned generally within the front opening 110 in the rear plate 102 of pressure jacket support 100. The small spacing between the hook tip 1330 of the hook element 1320 and the hook tip 630 of the hook element 620 is formed by a small distal or forward movement of the piston element 60, which remains generally within the front opening 110. Once the small space or clearance is defined between the hook tip 1330 of the hook element 1320 and the hook tip 630 of the hook element 620, the pressure jacket 136 may be pivoted upward as shown in FIGS. 44H-44I which pivotally disengages the hook elements 1320, 620 from one another and the syringe 1120 may be removed from the pressure jacket 136.

Figure 45A:
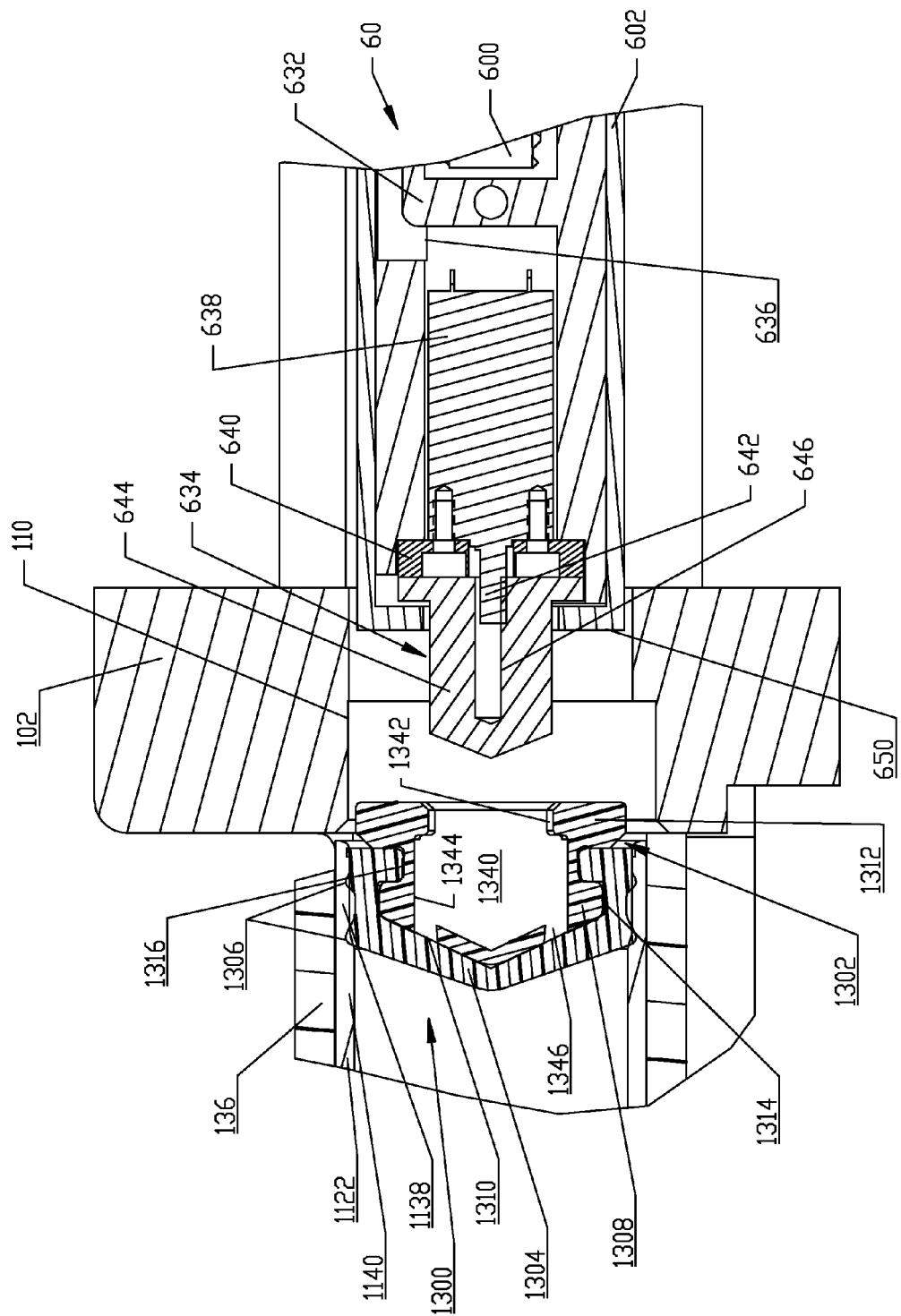

Another syringe plunger 1300 and piston element 60 interfacing arrangement is discussed hereinafter with reference to FIGS. 45A-45H, wherein like elements are identified with like reference numerals as used in the foregoing description of FIGS. 44A-44I. In FIGS. 45A-45H, a rotational piston interfacing arrangement is used to form the mechanical interface between the syringe plunger 1300 and piston element 60. In this embodiment, the plunger element 1302 is a hollow element defining a receiving cavity or bore 1340 and the rear flange portion 1312 defines an inward extending radial rib or rim 1342 at a proximal end for interfacing with piston element 60. Proximal radial rib or rim 1342 is formed on the rear flange portion 1312 of the plunger element 1302 which defines an annular recess 1344. The tapered distal end 1308 of plunger element 1302 may define openings 1346 therein as illustrated but may also be an entirely closed end wall as well. The radial rib or rim 1342 on rear flange portion 1312 defines a pair of opposed keyways or slots 1348, as shown in FIG. 45D and FIG. 45F, to allow access of elements associated with the piston element 60 into the receiving cavity or bore 1340.

Opposing piston element 60 in the present embodiment comprises an inner sleeve 632 that is disposed within the outer sleeve 602 and is further disposed about the ball screw shaft 600. The outer sleeve 602 and inner sleeve 632 are secured together to form a unitary device or component and, alternatively, may be formed as a single unitary structure if desired. A plunger interface element 634 is supported by the outer and inner sleeves 602, 632. The inner sleeve 632 defines an internal compartment or cavity 636 housing a motor 638 which is secured to the inner sleeve 632 via a motor mounting plate 640. An output shaft 642 from the motor 638 is mechanically interfaced with the plunger interface element 634 and is used to impart rotational movement to the plunger interface element 634. The plunger interface element 634 comprises a piston stem 644 defining a bore 646 wherein the motor output shaft 642 is disposed and in interference engagement with the plunger interface element 634 so that rotational motion of the motor output shaft 642 is imparted to the plunger interface element 634. The plunger interface element 634 comprises a pair of key or tab elements 648 for interfacing with the proximal radial rim 1342 provided on the rear flange portion 1312 of the plunger element 1302.

Figure 45B:
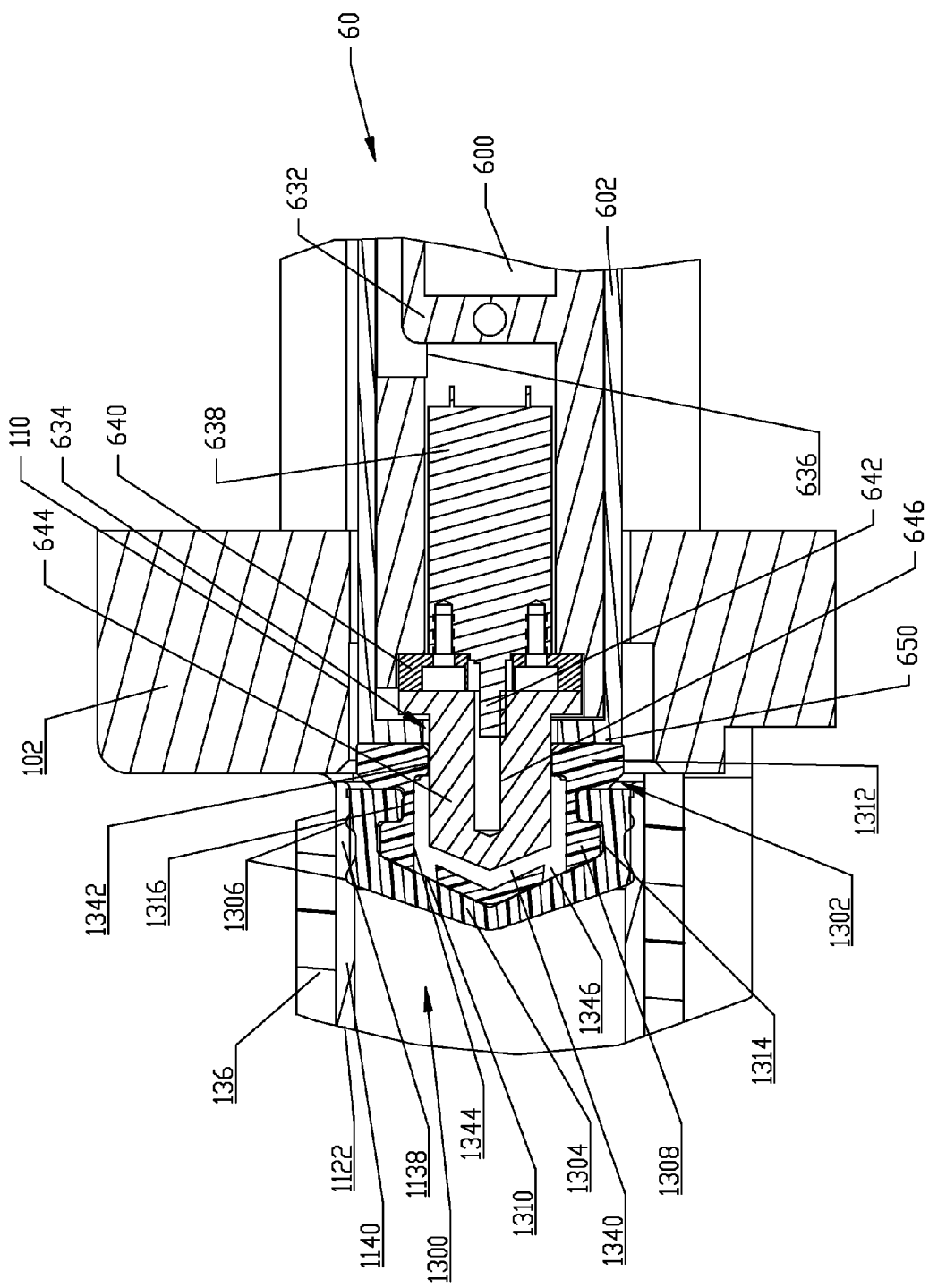
Figure 45C:
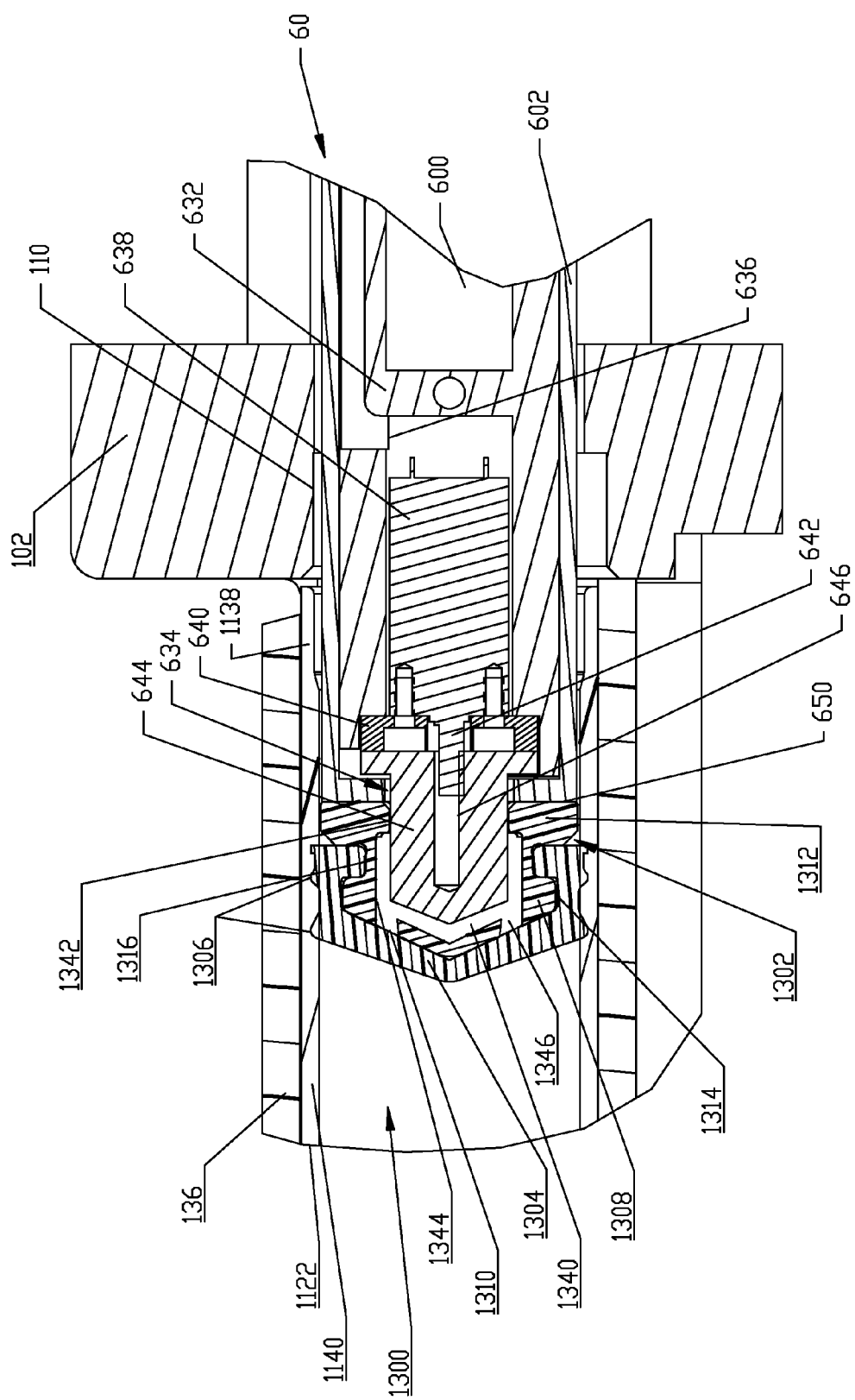
Figure 45E:
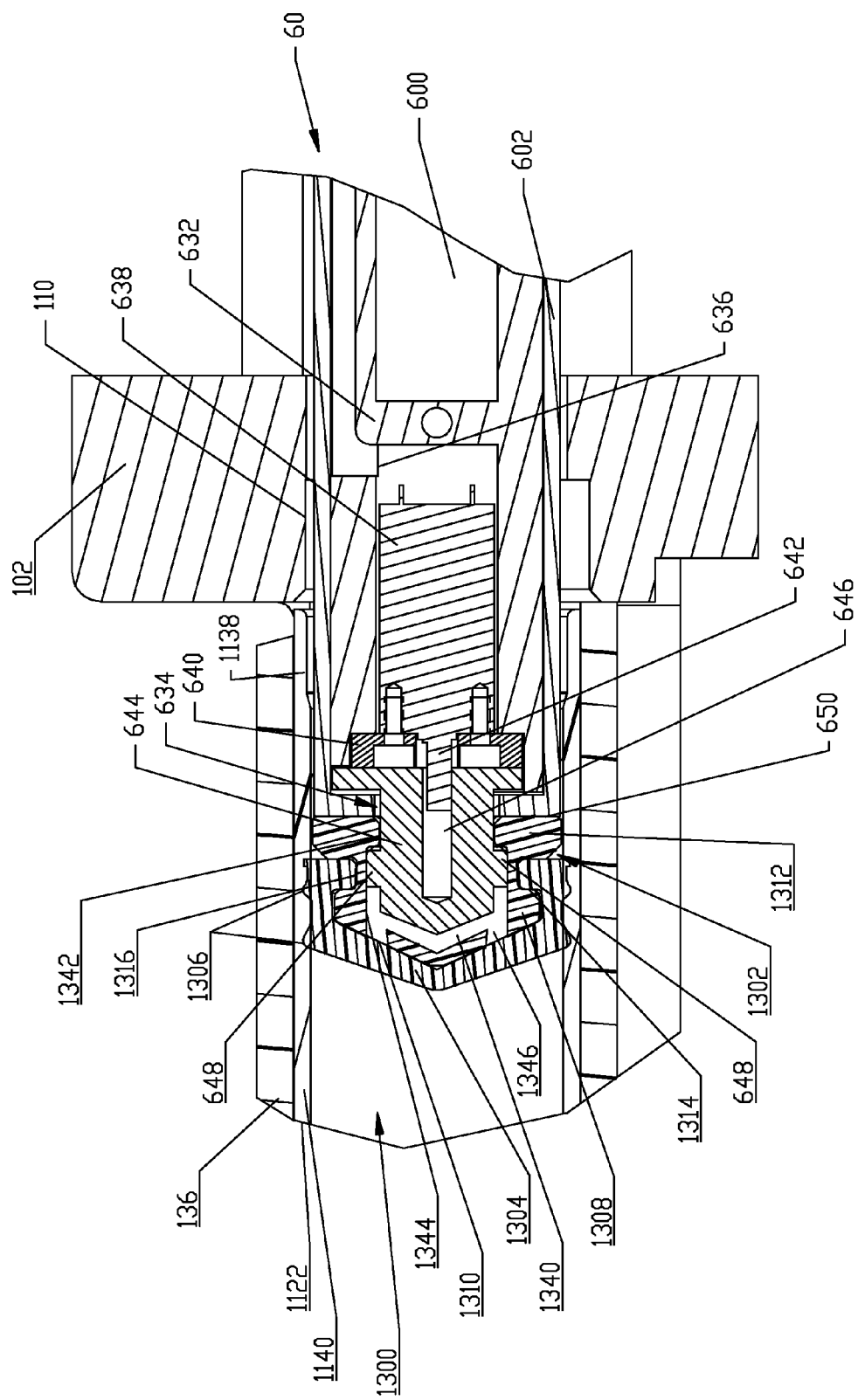
Figure 45G:
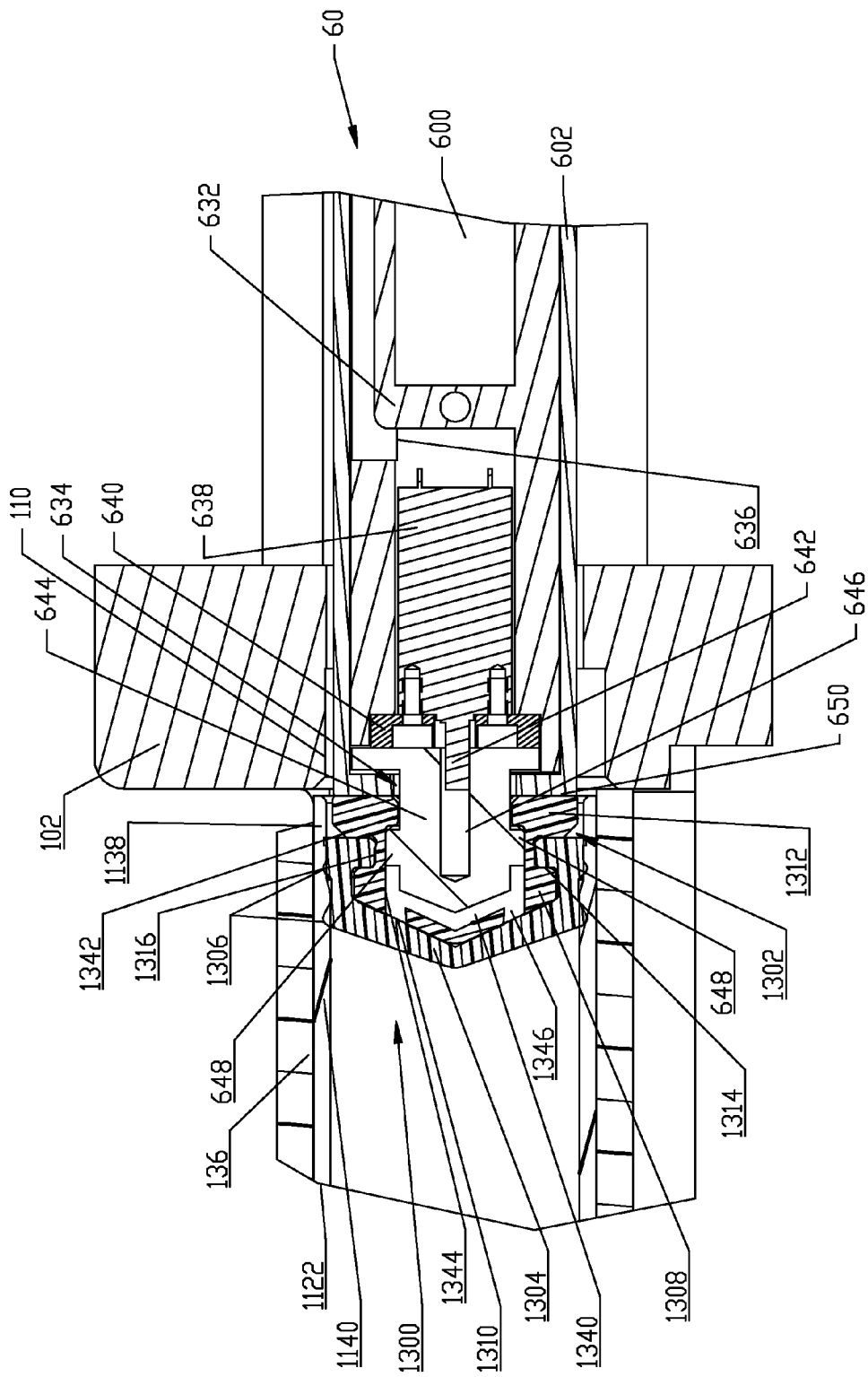
Figure 45H:
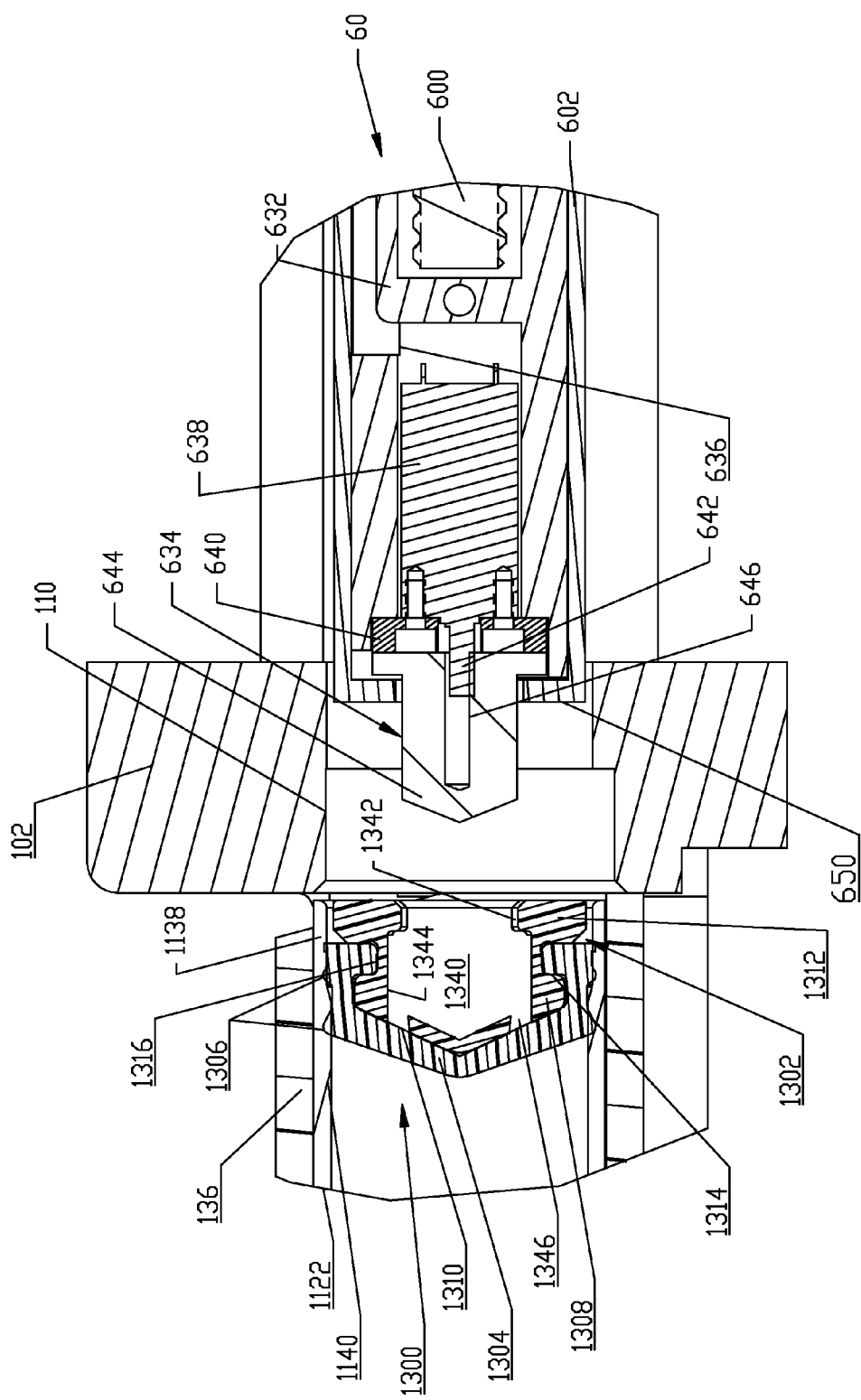

The operational sequence for interfacing the syringe plunger 1300 and piston element 60 begins in FIG. 45A which illustrates the fully-inserted position of the syringe 1120 in the receiving pressure jacket 136 and the pressure jacket 136 pivoted to a horizontal orientation. The loading steps for loading the syringe 1120 in the pressure jacket 136 are omitted but are similar to that described in connection with FIGS. 44A-44I, discussed previously. As shown in FIG. 45A, the piston stem 644 is spaced a distance from the rear flange portion 1312 of the plunger element 1302 but generally aligned with the receiving cavity or bore 1340 in the plunger element 1302. The orientation of the syringe plunger 1300 is such that the keyways 1348 in the radial rim 1342 on the rear flange portion 1312 are aligned with the opposed key or tab elements 648 on the piston stem 644. Accordingly, any distal or forward movement of the piston element 60 allows the key elements 648 to enter the receiving cavity or bore 1340 in the plunger element 1302 via the keyways 1348. Distal or forward movement of the piston element 60 is shown in FIGS. 45A-45C and the corresponding passage of the key elements 648 in keyways 1348 is shown in FIG. 45D. The distal or forward movement of the piston element 60 results in the piston stem 644 being received in the receiving cavity or bore 1340 in plunger element 1302. With the piston stem 644 extending into the receiving cavity or bore 1340 in the plunger element 1302, any distal or forward movement of the piston element 60 automatically imparts distal or forward motion to the syringe plunger 1300 by contact engagement between a distal end or face 650 of the outer sleeve 602 and the rear flange portion 1312 of the plunger element 1302.

Referring in particular to FIGS. 44E-44G, it will be appreciated that to cause proximal or rearward movement of the syringe plunger 1300 in the syringe body 1122 of the syringe 1120, an interference engagement between the syringe plunger 1300 and piston element 60 is required. To form the interference engagement between the syringe plunger 1300 and piston element 60, motor 638 is operated to rotate the motor output shaft 642 which causes the plunger interface element 634 to likewise rotate. The rotational movement imparted to the plunger interface element 634 is on the order of about 90.degree., whereby the key elements 648 on the piston stem 644 are oriented approximately orthogonal to the keyways 1348 in the radial rim 1342 in the rear flange portion 1312 of the plunger element 1302. Thus, the key elements 648 are placed in interference engagement with the radial rim 1342 on the rear flange portion 1312 of the plunger element 1302. The interference engagement between the key elements 648 and the radial rib 1342 on the rear flange portion 1312 of the plunger element 1302 may be established, if desired, immediately after the key elements 648 enter the receiving cavity or bore 1340 in the plunger element 1302 via keyways 1348 to thereby provide the interference engagement between the syringe plunger 1300 and piston element 60. Alternatively, the interference engagement may be established when the piston element 60 is directed to move in reverse or proximal direction by the electronic control device(s) associated with the injector 20. While rotational movement of the plunger interface element 634 of about 90.degree. is described in the foregoing as desirable, this is intended to be only exemplary and any rotational movement of plunger interface element 634 that places the key elements 648 in interference engagement with the radial rim 1342 on the rear flange portion 1312 of the plunger element 1302 is sufficient in accordance with this disclosure. With the interference engagement established between the key elements 648 and the radial rim 1342 on the rear flange portion 1312 of the plunger element 1302, proximal or rearward movement of the piston element 60 causes the syringe plunger 1300 to withdraw or move proximally or rearward in the syringe body 1122 of the syringe 1120.

When it is desired to release the interference engagement between the syringe plunger 1300 and piston element 60, the syringe plunger 1300 is returned to the storage position by the piston element 60 which corresponds to placement of the syringe plunger 1300 in the storage/expansion section 1138 of the syringe body 1122 of the syringe 1120 as described previously. The motor 638 is then operated to rotate the motor output shaft 642 which causes the plunger interface element 634 to likewise rotate. The rotational movement imparted to the plunger interface element 634 is again on the order of about 90.degree. (in either direction), whereby the key elements 648 on the piston stem 644 are oriented approximately in alignment with the keyways 1348 in the radial rim 1342 on the rear flange portion 1312 of the plunger element 1302. Thus, the key elements 648 are placed in an orientation to be removed of interference engagement with the radial rim 1342 in the rear flange portion 1312 of the plunger element 1302. Proximal or rearward movement of the piston element 60 withdraws plunger interface element 634 from engagement with the plunger element 1302 and the plunger interface element 634 may be withdrawn into the front opening 110 in the rear plate 102 of the pressure jacket support 100. Thereafter, the pressure jacket 136 may be pivoted upward to a removal orientation for removing the syringe 1120 from the barrel 162 of the pressure jacket 136 according to the unloading procedure set forth previously in this disclosure.

A further syringe plunger 1300 and piston element 60 interfacing arrangement is discussed hereinafter with reference to FIGS. 46A-46I, wherein like elements are identified with like reference numerals as used in the foregoing description of the previous embodiments of the syringe plunger 1300 and piston element 60 interfacing arrangements. In the present embodiment, a cam interfacing arrangement is used to form the mechanical interface between the syringe plunger 1300 and piston element 60. In this embodiment, the plunger element 1302 is again a hollow element defining a receiving cavity or bore 1340. However, whereas the rotational piston interfacing arrangement comprised the rear flange portion 1312 having an inward extending radial rib or rim 1342 for interfacing with the piston element 60, such an interfacing radial rib 1352 is now formed within the receiving cavity or bore 1340 and part of the distal end portion 1308. The radial rib 1352 defines a distal annular recess 1354 in cavity or bore 1340. Additionally, in contrast to the rotational piston interfacing arrangement, the interfacing radial rib or rim 1352 in the receiving cavity or bore 1340 does not define the opposed keyways or slots 1348 described previously but is instead a circumferentially extending radial rib or rim.

Opposing piston element 60 in the present embodiment comprises an outer sleeve 602 as in previous embodiments and comprises a plunger interface element 654 that is supported to a distal end of the outer sleeve 602. The plunger interface element 654 may be fixed to the distal end of the outer sleeve 602 by any suitable joining method including mechanical fastening, friction fit engagement, or possibly via use of an adhesive. Outer sleeve 602 defines an internal compartment or cavity 656 housing a solenoid 658 which is secured within the compartment 656 via mechanical fastening, friction fit engagement, or possibly via use of an adhesive to maintain the positioning of the solenoid 658 in the sleeve compartment 656. An output shaft 662 extends from the solenoid 658 to mechanically interface with the plunger interface element 654. The plunger interface element 654 comprises a piston stem 664 defining a bore 666 wherein the solenoid output shaft 662 is disposed and in mechanical engagement with a cam element 668 so that rotational motion of the solenoid output shaft 662 is imparted to the cam element 668. A hollow cap or end element 670 is disposed at the distal end of the plunger interface element 654 to enclose an open distal end of the piston stem 664. Cap element 670 defines a hollow cavity 672 therein and supports a pair of outward or radially extendable slide arms 674 in a pair of opposed apertures 676 in the cap element 670. A torsion spring 678 is also disposed in the hollow cavity 672 defined by the cap element 670 and is engaged with the respective slide arms 674. The torsion spring 678 is held fixed in the cap element 670 and acts to maintain the slide arms 674 in a retracted position within the hollow cavity 672. Each slide arm 674 comprises a first end 680 disposed in the respective opposed apertures 676 and a second end 682 extending interiorly into the hollow cavity 672 defined by the cap element 670. The torsion spring 678 acts upon the respective slide arms 674 so that the first end 680 of each of the slide arms 674 is positioned in the corresponding receiving aperture 676 to be generally flush with an exterior surface 684 of piston stem 664 (e.g., a retracted position). As further shown, the cam element 668 is operatively engaged with the second end 682 of each of the slide arms 674 within the hollow cavity 672 defined by cap element 670. The plunger interface element 654 further comprises a shoulder or flange 686 formed proximally of the piston stem 664 which is in engagement with an open distal end 688 in outer sleeve 602 to enclose the sleeve compartment 656 defined within the outer sleeve 602. The shoulder or flange 686 may be formed integrally with the piston stem 664 and is secured in the open distal end 688 in the outer sleeve 602 via mechanical fastening, interference engagement, adhesive engagement, and like methods.

Figure 46A:
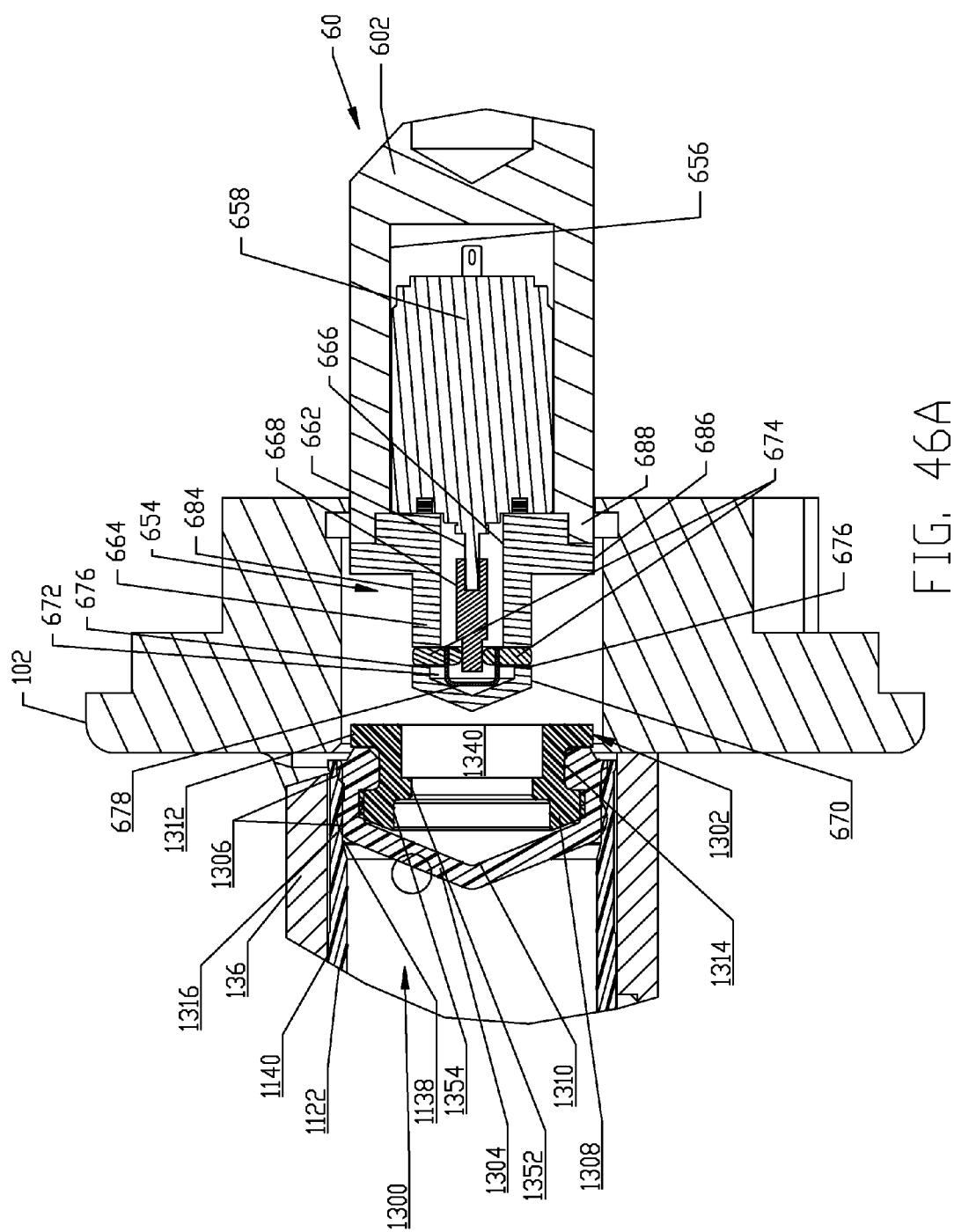
Figure 46C:
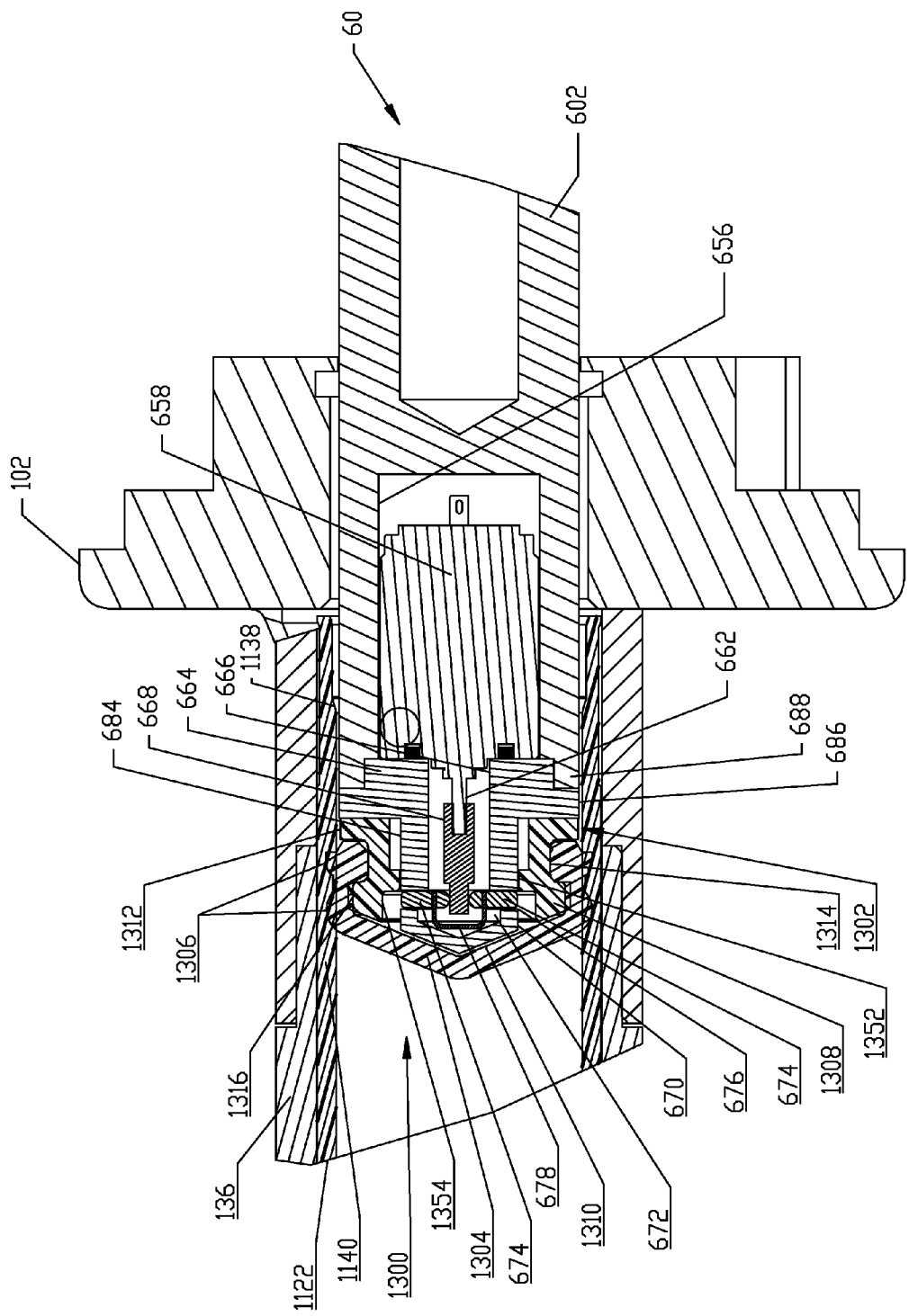

Referring in particular to FIG. 46A, this figure shows the pressure jacket 136 pivoted to a horizontal orientation and the syringe 1120 loaded therein ready for interfacing with piston element 60. Accordingly, the loading steps for loading syringe 1120 into pressure jacket 136 are again omitted in FIGS. 46A-46I, but follow the same methodology as described previously in this disclosure. As FIG. 46A shows, the piston stem 664 is spaced proximally from the syringe plunger 1300 and proximal of the rear flange portion 1312 of the plunger element 1302 of the syringe plunger 1300 but generally aligned with the receiving cavity or bore 1340 in the plunger element 1302. In the present embodiment, the orientation of syringe plunger 1300 is not a concern as in the previous embodiment described hereinabove. Distal or forward movement of piston element 60 allows the piston stem 664 to enter the receiving cavity or bore 1340 in the plunger element 1302. As will be appreciated, an outer diameter of the piston stem 664 is less than an inner diameter of the interfacing radial rim 1352 in the receiving cavity or bore 1340 of the plunger element 1302. Accordingly, distal or forward motion of the piston element 60 causes the piston stem 664 to enter the receiving cavity or bore 1340 until, desirably, the cap element 670 makes contact or is in close proximity with the plunger cover 1304. At this location, the slide arms 674 associated with cap element 670 are located distally forward of the radial rim 1352 and coextensive with the annular recess 1354. Moreover, with the piston stem 664 extending into the receiving cavity or bore 1340 in the plunger element 1302, any distal or forward motion of the piston element 60 automatically imparts distal or forward motion to the syringe plunger 1300 by contact engagement between the shoulder or flange 686 associated with the piston stem 664 and the rear flange portion 1312 of the plunger element 1302.

Figure 46F:
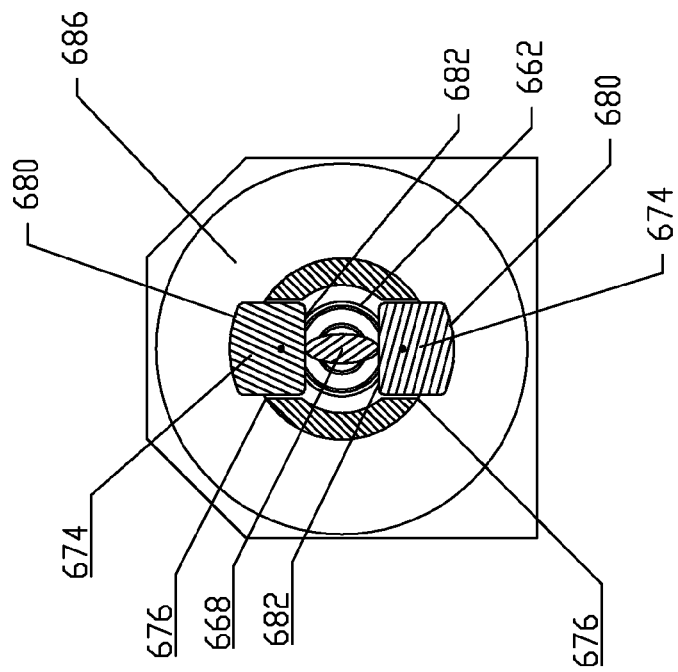
Figure 46D:
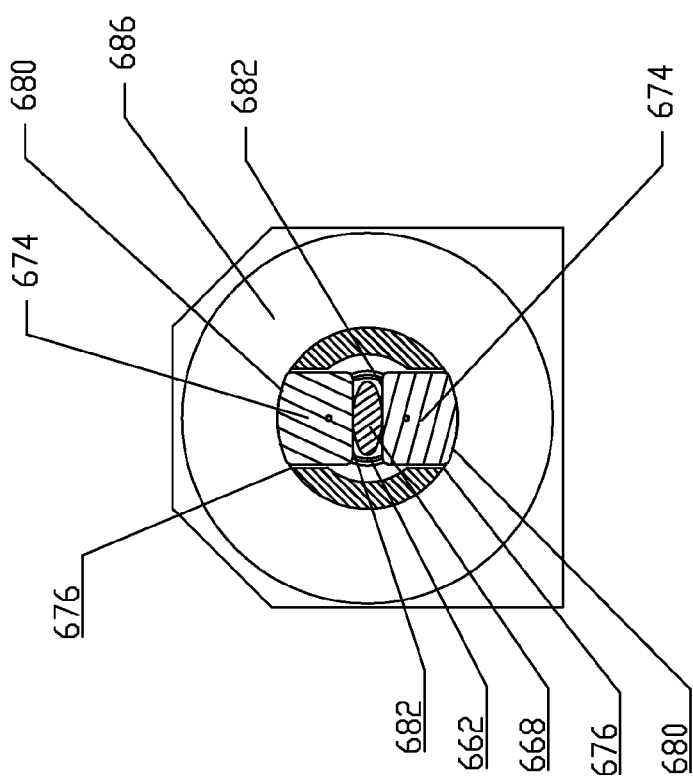
Figure 46G:
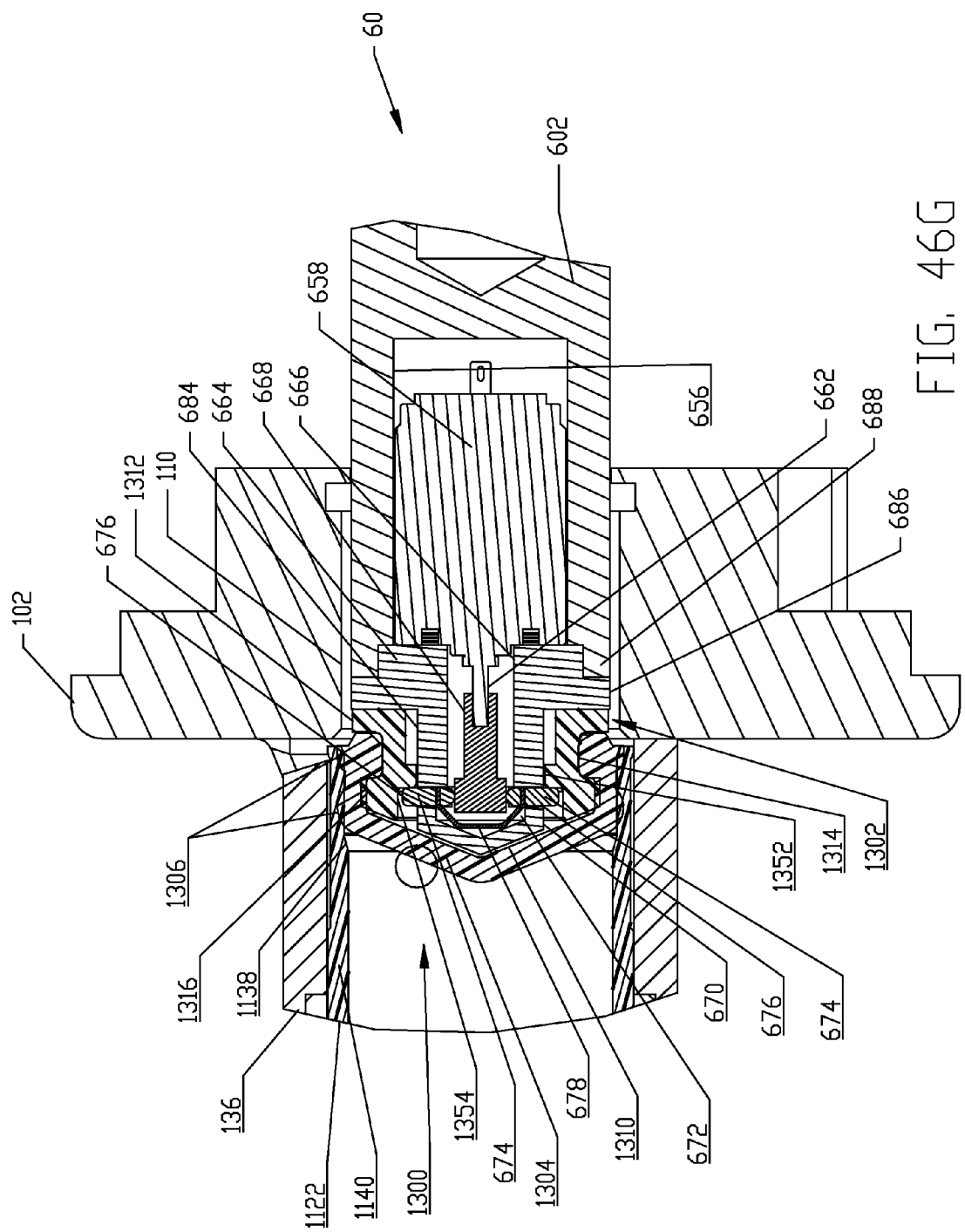
Figure 46H:
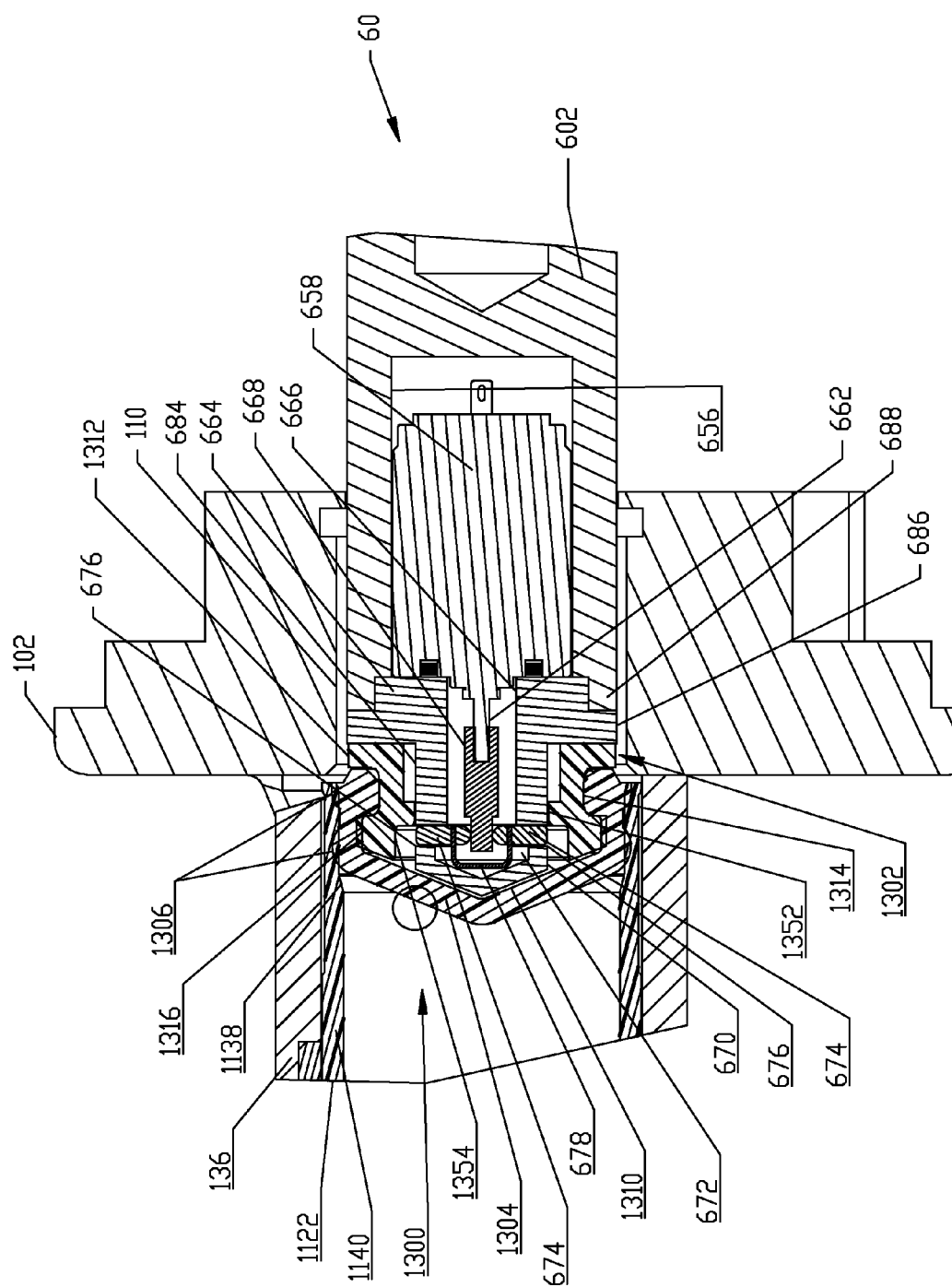
Figure 46I:
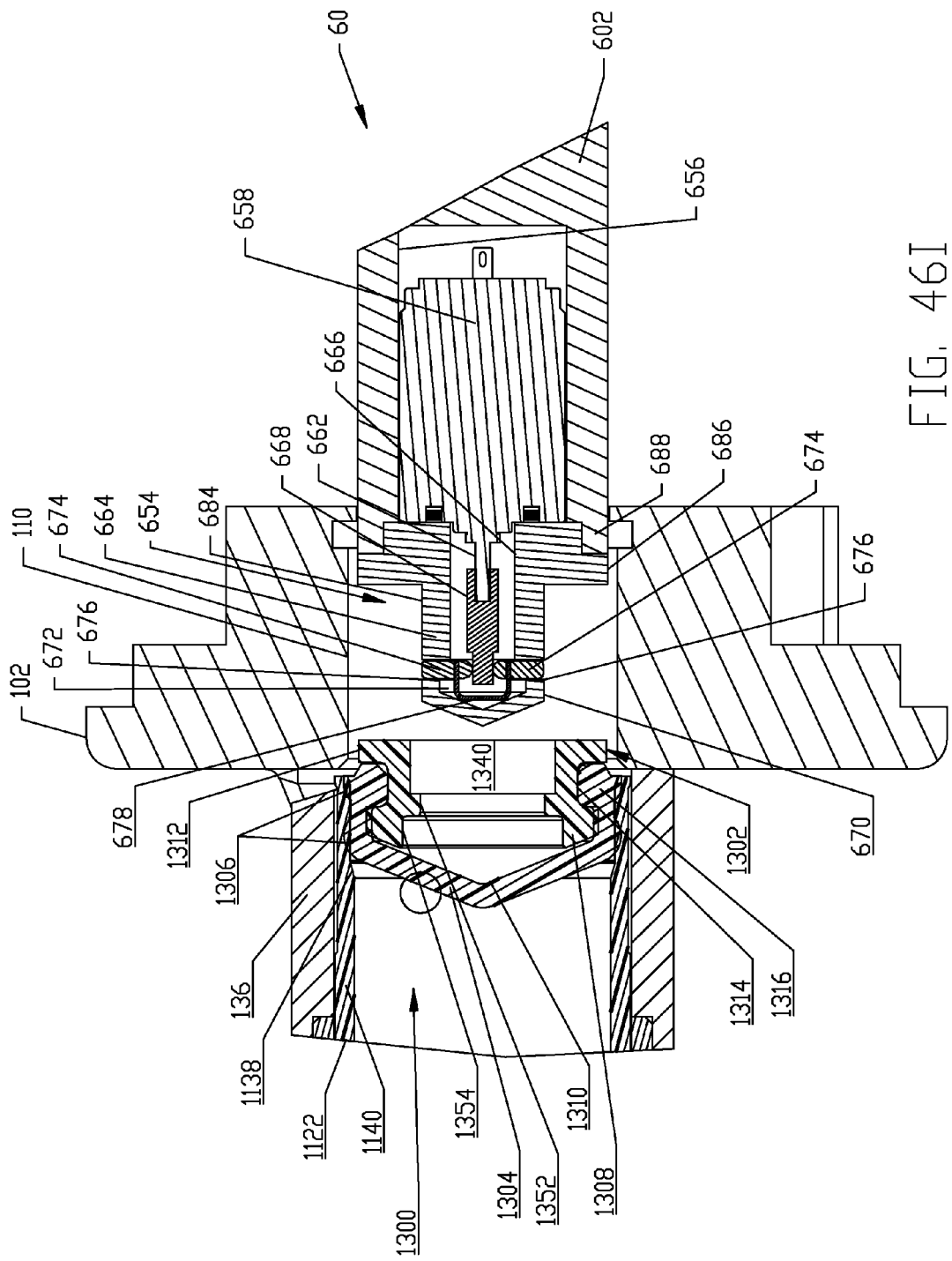

Referring in particular to FIGS. 46E-46G, as with the rotational piston interface arrangement discussed previously, to cause proximal or rearward movement of syringe plunger 1300 in the syringe body 1122 of the syringe 1120, an interference engagement between the syringe plunger 1300 and piston element 60 is required. To form the interference engagement between the syringe plunger 1300 and piston element 60, solenoid 658 is operated to rotate solenoid output shaft 662 which causes the cam element 668 to rotate and act upon slide arms 674; this rotated position of the cam element 668 is shown in FIG. 46F and the corresponding position of the slide arms 674 is also shown. The rotational movement of the cam element 668 causes radial movement of the slide arms 674 so that the slide arms 674 enter annular recess 1354 defined distally forward of the radial rim 1352. As a result, the slide arms 674 are placed in interference engagement with the radial rib or rim 1352 within receiving cavity or bore 1340. This interference engagement between the slide arms 674 and the radial rim 1352 within receiving cavity or bore 1340 may be established, if desired, immediately after the piston stem 664 fully enters the receiving cavity or bore 1340 and either contacts or comes into close proximity to the plunger cover 1304. Alternatively, the interference engagement may be established when the piston element 60 is directed to move in reverse or proximal direction by the electronic control device(s) associated with the injector 20. With the requisite interference engagement established between the slide arms 674 and the radial rim 1352 within the receiving cavity or bore 1340 in the plunger element 1302, proximal or rearward movement of the piston element 60 causes the syringe plunger 1300 to withdraw or move proximally or rearward in the syringe body 1122 of the syringe 1120.

If it is desired to release the interference engagement between the syringe plunger 1300 and piston element 60, the syringe plunger 1300 is desirably returned to the storage position by the piston element 60 which corresponds to placement of the syringe plunger 1300 in the storage/expansion section 1138 of the syringe body 1122 of the syringe 1120 as described previously. The solenoid 658 is then de-energized which allows the torsion spring 678 to act upon the slide arms 674 and return the slide arms 674 to their initial position, wherein the first end 680 of each of the slide arms 674 is positioned in the corresponding receiving aperture 676 to be generally flush with the exterior surface 684 of the piston stem 664. Subsequent proximal or rearward movement of the piston element 60 withdraws the piston stem 664 from the receiving cavity or bore 1340 in the plunger element 1302 and allows the plunger interface element 654 to disengage from the plunger element 1302. The plunger interface element 654 may be withdrawn into the front opening 110 in the rear plate 102 of the pressure jacket support 100. Thereafter, the pressure jacket 136 may be pivoted upward to a removal orientation for removing the syringe 1120 and the syringe 1120 removed from the barrel 162 of the pressure jacket 136 according to the unloading procedure set forth previously in this disclosure.

A fourth syringe plunger 1300 and piston element 60 is discussed hereinafter with reference to FIGS. 47A-47I, wherein like elements are identified with like reference numerals as used in the previously discussed embodiments of the interfacing arrangements between the syringe plunger 1300 and piston element 60. In the present embodiment, a sliding key arrangement is used to form the mechanical interface between the syringe plunger 1300 and piston element 60. In this embodiment, the plunger element 1302 is again a hollow element defining a receiving cavity or bore 1340. As with the rotational piston interfacing arrangement discussed previously, the rear flange portion 1312 comprises an inward extending rib or rim 1342 at a proximal end for interfacing with the piston element 60.

Opposing piston element 60 in the present embodiment comprises an outer sleeve 692 as in previous embodiments and comprises a plunger interface element 694 that is supported to a distal end of the outer sleeve 692. The plunger interface element 694 may be fixed to the distal end of the outer sleeve 692 by any suitable joining method including mechanical fastening, friction fit engagement, or possibly via use of an adhesive. A proximal end 696 of the plunger interface element 694 seats against an internal shoulder 698 defined within the outer sleeve 692. The plunger interface element 694 comprises an outward extending radial flange 700 seated against a distal end of the outer sleeve 692. The outer sleeve 692 defines an internal compartment or cavity 702 which is enclosed by the plunger interface element 694 and which houses a linear solenoid 710. Linear solenoid 710 may be secured within the sleeve compartment 702 via mechanical fastening, friction fit engagement, or possibly via use of an adhesive, and outer sleeve 692 defines a second, proximally located shoulder 704 in the sleeve compartment 702 against which the linear solenoid 710 seats or engages to maintain the positioning of the linear solenoid 710 in the sleeve compartment 702. The linear solenoid 710 comprises an energizing portion 712 with a proximal flange 714 that is seated against the second shoulder 704. The energizing portion 712 defines a central bore or cavity 716 wherein an extendable and retractable solenoid output shaft 722 is coaxially disposed. Extendable and retractable solenoid output shaft 722 has a distal interface portion 724 of reduced diameter as illustrated. The energizing portion 712 of the linear solenoid 710 is operable to extend and retract the solenoid output shaft 722 in a known manner in the electro-mechanical field of endeavor.

The plunger interface element 694 comprises a piston stem 730 defining a bore 732 enclosing a sliding key actuator 734 which is interfaced with the distal interface portion 724 of the solenoid output shaft 722. A fixed connection is provided between the sliding key actuator 734 and the distal interface portion 724 of the solenoid output shaft 722 so that the extending and retracting movement of the solenoid output shaft 722 is imparted directly to sliding key 740. The sliding key actuator 734 is adapted to mechanically interface with a sliding key 740. The sliding key actuator 734 comprises a plurality of distally extending angled key elements 736 that define a plurality (typically a pair) of angled slots 738 for interfacing with the sliding key 740. The sliding key 740 comprises a pair of opposed key teeth 742, 744 each having a radial tip 745. The opposed key teeth 742, 744 are engaged by the distal key elements 736 to effect radial movement of the key teeth 742, 744 from a first or retracted position wherein the key teeth 742, 744 are disposed within respective openings 746, 748 defined in the piston stem 730 so as to be generally flush with an outer surface 750 of the piston stem 730 of the plunger interface element 694, and an extended radial position wherein the key teeth 742, 744 extend radially outward from the respective openings 746, 748 to interface with the radial rib or rim 1342 formed on the rear flange portion 1312 of the plunger element 1302 in the present embodiment. Each key tooth 742, 744 defines an opening 751 for passage of one of the key elements 736 therethrough.

Figure 47A:
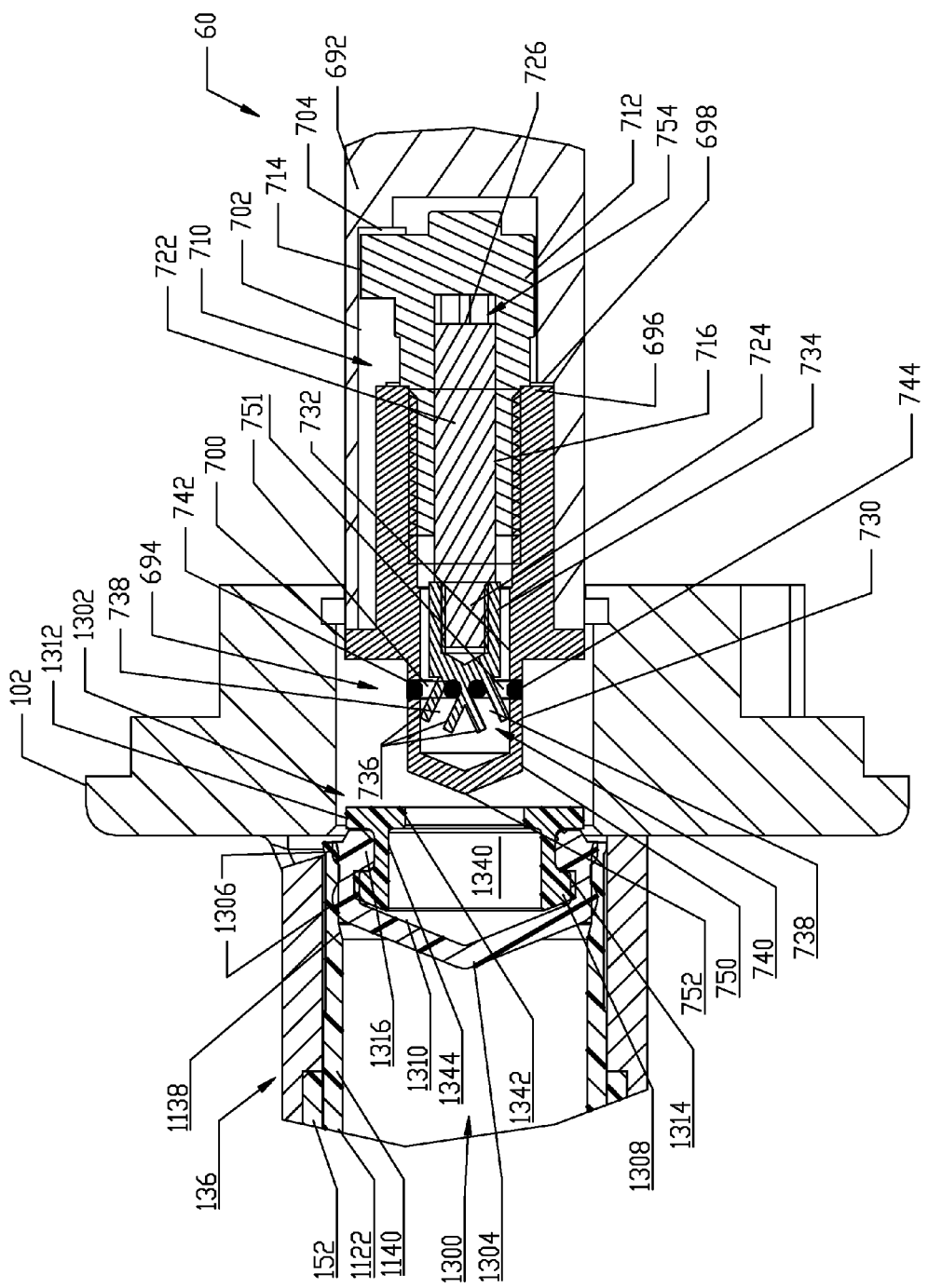
FIGS. 47A-47I are respective cross-sectional views illustrating a sequence of interfacing a syringe plunger in the syringe of FIG. 4 with a piston element of the powered injector of the fluid injector system of FIG. 1 according to a fourth embodiment.
Figure 47B:
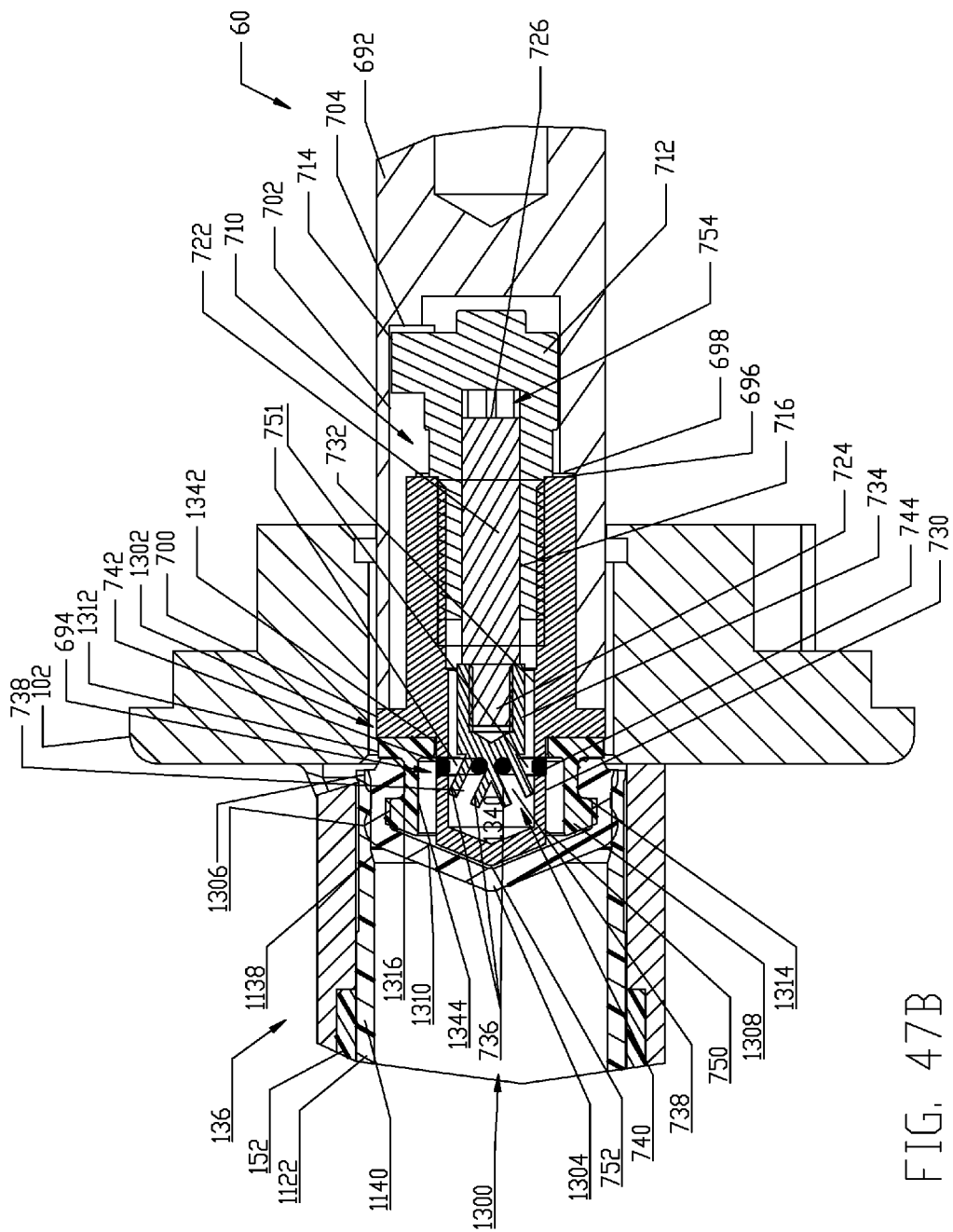
Figure 47C:
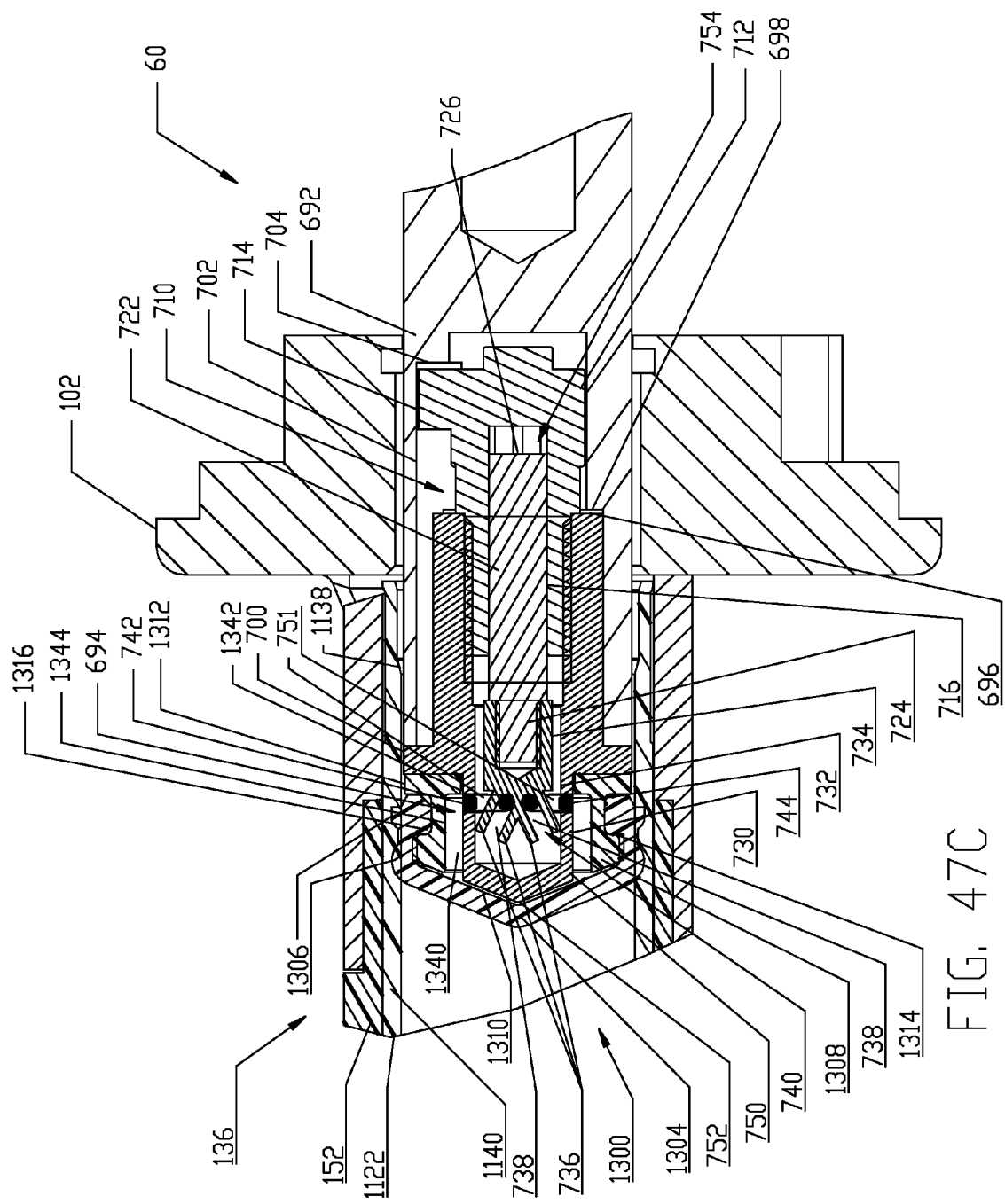

Referring in particular to FIG. 47A, this figure shows the pressure jacket 136 pivoted to a horizontal orientation and the syringe 1120 loaded therein ready for interfacing with piston element 60. Accordingly, the loading steps for loading the syringe 1120 into the pressure jacket 136 are omitted in FIGS. 47A-47I, but follow the same methodology as described previously in this disclosure. In FIG. 47A, the piston stem 730 is spaced proximally from the syringe plunger 1300 and proximal of the rear flange portion 1312 of the plunger element 1302 of the syringe plunger 1300 but generally aligned with the receiving cavity or bore 1340 in the plunger element 1302. In the present embodiment, the orientation of syringe plunger 1300 is also not a concern as the key teeth 742, 744 are operable to engage any portion of circumferential proximal rib or rim 1342 formed on the rear flange portion 1312 of the plunger element 1302. Distal or forward movement of piston element 60 allows the piston stem 730 to enter the receiving cavity or bore 1340 in the plunger element 1302. As will be appreciated, an outer diameter of the piston stem 730 is less than an inner diameter of the interfacing radial rib or rim 1342 formed on the rear flange portion 1312 of the plunger element 1302. Accordingly, distal or forward motion of the piston element 60 causes the piston stem 730 to enter the receiving cavity or bore 1340 until a distal tip or end 752 of the piston stem 730 contacts or is in close proximity with the plunger cover 1304. At this location, the opposed openings 746, 748 in the piston stem 730 are located distally forward of the radial rim 1342 and coextensive with the annular recess 1344. Moreover, with the piston stem 730 extending into the receiving cavity or bore 1340 in the plunger element 1302 any distal or forward motion of the piston element 60 automatically imparts distal or forward motion to the syringe plunger 1300 by contact engagement between the radial flange 700 on the plunger interface element 694 and the rear flange portion 1312 of the plunger element 1302.

In FIGS. 47A-47D, the energizing portion 712 of the linear solenoid 710 is in an energized state so that the solenoid output shaft 722 extends distally from the energizing portion 712 of the linear solenoid 710. In this state, the proximal end 726 of the solenoid output shaft 722 defines a proximal open space 754 within the bore 716 of the energizing portion 712. In this distally extending position, the opposed key teeth 742, 744 of the sliding key 740 are engaged in the angled slots 738 defined by the distal key elements 736 whereby the key teeth 742, 744 are retracted within the respective openings 746, 748 defined in the piston stem 730 and generally flush with the outer surface 750 of the piston stem 730 of the plunger interface element 694. This retracted orientation permits the piston stem 730 clear entry into the receiving cavity or bore 1340 in the plunger element 1302 of the syringe plunger 1300 and allows passage through the inner diameter of the radial rib or rim 1342 on the rear flange portion 1312 of the plunger element 1302.

Figure 47F:
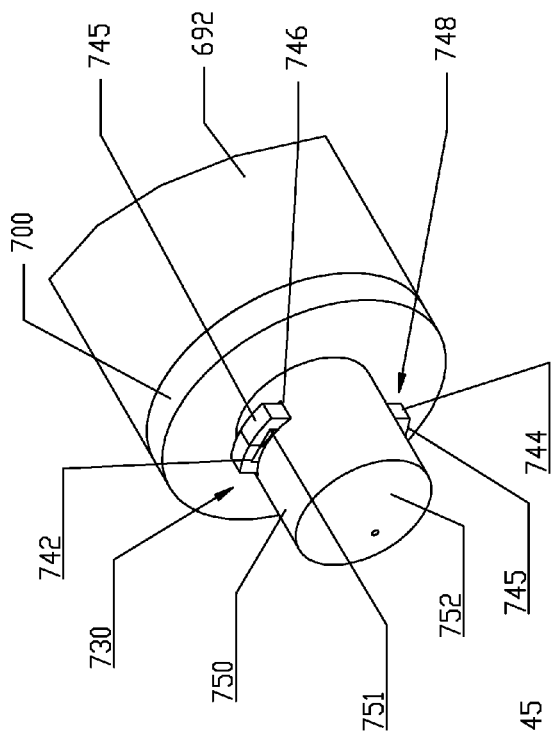
Figure 47D:
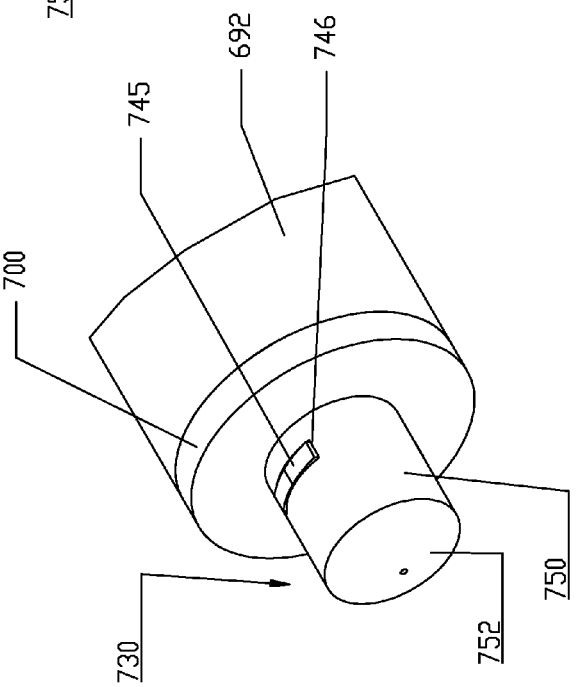
Figure 47E:
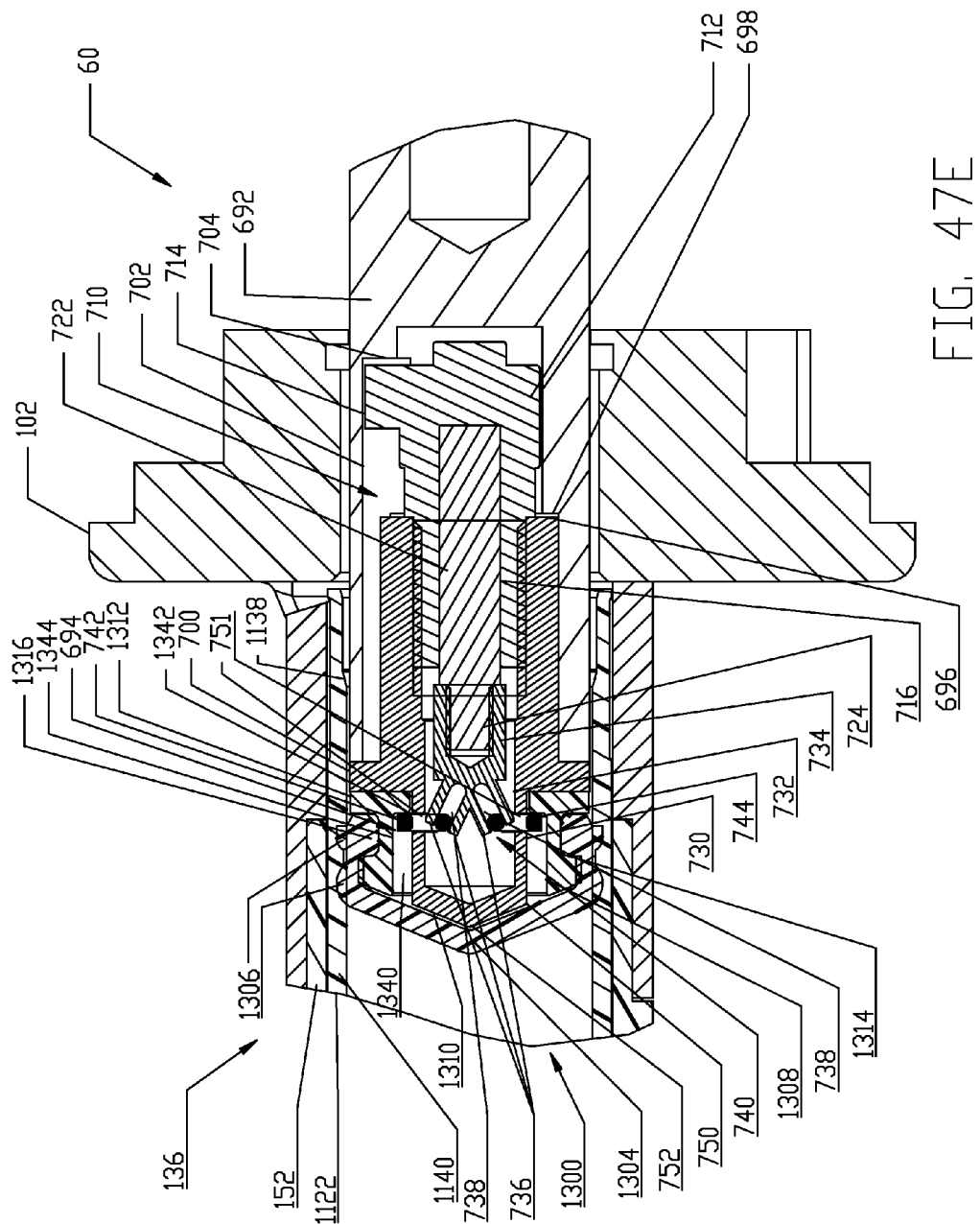
Figure 47G:
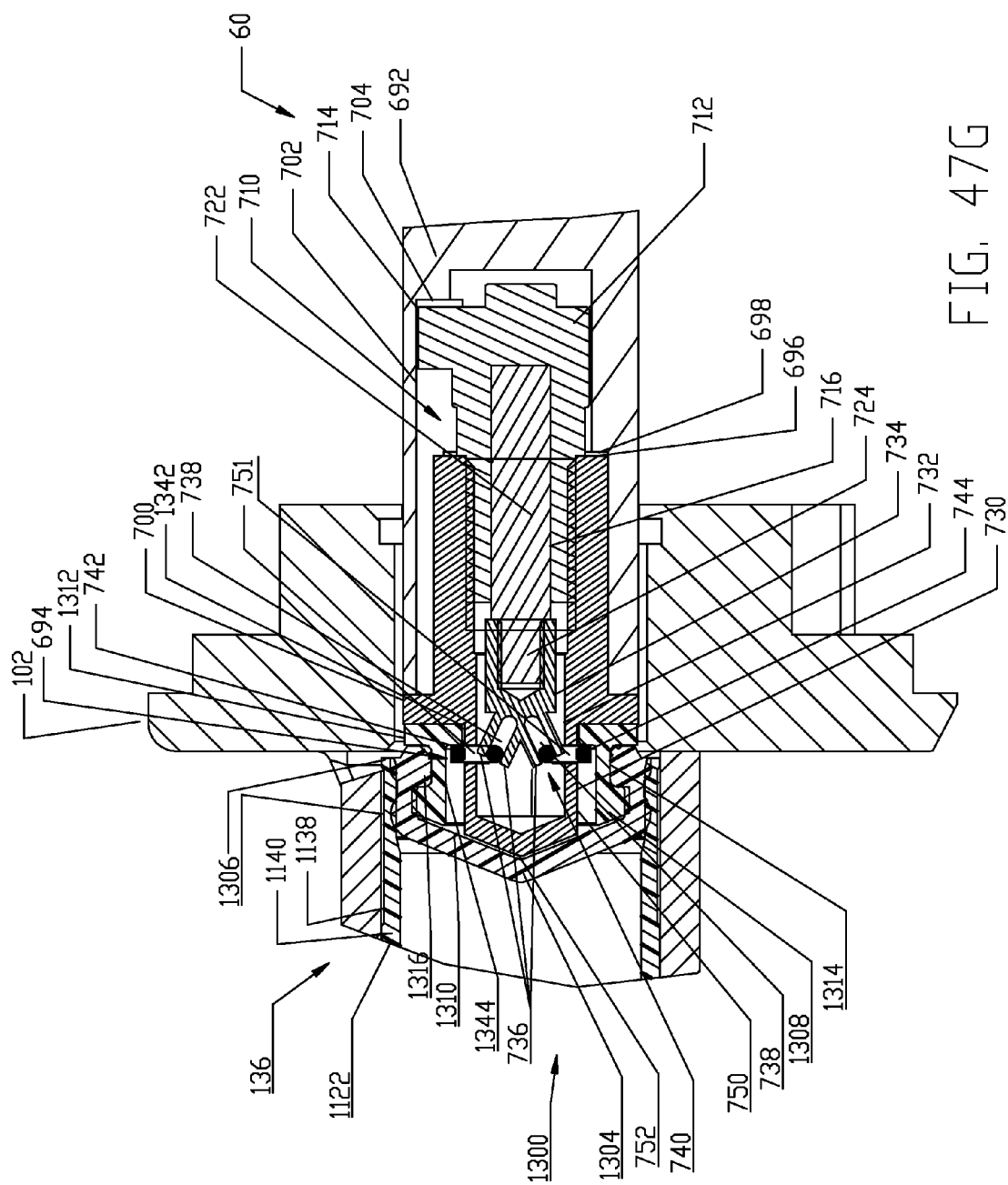
Figure 47H:
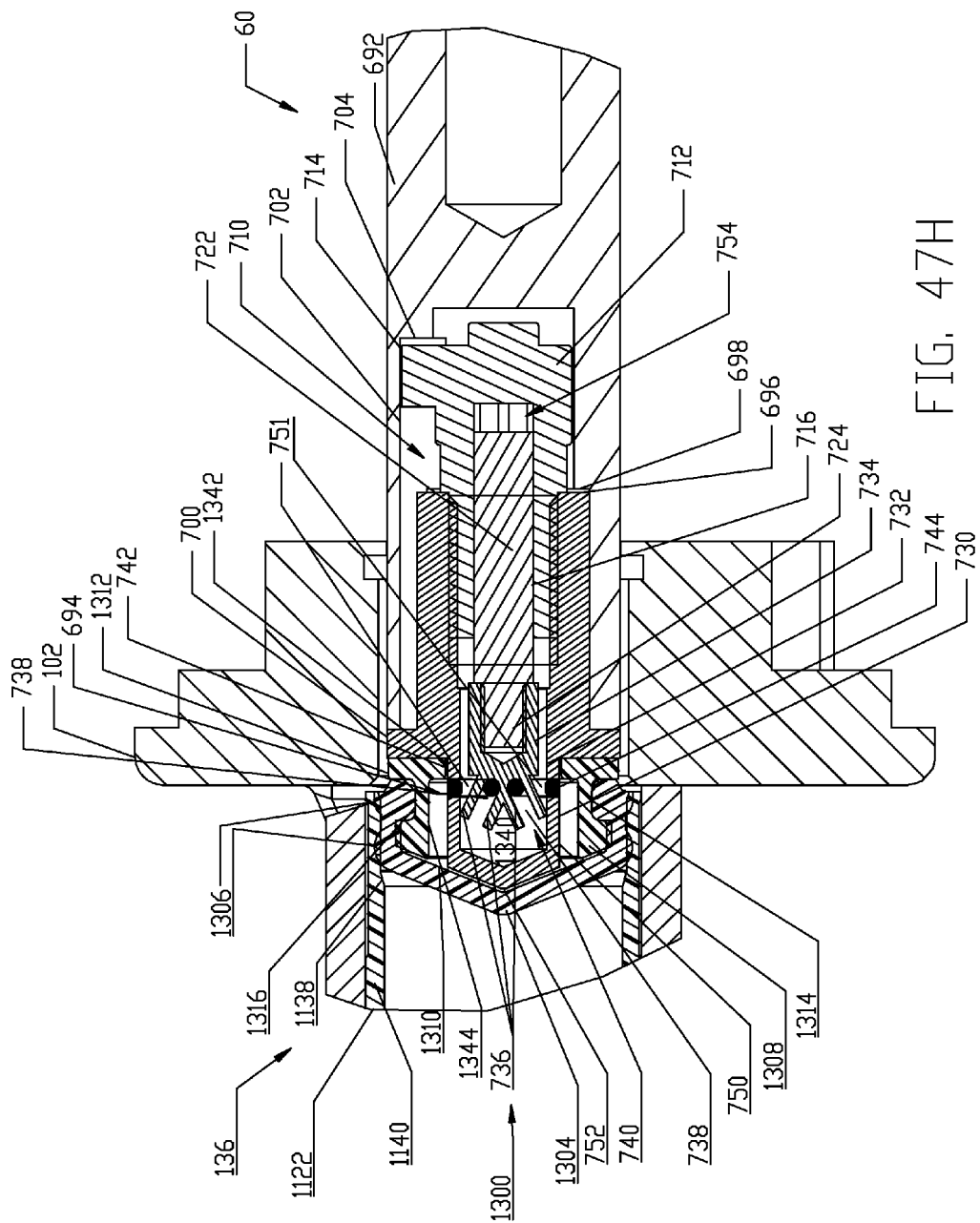
Figure 47I:
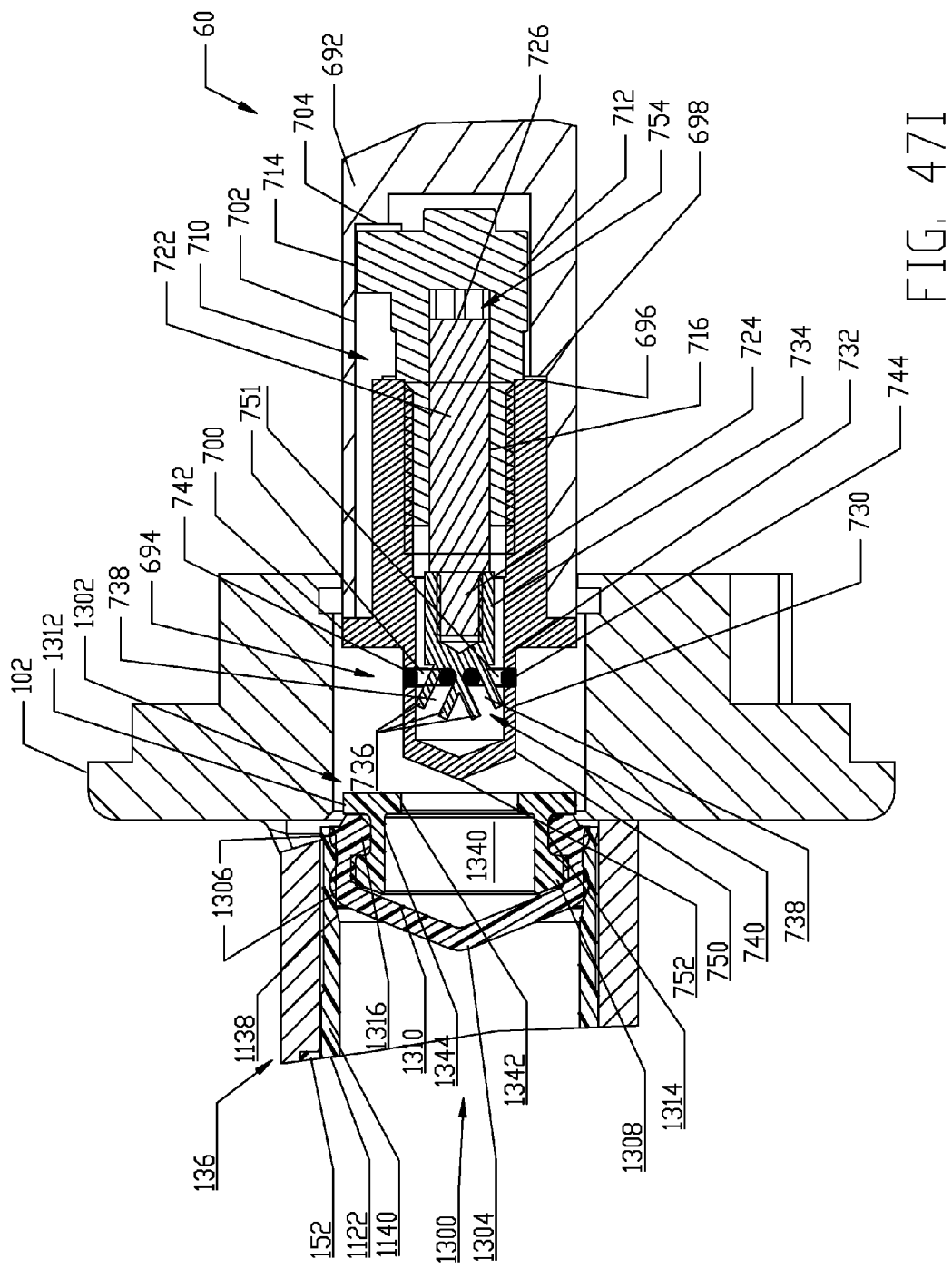

Referring in particular to FIGS. 47E-47G, as with certain previous embodiments, to cause proximal or rearward movement of the syringe plunger 1300 in the syringe body 1122 of the syringe 1120, an interference engagement between the syringe plunger 1300 and piston element 60 is required. To form the interference engagement between the syringe plunger 1300 and piston element 60, the energizing portion 712 of linear solenoid 710 is de-energized whereby the solenoid output shaft 722 retracts within the bore 716 of the energizing portion 712. As a result of this proximal or rearward movement of the solenoid output shaft 722, the proximal open space 754 in the bore 716 of the energizing portion 712 disappears. Further, as the solenoid output shaft 722 withdraws into the energizing portion 712, the sliding key actuator 734 moves proximally due to its fixed engagement with the distal interface portion 724 of the solenoid output shaft 722. Additionally, this proximal movement causes the key teeth 742, 744 to move radially outward as the key teeth 742, 744 are under the influence of the angled slots 738 defined by the distal key elements 736. More particularly, as the key actuator 734 moves proximally with the solenoid output shaft 722, the key teeth 742, 744 slide within their respective angled receiving slots 738 which, as illustrated, diverge outward from one another and this divergent or angled orientation imparts radial outward movement to the key teeth 742, 744. As the key teeth 742, 744 reach the opening of the slots 738, the radial tip 745 of each of the key teeth 742, 744 seats within the annular recess 1344 defined by the proximal radial rim 1342 on the rear flange portion 1312 of the plunger element 1302. The interference engagement between the key teeth 742, 744 and the radial rim 1342 is established immediately after the piston stem 664 fully enters the receiving bore 1340 and either contacts or comes into close proximity to the plunger cover 1304. Alternatively, the interference engagement may be established when the piston element 60 is directed to move in the reverse or proximal direction by the electronic control device(s) associated with the injector 20. With the requisite interference engagement established between the key teeth 742, 744 and the radial rim 1342 provided on the rear flange portion 1312, proximal or rearward movement of the piston element 60 causes the syringe plunger 1300 to withdraw or move proximally or rearward in the syringe body 1122 of the syringe 1120.

When it is desired to release the interference engagement between the syringe plunger 1300 and piston element 60, the syringe plunger 1300 is desirably first returned to the storage position by the piston element 60 which corresponds to placement of the syringe plunger 1300 in the storage/expansion section 1138 of the syringe body 1122 of the syringe 1120 as described previously. The linear solenoid 710 is then reenergized which moves the solenoid output shaft 722 distally or forward within the bore 716 of the energizing portion 712, thereby reestablishing a proximal space 954 within the bore 716 of the energizing portion 712. This forward or distal movement is imparted to the sliding key actuator 734 and results in the sliding key teeth 742, 744 tracking into their respective angled slots 738 defined by the distal key elements 736. As will be apparent, as the sliding key teeth 742, 744 track in their respective angled slots 738, the key teeth 742, 744 are radially withdrawn into the respective openings 746, 748 in the piston stem 730. Once withdrawn to be flush with the outer surface 750 of the piston stem 730, the piston stem 730 may be withdrawn from the receiving cavity or bore 1340 defined in the plunger element 1302 by the rearward movement of the piston element 60. When the plunger interface element 694 disengages from the plunger element 1302, further proximal or rearward movement of the plunger interface element 694 withdraws it into the front opening 110 in the rear plate 102 of the pressure jacket support 100. Thereafter, the pressure jacket 136 may be pivoted upward to a removal orientation for removing the syringe 1120 from the barrel 162 of the pressure jacket 136 according to the unloading procedure set forth previously in this disclosure.

A final syringe plunger 1300 and piston element 60 interfacing arrangement is discussed hereinafter with reference to FIGS. 48A-48D, wherein like elements are identified with like reference numerals as used in the previous embodiments of the interfacing arrangements between the syringe plunger 1300 and piston element 60. In FIGS. 48A-48D, an attachment arm arrangement is used to form the mechanical interface between the syringe plunger 1300 and piston element 60. In this embodiment, plunger element 1302 is now a substantially solid element that has a proximal tab or button element 1356 extending proximally from the rear flange portion 1312 for engagement by the flexible support arm arrangement as described herein. The proximal tab or button element 1356 defines a circumferential recess 1358 which is engaged by the flexible support arm arrangement as described herein.

Figure 48A:
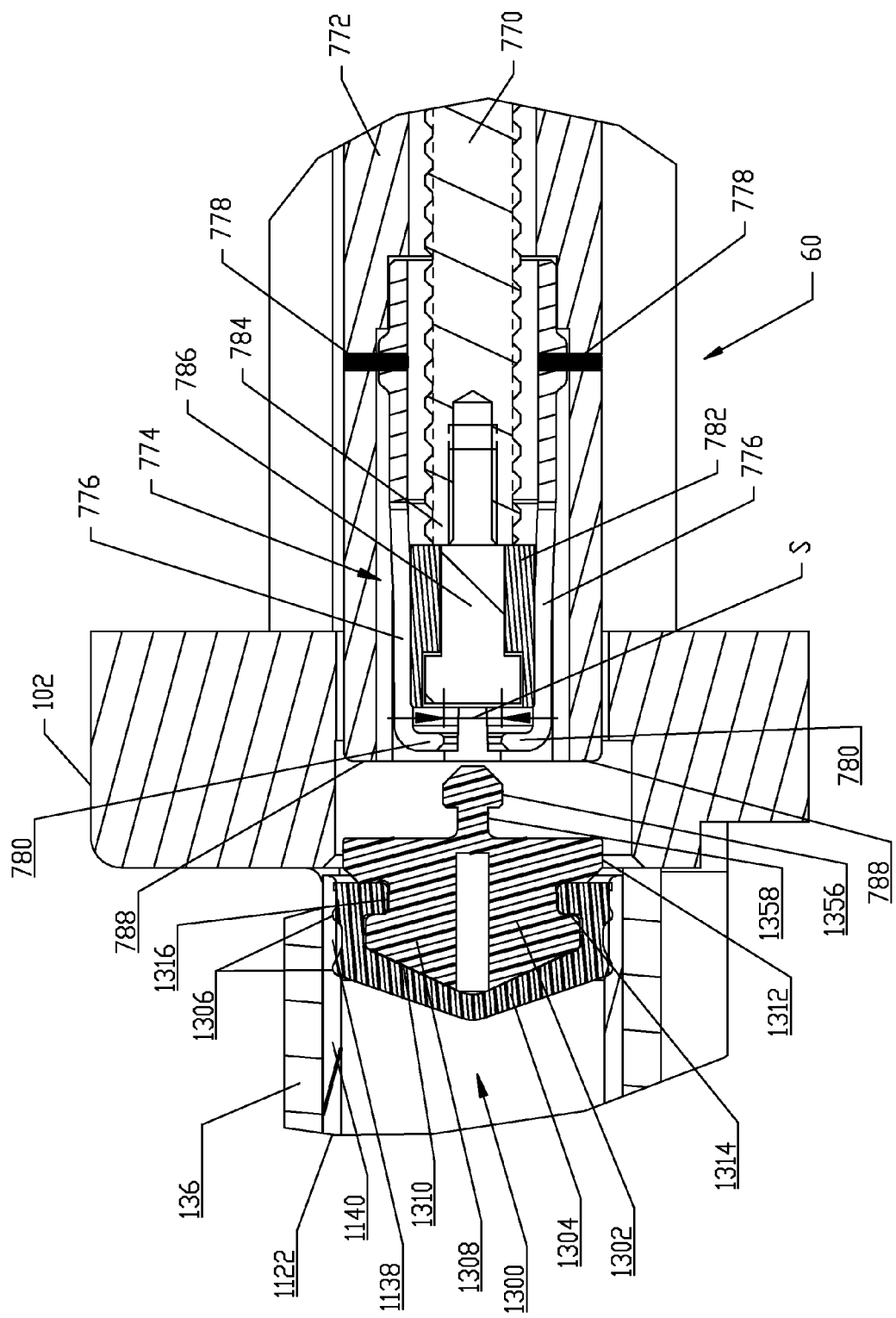
Figure 48C:
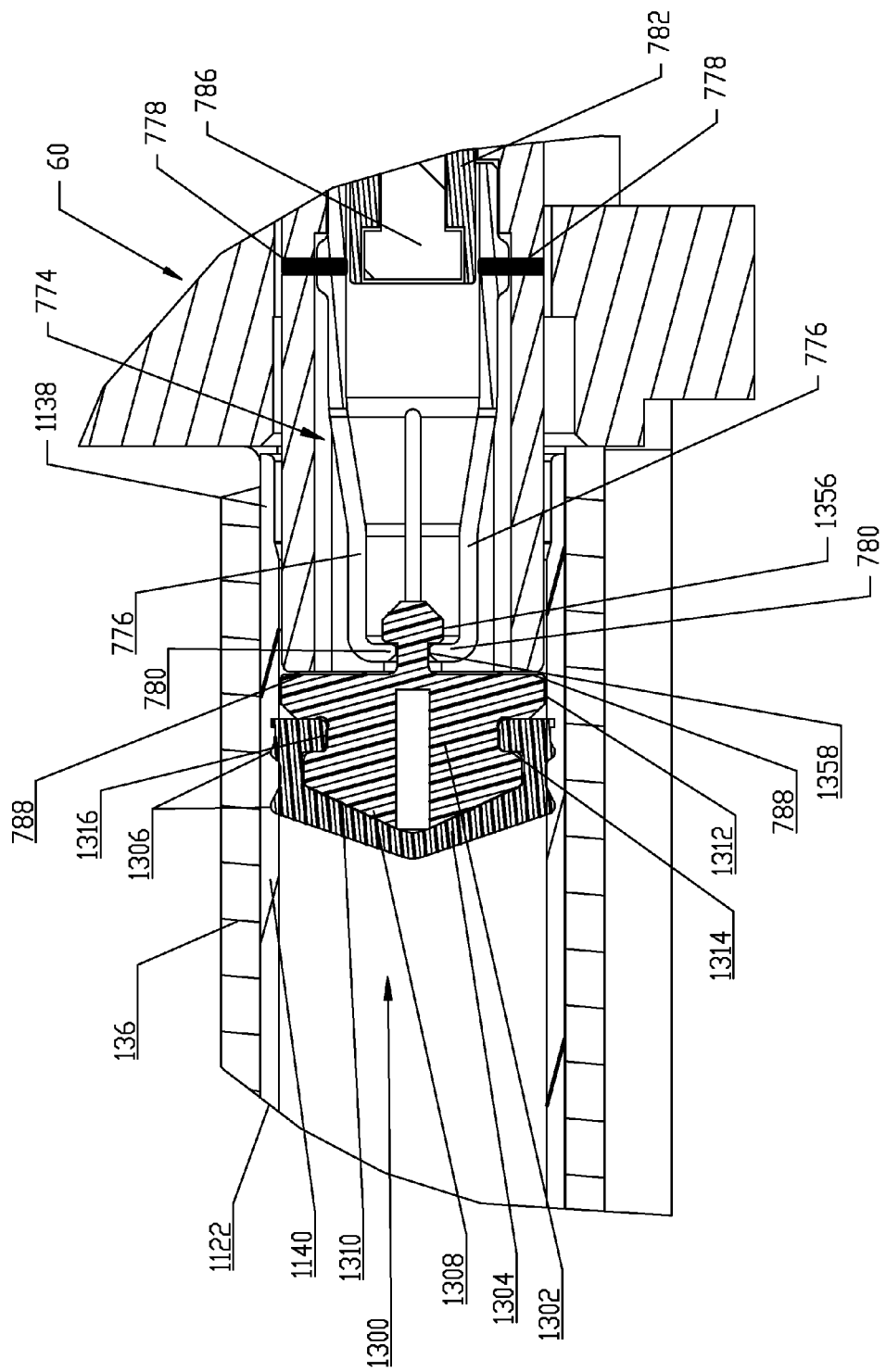
Figure 48D:
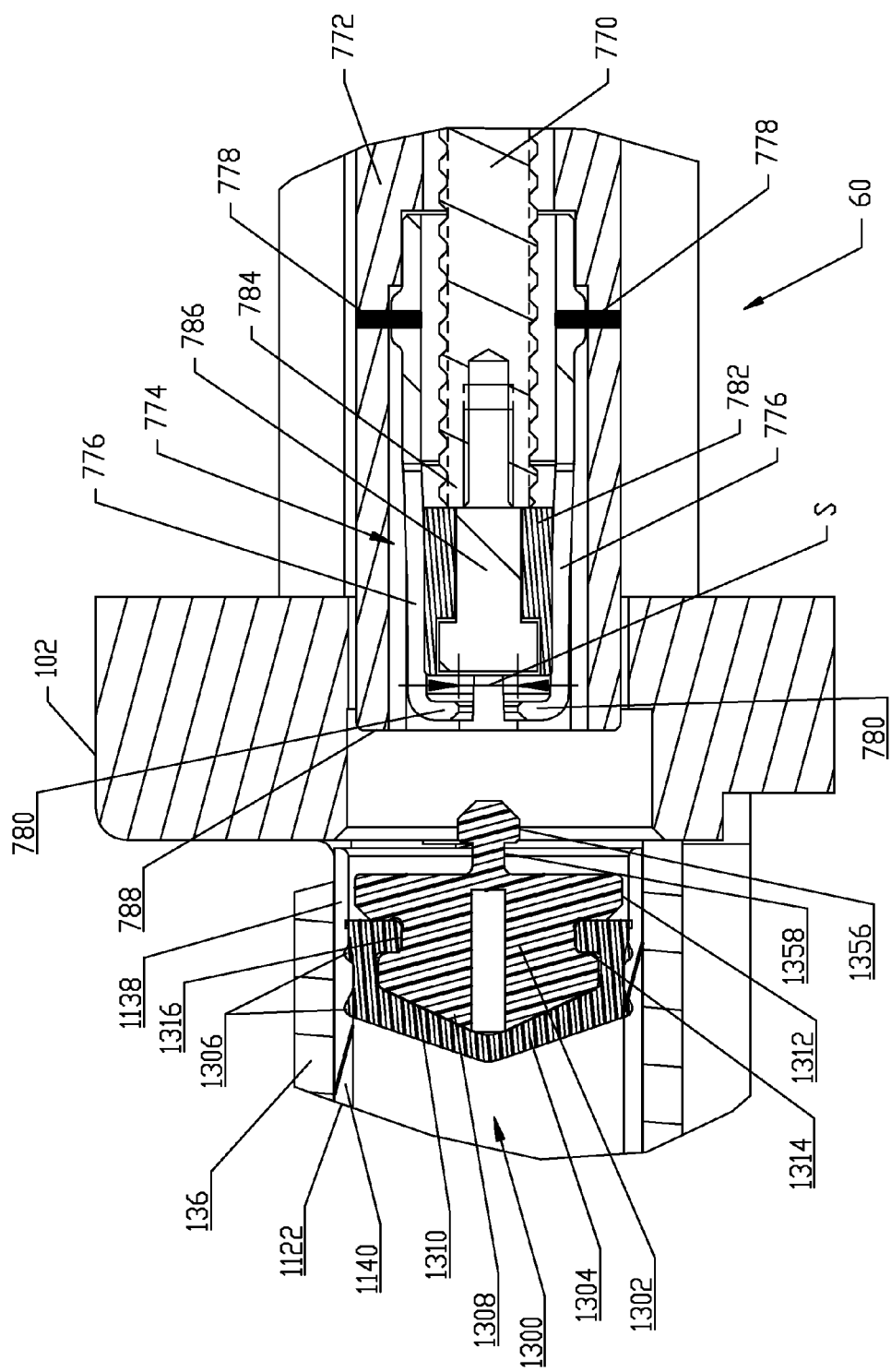
Figure 49:
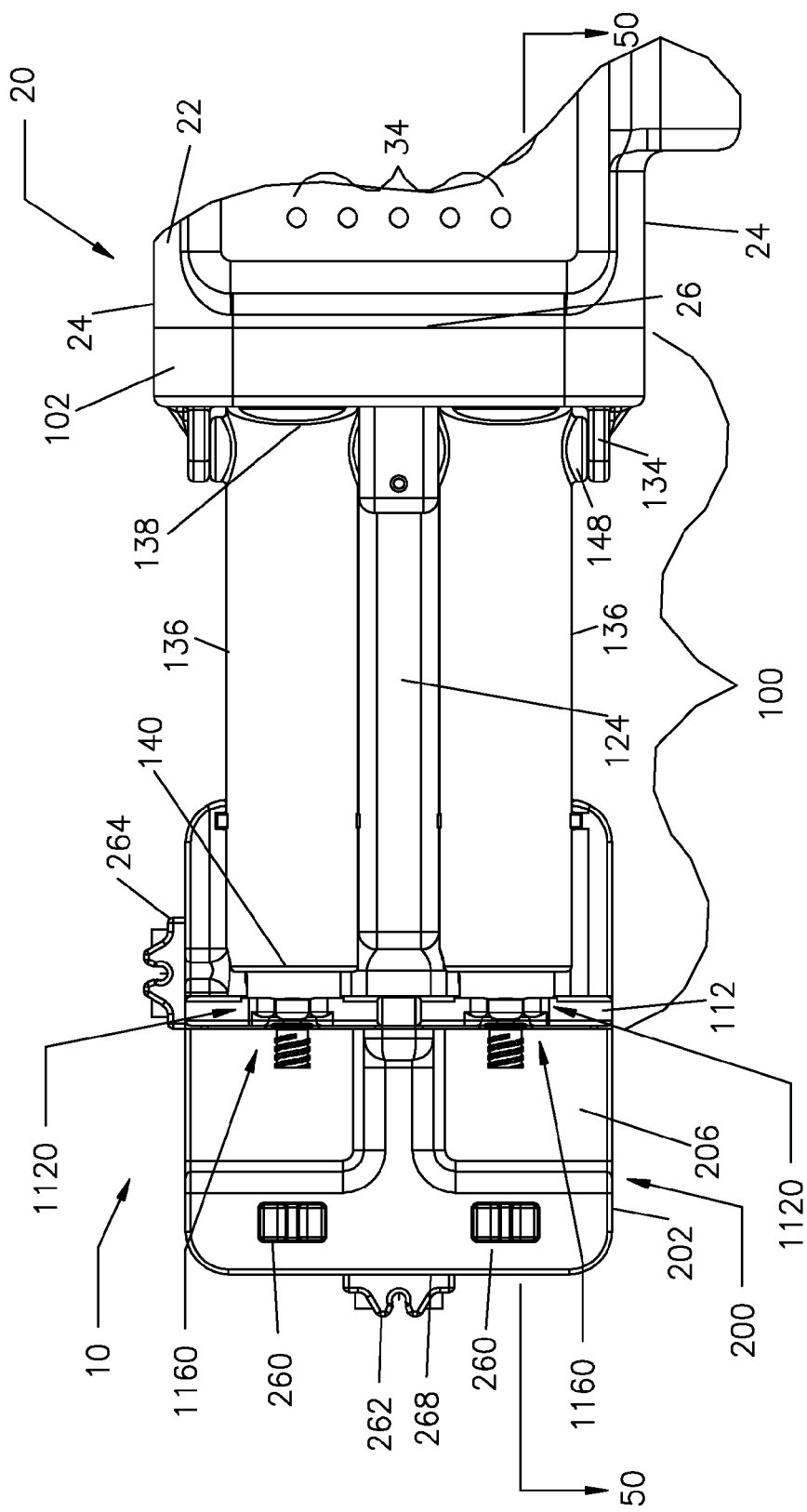
FIG. 49 is a top view of another embodiment of the fluid injector system of FIG. 1.
Figure 50:
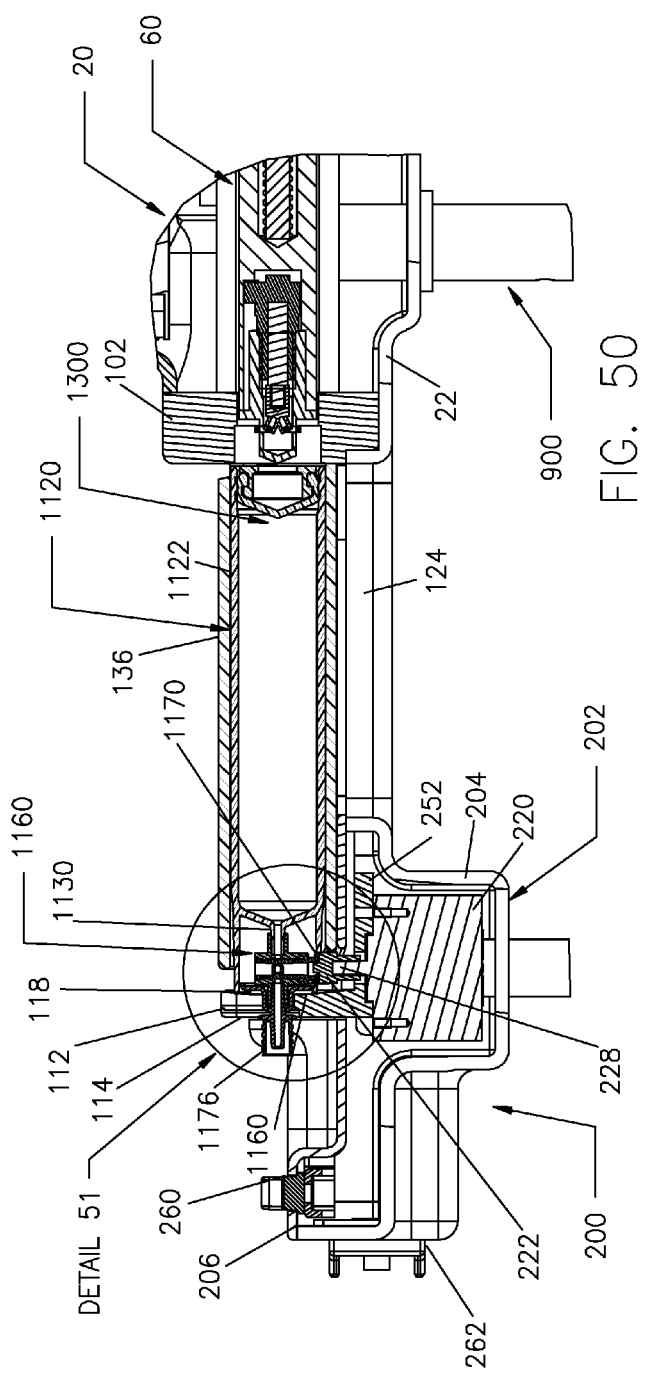
FIG. 50 is a cross-sectional view of the fluid injector system of FIG. 49 taken along Line 50-50 in FIG. 49.
Figure 51:
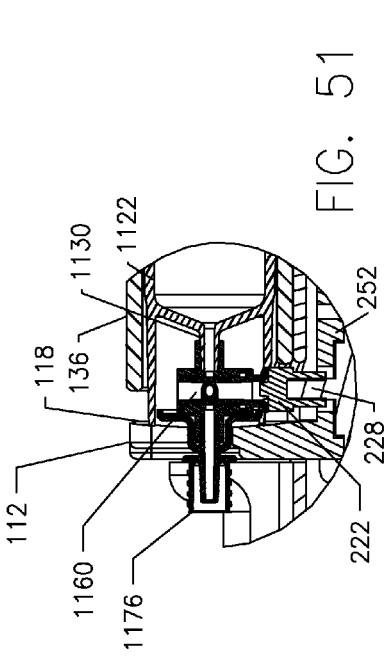
FIG. 51 is a detail cross-sectional view of Detail 51 in FIG. 50.

Opposing piston element 60 in the present embodiment comprises a ball screw shaft 770 disposed within an outer sleeve 772 and, as in previous embodiments, comprises a plunger interface element 774. The plunger interface element 774 comprises a pair of flexible attachment arms 776 that are fixed via pins 778 to the outer sleeve 772. The attachment arms 776 are biased inward toward one another and toward a central longitudinal axis of the ball screw shaft 770 and further comprise inward directed radial tips 780. A wedge 782 is fixed to a distal end 784 of the ball screw shaft 770 via a mechanical fastener 786. The wedge 782 is adapted to effect operation of the attachment arms 776 as described herein. Generally, the attachment arms 776 are maintained in a separated orientation and generally parallel to one another as shown in FIGS. 48A and 48B by the interspacing of the wedge 782 between the attachment arms 776. As the ball screw shaft 770 rotates in one direction, the outer sleeve 772 moves distally or proximally as is well-known in the powered medical injector field. As the outer sleeve 772 moves distally or forward, the attached attachment arms 776 likewise move distally or forward relative to the wedge 782 and this movement eventually removes the separating force exerted on the attachment arms 776 provided by the wedge 782. When this force is removed, the attachment arms 776 are permitted to move toward one another to engage the proximal tab or button element 1356 extending proximally from the rear flange portion 1312 of the plunger element 1302.

Referring in particular to FIG. 48A, this figure shows the pressure jacket 136 pivoted to a horizontal orientation and the syringe 1120 loaded therein ready for interfacing with piston element 60. Accordingly, the loading steps for loading the syringe 1120 into the pressure jacket 136 are again omitted in FIGS. 48A-48D, but follow the same methodology as described previously in this disclosure. As FIG. 48A shows, the proximal tab or button element 1356 extending proximally from the rear flange portion 1312 of plunger element 1302 is spaced distally from the attachment arms 776. As the ball screw shaft 770 rotates in one direction, the outer sleeve 772 moves distally or forward due to a threaded connection between a ball screw nut (not shown) and the ball screw shaft 770 and a fixed connection between the ball screw nut and the outer sleeve 772 as is well-known in the powered medical injector field. At some point, a distal end 788 of the outer sleeve 772 contacts the rear flange portion 1312 of the plunger element 1302. Moreover, as the outer sleeve 772 moves forward or distally so do the attached attachment arms 776, which move distally or forward relative to the wedge 782. The axial length of the wedge 782 is desirably selected so that a spacing S between the inward directed radial tips 780 of the attachment arms 776 is maintained substantially constant at least until the distal end 788 of the outer sleeve 772 contacts the rear flange portion 1312 of the plunger element 1302 so that the proximal tab or button element 1356 may pass between the radial tips 780. In this position, namely, when the distal end 788 of the outer sleeve 772 contacts the rear flange portion 1312 of the plunger element 1302, the radial tips 780 of the attachment arms 776 are generally aligned with the circumferential recess 1358 defined by the proximal tab or button element 1356. Further rotation of the ball screw shaft 770 causes further forward or distal movement of the outer sleeve 772 which imparts forward or distal movement to syringe plunger 1300 in the syringe body 1122 of the syringe 1120 and simultaneously forward or distal movement of the attached attachment arms 776. As a result of the rotational movement of the ball screw shaft 770 and the corresponding forward or distal movement of the outer sleeve 772 and attached attachment arms 776, the radial spacing or separating force provided by the wedge 782 against attachment arms 776 is eventually removed, allowing the inwardly-biased attachment arms 776 to capture the proximal tab or button element 1356 extending proximally from rear flange portion 1312 of the plunger element 1302.

When the wedging action of the wedge 782 is removed, the radial tips 780 of the attachment arms 776 engage the circumferential recess 1358 defined by the proximal tab or button element 1356, and a fixed engagement is now present between the syringe plunger 1300 and the piston element 60. Continued rotation of the ball screw shaft 770 causes advancement of the syringe plunger 1300 within the syringe body 1122 of the syringe 1120 due to the contact engagement between the distal end 788 of the outer sleeve 772 and the rear flange portion 1312 of the plunger element 1302 of syringe plunger 1300. Rotation of the ball screw shaft 770 in the opposite direction causes withdrawal of the syringe plunger 1300 within the syringe body 1122 of the syringe 1120 due to the interference engagement between the radial tips 780 of the attachment arms 776 and the circumferential recess 1358 defined by the proximal tab or button element 1356 extending from the rear flange portion 1312 of the plunger element 1302 of the syringe plunger 1300. When it is desired to release the fixed engagement between the syringe plunger 1300 and piston element 60, the syringe plunger 1300 is desirably withdrawn to the storage position by the piston element 60 which corresponds to placement of the syringe plunger 1300 in the storage/expansion section 1138 of the syringe body 1122 of the syringe 1120 as described previously. Continued rotation of the ball screw shaft 770 causes the attachment arms 776 to re-engage the wedge 782 and the wedge 782 begins to reassert a wedging action against the attachment arms 776 to reestablish the spacing S between the inward directed radial tips 780 of the attachment arms 776 of sufficient size to allow the distal radial tips 780 to disengage from the proximal tab or button element 1356 extending proximally from the rear flange portion 1312 of the plunger element 1302. Accordingly, additional rotation of the ball screw shaft 770 withdraws the piston element 60 from association with the syringe plunger 1300, and the proximal tab or button element 1356 extending proximally from rear flange portion 1312 of plunger element 1302 is again spaced distally from the attachment arms 776. Thereafter, the pressure jacket 136 may be pivoted upward to a removal orientation for removing the syringe 1120 from the barrel 162 of the pressure jacket 136 according to the unloading procedure set forth previously in this disclosure.

Referring to FIGS. 49-56, another embodiment of a multi-fluid medical injection/injector system 10 is shown and wherein like parts are designated with like reference numerals as designated previously in this disclosure. As the fluid injector system 10 shown in FIGS. 49-56 is generally similar to previous embodiments set forth in this disclosure only specific differences and/or modifications to the fluid injector system 10 shown in FIGS. 49-56 are described herein. As described previously, fluid injector system 10 comprises a powered injector administrator or device 20 and a fluid delivery set 1000 intended to be associated with the injector 20 to conduct one or more fluids under pressure into a patient intravenously via a patient catheter. In the present embodiment, the injector 20 is illustrated with the embodiment of piston elements 60 described in connection with FIGS. 47A-47I. The fluid delivery set 1000 in the present embodiment utilizes the single-use set 1500 described previously in this disclosure which is omitted from the various views for clarity purposes. Certain modifications to the multi-use sets 1100 are present in the current embodiment and such modifications are discussed in detail herein.

With respect to the pressure jacket support 100, the illustrated pressure jacket support 100 is substantially identical to that described previously in this disclosure with the pressure jacket support 100 having a rear plate 102 connected to the distal end 26 of the injector housing 22 of the injector 20 and a front plate 112, with the front and rear support plates 102, 112 connected by center beam 124. However, in the present embodiment, the respective slots 122 in the front plate 112 are located to be generally perpendicular to the central longitudinal axis L of the syringe body 1122 of syringe 1120 when the syringe 1120 is loaded within the receiving pressure jacket 136 and the pressure jacket 136 is in the generally horizontal position. Accordingly, the same pivotal movement of the pressure jacket 136, as described previously, automatically places the discharge conduit 1130 extending from the syringe body 1122 of the syringe 1120 into the receiving slot 122 in the front plate 112 of the pressure jacket support 100. As described herein, one difference in the present embodiment of the fluid injector system 10 lies in the orientation of the discharge conduit 1130 of the syringe body 1122 which now lies along the central longitudinal axis L of the syringe body 1122 of syringe 1120 rather than being offset therefrom as previously described in this disclosure. Therefore, as noted, the respective slots 122 in the front plate 112 of pressure jacket support 100 are no longer offset to accommodate the offset discharge conduit 1130 as described previously, but now are formed in the front plate 112 to be generally perpendicular to the central longitudinal axis L of the syringe body 1122 of syringe 1120 when the syringe 1120 is loaded within the receiving pressure jacket 136 and the pressure jacket 136 is in the generally horizontal position.

As discussed previously, the flange portion 142 and body portion 152 of each pressure jacket 136 may be separate components or be integrally formed as a single or unitary body portion 152. This type of pressure jacket 136 is illustrated in FIGS. 49-56. Unitary body portion 152 comprises all of the mounting features described previously in connection with flange portion 142. Other than the foregoing differences, the various components of the pressure jacket support 100 are the same as described previously in this disclosure.

Additionally, the fluid control module 200 in the present embodiment of fluid injector system 10 incorporates certain modifications as now described hereinafter. Initially, it is noted that the fluid control module housing 202 encloses and supports a pair of control valve actuators 220 within a depending enclosure 204 as described previously. However, the fluid control module housing 202 is now supported relative to the front plate 112 of pressure jacket support 100 so that the depending enclosure 204 locates the actuator output shaft 228 of each control valve actuator 220 on the rear or proximal side 116 of the front plate 112 for interfacing with a control valve associated with the syringe 1120 as described in detail herein. For this purpose, the front plate 112 may comprise a bottom support flange 252 to which the respective control valve actuators 220 may be secured using mechanical fasteners 254. A cover plate 206 encloses the depending enclosure 204 as described previously.

Further, the fluid control module housing 202 in the present embodiment supports a pair of top-mounted or top-located air detectors 260 to interface with the input lines 1502, 1504 associated with the single-use set 1500. Additionally, the fluid control module housing 202 supports a front-mounted or front-located air detector 262 and a side-mounted or side-located air detector 264 to interface with the respective connecting tubing 1174 to be associated with each syringe 1120 according to modifications to the syringe 1120 as described herein. The air detectors 260, 262, 264 are generally similar in form and function to the various air detectors described earlier in this disclosure. With reference to the plan view of the fluid injector system 10 of FIG. 49, it is noted that the "top" syringe 1120 in this view will have its associated connecting tubing 1174 interfaced with the side-mounted air detector 264 and the "lower" syringe 1120 in this view will have its associated connecting tubing 1174 interfaced with the front-mounted air detector 262. Additionally, the front and side mounted air detectors 262, 264 may comprise tubing attachment elements 268 in a similar manner to tubing attachment elements described previously in this disclosure.

As discussed in the foregoing, the syringe 1120 adapted for use in the fluid injector system 10 according to the present embodiment is modified, in one respect, so that the discharge conduit 1130 of the syringe body 1122 which now lies along the central longitudinal axis L of the syringe body 1122 of syringe 1120 rather than being offset therefrom as previously described in this disclosure. Nonetheless, the syringe 1120 comprises similar features to that described previously. Generally, syringe 1120 comprises an elongated, cylindrical syringe body 1122 having a front or distal end 1124 and a rear or proximal end 1126. However, in the present embodiment of the syringe 1120, the distal end 1124 of the syringe body 1122 comprises an outer skirt 1250 enclosing a conical-shaped distal portion or end 1252 and from which discharge conduit 1130 extends distally. The conical-shaped distal portion or end 1252 tapers inward at an angle of about 22.degree. in a similar manner to the way the distal portion or end 1124 of the syringe body 1122 tapers to the apex or cone point 1128 in the previously discussed embodiment of the syringe body 1122. The discharge conduit 1130 has a discharge port 1134 that is now coaxial with the central longitudinal axis L of the syringe body 1122 and the discharge conduit 1130 may be formed with a conventional luer fitting-type connection to mate with additional downstream components of the multi-use set 1100 adapted for use with the present embodiment of the fluid injector system 10.

The proximal end 1126 of the syringe body 1122 may also be formed with an expansion/storage section 1138. A generally cylindrical "working" section 1140 of the syringe body 1122 connects the distal and proximal ends 1124, 1126 of the syringe body 1122 and is defined essentially forward or distal of the expansion/storage section 1138 of the syringe body 1122. The cylindrical section 1140 of the syringe body 1122 has a relatively uniform outer diameter and the outer skirt 1250 extends distally from the cylindrical section 1140 of the syringe body 1122. The outer skirt 1250 generally tapers inward slightly from the outer diameter of the cylindrical section 1140 of the syringe body 1122. The expansion/storage section 1138 is provided generally as a storage section or area for the syringe plunger 1300, as described previously. The proximal end 1126 of the syringe body 1122 is desirably formed with an outward extending lip 1142 (not shown in FIGS. 49-56) to provide strength and rigidity to the storage/expansion section 1138 of syringe body 1122 or provide other functions as also described previously.

The outer skirt 1250 further defines a pair of side openings 1254, 1256. The side openings 1254, 1256 are formed in the outer skirt 1250 to be generally perpendicular to one another. As will be appreciated from viewing FIG. 52, for example, side opening 1256 is actually intended as a "bottom" opening in the outer skirt 1250 to allow passage of the actuator output shaft 228 of the control valve actuator 220. Accordingly, it will be appreciated that loading of the syringe 1120 into receiving pressure jacket 136 is orientation-specific and generally requires the syringe body 1122 to be oriented so that the side or bottom opening 1256 in outer skirt 1250 on the syringe body 1122 faces downward in the pressure jacket 136. The interfacing tab or key elements 1144 that mate with the keyway 158 in the body portion 152 of the pressure jacket 136 automatically orient the bottom opening 1256 into the correct orientation. Accordingly, as the pressure jacket 136 is pivoted to a generally horizontal or working position with the syringe 1120 present therein, the side or bottom opening 1256 permits the actuator output shaft 228 of the associated control valve actuator 220 to pass through the opening 1256. A distal edge 1258 of outer skirt 1250 desirably exhibits an arcuate or curved shape and the receiving recesses 118 in the rear or proximal side 116 of the front plate 112 are now desirably formed with a mating arcuate or curved shape. This mating configuration provides a similar self-centering function for the syringe 1120 when pressurized as that described previously in this disclosure.

As with previously discussed embodiments, the multi-use sets 1100 for use in the present embodiment comprise a fluid control valve 1150 and, particularly, a three-way stopcock valve 1160. Stopcock valve 1160 is generally similar to that described previously and comprises a valve body 1161 defining three ports, 1162, 1164, and 1166 and a plug 1168 actuated by an actuation handle 1170. In the present embodiment of the stopcock valve 1160, the actuation handle 1170 is disposed at the bottom end of the plug 1168 so as to be in a position to interface the actuator output shaft 228 of the associated control valve actuator 220. The first port 1162 is fluidly coupled to the discharge conduit 1130 on syringe body 1122 of syringe 1120 and this fluid coupling may be a permanent connection by the methods described previously or, alternatively, a disconnecting connection may be provided between the first port 1162 and the discharge conduit 1130 on the syringe body 1122. The second port 1164 is fluidly coupled to a conventional connector spike 1175 via connecting tubing 1174 as described previously in this disclosure but omitted in FIGS. 49-56 for clarity purposes. The third port 1166 is provided with a fluid connector 1176 which again is affixed to the third port 1166 via any of the conventional permanent joining methods described in the foregoing or a disconnecting arrangement may be provided as an alternative if desired. The fluid connector 1176 may comprise a radial skirt 1260 which faces the outer skirt 1250 on the syringe body 1122 to enclose an annular space 1262 around the discharge conduit 1130 for sterility purposes. As described previously, due to the pressures generated during operation of the syringe 1120, a permanent and robust fluid connection between the third port 1166 and the fluid connector 1176 and between the first port 1162 and the discharge conduit 1130 on the syringe body 1122 of syringe 1120 is generally preferred in accordance with this disclosure.

As described previously, each control valve actuator 220 is adapted to selectively position the stopcock actuation handle 1170 to achieve at least three set positions of the stopcock valve 1160, namely: (1) an inject or open position, wherein the first port 1162 is in fluid connection with the third or outlet port 1166; (2) a fill position, wherein the second port 1164 is in fluid connection with the first port 1162 to allow filling of the syringe 1120 via the connector spike 1175 and the connecting tubing 1174 associated with a fluid supply container 36, 38; and (3) a closed or isolation position, wherein the first and second ports 1162 and 1164 are isolated from the third or outlet port 1166.

The loading of syringes 1120 into the pressure jackets 136 of the pressure jacket support 100 is substantially identical to the procedure described previously in this disclosure other than for the differences noted in the foregoing. In particular, when loading the syringe 1120 into the pressure jacket 136 in the upward pivoted position of the pressure jacket 136, the bottom opening 1256 in the syringe skirt 1250 generally faces downward so as to orient the actuation handle 1170 disposed at the bottom end of the plug 1168 of the stopcock valve 1160 in a position to directly interface the actuator output shaft 228 of the associated control valve actuator 220. Accordingly, as the pressure jacket 136 is pivoted downward generally to a horizontal orientation in the pressure jacket operating space 104, the actuator output shaft 228 automatically engages the actuation handle 1170 to form the operative engagement between the actuation handle 1170 and the control valve actuator 220. Additionally, as the pressure jacket 136 is pivoted downward, the distal edge 1258 of the outer skirt 1250 matingly engages with the corresponding arcuate or curved shape of the receiving recesses 118 in the rear or proximal side 116 of the front plate 112. This mating configuration provides a similar self-centering function for the syringe 1120 when pressurized as that described previously in this disclosure.

Referring next to FIGS. 57-59 and with continued reference to FIGS. 49-56, the fluid injector system 10 according to the illustrated embodiment exhibits a different movement of the injector 20 as it moves from the syringe loading position or orientation to the fluid priming and air purge position and then to the inject position. As shown in FIGS.

58A-58C, the injector 20 is supported by a pedestal support 900 comprised of a support column 902 which may have a lower end 904 adapted to interface with a patient supporting surface such as an examination table. The injector housing 22 is pivotally supported to the support column 902 via pivot pin 906. Additionally, a conventional IV pole 908 is pivotally connected to the fluid control module housing 202 via a pivot pin 910. A link arm 912 has a first end 914 and a second end 916. First end 914 of link arm 912 is pivotally connected to the support column 902 via a pivot pin 918 and the second end 916 of the link arm 912 is pivotally connected via a pivot pin 920 to a lower end 922 of IV pole 908. The foregoing configuration defines a four bar linkage arrangement wherein the support column 902 defines the ground link, the injector housing 22 defines one grounded link, the link arm 912 defines the second grounded link, and the IV pole defines the coupler link as is well-known the field of kinematics.

In the present embodiment of the fluid injector system 10, association of the respective multi-use sets 1100 used with the injector 20 is substantially similar to that described previously and generally comprises inserting the respective syringes 1120 into the corresponding pressure jackets 136 according to the loading steps described previously. However, as FIG. 57A demonstrates, while the injector 20 is still in a horizontal orientation for loading syringe 1120 into the pressure jackets 136 in the present embodiment, the injector 20 is oriented on its side (e.g., one lateral side 24) so that the pressure jackets 136 are disposed one above the other. Accordingly, to load the respective pressure jackets 136 in the manner described previously in this disclosure requires that the pressure jackets 136 pivot laterally outward from the injector 20, rather than pivot upward relative to the injector 20 as described previously. Nonetheless, the loading steps set forth previously for loading the syringes 1120 into the respective pressure jackets 136 result in the discharge outlet 1130 extending distally from the syringe body 1122 of each syringe 1120 being seated into the corresponding slot 122 defined in the front plate 112 of the pressure jacket support 100. Now, however, the arcuate distal edge 1258 of the outer skirt 1250 on each syringe body 1122 engages the mating arcuate or curved shape of the receiving recesses 118 in the rear or proximal side 116 of the front plate 112 of the pressure jacket support 100. Additionally, the pivoting movement of the pressure jackets 136 to return the pressure jackets 136 into their respective pressure jacket operating spaces 104 defined by the pressure jacket support 100 results in the actuation handle 1170 disposed at the bottom end of the plug 1168 for each stopcock valve 1160 being automatically mechanically interfaced with the actuator output shaft 228 of the associated control valve actuator 220. With each pressure jacket 136 pivoted laterally into its pressure jacket operating space 104, each of the two multi-use sets 1100 is ready for use. The association of the single-use set 1500 with the respective multi-use sets 1100 is the same as described previously in this disclosure. Moreover, the details regarding associated the various tubing elements associated with the multi-use sets 1100 with the front and side mounted air detectors 262, 264 on the fluid control module 200 are available in the foregoing description of these detectors. Once the multi-use sets 1100 have been installed and fluid supplies are connected to the respective multi-use sets 1100 in the manner described previously in this disclosure, the electronic control device(s) associated with injector 20 causes the piston elements 60 to drive the captured syringe plungers 1300 distally forward to contact and seat against the conically-tapered distal end 1124 of the syringe body 1122. Once the foregoing initial set-up sequence is completed, the injector 20 may be moved to a fluid priming and air purge position as discussed hereinafter.

Figures 58A, 58B, 58C:
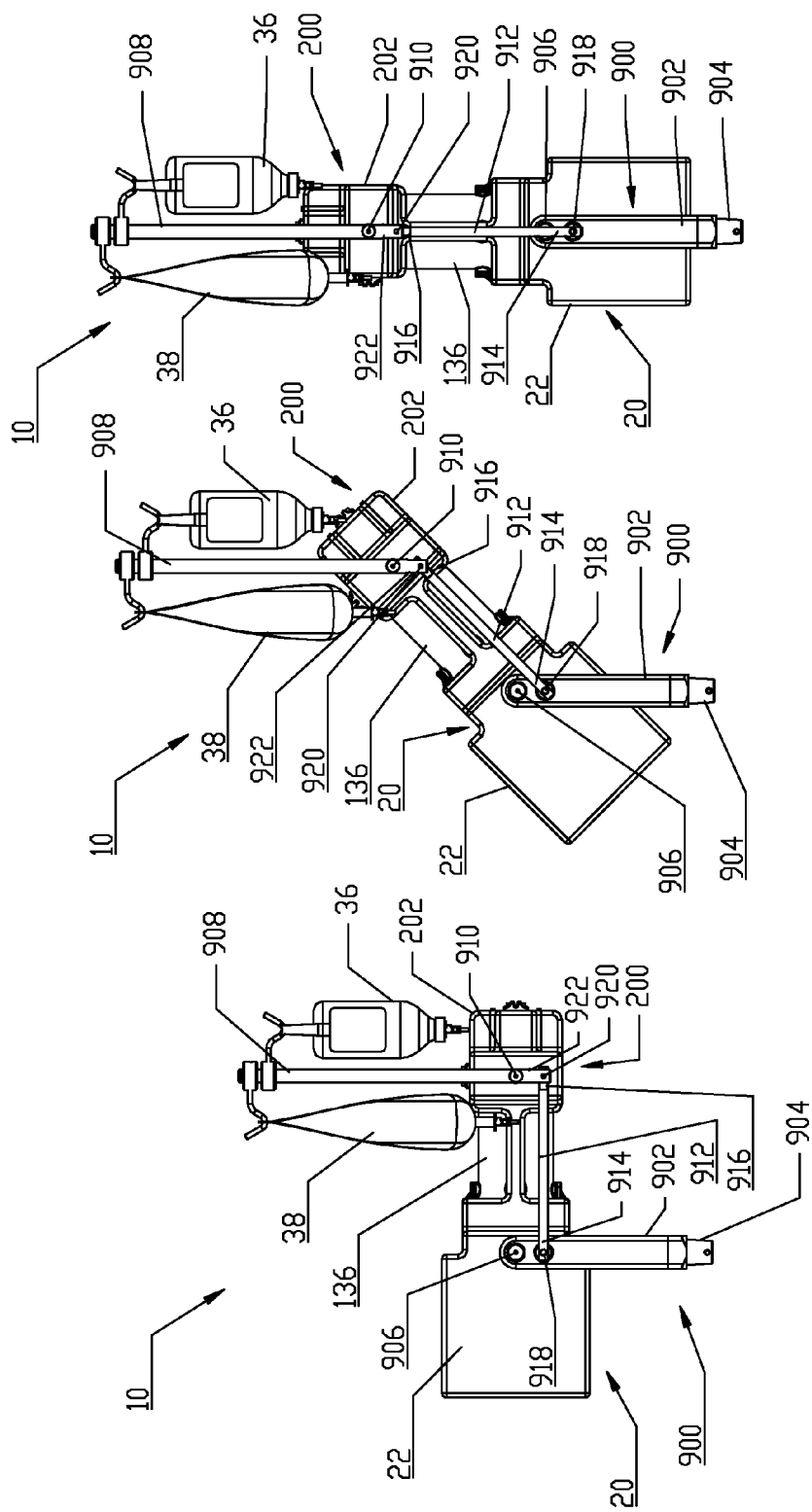
FIGS. 58A-58C are rear views of the fluid injector system of FIG. 49 illustrating the same sequence of movement shown in FIGS. 57A-57C but from the reverse side of the fluid injector system.

To reach the fluid priming and air purge position, the injector 20 pivots about pivot pin 906 connecting the injector housing 22 to the support column 902. As this pivoting movement occurs, the link arm 912 likewise pivots about pivot pin 918. IV pole 908 remains upright during the pivoting movement of the injector 20 and link arm 912 via the dual pivotal connections provided by pivot pins 910, 920. As the injector 20 pivots to reach a generally vertical orientation, as shown in FIGS. 57C, 58C, and 59C, the IV pole 908 and link arm 912 generally vertically align with the support column 902 along a generally vertical axis. In the vertical orientation of the injector 20, the syringes 1120 loaded in pressure jackets 136 are positioned vertically with the discharge conduit 1130 extending from the syringe body 1122 of each syringe 1120 loaded into the respective pressure jackets 136 pointed upward. With the syringes 1120 positioned with the discharge conduit 1130 on each syringe body 1122 pointed upward, any air bubbles associated with the filling of the respective syringes 1120 with fluid will be present at the tapered distal end 1124 of the syringe body 1122 of each syringe 1120 and in a position for easy purging from the syringe body 1122. Once the injector 20 is placed in the vertical position or orientation as illustrated, the attendant operator may press the "Fill/Purge" hard-wired button 34 on the injector 20 to fill the respective syringes 1120 with fluid and purge out air remaining in the syringe body 1122 of each syringe 1120. An exemplary automated sequence for the fluid priming and air purge cycle was described previously in this disclosure and is applicable to the present embodiment of fluid injector system 10.

Once the fluid fill and air purge cycle is complete, the injector 20 is returned to a horizontal orientation as shown in FIGS. 57A, 58A, and 59A, and is again positioned on its side wherein the pressure jackets 136 and syringes 1120 loaded therein are orientated one above the other. To reach this inject orientation, the injector 20 pivots about the pivot pin 906 connecting the injector housing 22 to the support column 902 but now in the reverse direction. As this pivoting movement occurs, the link arm 912 likewise pivots about pivot pin 918, again in the reverse direction. The IV pole 908 again remains upright during the pivoting movement of the injector 20 and link arm 912 via the dual pivotal connections provided by pivot pins 910, 920. As the injector 20 pivots to reach a horizontal orientation on its side, the syringes 1120 loaded in the pressure jackets 136 are again positioned generally horizontal with their discharge conduits 1130 pointed generally horizontally. It is when the injector 20 is rotated to the inject position that it is desirable to connect the single-use set 1500 to the respective multi-use sets 1100 operatively associated with the injector 20 and, further, optionally interface the single-use set 1500 to the downstream or secondary air detector module 360 (if present). Once the single-use set 1500 is joined to the respective multi-use sets 1100, the single-use set 1500 is primed with fluid and purged of air according to the exemplary procedure(s) described previously in this disclosure. When the fluid priming and air purging procedure for the single-use set 1500 is completed, the injector 20 may be used in a fluid delivery procedure. Moreover, any of the refilling procedures described previously may be conducted using the fluid injector system 10 described in connection with FIGS. 49-59. Likewise the removing, storing, and reuse of a used multi-use set 1100 as described previously in this disclosure may be conducted using the present embodiment of the fluid injector system 10. Further, it is also noted that the foregoing four-bar linkage pivoting motion of the injector 20 has distinct advantages in that the fluid supply containers 36, 38 may again be kept close to the syringes 1120 thereby decreasing the tubing lengths between the fluid supply container 36, 38 and syringes 1120 and, as a result, decreasing the fill or refill time for the syringes 1120.

The respective embodiments of the fluid injector system 10 set forth in this disclosure can provide simultaneous flow of two fluids, for example, contrast and saline in the foregoing embodiments at desired pressures during a diagnostic or therapeutic procedure, such as angiography. Simultaneous flow can have significant clinical benefits to a patient having the procedure. These benefits include improved image quality with less contrast dosing. The reduced contrast dosing is the result of delivering contrast agent with a flushing agent simultaneously. If excessive contrast can be reduced in this manner, it provides patient benefits through reduced toxicity levels, and provides more imaging options to patients with renal impairments. In an angiographic type procedure, for example, due to the fact that a clinician is observing the contrast in close proximity to the catheter where the fluid is delivered, phased delivery of such fluid would be readily observable in the vasculature. This differs from a computed tomography (CT) application, where imaging is often performed after a level of diffusion in the body.

Several fluid delivery techniques could be provided through the simultaneous delivery of saline and contrast utilizing the fluid injector systems 10 of this disclosure. One such fluid delivery technique is a pulse-type flow delivery. This would entail discrete motion of the piston elements 60. For example, one piston element 60 may move a discrete distance allowing a specific volume of saline to be injected into the patient; this could then be followed by a "pulse" of contrast initiated by the second piston element 60, then followed by saline initiated by the initial "saline" piston element 60. This pulsing effect may have clinical advantages in several areas. For example, in peripheral diagnostic applications, a discrete volume of contrast with a given volume that opacifies the blood vessel over a given length could be grouped together in an alternating saline-contrast-saline delivery. This discrete contrast volume is then pushed down the peripheral vasculature by a significant volume of saline. Typically, 70-100 ml volumes are used in such "run-off" type procedures. If this discrete contrast volume is synced with the movement of the imaging scanner through communication with the injector 20, a small volume of contrast could be tracked to illuminate any restrictions or blockages and, thereby, significantly reduce the amount of contrast agent that must be injected into the patient.

Additionally, through discrete coupled motion of the piston elements 60, saline flushing applications in diagnostics or therapeutics could have a "strobing" effect. This effect allows a discrete injection of saline to be initiated by the saline side piston element 60 followed by a discrete injection of contrast by the contrast side piston element 60, followed again by another discrete injection of saline. It may be desirable to make the discrete injections of saline to be a higher discrete volume than the discrete volumes of contrast so that the total volume of contrast delivered is reduced. This quick pulse or "strobing" effect could provide feedback information to the clinician during placement of a stent, angioplasty, or other therapeutic approach, while reducing the amount of contrast delivered to the patient. The "strobing" effect could be configured for a time base or pattern.

While the foregoing pulsed flow delivery could be accomplished through discrete motion of the piston elements 60, this effect could also be arrived at through operation of fluid control valves 1150 according to any of variations of the fluid control valves 1150 provided in this disclosure. However, this disclosure is not limited to the specific examples provided in the foregoing and suitable "valving" for these applications could take the form of stopcocks, pinch valves, check valves, or other mechanisms that enable flow to be alternately enabled and shut-off from the saline side syringe 1120 and the contrast side syringe 1120. This type of flow switching could take many forms from a very rapid succession with small volumes to a much larger drawn out pulsing effect when several milliliters of volume of one fluid are injected over several seconds then switched to the second fluid for a short or long interval, and then back to the first fluid.

Further, in a steady state, simultaneous flow situation, when the piston elements 60 are driven substantially simultaneously at a constant speed, adjusting the speed ratio of the piston elements 60 (e.g., saline piston element 60 speed to contrast piston element 60 speed) dynamically during a fluid injection procedure has the effect of increasing the image intensity or decreasing it as a function of time, volume, or user control. In addition, operational control of the "valving" as described in the foregoing paragraph provides the same effect as adjusting piston element speed.

To enable effective simultaneous flow delivery in fluid injector system 10 according to the embodiments of this disclosure, substantially equal pressure must be present in each line input line 1502, 1504 of the single-use set 1500 along with an accounting for the capacitance in the system. Algorithms may be provided in the electronic control device(s) associated with the injector 20 to generally adjust for system capacitance and equalize pressure in the fluid injector system 10 so as to enable fluids from two fluid sources associated with fluid injector system 10 to flow simultaneously. It is desirable to actuate the piston elements 60 substantially simultaneously in simultaneous flow delivery applications to equalize the pressure in each line. If the injector 20 is operated with differential pressure in each line input line 1502, 1504 of the single-use set 1500, the fluid in the lower pressure line may be stopped or reversed until sufficient capacitance is taken up in that line and sufficient pressure is achieved to enable flow. This time delay could reduce the usefulness of the image quality.

The foregoing multi-fluid injection techniques are desirable for reducing contrast dosing to a patient while providing effective imaging. By supplementing the overall fluid delivery procedure with saline, additional hydration of the patient occurs automatically and allows for flushing the renals enabling the body to remove the toxicity of the contrast media. In addition to improved patient comfort level and less toxicity, introduction of saline at clinically significant pressures and flow rates also allows higher flow rates to be achieved at lower pressure settings on the injector 20.

In another application, the embodiments of the fluid injector system 10 of this disclosure may be applied to calculate the blood flow rate in an artery. To obtain blood flow rate in an artery, two measurements are required. The first measurement is the inside diameter (ID) of the artery and, second, the linear velocity of the contrast bolus within the artery. The flow rate can then be calculated using the simple formula: $Q=AV$, where Q is the flow rate, A is the area of the inside cross-sectional area of the artery, and V is the linear velocity of the contrast bolus flow front. Measuring the artery inside diameter (ID) may be done on a fluoroscope when the bolus of contrast fills the artery and is routinely done to measure stent sizes needed for an interventional procedure. The linear velocity of the contrast bolus can also be measured on the fluoroscope after the sharp contrast bolus is injected by measuring the distance the flow front or bolus moves in a known time period. Velocity can be calculated by the formula: V=D/T, where V is the linear velocity, D is the distance the flow front of contrast traveled, and T is the unit of time that it takes for the flow front of contrast to travel the measured distance.

An important consideration in this method to obtain accurate flow rate information is delivering a tight, well defined contrast bolus in a short period of time. This can be accomplished in several ways. The contrast bolus can be preceded and followed by a volume of saline that is pre-positioned and primed into a tubing set. The injector 20 may then be triggered to deliver a high flow rate for a short period of time to flush the contrast bolus into the artery. The high instantaneous flow rate, in one example, can be accomplished by pre-pressurizing a syringe behind a closed valve, for example stopcock valve 1160, to remove all system compliance, and then opening the valve quickly for a short period of time to deliver the contrast bolus. These injection steps can be automated on the fluid injector system 10 via programming residing in the electronic control device(s) associated with the injector 20 for ease of use.

The single flow rate measurement described hereinabove only represents the flow rate in the artery at a given moment in time. The actual flow rate in an artery varies depending on the heart cycle. The injector 20 may be triggered based on the heart pulse to deliver the sharp contrast bolus at any desired point within the heart cycle to give maximum, minimum, or average flow rate measurements. Additionally the electronic control device(s) associated with the injector 20 may be programmed to give a multiple pulsatile flow, injecting saline followed by contrast followed by saline repeatedly, as described previously. This multiple pulsatile flow allows multiple measurements to be obtained that would characterize the artery flow rate for the complete heart cycle.

The actual measurements taken to obtain the flow rates as described above can be automated by either incorporating the measurement functions into the imaging scanner hardware and software or by employing a separate vision system looking at the display fluoroscope. The vision system could automatically measure the artery diameter, distance travel per unit time, and then perform the desired flow rate calculation automatically and display the results graphically for the clinician. This foregoing application represents a novel use of the injector 20 for measurement of blood flow rate using small volume pulsed contrast injections.

In another feature of fluid injector system 10 according to the embodiments of this disclosure, it is known that when simultaneous flow from two syringes is joined together in a "Y" joint or similar connection, both syringes encounter the same average pressure. In the present fluid injector system 10, syringes 1120 encounter this situation due to the presence of Y-connector 1508 in the single-use set 1500. This average pressure causes both syringes 1120 to swell or have extra capacitance. The capacitance swelling is a function of the average pressure, syringe material, syringe shape, and plunger design.

If one of the piston elements 60 pushing fluid in a syringe 1120 is significantly faster than the other, for example two to three times faster, the slower piston element 60-syringe 1120 combination has a faster growing capacitance or volume than the volume being taken up by the syringe plunger 1300 moving forward in the slower piston element 60-syringe 1120 combination. In this situation, fluid in the tubing line (e.g., either input line 1502 or input line 1504) from the faster piston element 60-syringe 1120 combination will be pushed into the tubing line that leads to the slower piston element 60-syringe 1120 combination, thereby exhibiting a reverse flow situation.

This reverse flow situation can be present in any two-syringe injector systems. The amount of back or reverse flow increases when the relative speed difference is large, the simultaneous fluid flow is through a small restriction, the speed of the total fluid injection is large, and the viscosity of the fluid is high. The back or reverse flow can prevent different ratios of simultaneously delivered fluid from ever occurring in certain injections, which can be a detriment for all two-syringe type injector systems. A solution to this problem is to speed up the slower moving piston element 60 in the fluid injector system 10 in proportion to the capacitive swelling that is occurring. Thus, the ratio of simultaneous fluid delivery can be maintained. The capacitance algorithm to accomplish this result first calculates the capacitive swelling as a function of pressure (P) for the fluid delivery set 1000 used in the fluid injector system 10, which can be represented as follows: Cap (P)=volume in milliliters. This function can be derived from empirical testing or derived from material and shape calculations of the fluid delivery set 1000. In the simplest case, it can be represented by a linear function. The capacitance algorithm then samples pressure at set time intervals and calculates the capacitance at this rate. At each sample measurement, the change in capacitance is calculated and divided by the sample rate time: Speed Up Flow={Cap(P(t1))–Cap(P(t2))}/Ts. The foregoing approach is advantageous because it can be done with just knowledge of the pressure in the syringe 1120 and knowledge about the characteristics of the fluid delivery set 1000.

Use of test injections can further allow for determination of a pressure drop across the fluid delivery set 1000 prior to entering a catheter. In this application, a series of either one continuous or multiple small test injections without a catheter connected to the catheter connector conduit 1514 may be conducted by the electronic control device(s) associated with the injector 20. These injections are preprogrammed, using slow rise times so as to obtain accurate pressure measurements of the fluid delivery set 1000. A prediction of the pressure loss over the fluid delivery set 1000 is generated by the electronic control device(s) associated with injector 20 for any flow rate. It is known that powered fluid injector systems typically use a variety of sensing mechanisms to determine pressure within a syringe and such sensing mechanisms are desirably part of the injector 20 in the present fluid injector system 10. Using the predicted pressure loss, electronic control device(s) associated with the injector 20 can calibrate the pressure offset at the end of the single-use set 1500 and effectively subtract the losses generated by the internal restriction pressure drops throughout the length of the fluid delivery set 1000. This pressure loss calculation allows the pressure at the catheter inlet to be established at the rated catheter pressure, thus enabling increased flow. This pressure loss predication can then be displayed on the graphical user interface (GUI) display windows 32 on the injector housing 22, or other associated GUI's. Additionally, control parameters may be preprogrammed based on the maximum fluid delivery possibility and this feature would provide clinicians a derived fluid injection profile and provide them with an enhanced range of fluid delivery.

In another feature of the fluid injector system 10, during a simultaneous flow application, the volume of the fluid in the fluid delivery set 1000 and the catheter connected thereto has a given ratio of fluids, typically saline and contrast, based on the last injection parameters. Further, it is often desirable to determine desired optimal fluid ratios of saline and contrast for upcoming injections. However, as noted, a fluid ratio may already be present in the fluid delivery set 1000 and the connected catheter, and this previous fluid mixture must be flushed from the fluid delivery set 1000 and the connected catheter so as to not contaminate the new desired fluid ratio. Another algorithm residing in the electronic control device(s) associated with the injector 20 makes use of the geometry of the fluid delivery set 1000 and connected catheter to adequately flush these elements to prepare for a new fluid ratio in an automated manner and have this new fluid ratio available at the catheter tip. As a result, simultaneous flow applications using the fluid injector system 10 have increased effectiveness particularly in cardiology procedures.

Figure 60:
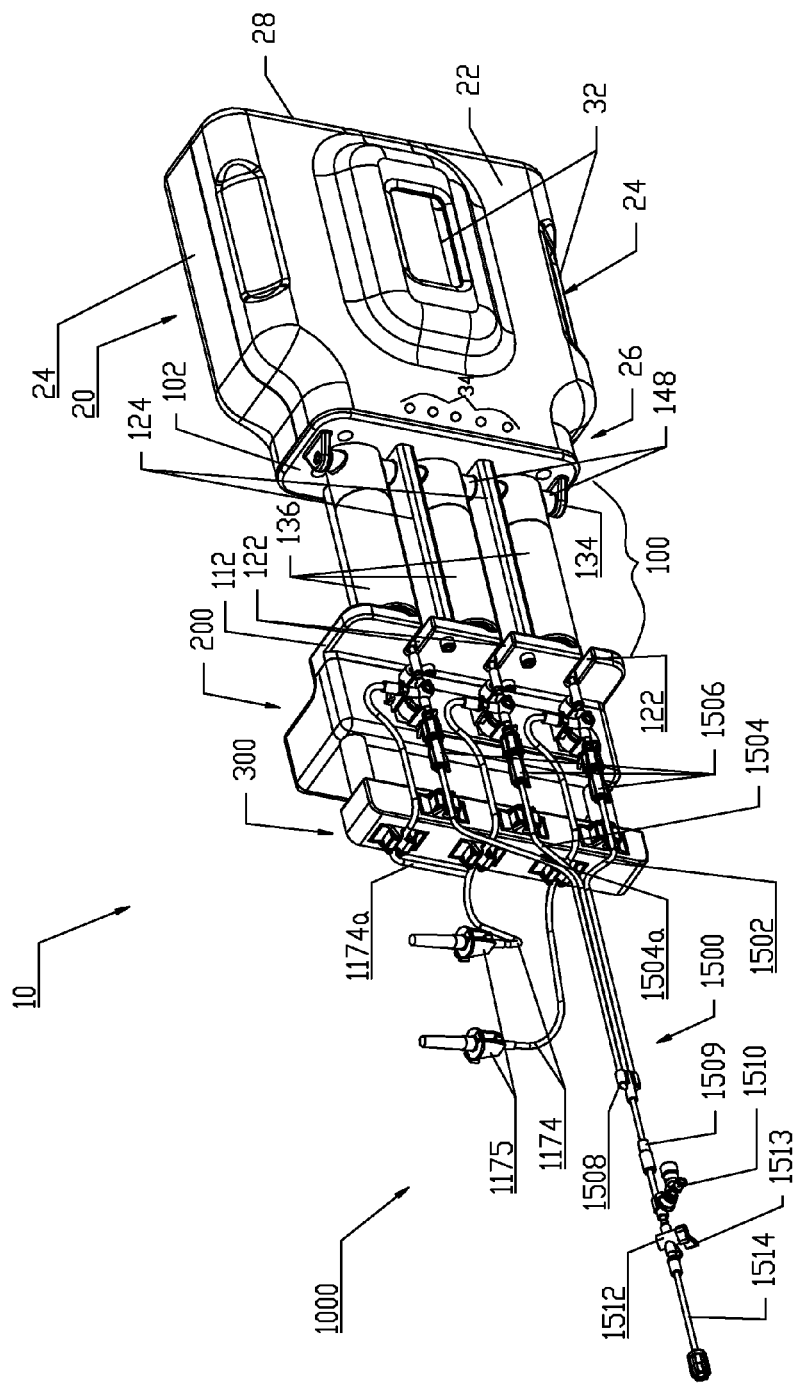
FIG. 60 is a perspective view of another embodiment of the fluid injector system of FIG. 1.
Figure 61:
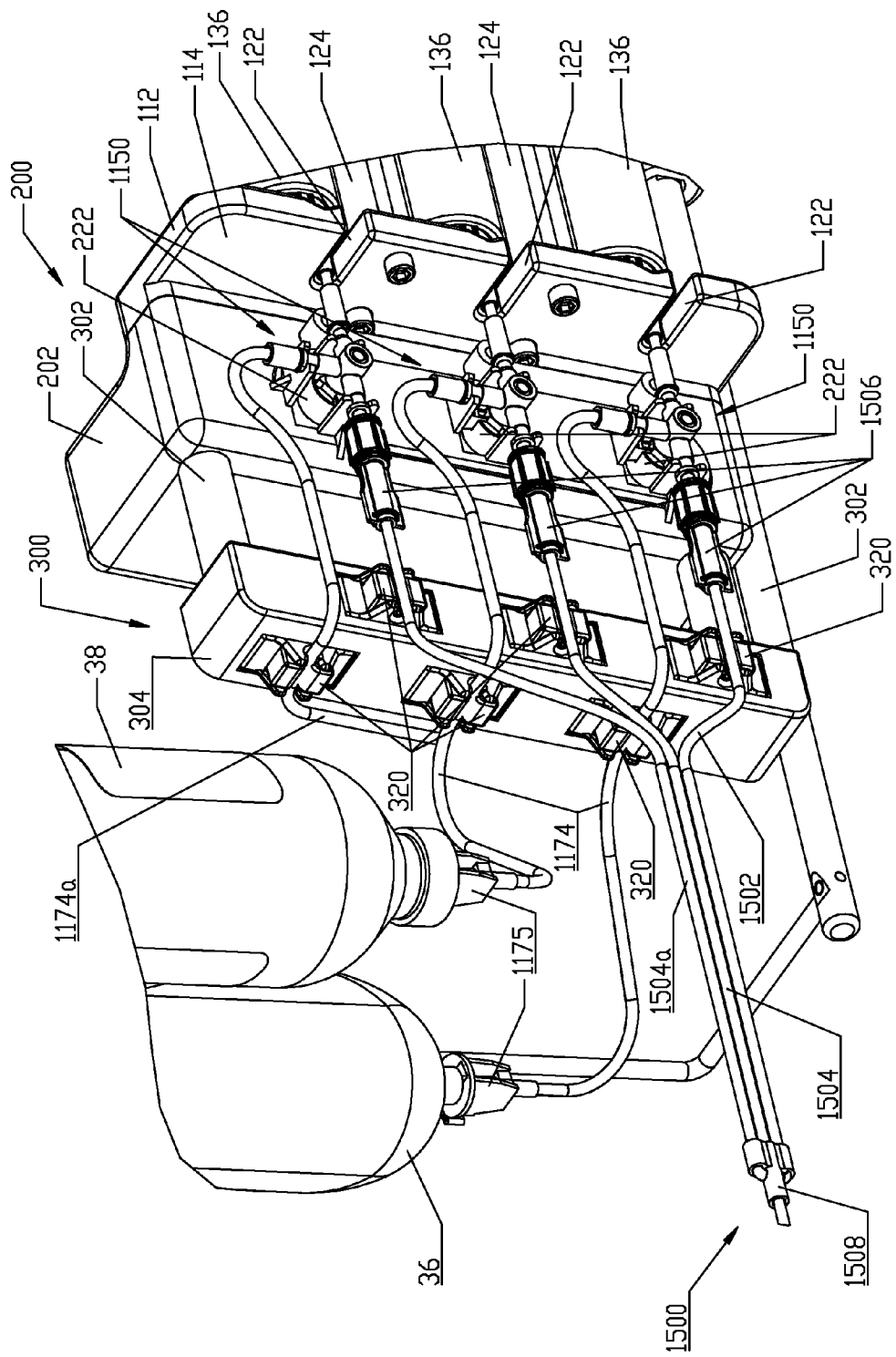
FIG. 61 is a front perspective view of a forward portion of the fluid injector system of FIG. 60.
Figure 62:
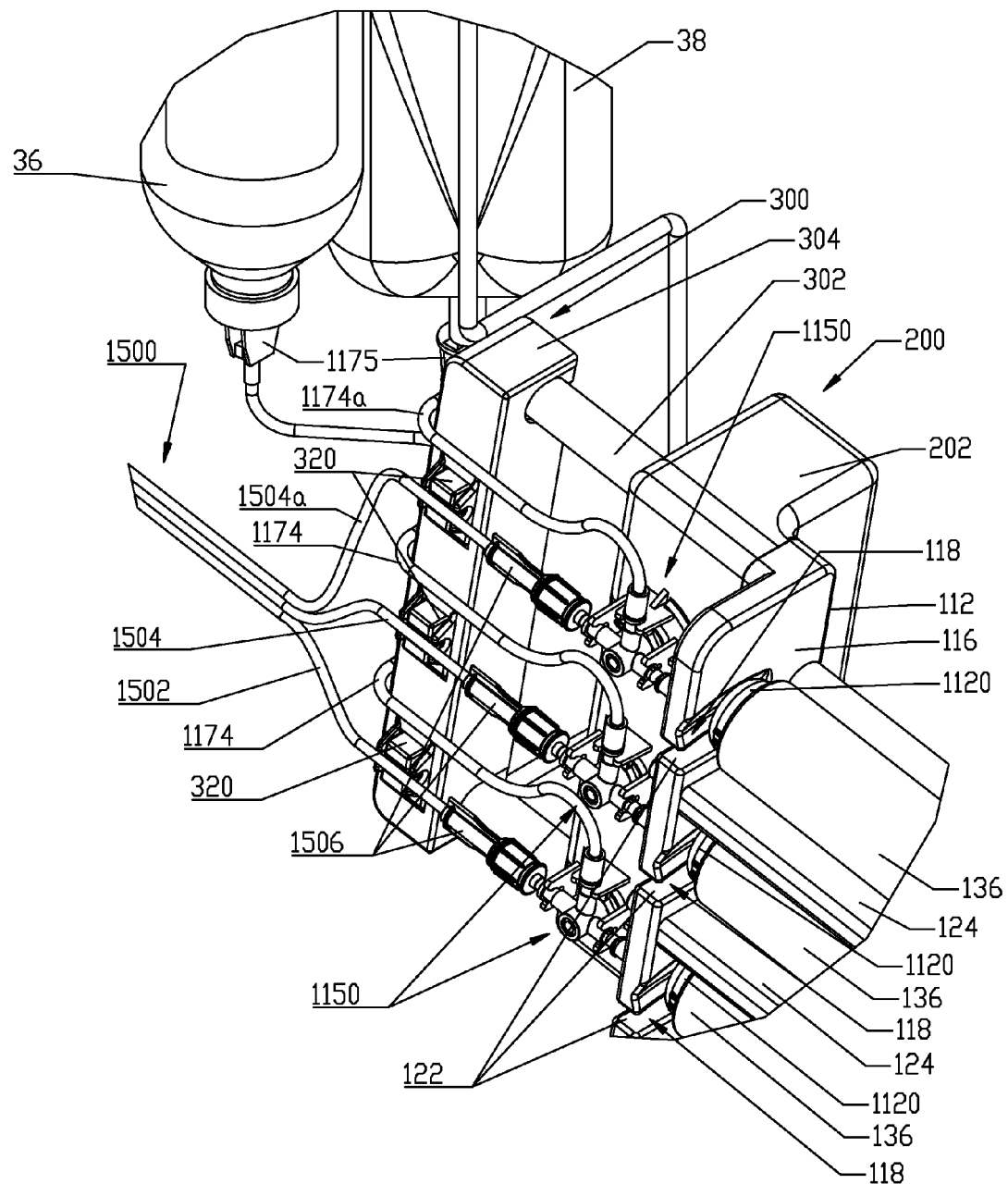
FIG. 62 is a top perspective view of the forward portion of the fluid injector system of FIG. 60.

While the foregoing discussion of the various embodiments of the fluid injector system 10 was directed to the use of a dual syringe arrangement for the delivery of two fluids such as contrast and saline, this arrangement should not be considered limiting as revealed by FIGS. 60-62, wherein a fluid injector system 10 comprising a multi-syringe 1120 arrangement is shown. This embodiment comprises the same components as the embodiment of fluid injector system 10 shown in, for example, FIGS. 1-3 but adds an additional syringe 1120-pressure jacket 136 combination or stage to the dual fluid injector system 10 described previously. As the previous discussion regarding the fluid injector system 10 generally shown in FIGS. 1-3 et seq. is applicable to the embodiment shown in FIGS. 60-62, only the relevant differences between these systems are discussed hereinafter.

In FIGS. 60-62, for illustrative purposes, two of the syringes 1120 are shown in fluid connection with fluid supply container 38 via connecting tubing line 1174 which terminates in a conventional end connector spike 1175. In particular, connecting tubing line 1174 further comprises a branch line 1174a which connects to the second port 1164 on the stopcock valve 1160 associated with the upper most syringe 1120 in the views shown in FIGS. 60-62 to provide fluid to this syringe 1120 from fluid supply container 38. The upper most syringe 1120 comprises an ultimate fluid connection with Y-connector 1508 via a third input line 1504a in the single-use set 1500 which is modified to include a Y-connector 1508 that can accommodate such a third input line 1504a. The association between the upper most syringe 1120 and the single-use set 1500 mirrors that described previously in this disclosure in connection with the two lower syringes shown in the views of FIGS. 60-62. The two lower syringes 1120 in the views shown in FIGS. 60-62 otherwise have identical fluid connections as to the dual syringe arrangement shown in FIGS. 1-3 et seq. Accordingly, it will be apparent that the upper most syringe 1120 and the middle syringe 1120 in FIGS. 60-62 are connected to the same fluid source, for example, a source of saline present in fluid supply container 38. As both of the foregoing upper and middle syringes 1120 are available to access a saline source, staggered or alternate operation of these syringes 1120 allows the clinician to have a continuous supply of saline, in the present instance, available for contrast flushing operations or other operations involving the use of saline, with such operations only limited by the fluid available in fluid supply container 38. As a result, a continuous flow of fluid from the upper and middle syringes 1120 may be available during operation of the fluid injector system 10 shown in FIGS. 60-62 only limited by the fluid available in fluid supply container 38.

While the foregoing illustrative example has two syringes 1120 coupled to a single fluid source, a distinct or separate fluid source may be dedicated to the uppermost syringe 1120 in FIGS. 60-62 and, thus, the depicted fluid injector system 10 would then be capable of delivering a mixture of three different fluids to the single-use set 1500 (e.g., simultaneous delivery in any desired mixture ratio), or sequential delivery of each of the three different fluids in any order desired with appropriate programming of the electronic control device(s) associated with the injector 20. Moreover, based on the foregoing concepts, it is possible to add additional "stages" of syringe-pressure jacket combinations to allow for the handling of additional fluids of different or like kinds. In these multi-stage embodiments, the syringes 1120 may be individually associated with individual fluid sources such as is the case with the lowermost syringe 1120 shown in FIGS. 60-62, or two or more syringes 1120 may each have a connection to a common fluid source such as is the case with the two upper syringes 1120 shown in FIGS. 60-62; any combination of single-fluid source syringes 1120 or multiple syringes 1120 drawing from the same fluid source may be provided in the foregoing multi-stage embodiments.

Figures 37A, 37B:
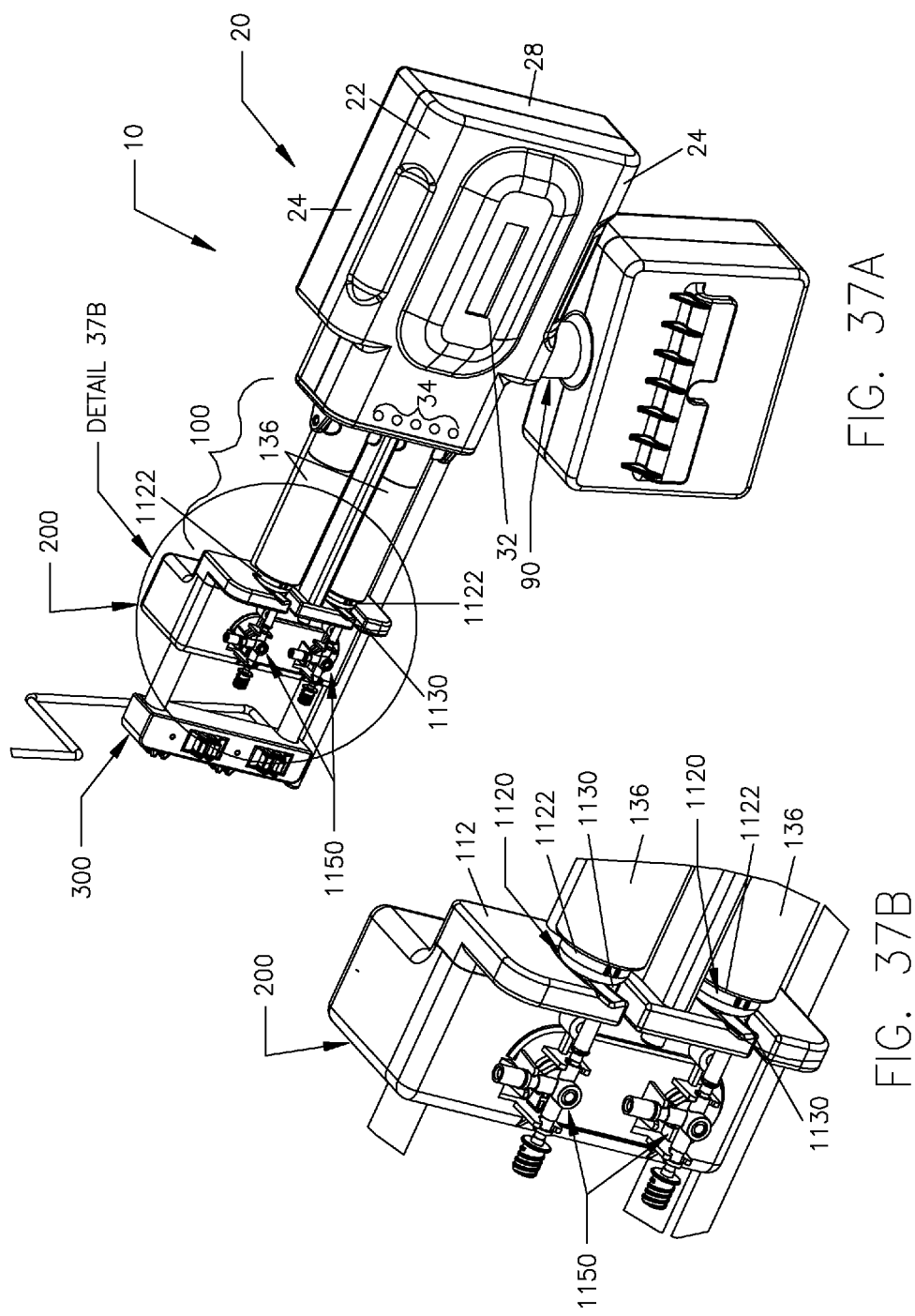
FIG. 37A is a perspective view showing the injection orientation of the fluid injector system of FIG. 1.
FIG. 37B is a detail view of Detail 37B in FIG. 37A.
Figure 63:
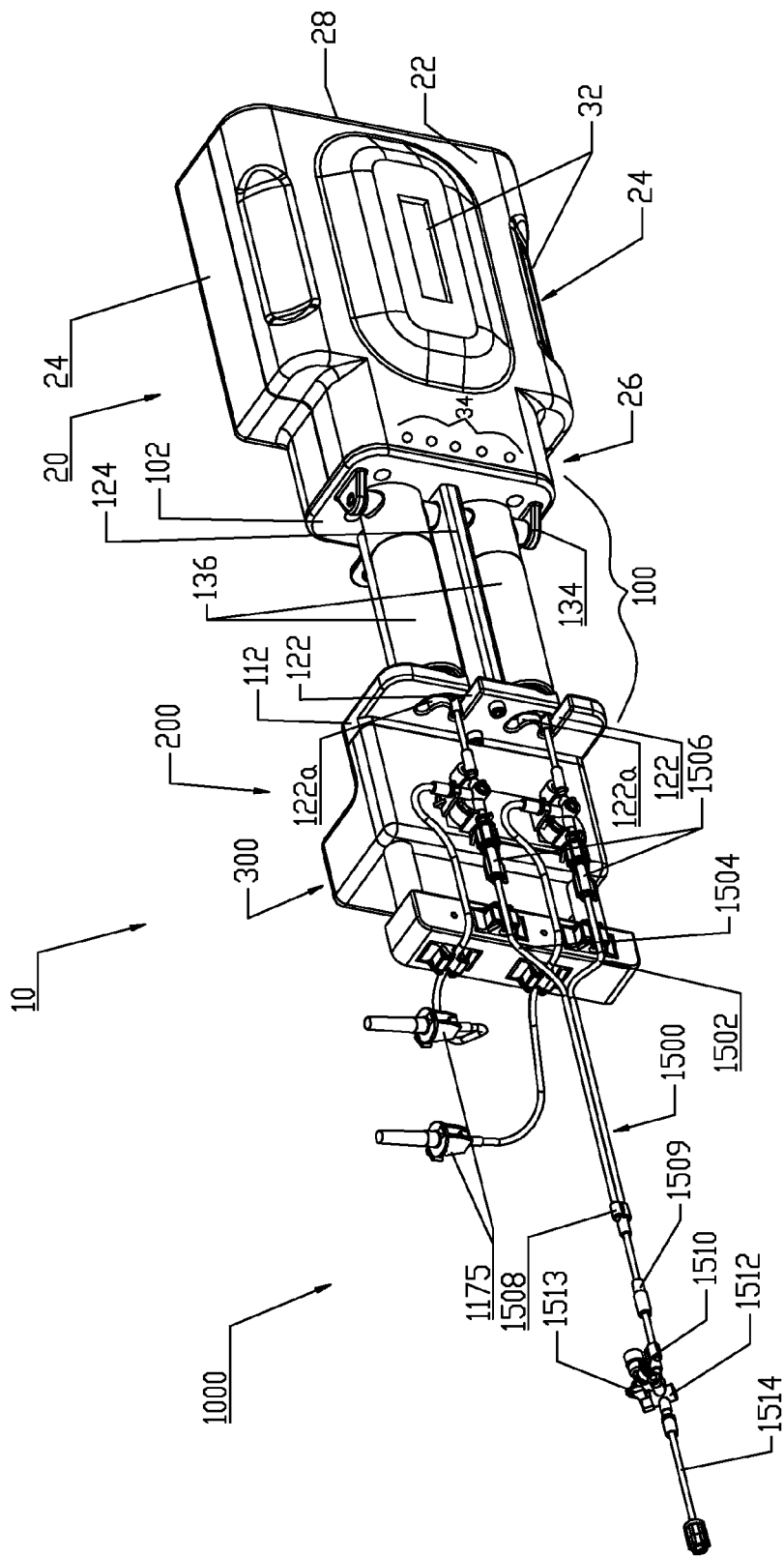
FIG. 63 is a perspective view of another embodiment of the fluid injector system of FIG. 1.
Figure 64:
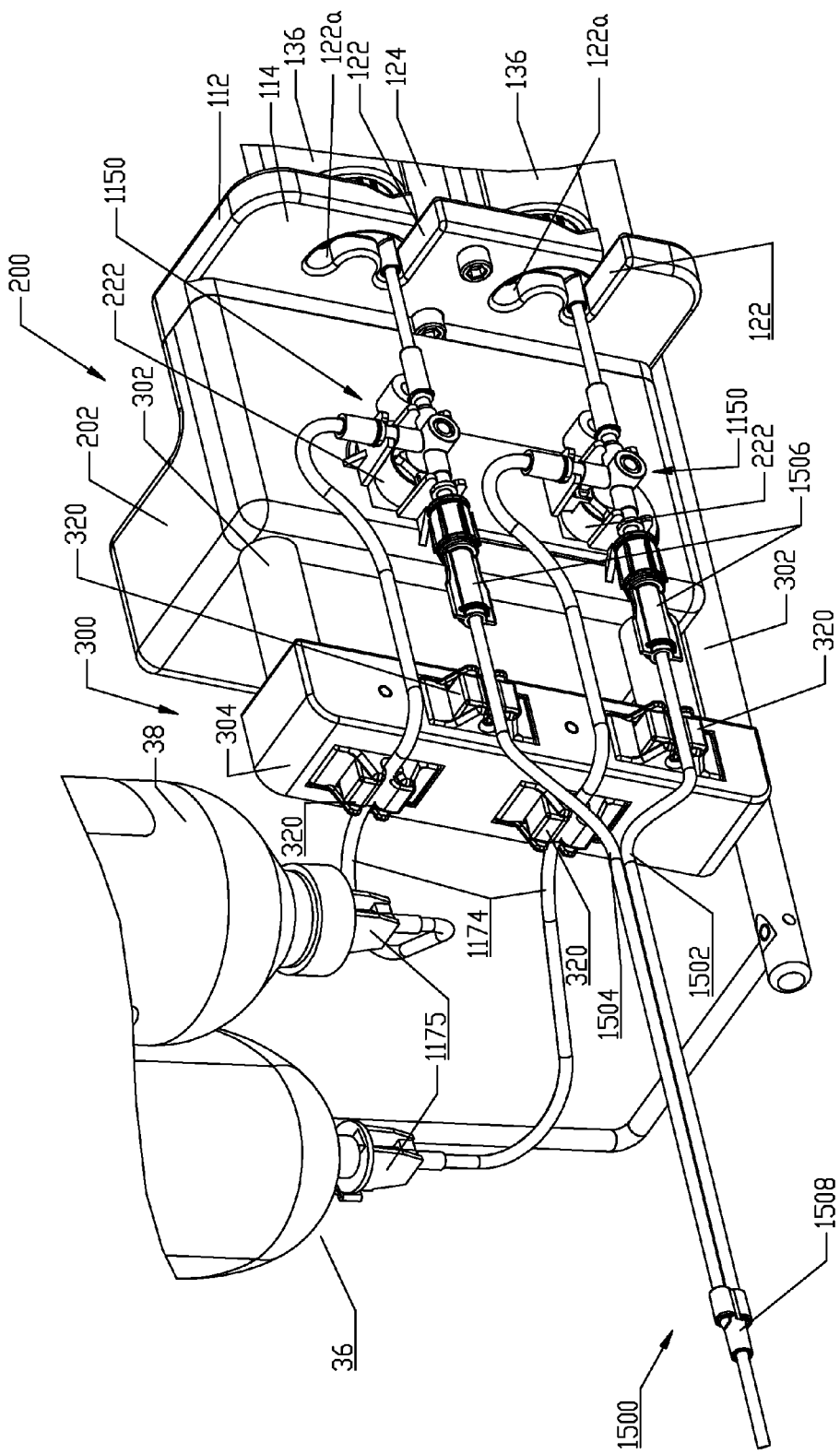
FIG. 64 is a front perspective view of the fluid injector system of FIG. 63.
Figure 65:
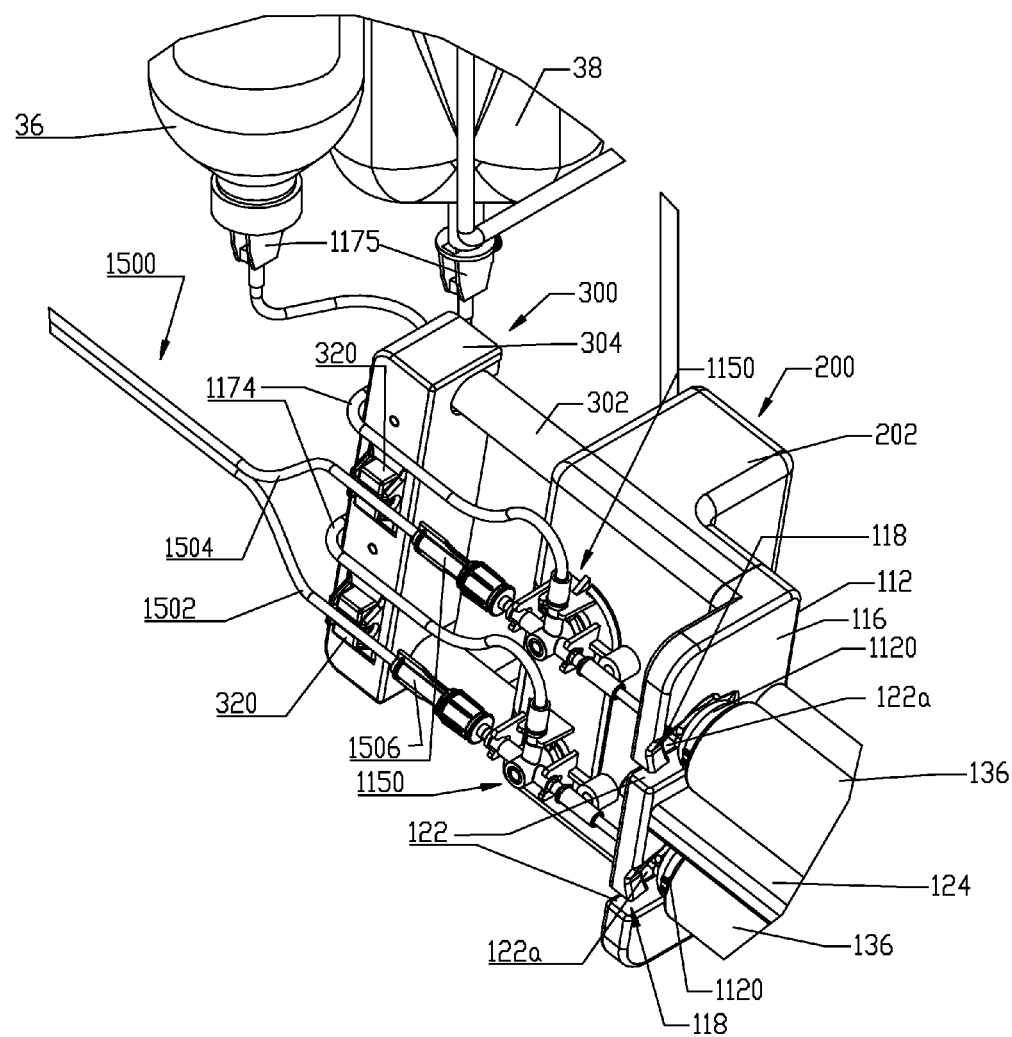
FIG. 65 is a top perspective view of a forward portion of the fluid injector system of FIG. 62.

Further, the foregoing discussion relating to FIGS. 33-37 described the sequential movement of the injector 20 as it pivots from the fluid priming and air purge orientation shown in FIG. 33 to the inject orientation shown in FIG. 37. As noted in this discussion, to reach the injection position, the pivoting movement of injector 20 results in the injector 20 "rolling" and traversing approximately 180.degree. of rotation to pivot from the fluid priming and air purge orientation to the inject orientation Likewise, the discussion relating to FIGS. 57-59 described movement of the injector 20 from a generally horizontal orientation to a generally vertical fluid fill and air purge orientation and then a return to the generally horizontal orientation wherein the pressure jackets 136 and syringes 1120 are orientated generally horizontally and ready for an injection procedure. While such "global" movement of the injector 20 has numerous advantages, as an alternative, FIGS. 63-65 illustrate the fluid injector system 10 of FIGS. 1-3 et seq. wherein only the syringes 1120 are rotated between the fluid priming and air purge orientation (e.g., wherein the discharge outlet or conduit 1130 is located at the "top") and the inject orientation (e.g., wherein the discharge outlet or conduit 1130 is located at the "bottom"). FIGS. 63-65 illustrate that the slots 122 defined vertically in front plate 112 may have a curved extension 122a in the form of a generally semicircular arc to accommodate rotational movement of the syringe 1120 in the associated pressure jacket 136 so that the discharge outlet or conduit 1130 may be rotationally moved between the fluid priming and air purge "top" orientation and the inject "bottom" orientation.

Numerous methods may be applied to obtain the desired rotational movement of the syringe 1120 in the associated pressure jacket 136. For example, the piston element 60 that captures the plunger 1300 in the syringe 1120 may be adapted for rotational movement which is imparted to the plunger 1300 via frictional contact between the plunger cover 1304 and the interior wall of the syringe body 1122 of the syringe 1120; this frictional contact is desirably sufficient to effect the rotation of the syringe 1120 in the pressure jacket 136 without "slippage" between the plunger 1300 and syringe 1120. Alternatively, interfering engagement structures may be provided between, for example, the plunger element 1302 of the plunger 1300 and a corresponding interior element (not shown) extending radially-inward from the interior wall of the syringe body 1122 so that rotation of the plunger 1300 causes the structure on the plunger element 1302 to engage the radial structure extending from the interior wall of the syringe body 1122 and thereby transfer the rotational motion of the piston element 60 to the syringe body 1122. Another suitable rotating arrangement includes a direct mechanical engagement of the syringe 1120 while seated within the pressure jacket 136 to cause rotation of the syringe 1120 therein. One such mechanical arrangement includes the use of a frictional wheel that extends through a bottom opening in the pressure jacket 136 to frictionally engage the exterior surface of the syringe body 1122. Accordingly, rotational movement of the friction wheel and the frictional contact thereof with the exterior surface of the syringe body 1122 desirably rotates the syringe 1120 in the pressure jacket 136 while the plunger 1300 in the syringe 1120 remains stationary under a restraining force provided by the associated piston element 60 of the injector 20. Alternatively, the plunger 1300 may be allowed to rotate at least to some degree (or entirely) with the syringe 1120 by a suitable mechanical connection to the associated piston element 60. The foregoing friction wheel arrangement may be supported by the center beam 124 connecting the support plates 102, 112 and include suitable electro-mechanism drive elements to effect rotation of the friction wheel and, further, include suitable mechanical structure to allow the friction wheel to move into and out of engagement within the bottom opening in the pressure jacket 136 so as not to impede the loading and unloading of the pressure jacket 136. As an alternative, the friction wheel may have gear teeth and like structures for interfacing with suitable profiling on/in the surface of the syringe body 1122 of the syringe 1120 to allow the gear teeth or profiling on the friction wheel to engage corresponding gear structures or other profiling on the surface of the syringe body 1122 of the syringe 1120 to cause the desired rotation of the syringe 1120 in the pressure jacket 136.

Another direct mechanical engagement arrangement for imparting rotational movement to the syringe 1120 includes a driven belt (or rope) arrangement wherein a frictional belt engages the syringe body 1122 while positioned within the pressure jacket 136. Such a driven belt arrangement shares common characteristics with the foregoing driven wheel arrangement and may be driven in either direction to effect movement of the syringe 1120 in the pressure jacket 136 in either rotational direction. In each of the foregoing arrangements for effecting rotation of the syringe 1120 in the pressure jacket 136, it is desirable for the intermediate conduit element 1172 to have sufficient length and flexibility to accommodate the rotational movement of the syringe 1120 in the pressure jacket 136. As a reminder, the conduit element 1172 is bonded to the first port 1162 of the stopcock valve 1160 and to the discharge conduit 1130 on the syringe body 1122 of the syringe 1120 but is also present in other embodiments of the fluid control valve 1150 for connecting the first port on the various embodiments of the fluid control valve 1150 with the discharge conduit 1130 on the syringe body 1122 of the syringe 1120.

Figure 66:
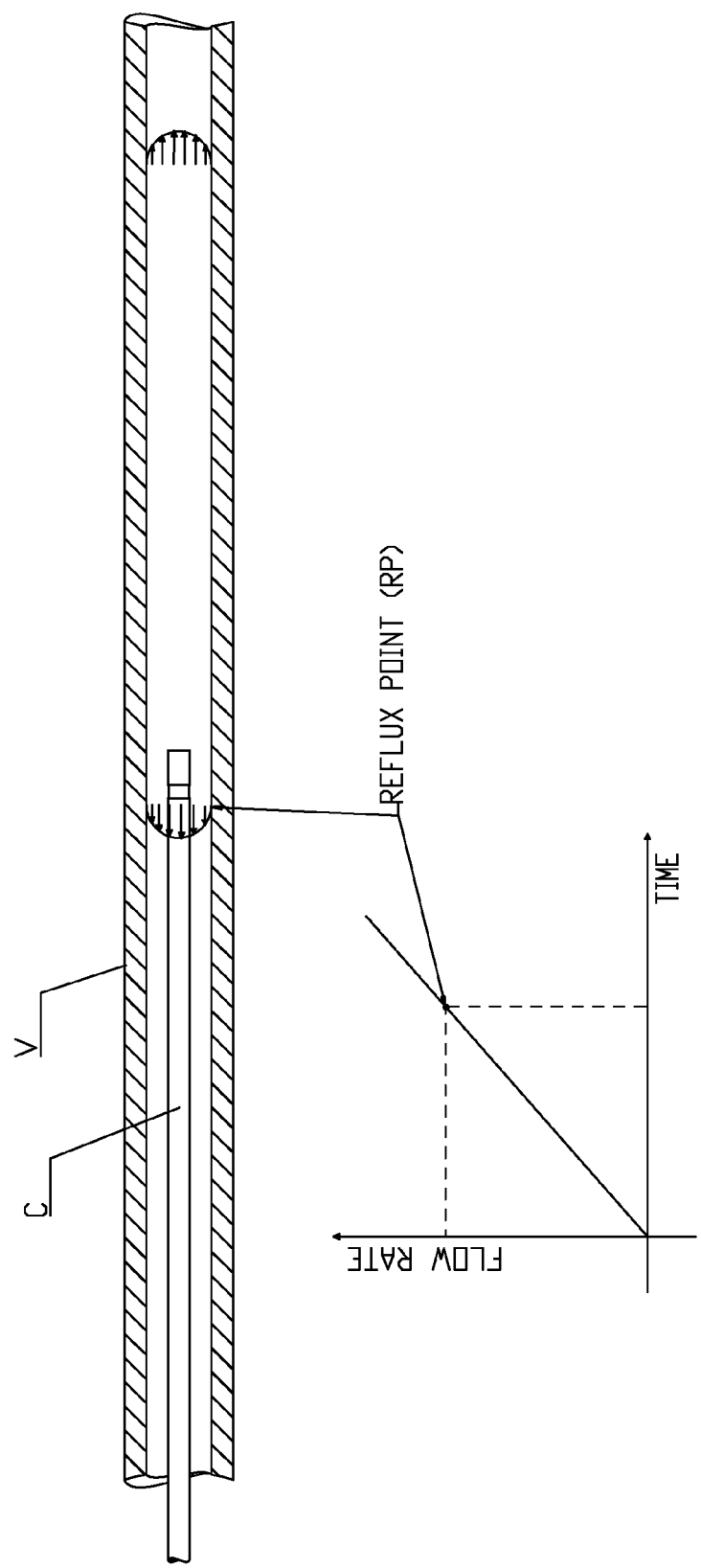
FIG. 66 is a schematic view of a blood vessel shown with an indwelling catheter for illustrating an application use of the various embodiments of the fluid injector system.

Referring next to FIG. 66, the foregoing embodiments of the fluid injector system 10 have additional applications in the medical field such as for non-invasive assessment of blood flow in a blood vessel. In many vascular procedures it is desirable to know the flow in a blood vessel V to assess the significance of a stenosis, the suitability for a transplant, or possibly to assess the presence of microvascular disease which cannot be detected any other way. Using the foregoing fluid injector system(s) 10, the system(s) 10 may be programmed for an injection of diluted contrast into the blood vessel V through a catheter C with a long, for example, more than 1 second, linearly rising flow rate, and the resulting flow rate may be displayed real time on the fluoroscopy image of the procedure displayed on a suitable monitor. An attending physician (or possibly a computer) can review the images and select the one where reflux begins (e.g., the reflux point RP), and the flow in the blood vessel is approximately equal to the injection rate on the image. This application is well-suited for a real time injector-imager communication interface, or the ability to post-process synchronize the injections. It is desirable to use diluted contrast media so that its viscosity does not significantly affect the flow and diluted contrast also reduces the contrast loading to the patient. While a real time injector interface to the imaging system and a display monitor are preferable, alternatively, before there is a real time connection between the injector and the imager, the injector could be enunciating the flow rates in, for example, 0.5 ml/sec increments, and when the physician identifies the reflux point RP on the displayed image, he or she or another attendant person can record the last recited flow rate or, when the reflux is identified, a clinician may touch one of the display windows 32 on the injector 20 or one of the control buttons 34 on the injector 20 such as the "Acknowledge/Start" button, and the injector 20 saves the latest flow rate. The catheter C is desirably a multi-opening catheter with side openings for accuracy purposes as a single end-opening catheter could exhibit a streaming of fluid from the end opening which could affect measurements. Desirably, the selected catheter may have several lumens all the way to the tip so that saline could be injected out of the side openings distally at the tip while contrast is injected from the more proximally-located side openings. The contrast flow rate is desirably relatively slow and constant. The saline flow could ramp-up and, at the point where the contrast starts to reflux, the contrast flow rate plus the saline flow rate equals the vessel natural flow rate. The injection may start at a flow rate other than zero, thereby bracketing the expected flow rate, or the injection flow rate could start at zero if the expected flow is low. If images are acquired at, for example, 30 frames per second, the injection only needs to last a few seconds to be reasonably accurate, subject to the need for some time to allow the fluid injector system 10 to get up to speed and pressurize the system 10 to fill all the mechanical capacitance of the system 10. Optionally, the physician may select an area of interest on the displayed image, and the injector 20 can increase flow until contrast refluxes into the selected area. The change in flow rate does not have to be linearly rising and could be stepped, decreasing, or varying in some other way. In the case where there is automatic feedback, the injector 20 could start reasonably low, then jump high, and eventually identify the right flow rate.

While embodiments of a multi-fluid medical injector system and methods of operation thereof were provided in the foregoing description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are to be embraced within their scope.

The invention claimed is:

1. An automatic refill procedure for a fluid injector system comprising a fluid injector and an operably engaged syringe, the procedure comprising:
   providing at least one hand controller configured to operate at least a portion of the fluid injector system;
   providing at least one sensor disposed in the at least one hand controller, the at least one sensor comprising at least one of the following: an accelerometer, a position sensor, an orientation sensor, a capacitance touch sensor, a thermal sensor, or any combination thereof;
   providing at least one processor in communication with the fluid injector system;
   determining, with the at least one processor, if a fluid injection procedure involving the syringe is impending based at least partially on inactivity of the at least one hand controller of the fluid injector system for a certain period of time, wherein the inactivity of the at least one hand controller for the certain period of time is determined based at least partially on the at least one sensor in the at least one hand controller, and indicates that the fluid injection procedure involving the syringe is not impending; and
   initiating, with the at least one processor, an automatic refill of the syringe in response to determining that the fluid injection procedure involving the syringe is not impending, such that the automatic refill does not interfere with an impending fluid injection procedure.

2. The automatic refill procedure of claim 1, wherein the at least one processor comprises a timer for monitoring the inactivity of the at least one hand controller of the fluid injector system, and wherein the inactivity of the at least one hand controller for the certain period of time indicates that the automatic refill of the syringe will not interfere with the impending fluid injection procedure.

3. The automatic refill procedure of claim 1, wherein the at least one sensor in the at least one hand controller signals to the at least one processor that the at least one hand controller is inactive.

4. The automatic refill procedure of claim 1, further comprising:
   determining if a preprogrammed trigger minimum volume is present in the syringe.

5. The automatic refill procedure of claim 4, wherein the preprogrammed trigger minimum volume is at least partially determined by or from at least one of the following: tracking a fluid volume dispensed from the syringe during operation of the fluid injector system, a fluid level sensor associated with the syringe, an amount of fluid to perform a next fluid injection procedure, or any combination thereof.

6. The automatic refill procedure of claim 4, wherein the preprogrammed trigger minimum volume is determined to be present in the syringe when, at the completion of a fluid injection procedure, there is not enough fluid to perform a next fluid injection procedure.

7. The automatic refill procedure of claim 1, wherein the initiated automatic refill refills the syringe without inducing a vacuum condition in the syringe.

8. A fluid injector system comprising a fluid injector and an operably engaged syringe, comprising:
   at least one hand controller configured to operate at least a portion of the fluid injector system;
   at least one sensor disposed in the at least one hand controller, the at least one sensor comprising at least one of the following: an accelerometer, a position sensor, an orientation sensor, a capacitance touch sensor, a thermal sensor, or any combination thereof; and
   at least one processor in communication with the fluid injector system, the at least one processor configured to:
      determine if at least one fluid injection procedure involving the syringe is impending based at least partially on inactivity of the at least one hand controller of the fluid injector system for a certain period of time, wherein the inactivity of the at least one hand controller for the certain period of time is determined based at least partially on the at least one sensor in the hand controller, and indicates that the fluid injection procedure involving the syringe is not impending; and
      initiate an automatic refill of the syringe if the at least one fluid injection procedure is not determined to be impending, such that the automatic refill of the syringe will not interfere with the fluid injection procedure.

9. The fluid injector system of claim 8, wherein the determination if at least one fluid injection procedure involving the syringe is impending is based at least partially on at least one of the following: a movement of the at least one hand controller, an orientation of the at least one hand controller, a physical contact between the at least one hand controller and an individual, or any combination thereof.

* * * * *